(12) United States Patent
Berry et al.

(10) Patent No.: US 8,173,638 B2
(45) Date of Patent: May 8, 2012

(54) COMPOUNDS WHICH MODULATE THE CB2 RECEPTOR

(75) Inventors: Angela Berry, Gaylordsville, CT (US); Pier Francesco Cirillo, Woodbury, CT (US); Eugene Richard Hickey, Danbury, CT (US); Doris Riether, Newtown, CT (US); David Smith Thomson, Ridgefield, CT (US); Lifen Wu, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 265 days.

(21) Appl. No.: 12/513,680

(22) PCT Filed: Nov. 15, 2007

(86) PCT No.: PCT/US2007/084770
§ 371 (c)(1),
(2), (4) Date: May 6, 2009

(87) PCT Pub. No.: WO2008/064054
PCT Pub. Date: May 29, 2008

(65) Prior Publication Data
US 2010/0009964 A1    Jan. 14, 2010

Related U.S. Application Data

(60) Provisional application No. 60/866,612, filed on Nov. 21, 2006.

(51) Int. Cl.
*A61P 25/00* (2006.01)
*A61K 31/55* (2006.01)
*C07D 295/13* (2006.01)
*C07D 413/12* (2006.01)

(52) U.S. Cl. .................. 514/211.15; 514/218; 540/544; 540/597; 540/598; 540/603; 540/607

(58) Field of Classification Search ............. 514/211.15, 514/218; 540/544, 597, 603, 607, 598
See application file for complete search history.

(56) References Cited

U.S. PATENT DOCUMENTS

| | | |
|---|---|---|
| 7,595,397 B2 | 9/2009 | Zindell et al. |
| 7,935,715 B2 | 5/2011 | Berry et al. |
| 2004/0067999 A1 | 4/2004 | Block et al. |
| 2005/0059663 A1 | 3/2005 | Martin et al. |
| 2007/0179126 A1 | 8/2007 | Casellas et al. |
| 2007/0191340 A1 | 8/2007 | Zindell et al. |
| 2008/0039464 A1 | 2/2008 | Berry et al. |
| 2008/0064690 A1 | 3/2008 | Atkinson et al. |
| 2008/0081822 A1 | 4/2008 | Berry et al. |
| 2009/0275611 A1 | 11/2009 | Riether et al. |
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2010/0331304 A1 | 12/2010 | Berry et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0136869 A1 | 6/2011 | Bartolozzi et al. |
| 2011/0190256 A1 | 8/2011 | Cirillo et al. |

FOREIGN PATENT DOCUMENTS

| | | |
|---|---|---|
| JP | 2003/155285 | 5/2003 |
| WO | 2007070760 A2 | 6/2007 |
| WO | 2007118041 A1 | 10/2007 |
| WO | 2008014199 A2 | 1/2008 |
| WO | 2008039645 A1 | 4/2008 |
| WO | 2008048914 A1 | 4/2008 |
| WO | 2008064054 A2 | 5/2008 |
| WO | 2008098025 A1 | 8/2008 |
| WO | 2009055357 A1 | 4/2009 |
| WO | 2009061652 A1 | 5/2009 |
| WO | 2009105509 A1 | 8/2009 |
| WO | 2009140089 A2 | 11/2009 |
| WO | 2010005782 A1 | 1/2010 |
| WO | 2010036630 A2 | 4/2010 |
| WO | 2010036631 A2 | 4/2010 |
| WO | 2010077836 A2 | 7/2010 |
| WO | 2010096371 A2 | 8/2010 |
| WO | 2010147791 A1 | 12/2010 |
| WO | 2010147792 A2 | 12/2010 |
| WO | 2011037795 | 3/2011 |

OTHER PUBLICATIONS

Carenzi et al., New Isoxazole Derivatives Provided with Antihypertensive Activity, Arzneimittel-Forschung, vol. 39, No. 6, pp. 642-646, 1989.*
Written Opinion of the International Searching Authority for PCT/US2007/084770 mailed Sep. 17, 2008.
International Search Report for PCT/US2007/084770 mailed Sep. 17, 2008.

(Continued)

*Primary Examiner* — Brenda Coleman
(74) *Attorney, Agent, or Firm* — Michael P. Morris; Anthony P. Bottino

(57) ABSTRACT

Compounds of formula (I) are disclosed. Compounds according to the invention bind to and are agonists, antagonists or inverse agonists of the CB2 receptor, and are useful for treating inflammation. Those compounds which are agonists are additionally useful for treating pain.

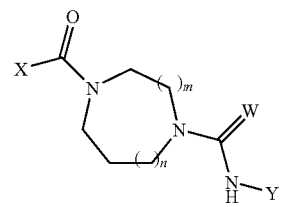

8 Claims, No Drawings

OTHER PUBLICATIONS

X.L. Cockcroft, et al., "Phthalazinones 2: optimization and synthesis of novel potent inhibitors of ply(ADP-ribose)polymerase". Bioorganic & Medicinal Chemistry Letters, 16, 2006, pp. 1040-1044.

M.M. Vogtle, et al., "An efficient protocol for the solid-phase synthesis of malondiamides". Molecules, 2005, 10, pp. 1438-1445. XP002481324.

* cited by examiner

COMPOUNDS WHICH MODULATE THE CB2 RECEPTOR

APPLICATION DATA

This application is a 371 National Stage filing of PCT/US2007/084770 filed on Nov. 15, 2007. This application also claims benefit to U.S. provisional application Ser. No. 60/866,612 filed on Nov. 21, 2006.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various imflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J. Pharmacol. (2005) 520:164-171 and Smith et al., The anti-inflammatory activities of cannabinoid receptor ligands in mouse peritonitis models Eur J. Pharmacol. (2001) 432:107-119). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J. Neurosci. (2003) 23:2511-2516). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332). The foregoing results confirm that CB2 agonists can be used for the treatment of inflammatory and neuropathic pain as well as emesis.

BRIEF SUMMARY OF THE INVENTION

The present invention provides novel compounds which bind to and are agonists, antagonists or inverse agonists of the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In its broadest generic aspect the invention provides compounds of the formula

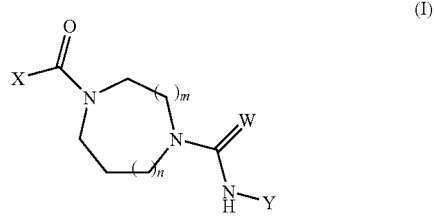

(I)

wherein,
W is O or S,
X is $C_1$-$C_6$ alkyl, $C_1$-$C_6$ alkenyl, $C_3$-$C_{10}$ cycloalkyl, aryl, 3-10 membered heterocyclyl or heteroaryl, each optionally substituted with 1 to 3 substituents; or, X is $R^2R^3N-$, wherein $R^2$ and $R^3$ are independently hydrogen, $C_1$-$C_6$ alkyl, $C_3$-$C_{10}$ cycloalkyl, aryl, 3-10 membered heterocyclyl or heteroaryl, each optionally substituted with 1 to 3 substituents; or $R^2$ and $R^3$ together with the nitrogen to which they are attached form a ring containing 1 to 3 heteroatoms and which is optionally substituted with 1 to 3 substituents;

Y is $C_1$-$C_6$ alkyl, $C_3$-$C_{10}$ cycloalkyl, aryl, 3-10 membered heterocyclyl or heteroaryl, each optionally substituted with 1 to 3 substituents;

m and n are each independently 1 or 2 wherein both cannot be 2.

In a first subgeneric aspect, the invention provides compounds of the formula I wherein, W is O or S, X is $C_1$-$C_6$ alkyl, $C_3$-$C_{10}$ cycloalkyl, phenyl, naphthyl, quinolinyl, morpholinyl, thiomorpholinyl, dioxo-thiomorpholinyl, oxo-thiomorpholinyl, piperidinyl, piperazinyl, tetrahydropyranyl, tetrahydrofuranyl, pyridinyl, thiazolyl, oxazolyl, isoxazolyl, imidazolyl, hexahydrothiopyran, dioxo-hexahydrothiopyran, oxazepanyl or thienyl, each X is optionally substituted with 1-3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, amino$C_1$-$C_6$ acyl, $C_1$-$C_6$ acylamino, $C_1$-$C_6$ alkoxycarbonyl, $C_1$-$C_6$ alkoxycarbonylamino, $C_3$-$C_6$ cycloalkyl, morpholinyl, thiomorpholinyl, dioxothiomorpholinyl, piperidinyl, pyrrolidinyl, tetrahydrofuranyl, tetrahydropyranyl, phenoxy, phenylamino, halogen, cyano, $C_1$-$C_6$ dialkylamino, oxo, hydroxyl, phenyl, pyridinyl and $SO_2R^4$, each of the above ring substituents for X are further optionally substituted with 1 to 2 halogen or $C_1$-$C_4$ alkyl optionally substituted with halogen; or X is $R^2R^3N-$, wherein $R^2$ and $R^3$ are independently hydrogen, $C_1$-$C_6$ alkyl (optionally substituted by 1 to 3 halogen atoms), $C_3$-$C_6$ cycloalkyl, phenyl, benzyl, quinolinyl, morpholinyl, thiomorpholinyl, piperidinyl, piperazinyl, thiazolyl, oxazolyl, isoxazolyl, imidazolyl, triazolyl, oxadiazolyl, thiadiazolyl, indolyl, azaindolyl, benzoxazolyl, benzothiazolyl, benzimidazolyl, tetrahydrobenzothiazolyl, tetrahydrobenzimidazolyl, tetrahydrobenzoxazolyl, tetrahydroisoquinolinyl or pyridinyl each of the above ring substituents are optionally substituted with 1 to 2 $C_1$-$C_4$ alkyl optionally substituted with halogen;

$R^4$ is $C_1$-$C_6$ alkyl (optionally substituted by 1 to 3 halogen atoms), $C_3$-$C_6$ cycloalkyl, phenyl or benzyl;

Y is $C_1$-$C_6$ alkyl, $C_3$-$C_{10}$ cycloalkyl, phenyl, naphthyl, quinolinyl, morpholinyl, thiomorpholinyl, piperidinyl, piperazinyl, tetrahydropyranyl, tetrahydrofuranyl, pyridinyl, thiazolyl, oxazolyl, isoxazolyl, imidazolyl, triazolyl, oxadiazolyl, thiadiazolyl, indolyl, azaindolyl, benzoxazolyl, benzothiazolyl, benzimidazolyl, tetrahydrobenzothiazolyl, tetrahydrobenzimidazolyl, tetrahydrobenzoxazolyl, tetrahydroisoquinolinyl, and thienyl each optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, $C_3$-$C_6$ cycloalkyl, phenoxy, $C_1$-$C_6$ alkylthio (which is optionally substituted with 1 to 3 halogen atoms), halogen, cyano, $C_1$-$C_6$ dialkylamino, $C_1$-$C_6$ dialkylamino$C_1$-$C_6$ alkyl, phenyl (which is optionally substituted with 1 to 2 halogen atoms or $C_1$-$C_4$ alkyl optionally substituted with halogen), thienyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^5$ wherein $R^5$ is $C_1$-$C_6$ alkyl (optionally substituted by one to 3 halogen atoms).

In a further subgeneric aspect, the invention provides compounds of the formula I wherein, W is O, X is methyl, ethyl, propyl, butyl, pentyl, cyclopropyl, cyclobutyl, cyclopentyl, cyclohexyl, cycloheptyl, phenyl, naphthyl, quinolinyl, morpholinyl, thiomorpholinyl, dioxothiomorpholinyl, oxo-thiomorpholinyl, piperidinyl, piperazinyl, tetrahydropyranyl, tetrahydrofuranyl, pyridinyl, thiazolyl, oxazolyl, isoxazolyl, imidazolyl, hexahydrothiopyran, dioxo-hexahydrothiopyran, oxazepanyl, and thienyl, each X is optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, $C_1$-$C_6$ acylamino, $C_3$-$C_6$ cycloalkyl, phenoxy, halogen, cyano, $C_1$-$C_6$ dialkylamino, morpholinyl, tetrahydrofuranyl, tetrahydropyranyl, piperidinyl, pyrrolidinyl, thiomorpholinyl, dioxo-thiomorpholinyl, oxo, hydroxyl, phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^4$;

or X is $R^2R^3N-$, wherein $R^2$ and $R^3$ are independently hydrogen, $C_1$-$C_6$ alkyl (optionally substituted by 1 to 3 halogen atoms), $C_3$-$C_6$ cycloalkyl, phenyl, benzyl or morpholinyl;

Y is methyl, ethyl, propyl, butyl, pentyl, cyclopropyl, cyclobutyl, cyclopentyl, cyclohexyl, cycloheptyl, phenyl, naphthyl, quinolinyl, morpholinyl, thiomorpholinyl, piperidinyl, piperazinyl, tetrahydropyranyl, tetrahydrofuranyl, pyridinyl, thiazolyl, oxazolyl, isoxazolyl, imidazolyl, indolyl, azaindolyl, benzoxazolyl, benzothiazolyl, benzimidazolyl, tetrahydrobenzothiazolyl, tetrahydrobenzimidazolyl, tetrahydrobenzoxazolyl and thienyl each optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_3$-$C_6$ cycloalkyl, phenoxy, $C_1$-$C_6$ alkylthio (which is optionally substituted with 1 to 3 halogens), halogen, cyano, dimethylamino $C_1$-$C_6$ alkyl, phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^5$ wherein $R^5$ is $C_1$-$C_6$ alkyl (optionally substituted by one to 3 halogen atoms), $C_3$-$C_6$ cycloalkyl, phenyl or benzyl;

$R^4$ is $C_1$-$C_6$ alkyl (optionally substituted by 1 to 3 halogen atoms), $C_3$-$C_6$ cycloalkyl, phenyl or benzyl;

m and n are each 1.

In a still further subgeneric aspect, the invention provides compounds of the formula I wherein, W is O, X is methyl, ethyl, propyl, cyclopentyl, cyclohexyl, phenyl, naphthyl, quinolinyl, tetrahydropyranyl, cycloheptyl, dioxohexahydrothiopyran, each optionally substituted with 1-3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, $C_1$-$C_6$acylamino, $C_3$-$C_6$ cycloalkyl, phenoxy, halogen, hydroxyl, oxo, cyano, $C_1$-$C_6$dialkylamino, morpholinyl, thiomorpholinyl, dioxo-thiomorpholinyl, piperidinyl (optionally substituted with 1-2 halogen atoms), pyrrolidinyl (optionally substituted with 1-2 halogen atoms), phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^4$;

Y is phenyl, naphthyl, quinolinyl, pyridinyl, thiazolyl, oxazolyl, isoxazolyl, imidazolyl, tetrahydrobenzothiazolyl, and thienyl each optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_3$-$C_6$ cycloalkyl, phenoxy, halogen, cyano, $C_1$-$C_6$ alkylthio (which is optionally substituted with 1-3 halogens) dimethylamino $C_1$-$C_6$ alkyl, phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^5$ wherein $R^5$ is $C_1$-$C_6$ alkyl (optionally substituted by 1 to 3 halogen atoms), $C_3$-$C_6$ cycloalkyl, phenyl or benzyl.

or X is $R^2R^3N$—, wherein $R^2$ and $R^3$ are independently hydrogen, $C_1$-$C_6$ alkyl (optionally substituted by 1 to 3 halogen atoms), or morpholinyl;

$R^4$ is $C_1$-$C_6$ alkyl (optionally substituted by 1 to 3 halogen atoms), $C_3$-$C_6$ cycloalkyl, phenyl or benzyl.

All terms as used herein in this specification, unless otherwise stated, shall be understood in their ordinary meaning as known in the art. In all the compounds disclosed hereinabove in this application, in the event the nomenclature is in conflict with the structure, it shall be understood that the compound is defined by the structure.

The term "alkyl", or any substituent containing an alkyl group such as alkoxy or acylamino, shall be understood to be branched or unbranched alkyl groups, preferably $C_1$-$C_6$ and shall be understood to be optionally partially or fully halogenated.

The term "aryl" refers to phenyl and naphthyl.

Each aryl or heteroaryl unless otherwise specified includes it's partially or fully hydrogenated derivative. For example, naphthyl may include it's hydrogenated derivatives such as tetrahydronaphthyl. Other partially or fully hydrogenated derivatives of the aryl and heteroaryl compounds described herein will be apparent to one of ordinary skill in the art.

The invention also includes tautomers, prodrugs and pharmaceutically acceptable salts of the above-described compounds of formula I. In addition, the invention includes amorphous or crystalline forms of the compounds, and isolated isomorphs or polymorphic mixtures, if present.

Compounds of the formula I modulate the activity of the CB2 receptor. By virtue of this fact the compounds of the formula I can be used for treating inflammation, in a manner described more fully below.

Those compounds of the formula I which are agonists of the CB2 receptor can additionally be used for treating pain, in a manner described more fully below.

The compounds of formula I may be made using the general synthetic methods described below, which also constitute part of the invention.

General Synthetic Methods

The invention also provides processes for making compounds of Formula (I). In all schemes, unless specified otherwise, W, X, Y, m and n in the formulas below shall have the meaning of W, X, Y, m and n in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the schemes below, are either commercially available or easily prepared from commercially available materials by those skilled in the art.

The compounds in this application may be synthesized according to schemes 1 and 2 below:

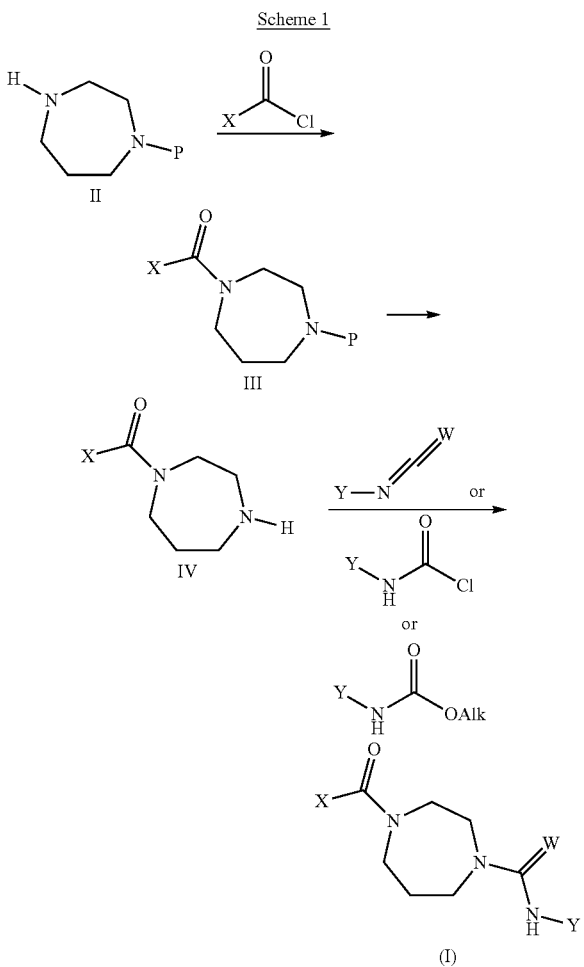

As illustrated in scheme 1, an appropriately-protected 1,4-diazapane II, wherein P is a protecting group, is allowed to react with an acid chloride of formula XCOCl or carbamoyl chloride of formula XCOCl (wherein X=$R^2R^3N$—), in the presence of a suitable base, resulting in the formation of either an amide- or urea-substituted diazapane III. Deprotection of this resulting product of formula III provides a compound of formula IV. Reaction of the compound of formula IV with an appropriate isocyanate or isothiocyanate of formula Y—NCW, provides the corresponding, desired compound of formula (I). Alternatively, reaction of the compound of formula IV with an appropriate, carbamoyl chloride of formula Y—NHCOCl, or an activated carbamate of formula Y—NH-COOAlk, in the presence of a base, provides the corresponding, desired compound of formula (I).

Alternatively, compounds of formula (I) may also be prepared by the method outlined in scheme 2.

Scheme 2

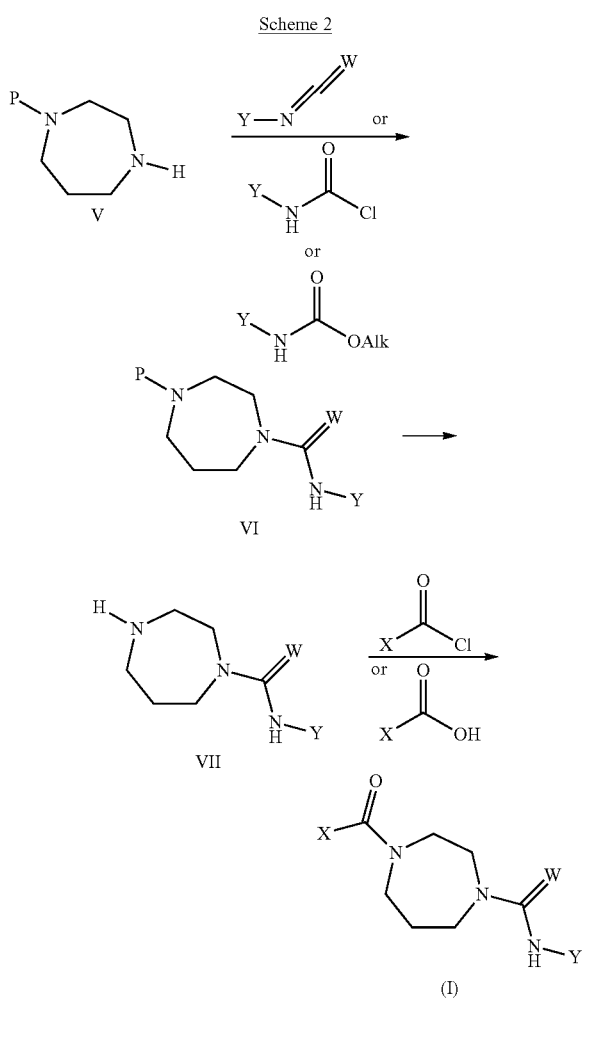

the corresponding, desired compound of formula (VI). Alternatively, reaction of the compound of formula V with an appropriate, carbamoyl chloride of formula Y—NHCOCl, or an activated carbamate of formula Y—NHCOOAlk, in the presence of a base, provides the corresponding urea-substituted diazapane of formula VI. Deprotection of the compound of formula VI provides the free amine of formula VII. This compound of formula VII is then reacted with an acid chloride of formula XCOCl to provide a compound of formula (I). Alternatively, the compound of formula VII may be reacted with a carboxylic acid of formula XCOOH, under standard peptide coupling conditions to provide the corresponding desired compound of formula (I). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine. Further modification of the initial product of formula (I) by methods known in the art and illustrated in the Examples below, may be used to prepare additional compounds of this invention The experimental procedures described below are included as examples.

EXAMPLES

The manner in which the compounds of the invention can be made will be further understood by way of the following examples.

Example 1

Synthesis of 4-(3-Cyclopentyl-propionyl)-[1,4]diazepane-1-carboxylic acid (4-butyl-phenyl)-amide
(Compound 1 in Table 1, Method A)

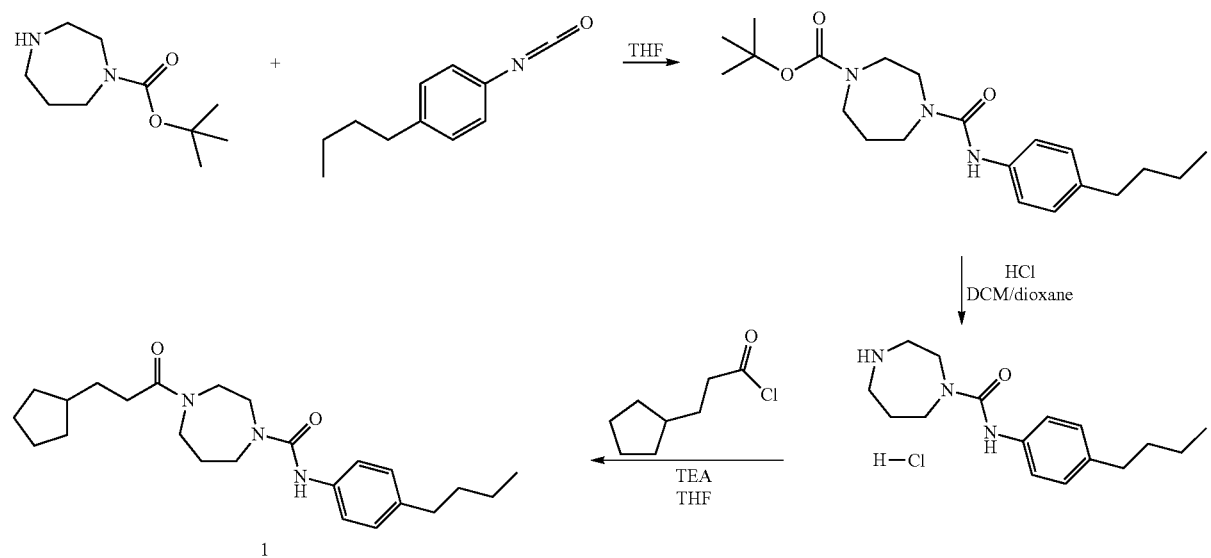

As shown in scheme 2, reacting an appropriately-protected 1,4-diazapane V, wherein P is a protecting group, with an isocyanate or isothiocyanate of formula Y—NCW, provides To a solution of the Boc-protected homopiperazine (0.426 g; 2.13 mmol) in 5 mL anhydrous tetrahydrofuran (THF) was added the 4-n-butylphenyl isocyanate (0.36 mL; 2.13 mmol).

The mixture was left stirring at room temperature overnight, then the solvent was removed in vacuo to afford a white solid. Purification by flash column chromatography on silica gel afforded pure product as a white foam, 749 mg (94% yield).

The Boc-protected diazapane urea from above (0.70 g; 1.86 mmol; 1 equiv.) was dissolved in 20 mL anhydrous dichloromethane (DCM) and treated at room temperature with a solution of HCl in 1,4-dioxane (4 M; 2.3 mL). A thick white precipitate formed after 1 h. The mixture was left stirring for 3 h, then the solvent was removed in vacuo to afford the diazapane urea hydrochloride salt as a white solid. It was used without purification in the next step.

To a mixture of the diazapane urea hydrochloride salt (84 mg; 0.27 mmol) and triethylamine (TEA) (0.084 mL; 0.60 mmol) in 1 mL anhydrous THF was added the 3-cyclopentanepropionic acid chloride (0.043 mL; 0.28 mmol). An exotherm was observed after the addition. The reaction mixture was left stirring overnight, then quenched with water and extracted 3 times with ethyl acetate (EtOAc). The combined organic extracts were dried over anhydrous sodium sulfate, filtered, and evaporated in vacuo. The resulting orange oil, was purified by flash column chromatography on silica gel. The title compound was isolated as a colorless glass (90 mg; 84% yield).

According to this method, compounds listed in Table 1, method A were made.

Example 2

Synthesis of 4-(3-Cyclopentyl-propionyl)-[1,4]diazepane-1-carboxylic acid (4-isopropyl-phenyl)-amide (Compound 2 in Table 1, Method B)

To a solution of the Boc-protected homopiperazine (0.45 g; 2.25 mmol) and TEA (0.31 mL; 2.25 mmol) in 5 mL anhydrous THF was added the 3-cyclopentyl-propionyl chloride (0.34 mL; 2.25 mmol). The mixture was left stirring at room temperature overnight, then was quenched with water and extracted with EtOAc twice. Combined organic extracts were washed with brine, dried over sodium sulfate, filtered, and evaporated in vacuo. The crude product was purified by flash column chromatography on $SiO_2$ using 0-40% EtOAc in hexanes mixtures as eluent to provide the amide as a colorless oil, 0.60 g.

The boc-protected diazepane amide was dissolved in 20 mL anhydrous DCM and treated at room temperature with excess HCl in 1,4-dioxane (4N, 4.6 mL). The mixture was left stirring at room temperature for 5 h, then the solvent was removed in vacuo. The desired salt was obtained as a white solid, 0.465 g.

To a suspension of the diazapane amide hydrochloride salt (100 mg; 0.38 mmol) and triethylamine (TEA) (0.10 mL; 0.72 mmol) in 2 mL THF was added the 4-isopropyl-phenyl isocyanate (62 mg; 0.38 mmol). The mixture was left stirring at room temperature overnight, then the solvent was evaporated in vacuo and the residue was purified by flash chromatography on silica gel using 5% methanol in DCM as eluent mixtures. The title compound was isolated as a slightly yellow glassy material (138 mg; 93%). According to this method, compounds listed in Table 1, method B were made.

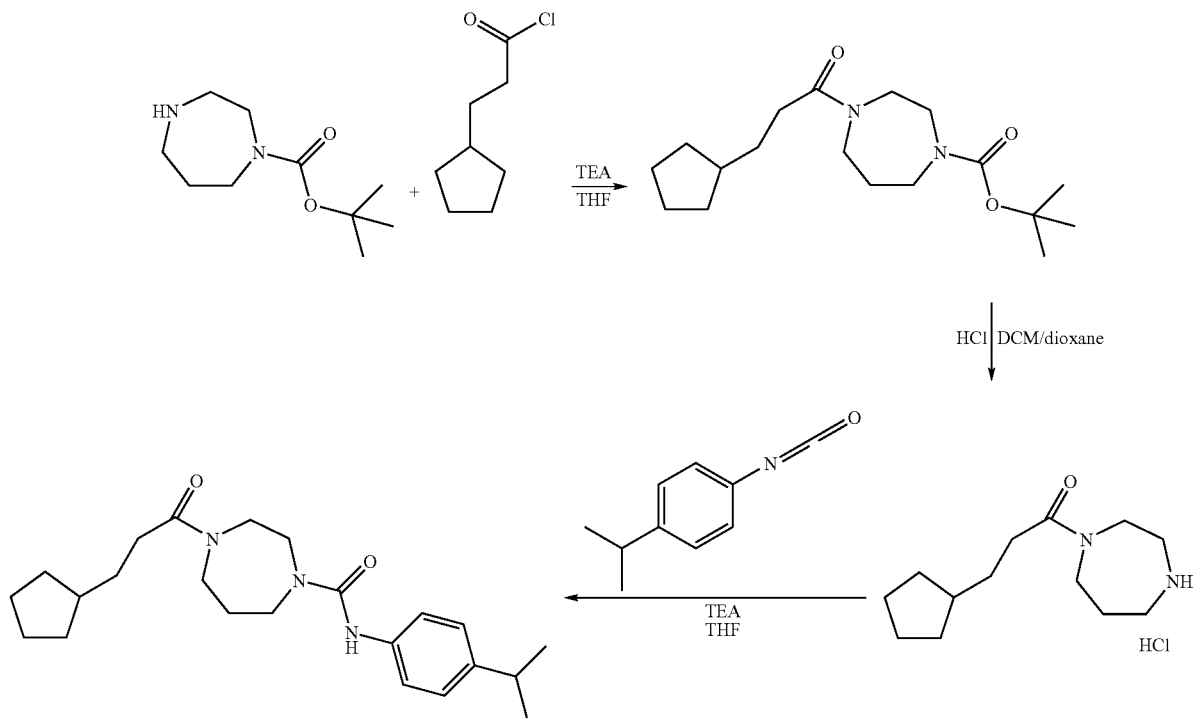

2

Example 3

Synthesis of 4-(2-Cyclopentyl-acetyl)-[1,4]diazepane-1-carboxylic acid (4-butyl-phenyl)-amide (Compound 11 in Table 1, Method C)

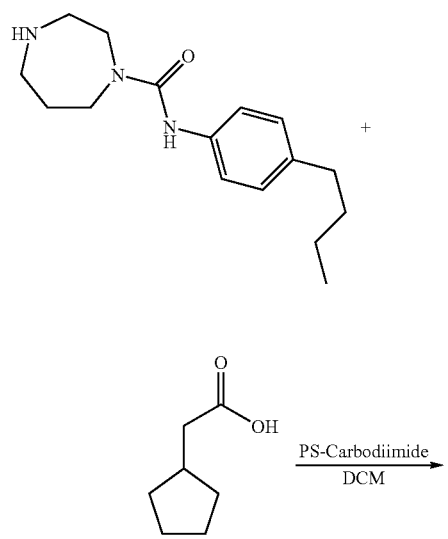

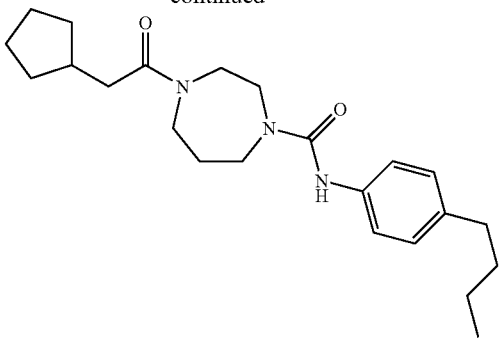

11

To a solution of the 2-cyclopentaneacetic acid (38.5 mg; 0.30 mmol) in 2 mL DCM was added the PS-Carbodiimide (0.94 mmol/g; 400 mg). After shaking for 20 min the amine was added and the mixture was shaken overnight. The mixture was filtered though a solid-phase extraction (SPE) column packed with amine anion exchange sorbent, the solids were washed with 15 mL 3% methanol in DCM, then the combined filtrate and washings were eluted through a SPE column packed with sulfonic acid cation exchange sorbent, using 20 mL 3% MeOH in DCM. The collected organics were evaporated in vacuo to afford the title compound as a colorless foam, 85 mg (87% yield), in 94.1% purity by HPLC.

According to this method, compounds listed in Table 1, method C were made.

Example 4

Synthesis of 4-(3-Cyclohexyl-propionyl)-[1,4]diazepane-1-carboxylic acid (4-isopropyl-phenyl)-amide (Compound 56 in Table 1, Method D)

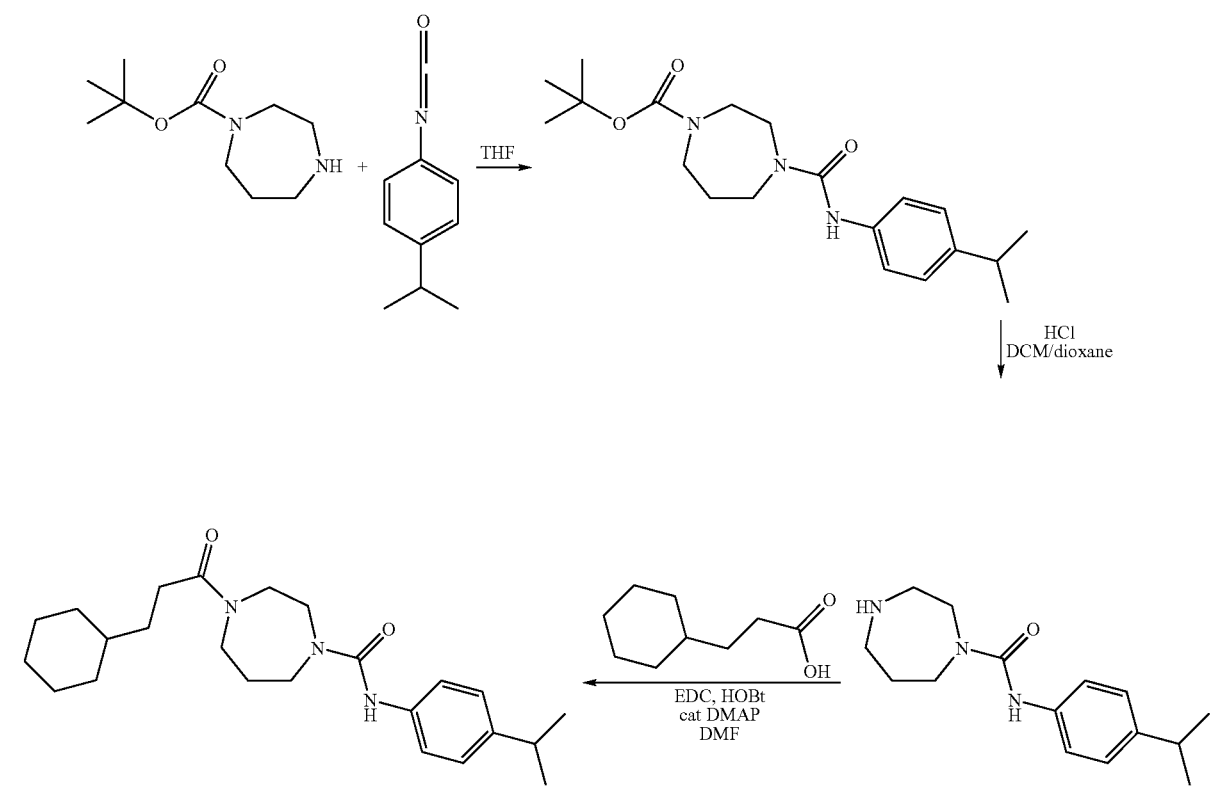

56

To a solution of mono-Boc-homopiperazine (1.00 g; 5.0 mmol) in 30 mL anhydrous THF was added 4-isopropylphenyl isocyanate (0.80 mL; 5.0 mmol) and the mixture was left stirring overnight. The solvent was then evaporated in vacuo and the product was recrystallized from hot EtOAc to afford a white solid, 1.45 g (80% yield).

This resulting Boc-protected diazapane was dissolved in 40 mL anhydrous DCM and treated with excess HCl in dioxane (4 M solution, 5 mL). After stirring vigorously overnight the reaction mixture was slowly quenched with saturated aqueous sodium bicarbonate solution, and the product was extracted with DCM twice. Combined organic fractions were dried over sodium sulfate, filtered, and the solvent was evaporated in vacuo to afford the product diazapane urea free base as a glassy pale yellow solid (0.95 g; 90.6% yield).

To a solution of 3-cyclohexane-propionic acid (55 mg; 0.35 mmol) and 1-hydroxybenzotriazole (HOBt) (68 mg; 0.5 mmol) in 1 mL anhydrous N,N-dimethylformamide (DMF) was added N-(3-dimethylaminopropyl)-N'-ethylcarbodiimide hydrochloride (EDC) (96 mg; 0.50 mmol) and the mixture was stirred for 20 minutes at room temperature. The diazapane urea (70 mg; 0.27 mmol) was then added as a solution in 1 mL DMF, together with a catalytic amount of 4-dimethylaminopyridine (DMAP). The mixture was stirred for 2 days, then water was added and the product was extracted with ether twice. Combined organic extracts were washed with saturated aqueous sodium bicarbonate solution, then with brine. The washed extracts were then dried over sodium sulfate, filtered, and the solvent was removed in vacuo to afford the crude product, which was purified by flash column chromatography on silica gel. The title compound was isolated as a colorless foam, 89 mg (83%).

According to this method, compounds listed in Table 1, method D were made.

Example 5

Synthesis of 4-(2-Tetrahydro-pyran-4-yl-acetyl)-[1,4]diazepane-1-carboxylic acid (4-trifluoromethoxyphenyl)-amide (Compound 27 in Table 1, Method E)

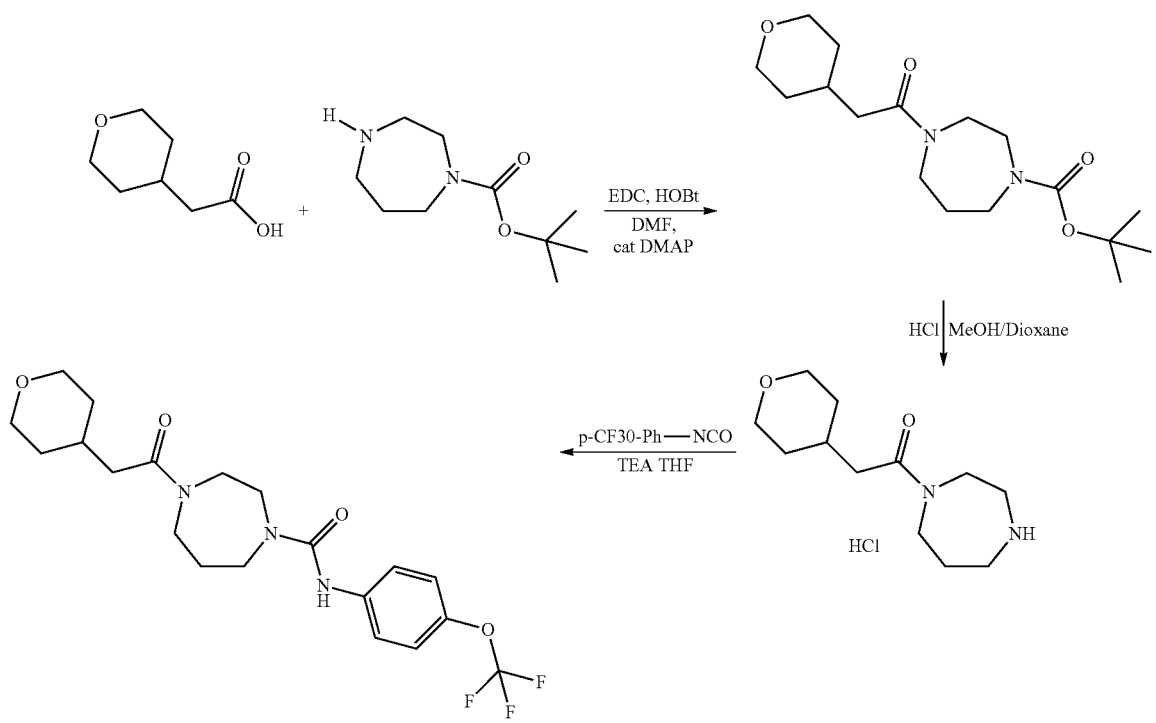

27

To a solution of 4-tetrahydropyran acetic acid (669 mg; 4.64 mmol) and HOBt (531 mg; 5.52 mmol) in 10 mL DMF was added EDC (1.06 g; 5.52 mmol). After stirring 15 min at room temperature the diazapane amine was added (0.78 mL; 4.03 mmol), then a catalytic amount of DMAP was added, and the mixture was left stirring overnight.

Water was added and the product was extracted with EtOAc. The combined extracts were washed sequentially with water, saturated aqueous sodium bicarbonate solution, saturated ammonium chloride aqueous solution, and brine. The extracts were then dried over anhydrous sodium sulfate, filtered, and the solvent was removed in vacuo. The product was purified by flash column chromatography on silica gel using 50% EtOAc in hexanes as eluent mixture, followed by to 5% methanol in DCM. An off-white solid was isolated, 738 mg (56% yield). The Boc-protected diazapane amide from above (738 mg; 2.26 mmol) was dissolved in 10 mL methanol. HCl in dioxane was added (4M; 5.7 mL). The mixture was stirred at room temperature for 2 hours. Thin layer chromatography (TLC) showed complete conversion, whereupon solvent was removed in vacuo to afford 599 mg of the salt as a waxy solid. To a suspension of the above salt (50 mg; 0.19 mmol) and TEA (0.053 mL; 0.38 mmol) in 2 mL THF was added the isocyanate (0.029 mL; 0.19 mmol). The mixture was left stirring at room temperature for 3 hours, then the solvent was removed in vacuo, water was added, and the product was extracted with EtOAc twice. The combined organic extracts were washed with brine, dried over anhydrous sodium sulfate, filtered, and the solvent was evaporated in vacuo. The resulting oil was purified by flash column chromatography on silica gel using 5% methanol in DCM mixtures as eluent. The title compound was obtained as a colorless oil, 74 mg (88% yield).

According to this method, compounds listed in Table 1, method E were made. When the isocyanates were not commercially available they were generated by standard procedures using phosgene or triphosgene (e.g. Norwick et al, *J. Org. Chem.* 1996, 61, 3929-3934).

Example 6

Synthesis of 4-(2-Tetrahydro-pyran-4-yl-acetyl)-[1,4]diazepane-1-carboxylic acid (4-methanesulfonyl-phenyl)-amide
(Compound 136 in Table 1, Method F)

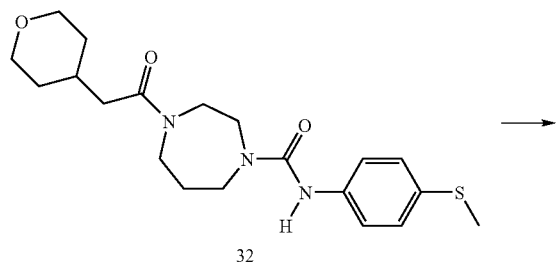

32

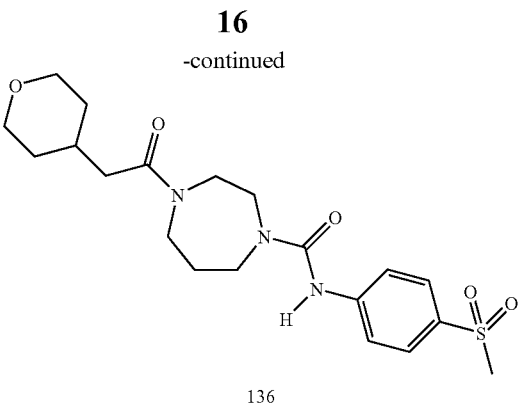

136

Methyl thioether compound 32 (94 mg; 0.24 mmol) was dissolved in 5 mL acetone. A solution of oxone (326 mg; 0.53 mmol) in 2 mL water was added. The mixture was stirred at room temperature for 3 hours, then the solvent was removed in vacuo. Water was added to the residue and the product was extracted with DCM twice. Combined organic extracts were washed with brine, dried over anhydrous sodium sulfate, and filtered. The solvent was removed in vacuo to afford the title compound as a white solid (82 mg; 80.6% yield).

A similar procedure as above was used for the synthesis of compounds 137 and 138 in Table 1, starting from the corresponding thioethers (23 and 24).

Example 7

Synthesis of 4-(Tetrahydro-pyran-4-carbonyl)-[1,4]diazepane-1-carboxylic acid [4-(2,2,2-trifluoro-1-methyl-ethyl)-phenyl]-amide (Compound 139 in Table 1, Method G)

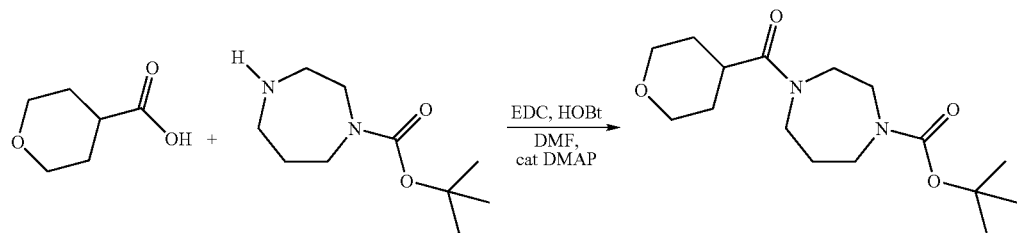

HCl | DCM

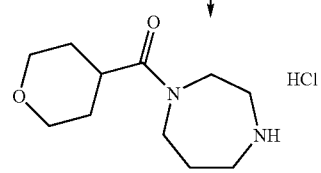

HCl

+

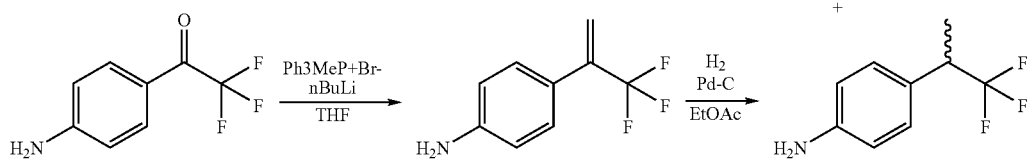

triphosgene
DIPEA

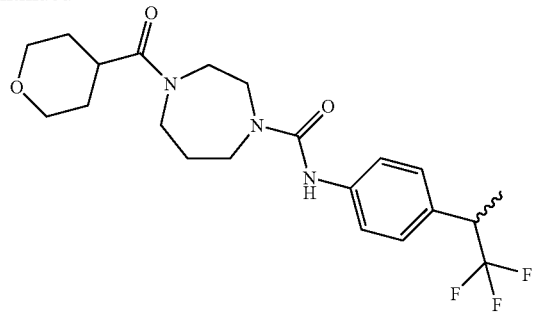

139

To a solution of tetrahydropyranyl-4-carboxylic acid (0.69 g; 5.3 mmol) and HOBt (1.08 g; 8.0 mmol) in 35 mL anhydrous DMF was added EDC (1.53 g; mmol). The mixture was stirred for 20 minutes, and then the Boc-protected homopiperazine was added (0.80 mL; 4.1 mmol). The reaction was stirred for 2 days and then water and EtOAc were added. The layers were separated and the aqueous was extracted twice more with EtOAc. The combined organic layers were washed sequentially with water, saturated aqueous sodium bicarbonate, and brine. The extracts were dried over anhydrous sodium sulfate, filtered, and the solvent was evaporated in vacuo, to afford 1.17 g of crude product as a colorless glass. Purification by flash column chromatography on silica gel afforded 1.00 g (78% yield) of product as a pale yellow solid.

The Boc-protected diazapane amide from above (1.0 g; 3.2 mmol) was dissolved in 40 mL DCM and treated at room temperature with a solution of HCl in 1,4-dioxane (1 M; 12 mL). The mixture was left stirring overnight, then the solvent was removed in vacuo. This hydrochloride salt was used without purification.

To a suspension of dry methyltriphenylphosphonium bromide (1.22 g; 3.4 mmol) in anhydrous THF (5 mL) under inert atmosphere and at 0° C. was added dropwise a solution of n-butyllithium (1.5 M; 2.2 mL; 3.3 mmol). The resulting yellow mixture was stirred 1 hour at 0° C., then cooled to −78° C. A solution of the 4-aminophenyl-trifluoromethyl ketone (500 mg; 2.64 mmol) in 5 mL THF was added and the mixture was allowed to slowly warm to room temperature and stirred 2 h. The reaction was finally stopped by addition of saturated aqueous ammonium chloride solution, and the product extracted with EtOAc three times. The combined organic extracts were washed with brine, dried over anhydrous sodium sulfate, filtered, and the solvent was evaporated in vacuo. The resulting crude oil was purified by flash column chromatography on silica gel to afford 321 mg of product styrene as a yellow oil (65% yield).

This styrene was dissolved in 5 mL EtOAc and treated with 10% palladium-on-carbon under an atmosphere of hydrogen. After 2 hours the catalyst was filtered off and washed with EtOAc. The solvent was removed in vacuo to afford the aniline as a colorless oil (322 mg, quantitative yield), which was used without purification.

To a stirred solution of triphosgene (78 mg; 0.26 mmol) in 8 mL DCM was added dropwise over 15 min via syringe a solution of the aniline from above (124 mg; 0.66 mmol) and diisopropylethylamine (DIPEA) (0.13 mL) in 5 mL DCM. After 15 min of stirring a solution of the diazapane amide hydrochloride salt (164 mg; 0.66 mmol) and excess Hunigs base (0.26 mL) was added in one portion. The mixture was left stirring at room temperature overnight, then quenched with saturated aqueous sodium bicarbonate solution. The layers were separated and the organic was dried over anhydrous sodium sulfate, and filtered. The solvent was evaporated in vacuo to afford 286 mg of a pale yellow foam. Purification by flash column chromatography on silica gel afforded 154 mg of the title compound as a colorless glass (55% yield) ES+MS: 428 amu (MH+).

Example 8

Synthesis of 4-(4-Hydroxy-cyclohexanecarbonyl)-[1,4]diazepane-1-carboxylic acid (5-tert-butyl-isoxazol-3-yl)-amide (Compound 145 in Table 1, Method H)

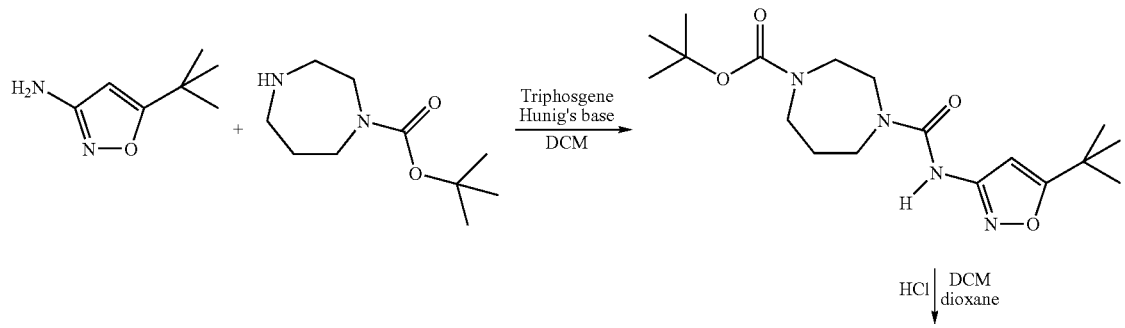

-continued

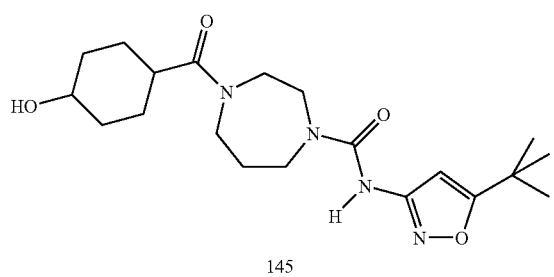 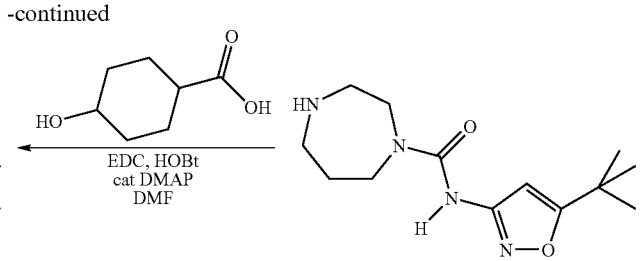

145

Triphosgene (3.05 g; 10.3 mmol) was dissolved in 120 mL DCM. A mixture of 3-amino-5-tert-butyl-isoxazole (3.60 g; 25.7 mmol) and DIPEA (4.9 mL; 28.2 mmol) in 210 mL DCM was slowly added dropwise over 2 hours via an addition funnel. After the reaction was stirred for an additional 30 minutes, a solution of the Boc-protected diazapane (5 mL; 25.7 mmol) and 4.9 mL DIPEA in 40 mL DCM was added rapidly in one portion. The mixture was stirred for 3 hours at room temperature, then washed with saturated aqueous sodium bicarbonate solution. The organic fraction was dried over anhydrous sodium sulfate, filtered, and the solvent was removed in vacuo to afford 10.3 g of crude material. The solid was recrystallized from hot EtOAc to afford 5.45 g of product as a pure, white solid (58% yield).

The Boc-protected diazapane urea from above (5.45 g; 14.9 mmol) was dissolved in 50 mL DCM and treated at room temperature with HCl in dioxane (4N, 16.5 mL). The mixture was stirred overnight, during which time a white precipitate formed. The mixture was then poured onto saturated aqueous sodium bicarbonate solution and the pH was brought to approximately 10 by addition of some saturated sodium carbonate solution. The resulting mixture was then diluted with DCM and the layers separated. The aqueous layer was extracted once with DCM and the combined organics were dried over anhydrous sodium sulfate, and filtered. Evaporation of solvent in vacuo afforded an off-white foam, 2.87 g (73% yield). The crude product was used without purification.

To a solution of the 4-hydroxy-cyclohexane-carboxylic acid (50 mg; 0.35 mmol) and HOBt (56 mg; 0.41 mmol) in 2 mL anhydrous DMF was added EDC (79 mg; 0.41 mmol). After stirring for 15 minutes at room temperature, the diazapane-isoxazole urea was added (80 mg; 0.30 mmol), followed by a catalytic amount of DMAP. The mixture was left stirring overnight. Water was then added and the product was extracted twice with EtOAc. The combined organics were sequentially washed with saturated aqueous sodium bicarbonate solution, saturated aqueous ammonium chloride solution, and brine. They were then dried over anhydrous sodium sulfate, filtered, and the solvent was evaporated in vacuo. The residue was purified by flash column chromatography on silica gel using 2.5% to 10% methanol in DCM mixtures as eluent. The title compound was obtained in >90% purity (HPLC) as a colorless oil (42 mg; 36% yield).

According to this method, compounds listed in Table 1, method H were made.

Example 9

Synthesis of 4-(4-Acetylamino-cyclohexanecarbonyl)-[1,4]diazepane-1-carboxylic acid (5-tert-butyl-isoxazol-3-yl)-amide (Compound 160, Table 1, Method J)

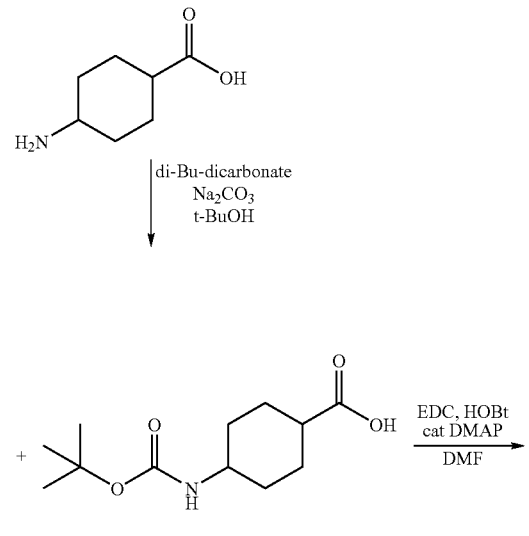

-continued

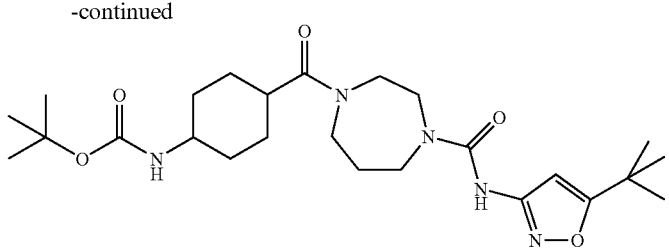

↓ HCl
  DCM

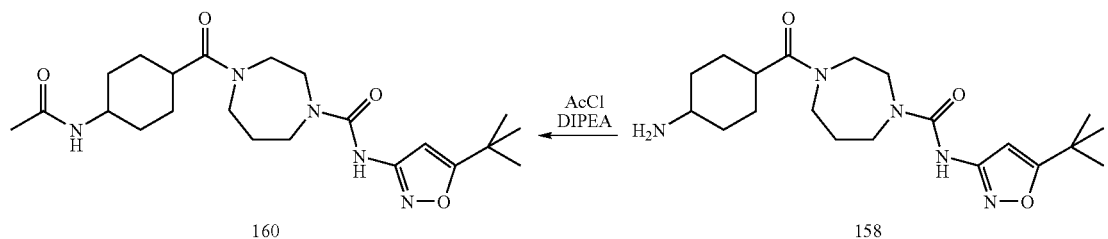

160                                                                    158

Di-tert-butyl dicarbonate (698 mg; 3.20 mmol) was added with stirring to a solution of 4-amino-cyclohexane-carboxylic acid (300 mg; 2.1 mmol) in 3 mL of tert-butanol and 1.7 mL of aqueous sodium carbonate solution (2 M). The mixture was stirred at room temperature overnight. The tert-butanol was then removed under reduced pressure and water (5 mL) was added. The product was extracted twice with DCM. The aqueous layer was acidified to pH 2 with an aqueous solution of potassium hydrogen sulfite and extracted three times with EtOAc. All the organics were combined, washed with brine, dried over anhydrous sodium sulfate, and filtered. Removal of solvent in vacuo afforded desired Boc-protected amino acid as a white solid, 601 mg (>100% yield containing solvent traces).

To a solution of the Boc-protected cyclohexane amino acid (124 mg; 0.51 mmol) and HOBt (82 mg; 0.61 mmol) in 2 mL anhydrous DMF was added EDC (116 mg; 0.61 mmol). After stirring at room temperature for 15 minutes, the diazapane-isoxazole urea dihydrochloride salt (150 mg; 0.44 mmol) was added, followed by DIPEA (0.17 mL; 0.97 mmol) and a catalytic amount of DMAP. The mixture was stirred at room temperature overnight. Water was then added and the product was extracted with EtOAc three times. The combined organic extracts were washed sequentially with saturated aqueous sodium bicarbonate solution, saturated aqueous ammonium chloride solution, and brine. They were then dried over anhydrous sodium sulfate, filtered, and the solvent was removed in vacuo. The residue was purified by flash column chromatography on silica gel using 2.5% methanol in DCM mixture as eluent. The product was obtained in >90% purity (HPLC) as an off white foam (188 mg; 87% yield). The Boc-protected diazapane-amide-urea (107 mg; 0.22 mmol) was dissolved in 1 mL methanol and treated with excess 4 N HCl in 1,4-dioxane (0.55 mL). The mixture was left stirring at room temperature overnight. The solvents were then removed in vacuo to afford 108 mg of product as the hydrochloride salt, an off white foam, which was used without purification in the next step The amido-cyclohexane amine hydrochloride salt (50 mg; 0.12 mmol) and DIPEA (0.045 mL; 0.26 mmol) were dissolved in 1 mL acetonitrile and treated with acetyl chloride. After 20 minutes the reaction was quenched with water and the amide product extracted twice with DCM. The combined organic extracts were washed with brine, dried over anhydrous sodium sulfate, and filtered. The solvent was removed in vacuo. The crude product was purified by flash column chromatography on silica gel using 2.5% to 5% methanol in DCM mixture as eluent. Obtained 36 mg of the title compound as a colorless oil, which slowly solidified to a white crystalline solid (61% yield).

Similar procedures were used for the synthesis of compounds in Table 1, method J. Methanesulfonyl chloride was used instead of acetyl chloride for the synthesis of compounds 161, 163 and 165.

Example 10

Synthesis of 4-(Tetrahydro-pyran-4-carbonyl)-[1,4]diazepane-1-carboxylic acid (5-tert-butyl-thiazol-2-yl)-amide (Compound 171 in Table 1, Method K)

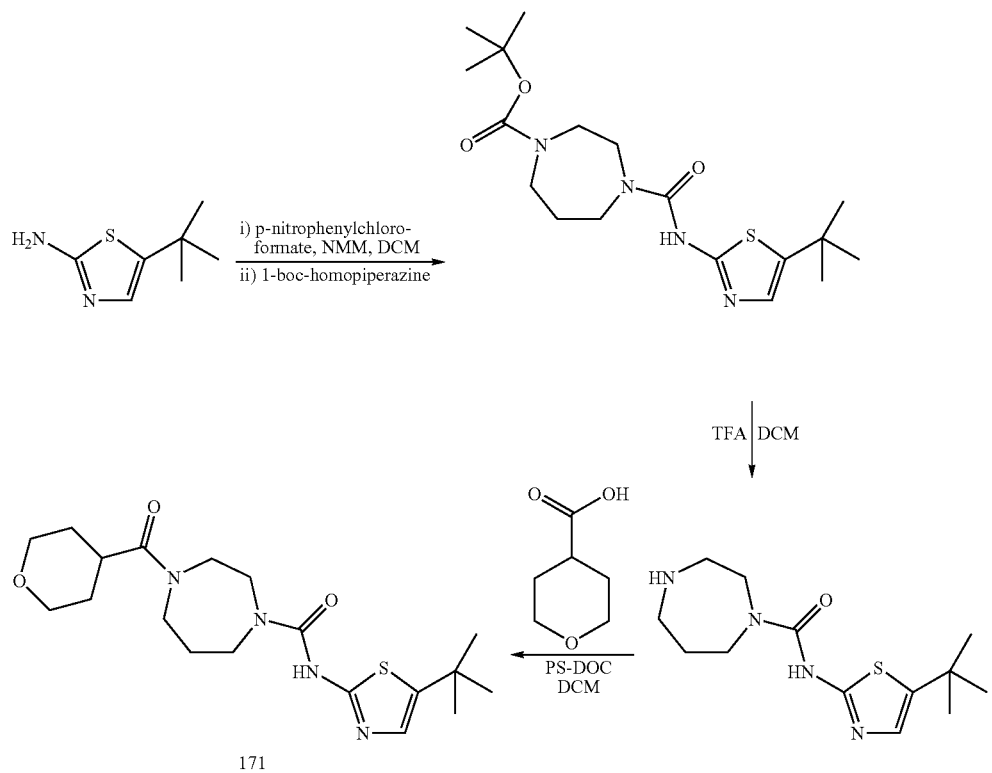

Aminothiazole (100 mg; 0.64 mmol) was dissolved in 2 mL anhydrous DCM under nitrogen atmosphere and was cooled in an ice-bath. N-Methylmorpholine (70.4 µL) was then added, followed by p-nitrophenylchloroformate (129 mg; 0.64 mmol). After 2 hours Boc-homopiperazine (126.2 µL, 0.64 mmol) was added to the reaction mixture to give a bright yellow solution. After 1 hour, the mixture was diluted with DCM (5 mL), washed with 1M aqeuous sodium hydroxide solution (2×5 mL or until basic washes are no longer yellow), then water (5 mL), and brine. Concentration in vacuo provided 255 mg of crude product as a dark yellow oil. Purification by flash column chromatography on silica gel afforded 188 mg of impure material that was used in the next step.

Crude N-Boc-homopiperazine urea from above (188 mg; 0.49 mmol) was dissolved in 2 mL of 10% trifluoroacetic acid (TFA) in DCM solution, and shaken at room temperature. After 2 hours of 300 µL more TFA was added; and after 3 hours more shaking complete de-protection was achieved.

The reaction mixture was concentrated in vacuo, the residue was re-dissolved in DCM and extracted with 1M HCl (5×5 mL); the combined acidic extracts were made basic (pH 9) with sodium carbonate and extracted with DCM (7×5 mL). The combined basic organic extracts were washed with brine, dried over anhydrous sodium sulfate, filtered and concentrated in vacuo to give the desired diazapane amine (95.6 mg, 69% yield).

Alternatively, the Boc-deprotection was carried out with solid-supported tosic acid resin (MP-TsOH) as follows:

A mixture of Boc-piperazine urea (100 mg; UV purity only 56%) and 3 equivalents of MP-TsOH in DCM was shaken at room temperature overnight. The resin was collected by filtration, washed with DCM, then with methanol. The product was then released from the resin with 2M ammonia in methanol. Concentration in vacuo gave 48 mg of pure diazapane amine (62% yield).

Homopiperazine urea (95.6 mg; 0.34 mmol) and tetrahydropyran carboxylic acid (44 mg, 0.406 mmol) were dissolved in 4 mL DCM. Polymer-supported carbodiimide resin (PS-DCC, loading 1.6 mmol/g; 420 mg) was added to this solution and the reaction mixture was shaken at room temperature for 2 days. The resins were filtered off and washed with DCM. The organic layer was washed with saturated aqueous sodium bicarbonate solution (3 mL), then with a 1:1 mixture of 10% citric acid and brine (2×3 mL). The organic layer was then dried over anhydrous sodium sulfate, and concentrated in vacuo, to afford the title compound as a tan foam.

Similar procedures as above were used for the synthesis of compounds in Table 1, method K. The 2-amino-5-phenylthiazole used to make compound 173 was made according to the procedure described by K. D. Hargrave et al *J. Med. Chem.* 1983. 26(8), 1158-1163.

Example 11

Synthesis of 4-(Tetrahydro-pyran-4-carbonyl)-[1,4]diazepane-1-carboxylic acid (4,5-dimethyl-isoxazol-3-yl)-amide (Compound 233 in Table 1, Method L)

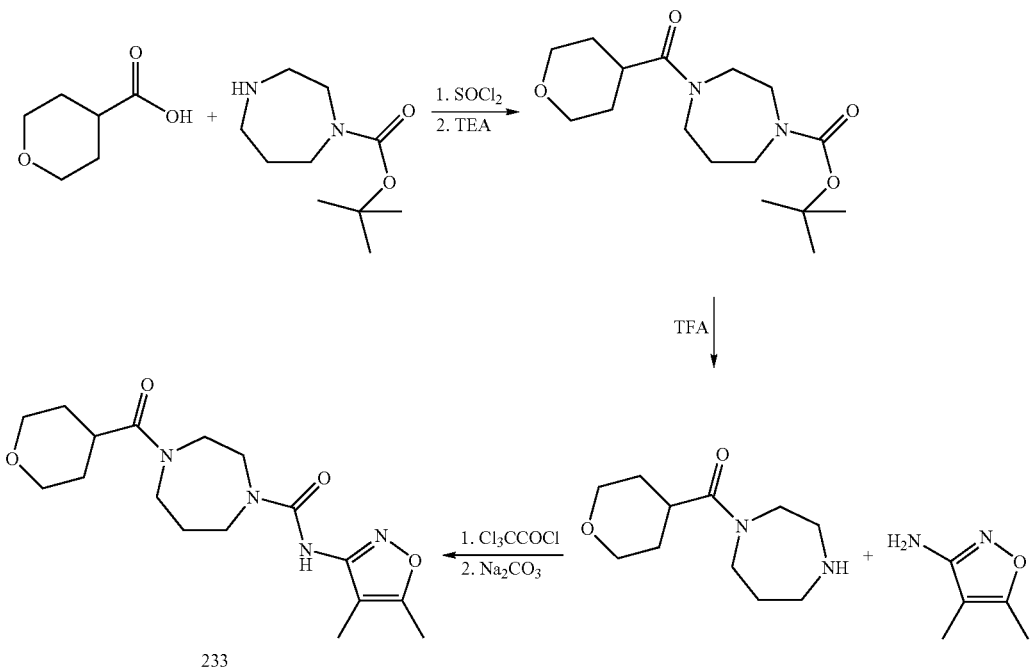

To a solution of 6 g (46.1 mmol) of tetrahydro-pyran-4-carboxylic acid in anhydrous DCM (60 mL) were added dropwise 8.4 mL (115.3 mmol) of thionyl chloride at 0° C. under a nitrogen atmosphere. The reaction was allowed to warm to room temperature and stirred for 18 h. The solvent was removed under reduced pressure to give the crude acid chloride, which was dissolved in anhydrous THF (60 mL).

A solution of 8.85 g (44.3 mmol) of [1,4]diazepane-1-carboxylic acid tert-butyl ester and 30.6 mL (277 mmol) of N,N-triethylamine in THF (60 mL) was added dropwise over 15 minutes to the acid chloride solution at 0° C. After the addition was complete, the reaction was allowed to warm to room temperature and stirred for 40 h. The reaction mixture was concentrated under reduced pressure. The residue was dissolved in DCM (150 mL) and washed with an aqueous citric acid (10 wt %)/brine solution (1/1, 2×50 mL). The organic layer was dried over $Na_2SO_4$ and filtered. The filtrate was concentrated under reduced pressure to afford 13.1 g of 4-(tetrahydro-pyran-4-carbonyl)-[1,4]diazepane-1-carboxylic acid tert-butyl ester; ES–MS: m/z 313 [M+H$^+$].

To a solution of 13 g (41.7 mmol) of 4-(tetrahydro-pyran-4-carbonyl)-[1,4]diazepane-1-carboxylic acid tert-butyl ester in DCM (260 mL) were added 32.5 mL of trifluoroacetic acid. The reaction was stirred for 6 h at room temperature. The solvent was removed under reduced pressure. The residual oil was azeotroped with DCM (3×20 mL), chloroform (2×20 mL) and toluene (3×20 mL) to afford 22.9 g of [1,4]diazepan-1-yl-(tetrahydro-pyran-4-yl)-methanone as triple trifluoroacetic acid salt; ES–MS: m/z 213 [M+H$^+$]

4,5-Dimethyl-isoxazol-3-ylamine was converted into its isocyanate by adaptation of the following reference: Nishikawa T. et al. *Org. Lett.* 2006, 8, 3263-3265.

To a solution of 90 mg (0.8 mmol) of 4,5-dimethyl-isoxazol-3-ylamine in DCM (2 mL) was added N,N-diisopropylethylamine (278 μL, 1.6 mmol), followed by 89 μL (0.8 mmol) of trichloroacetylchloride. The reaction mixture was shaken on an orbital shaker for 18 h. Saturated aqueous $NaHCO_3$ solution (3 mL) was added to the reaction mixture. The organic layer was dried over $Na_2SO_4$, filtered and the filtrate was concentrated under reduced pressure. The residue was dissolved in DMF (3 mL) and added to 487 mg (0.88 mmol) of [1,4]diazepan-1-yl-(tetrahydro-pyran-4-yl)-methanone (triple trifluoroacetic acid salt). To this solution 339 mg (3.2 mmol) of $Na_2CO_3$ were added and the mixture was heated in a sealed tube at 100° C. for 18 h. The reaction was cooled to room temperature, filtered and the filtrate was concentrated under reduced pressure. The residue was purified by mass-triggered preparative LC-MS to afford 12 mg of 4-(tetrahydro-pyran-4-carbonyl)-[1,4]diazepane-1-carboxylic acid (4,5-dimethyl-isoxazol-3-yl)-amide.

According to this method, compounds listed in Table 1, method L were made.

Example 12

Synthesis of 4-(Tetrahydro-pyran-4-carbonyl)-[1,4]diazepane-1-carboxylic acid (4-tert-butyl-thiazol-2-yl)-amide (Compound 182 in Table 1, Method M)

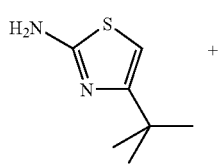

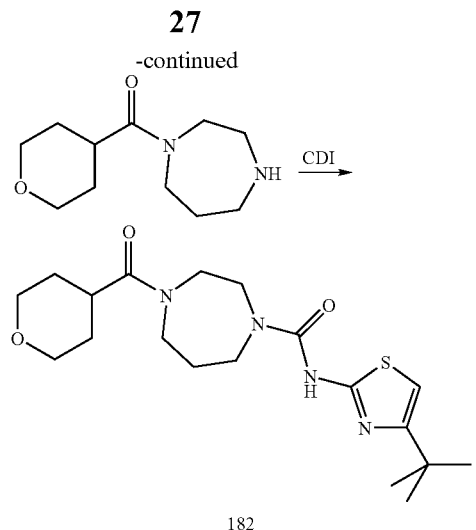

182

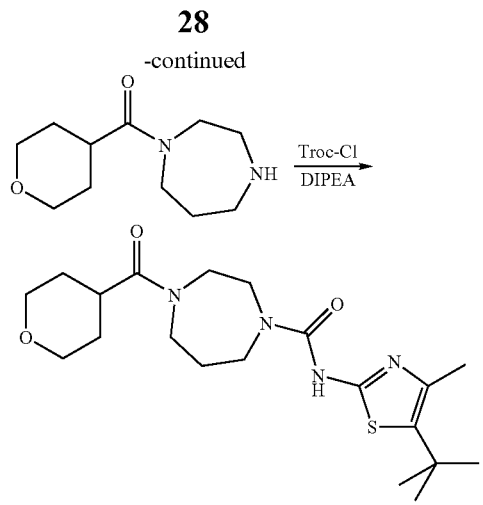

183

To a solution of 62.8 mg (0.4 mmol) of 4-tert-butyl-thiazol-2-ylamine in DCM (2 mL) were added 98 mg (0.6 mmol) of 1,1'-carbonyldiimidazole and the reaction was stirred for 4 h at room temperature. A solution of 354 mg (0.8 mmol) of [1,4]diazepan-1-yl-(tetrahydro-pyran-4-yl)-methanone (triple trifluoroacetic acid salt, prepared according to Method L, above) in DCM (3 mL) was added and the reaction stirred for 18 h at room temperature. The reaction mixture was washed with 10% aqueous citric acid solution (5 mL). The organic layer was dried over Na$_2$SO$_4$, filtered and the filtrate was concentrated under reduced pressure. The crude product was purified by mass-triggered preparative LCMS to afford 27.6 mg of 4-(tetrahydro-pyran-4-carbonyl)-[1,4]diazepane-1-carboxylic acid (4-tert-butyl-thiazol-2-yl)-amide.

According to this method, compounds listed in Table 1, method M were made.

Example 13

Synthesis of 4-(Tetrahydro-pyran-4-carbonyl)-[1,4]diazepane-1-carboxylic acid (5-tert-butyl-4-methyl-thiazol-2-yl)-amide (Compound 183 in Table 1, Method N)

To a solution of 137.8 mg (0.8 mmol) of 5-tert-butyl-4-methyl-thiazol-2-ylamine in DCM (4 mL) were added 169.5 mg (0.8 mmol) of 2,2,2-trichloroethyl chloroformate and 0.21 mL (1.2 mmol) of N,N-diisopropylethylamine. The reaction was stirred for 18 h at room temperature. The reaction mixture was washed with saturated aqueous NaHCO$_3$ solution and the aqueous layer was back-extracted with DCM (2×2 mL). The combined organic layers were dried over Na$_2$SO$_4$, filtered and the filtrate was concentrated under reduced pressure. The residue was dissolved in DCE (4 mL) and a solution of 443 mg (0.8 mmol) of [1,4]diazepan-1-yl-(tetrahydro-pyran-4-yl)-methanone (triple trifluoroacetic acid salt, prepared according to Method L, step 1-2) in DCE (2 mL) and 0.42 mL (2.4 mmol) of N,N-diisopropylethylamine were added. The reaction was stirred for 18 h at 80° C. The reaction mixture was washed with 10% aqueous citric acid solution (3 mL). The aqueous layer was back-extracted with DCM (2×2 mL). The combined organic extracts were dried over Na$_2$SO$_4$, filtered and the filtrate was concentrated under reduced pressure. The crude product was purified by mass-triggered preparative LCMS to afford 92.7 mg of 4-(tetrahydro-pyran-4-carbonyl)-[1,4]diazepane-1-carboxylic acid (5-tert-butyl-4-methyl-thiazol-2-yl)-amide.

According to this method, compounds listed in Table 1, Method N were made.

Example 14

Synthesis of 4-(Tetrahydro-pyran-4-carbonyl)-[1,4]diazepane-1-carboxylic acid (3-sec-butyl-isoxazol-5-yl)-amide (Compound 193 in Table 1, Method P)

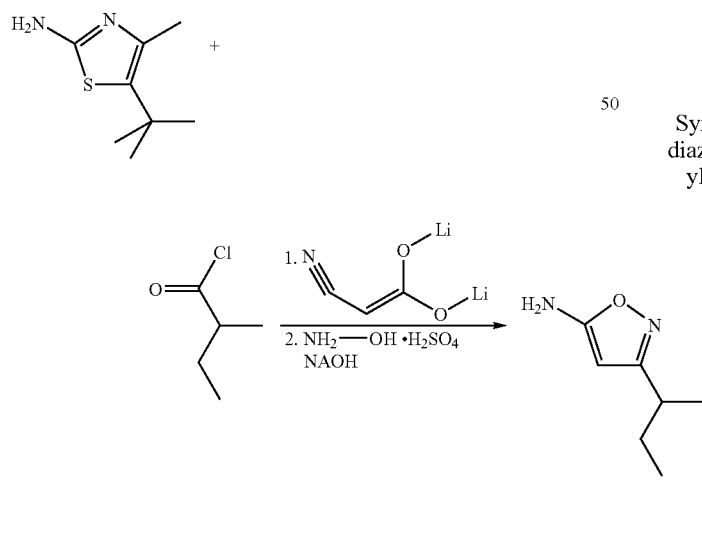

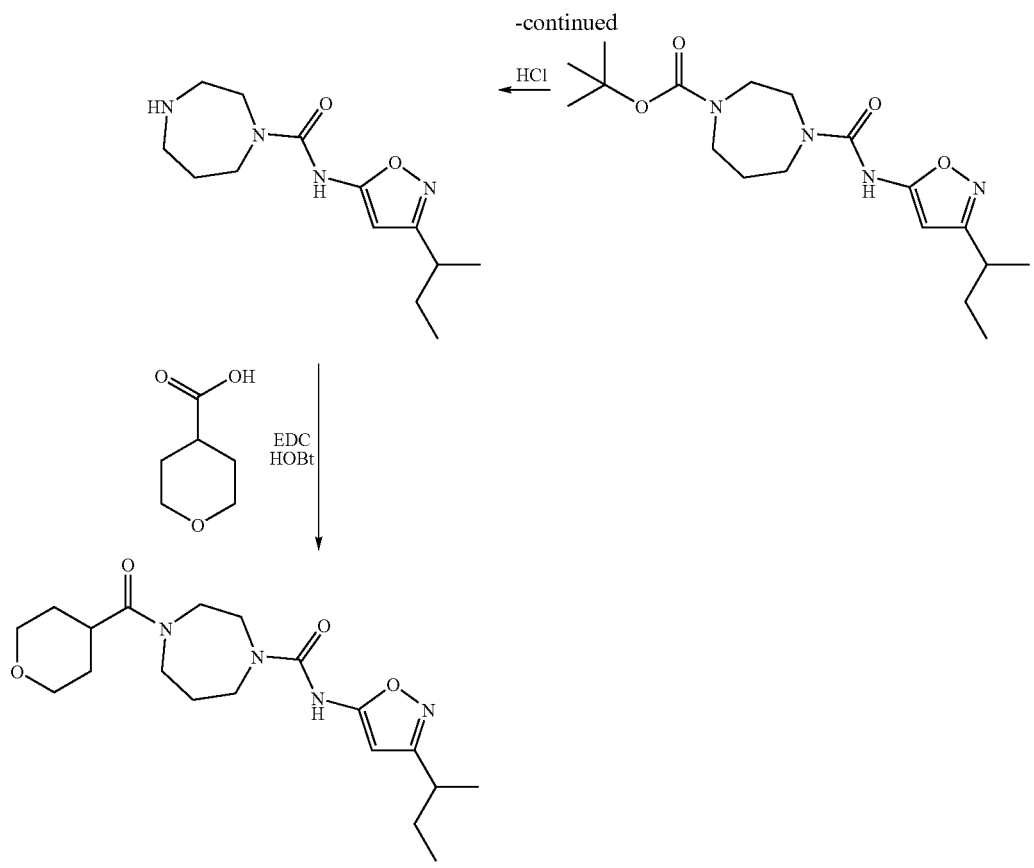

The 5-amino-3-sec-butyl-isoxazole used to make this compound was synthesized according to the procedures described in Krauss et al, Synthesis 1983, 308-309 and Takase et al, *Heterocycles* 1991, 32(6), 1153-1158.

To a solution of 5-amino-3-sec-butylisoxazole (500 mg; 3.57 mmol; 1 equiv.) and pyridine (0.58 mL; 7.13 mmol; 2 equiv.) in DCM (30 mL) was added 0.74 mL (5.35 mmol; 1.5 equiv.) of 2,2,2-trichloroethyl chloroformate dropwise. The reaction mixture was stirred overnight at room temperature, then diluted with DCM, and washed sequentially with water, 1N HCL aqueous solution, saturated aqueous NaHCO$_3$ solution and brine. The organic layer was dried over Na$_2$SO$_4$, filtered, and the filtrate was concentrated under reduced pressure. The residue, 1.58 g of (3-sec-Butyl-isoxazol-5-yl)-carbamic acid 2,2,2-trichloro-ethyl ester was isolated as a pale yellow oil, and used as is in the next step.

To a solution of (3-sec-Butyl-isoxazol-5-yl)-carbamic acid 2,2,2-trichloro-ethyl ester (1.126 g; 3.57 mmol; 1 equiv.) in 15 mL anhydrous DMSO was added Boc-protected diazapane (0.69 mL; 3.57 mmol; 1 equiv.) and DIPEA (0.845 mL; 4.85 mmol; 1.4 equiv.). The reaction mixture was heated while stirring in a 55° C. oil bath for 18 h. The resulting dark orange solution was cooled to room temperature, quenched with water and extracted twice with EtOAc. The combined organic extracts were washed with water, brine, and dried over Na$_2$SO$_4$. After concentration in vacuo, the residue was purified by flash column chromatography using 2.5% MeOH/DCM as eluent mixtures. The enriched fractions were concentrated and the chromatography repeated using 50% EA/Hex as eluent mixture. The desired product, 4-(3-sec-Butyl-isoxazol-5-ylcarbamoyl)-[1,4]diazepane-1-carboxylic acid tert-butyl ester was obtained as a yellow oil (749 mg).

4-(3-sec-Butyl-isoxazol-5-ylcarbamoyl)-[1,4]diazepane-1-carboxylic acid tert-butyl ester (749 mg; 2.044 mmol; 1 equiv.) was dissolved in DCM (10 mL) and a 4M solution of HCl in 1,4-dioxane (2.56 mL; 10.22 mmol; 5 equiv.) was added. The reaction mixture was stirred overnight at room temperature. The solvents were then removed in vacuo and 630 mg yellow foam (hydroscopic) was obtained. THF/EtOAc (50:50) was added and the organic layer was washed sequentially with saturated aqueous NaHCO$_3$ solution and brine. The organics were dried over Na$_2$SO$_4$, filtered, and concentrated to afford 372 mg of [1,4]Diazepane-1-carboxylic acid (3-sec-butyl-isoxazol-5-yl)-amide as a brown oil.

4-Tetrahydropyran-carboxylic acid (66 mg; 0.50 mmol; 1.1 equiv.), HOBt (81 mg; 0.6 mmol; 1.4 equiv.) and EDC (115 mg; 0.6 mmol; 1.4 equiv.) were combined in 2 mL anhydrous DMF. After 15 minutes [1,4]Diazepane-1-carboxylic acid (3-sec-butyl-isoxazol-5-yl)-amide from above (117 mg; 0.44 mmol; 1.0 equiv.) was added, followed by 2 mg of DMAP (catalytic). The mixture was left stirring overnight. Water was added to the reaction mixture and it was extracted with EtOAc. The organic layer was washed with water once then saturated aqueous NaHCO$_3$ solution, saturated aqueous NH$_4$Cl solution, then brine. The organics were dried over Na$_2$SO$_4$, filtered, and concentrated in vacuo. The residue was purified by flash column chromatography using 2.5% MeOH/DCM mixtures as eluent, then switched to 10% MeOH/DCM. Solvents were removed from the enriched fractions and 61 mg of 4-(Tetrahydro-pyran-4-carbonyl)-[1,4]diazepane-1-carboxylic acid (3-sec-butyl-isoxazol-5-yl)-amide was obtained (36% yield) as a light yellow solid.

According to this method, compounds listed in Table 1, Method P were made.

Example 15

Synthesis of 4-(Tetrahydro-pyran-4-carbonyl)-[1,4]diazepane-1-carboxylic acid (5-sec-butyl-pyridin-2-yl)-amide (Compound 196, Table 1, Method Q)

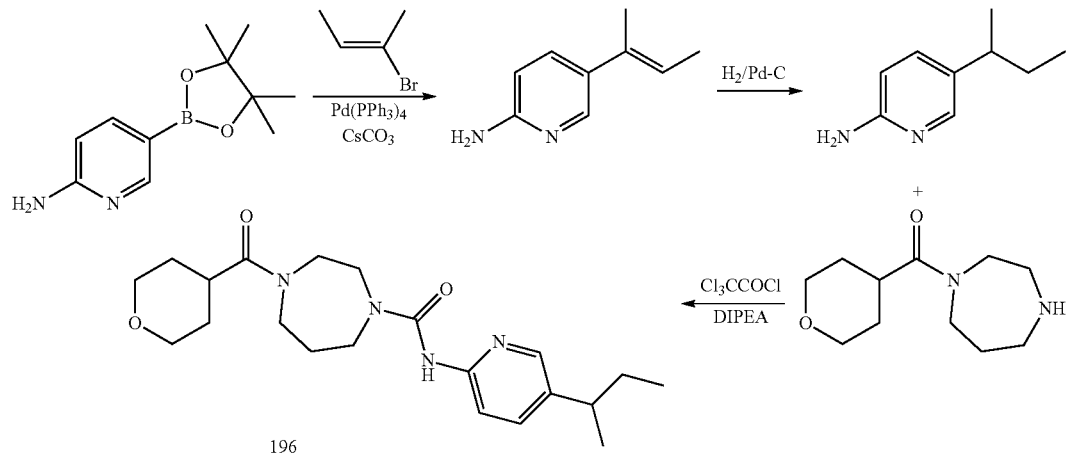

A reaction flask was charged with 0.5 g (2.27 mmol) of 5-(4,4,5,5-tetramethyl-[1,3,2]dioxa borolan-2-yl)-pyridin-2-ylamine, 0.31 g (2.50 mmol) of 2-bromo-but-2-ene, 1.48 g (4.54 mmol) of Cs$_2$CO$_3$ and 52 mg (0.045 mmol) of tetrakis(triphenylphosphine)palladium under nitrogen atmosphere. The solids were dissolved in a degassed toluene/ethanol mixture (20 mL, 1/1) and the reaction heated to 90° C. for 7 h. The reaction was quenched with water (5 mL) and TBME (5 mL). The reaction mixture was filtered. The filtrate was extracted with TBME (20 mL). The organic extract was washed with brine and concentrated under reduced pressure. The residue was purified twice by column chromatography (silica, eluent DCM, 0-50% ethyl acetate) to afford 134 mg of 5-(1-methyl-propenyl)-pyridin-2-ylamine. ES–MS: m/z 149 [M+H$^+$];

A solution of 130 mg (0.87 mmol) of 5-(1-methyl-propenyl)-pyridin-2-ylamine in ethanol (5 mL) was reduced over palladium on charcoal (10 wt %, 13 mg) under a hydrogen atmosphere at room temperature for 18 h. The catalyst was separated by filtration through Celite® and washed with ethanol (5 mL). The filtrate was concentrated under reduced pressure. The residue was purified by column chromatography (silica, eluent ethyl acetate) to afford 90 mg of 5-sec-butyl-pyridin-2-ylamine. ES–MS: m/z 151 [M+H$^+$];

4-(Tetrahydro-pyran-4-carbonyl)-[1,4]diazepane-1-carboxylic acid (5-sec-butyl-pyridin-2-yl)-amide was prepared according to example 11, Method F.

To a solution of 90 mg (0.6 mmol) of 5-sec-butyl-pyridin-2-ylamine in DCM (2 mL) was added N,N-diisopropylethylamine (348 µL, 1.2 mmol), followed by 67 µL (0.6 mmol) of trichloroacetylchloride. The reaction mixture was shaken on an orbital shaker for 18 h. Saturated aqueous NaHCO$_3$ solution (3 mL) was added to the reaction mixture. The organic layer was dried over Na$_2$SO$_4$, filtered and the filtrate was concentrated under reduced pressure. The residue was dissolved in DMF (2 mL) and added to 332 mg (0.6 mmol) of [1,4]diazepan-1-yl-(tetrahydro-pyran-4-yl)-methanone (triple trifluoroacetic acid salt). To this solution 254 mg (2.4 mmol) of Na$_2$CO$_3$ were added and the mixture was heated in a sealed tube at 100° C. for 18 h. The reaction was cooled to room temperature, filtered and the filtrate was concentrated under reduced pressure. The residue was purified by mass-triggered preparative LC-MS to afford 21 mg of 4-(tetrahydro-pyran-4-carbonyl)-[1,4]diazepane-1-carboxylic acid (5-sec-butyl-pyridin-2-yl)-amide. ES–MS: m/z 389;

Example 16

Synthesis of 4-(1,1-Dioxo-1λ$^6$-thiomorpholine-4-carbonyl)-[1,4]diazepane-1-carboxylic acid (5-tert-butyl-isoxazol-3-yl)-amide (Compound 200 in Table 1, Method R)

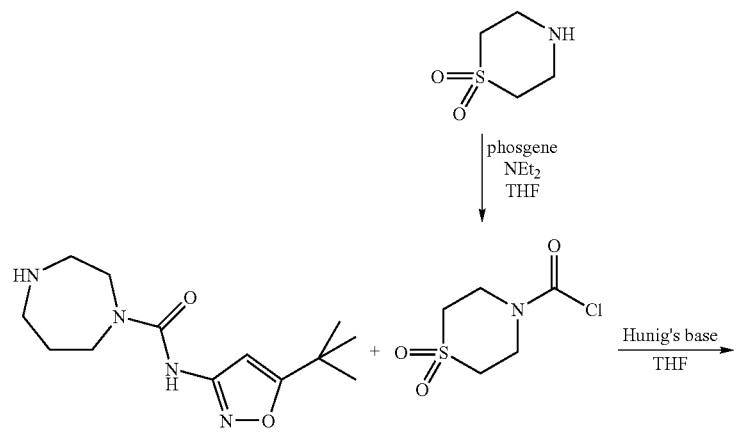

-continued

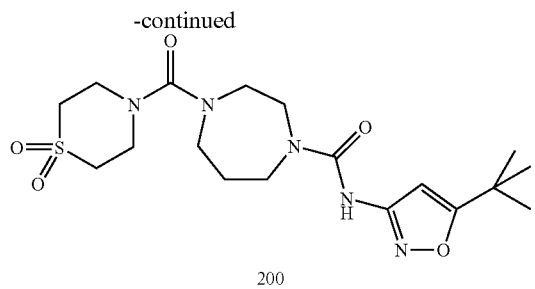

200

Thiomorpholine 1,1-dioxide (1.00 g; 7.40 mmol) was dispersed in 50 mL anhydrous THF, followed by addition of triethylamine (1.24 mL; 8.88 mmol) and 20% solution of phosgene in toluene (11.74 mL; 22.2 mmol). The reaction mixture was stirred vigorously overnight at room temperature, then diluted with ether, and filtered though Celite. The Celite was washed with ether and the filtrate was concentrated in vacuo to afford the desired carbamoyl chloride (1.43 g; 7.21 mmol; 97.5% yield) as an off-white solid. This material was used without purification.

To a solution of the diazapane-isoxazole urea (683 mg; 3.46 mmol) in 20 mL anhydrous THF was added dioxothiomorpholine carbamoyl chloride (1.09 g of 84% material; 3.46 mmol) followed by DIPEA (0.72 mL; 4.15 mmol). The mixture was left stirring at room temperature for 2 hours, then quenched with water. It was extracted twice with DCM, and dried over anhydrous sodium sulfate to afford a yellow foam. This material was triturated in DCM to afford 456 mg of the title compound as a white solid. A further 186 mg of product precipitated out of the mother liquor, and this solid was combined with the previous and dried in high vacuum at 60° C. overnight. A total 632 mg of the title compound were isolated in 97.6% purity (HPLC), 42.8% yield.

Similar procedures as above were used for the synthesis of compounds in Table 1, method R. Where appropriate the isocyanate was used in place of the carbamoyl chloride.

Example 17

Synthesis of 4-[2-(1,1-Dioxo-1λ$^6$-thiomorpholin-4-yl)-acetyl]-[1,4]diazepane-1-carboxylic acid (5-tert-butyl-isoxazol-3-yl)-amide (Compound 228 in Table 1, Method S)

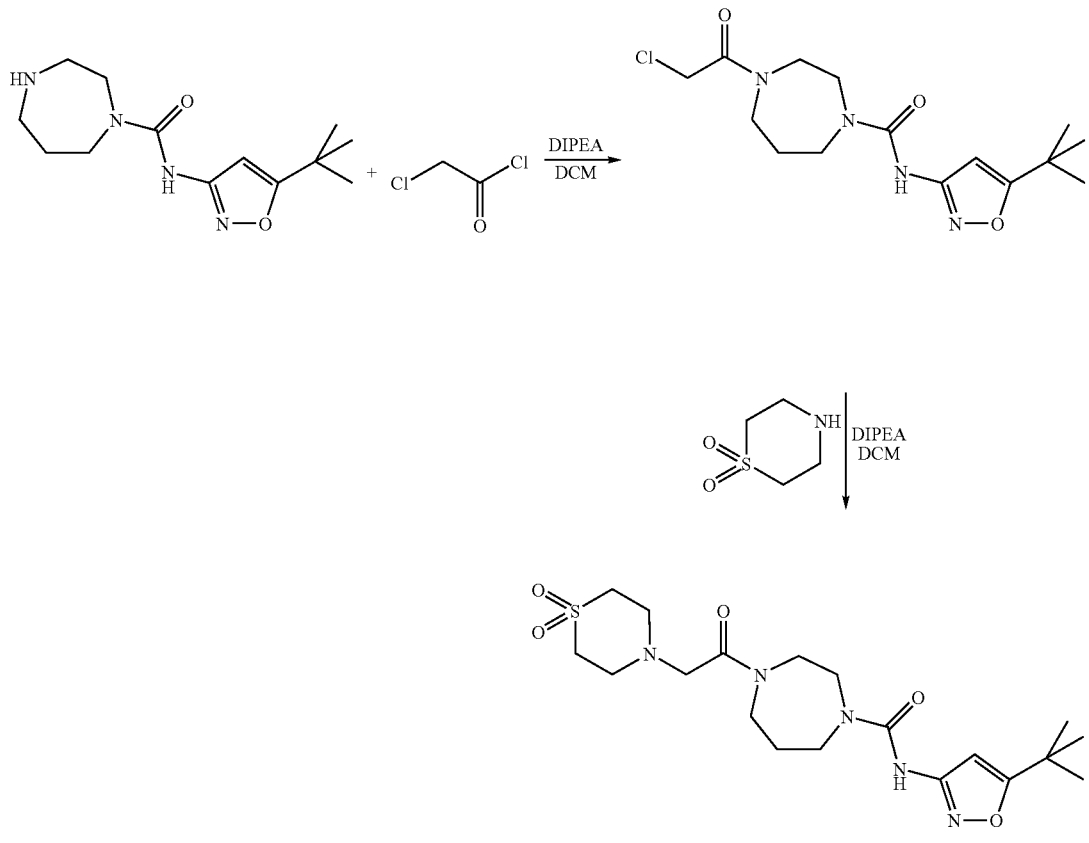

228

To a solution of the diazapane-isoxazole urea (1.8 g; 6.76 mmol) in 20 mL DCM (cooled to 0° C.), was added DIPEA (1.29 mL; 7.42 mmol) followed by the dropwise addition of chloroacetyl chloride (0.59 mL; 7.43 mmol). The mixture was stirred for 1 hour as the reaction slowly warmed to room temperature. Saturated aqueous ammonium chloride solution was added to the mixture and it was extracted with DCM twice. The combined organics were washed with brine, dried over anhydrous sodium sulfate, filtered, and concentrated in vacuo. The yellow residue was purified by flash column chromatography on silica gel using 2.5% methanol in DCM mixture as eluent. The product was obtained as a pale yellow foam (1.16 g; 50.2% yield).

The above acteyl chloride (1.122 g; 3.27 mmol) was dissolved in 10 mL DMF. Thiomorpholine 1,1-dioxide (0.442 g; 3.27 mmol) was added followed by DIPEA (0.63 mL; 3.6 mol) and DMAP (16 mg; 0.131 mmol). The reaction mixture was heated in a 60° C. oil bath overnight. Water was added to the reaction mixture, and it was extracted with EtOAc three times. The organics were combined and washed with brine, dried over anhydrous sodium sulfate, filtered and concentrated. The yellow residue obtained was purified by flash column chromatography on silica gel using 2.5% methanol in DCM mixture as eluent then switched to 5% methanol in DCM. The title compound was obtained in >95% purity (HPLC) as a white foam (781 mg; 54% yield).

According to this method, compounds listed in Table 1, method S were made.

TABLE 1

| Example | Name | Structure | LC-MS MH+ (amu) | Method |
|---------|------|-----------|-----------------|--------|
| 1 | 4-(3-Cyclopentyl-propionyl)-[1,4]diazepane-1-carboxylic acid (4-butyl-phenyl)-amide | 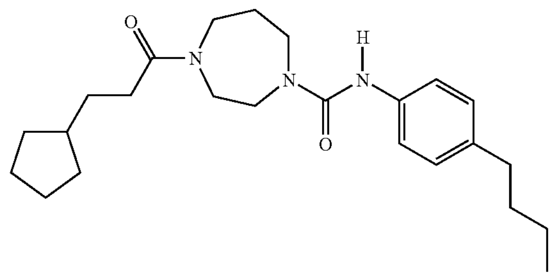 | 401 | A |
| 2 | 4-(3-Cyclopentyl-propionyl)-[1,4]diazepane-1-carboxylic acid (4-isopropyl-phenyl)-amide | 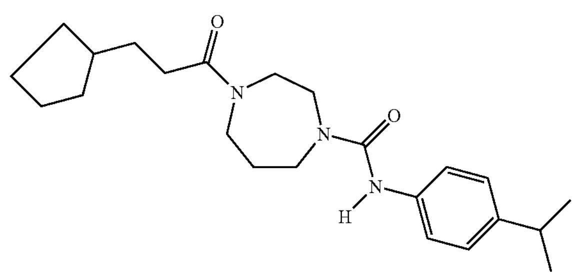 | 386 | B |
| 3 | 4-(3-Cyclopentyl-propionyl)-[1,4]diazepane-1-carboxylic acid (4-ethyl-phenyl)-amide | 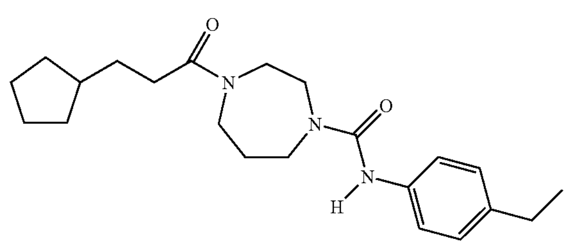 | 372 | B |
| 4 | 4-(3-Cyclopentyl-propionyl)-[1,4]diazepane-1-carboxylic acid (4-cyano-phenyl)-amide | 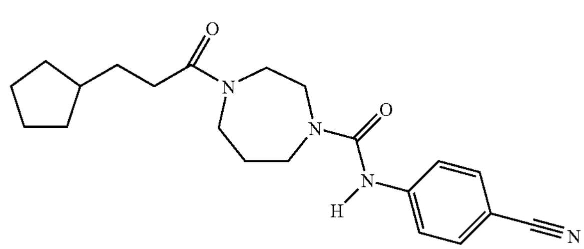 | 369 | B |

TABLE 1-continued

| Example | Name | Structure | LC-MS MH+ (amu) | Method |
|---|---|---|---|---|
| 5 | 4-(3-Cyclopentyl-propionyl)-[1,4]diazepane-1-carboxylic acid naphthalen-1-ylamide | 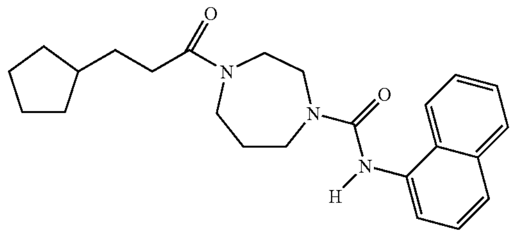 | 394 | B |
| 6 | 4-(3-Cyclopentyl-propionyl)-[1,4]diazepane-1-carboxylic acid naphthalen-2-ylamide | 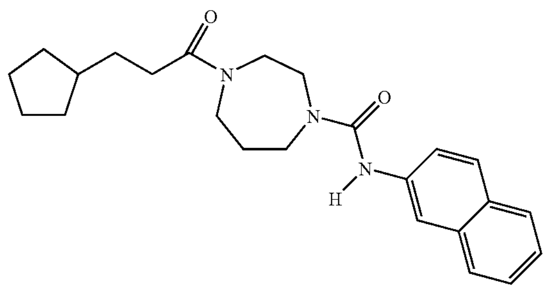 | 394 | B |
| 7 | 4-(3-Cyclopentyl-propionyl)-[1,4]diazepane-1-carboxylic acid (4-chloro-phenyl)-amide | 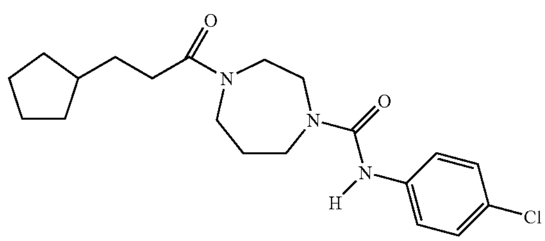 | 379 | B |
| 8 | 4-(3-Cyclopentyl-propionyl)-[1,4]diazepane-1-carboxylic acid m-tolylamide | 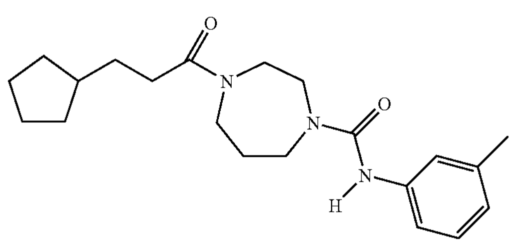 | 358 | B |
| 9 | 4-(3-Cyclopentyl-propionyl)-[1,4]diazepane-1-carboxylic acid (4-dimethylamino-phenyl)-amide | 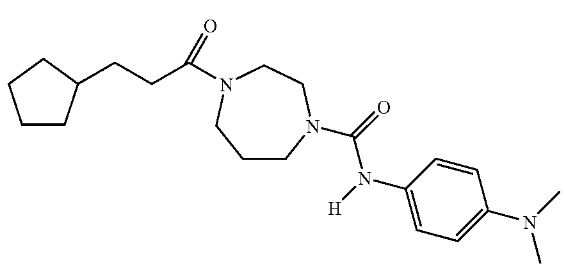 | 387 | B |

TABLE 1-continued

| Example | Name | Structure | LC-MS MH+ (amu) | Method |
|---|---|---|---|---|
| 10 | 4-(3-Cyclohexyl-propionyl)-[1,4]diazepane-1-carboxylic acid (4-butyl-phenyl)-amide | 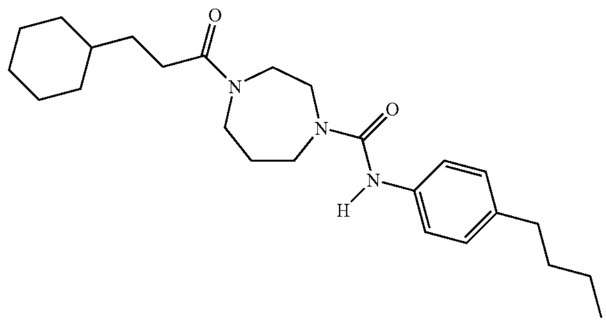 | 414 | C |
| 11 | 4-(2-Cyclopentyl-acetyl)-[1,4]diazepane-1-carboxylic acid (4-butyl-phenyl)-amide | 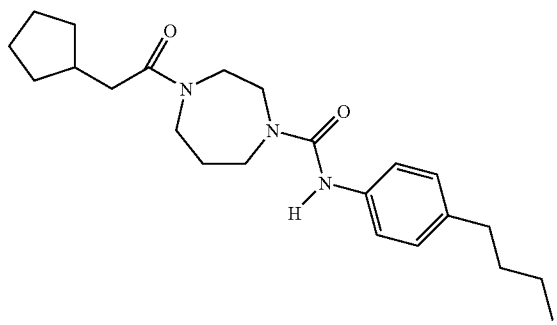 | 386 | C |
| 12 | 4-Cyclopentanecarbonyl-[1,4]diazepane-1-carboxylic acid (4-butyl-phenyl)-amide | 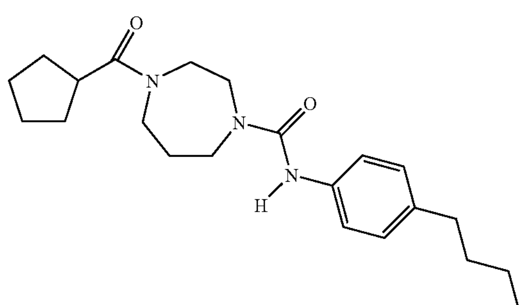 | 372 | C |
| 13 | 4-(4-Methyl-pentanoyl)-[1,4]diazepane-1-carboxylic acid (4-butyl-phenyl)-amide | 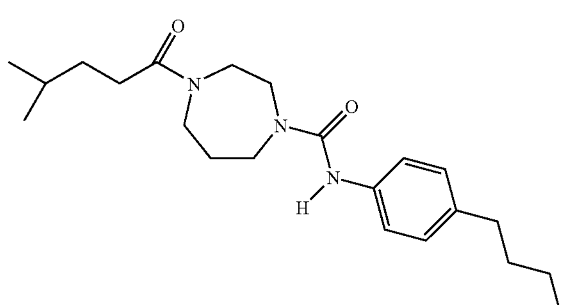 | 374 | C |

TABLE 1-continued
| Example | Name | Structure | LC-MS MH+ (amu) | Method |
|---|---|---|---|---|
| 14 | 4-(3-Cyclopentyl-propionyl)-[1,4]diazepane-1-carboxylic acid (4-pentyl-phenyl)-amide | 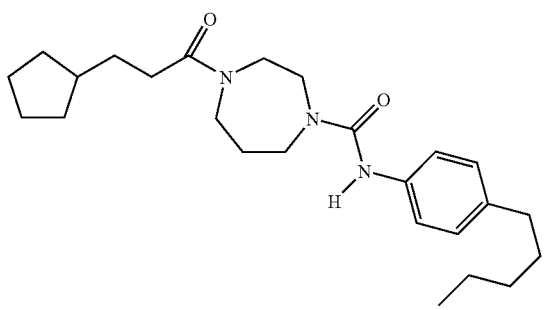 | 414 | B |
| 15 | 4-(3-Cyclopentyl-propionyl)-[1,4]diazepane-1-carboxylic acid (4-trifluoromethyl-phenyl)-amide | 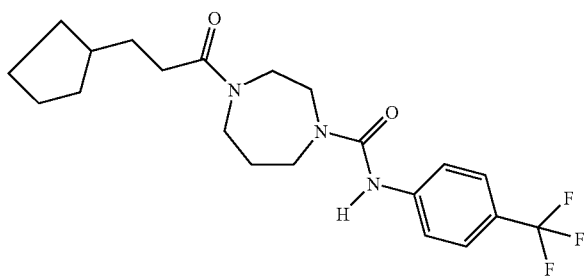 | 412 | B |
| 16 | 4-Benzoyl-[1,4]diazepane-1-carboxylic acid (4-butyl-phenyl)-amide | 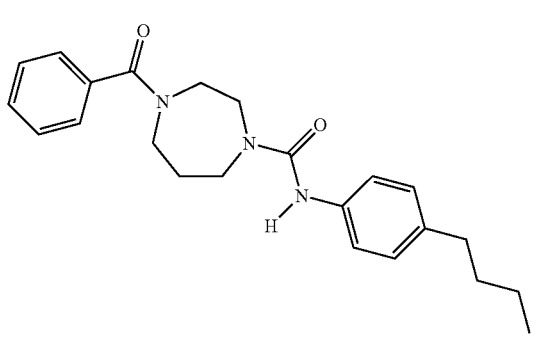 | 380 | C |
| 17 | 4-(2-Cyclohexyl-acetyl)-[1,4]diazepane-1-carboxylic acid (4-butyl-phenyl)-amide | 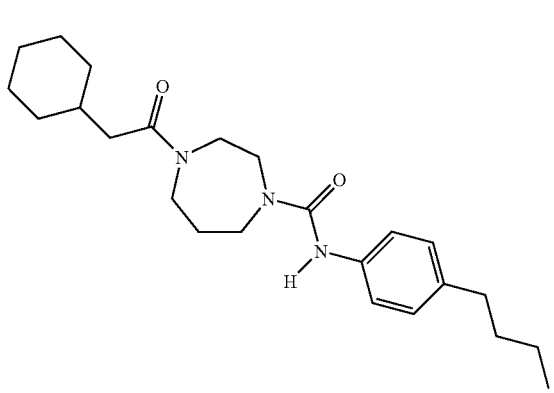 | 400 | C |

TABLE 1-continued

| Example | Name | Structure | LC-MS MH+ (amu) | Method |
|---|---|---|---|---|
| 18 | 4-(3-Cyclopropyl-propionyl)-[1,4]diazepane-1-carboxylic acid (4-butyl-phenyl)-amide | 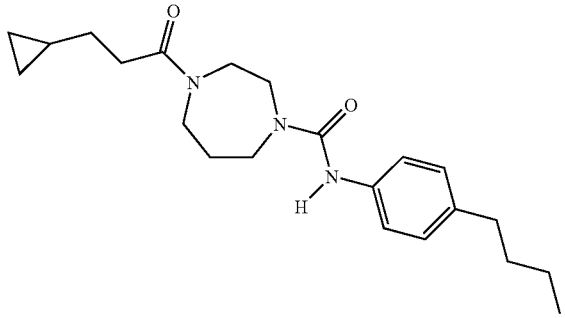 | 372 | D |
| 19 | 4-Cyclohexanecarbonyl-[1,4]diazepane-1-carboxylic acid (4-butyl-phenyl)-amide | 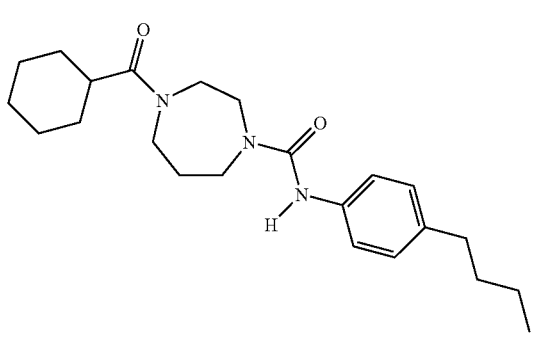 | 386 | D |
| 20 | 4-(Tetrahydro-pyran-4-carbonyl)-[1,4]diazepane-1-carboxylic acid (4-butyl-phenyl)-amide | 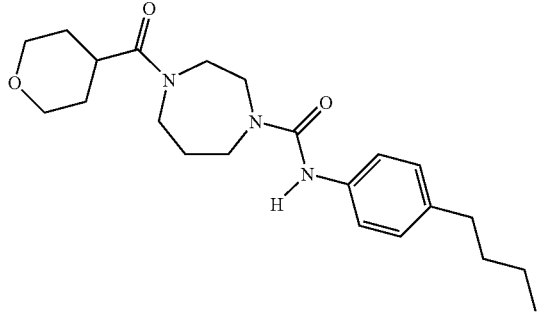 | 388 | D |
| 21 | 4-(2-Cyclopentyl-acetyl)-[1,4]diazepane-1-carboxylic acid (4-trifluoromethoxy-phenyl)-amide | 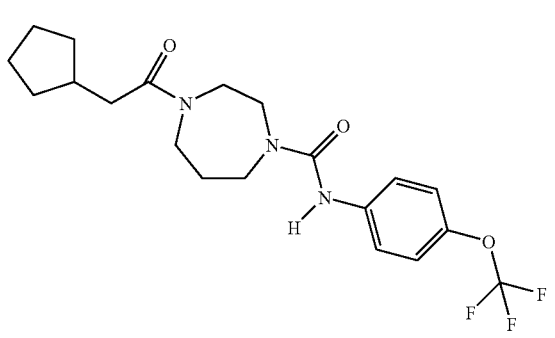 | 414 | E |
| 22 | 4-(2-Cyclopentyl-acetyl)-[1,4]diazepane-1-carboxylic acid (4-isopropyl-phenyl)-amide | 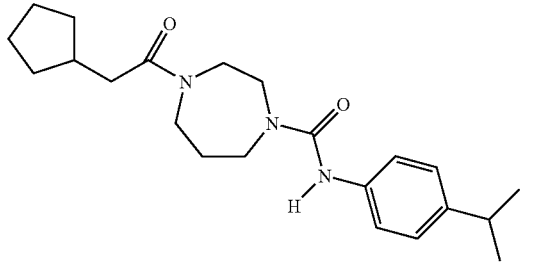 | 372 | E |

TABLE 1-continued

| Example | Name | Structure | LC-MS MH+ (amu) | Method |
|---|---|---|---|---|
| 23 | 4-(3-Cyclopentyl-propionyl)-[1,4]diazepane-1-carboxylic acid (4-methylsulfanyl-phenyl)-amide | 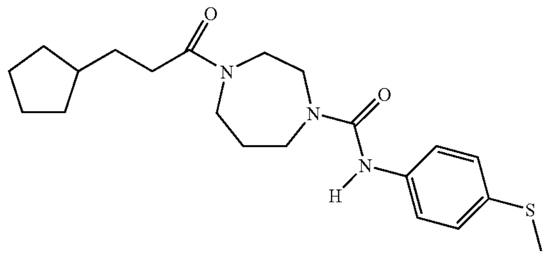 | 390 | B |
| 24 | 4-(2-Cyclopentyl-acetyl)-[1,4]diazepane-1-carboxylic acid (4-methylsulfanyl-phenyl)-amide | 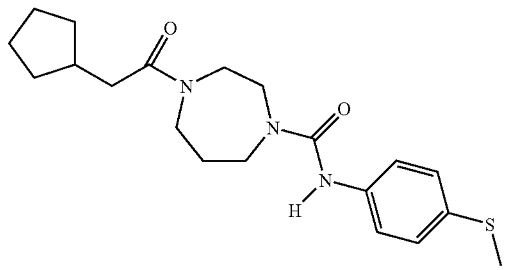 | 376 | E |
| 25 | 4-(2-Tetrahydro-pyran-4-yl-acetyl)-[1,4]diazepane-1-carboxylic acid (4-isopropyl-phenyl)-amide | 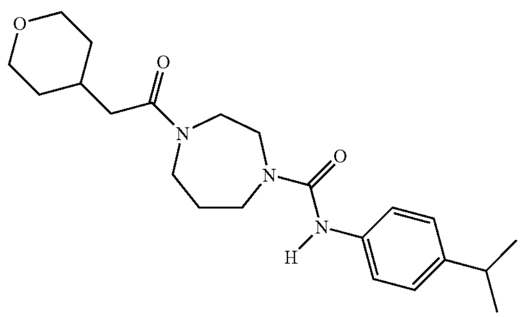 | 388 | C |
| 26 | 4-(2-Tetrahydro-pyran-4-yl-acetyl)-[1,4]diazepane-1-carboxylic acid (4-ethyl-phenyl)-amide | 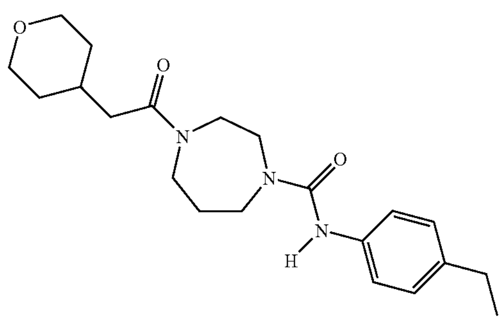 | 374 | C |
| 27 | 4-(2-Tetrahydro-pyran-4-yl-acetyl)-[1,4]diazepane-1-carboxylic acid (4-trifluoromethoxy-phenyl)-amide | 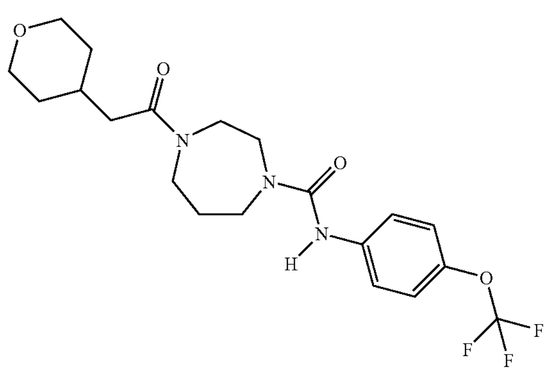 | 430 | E |

TABLE 1-continued

| Example | Name | Structure | LC-MS MH+ (amu) | Method |
|---|---|---|---|---|
| 28 | 4-(2-Tetrahydro-pyran-4-yl-acetyl)-[1,4]diazepane-1-carboxylic acid (4-sec-butyl-phenyl)-amide | 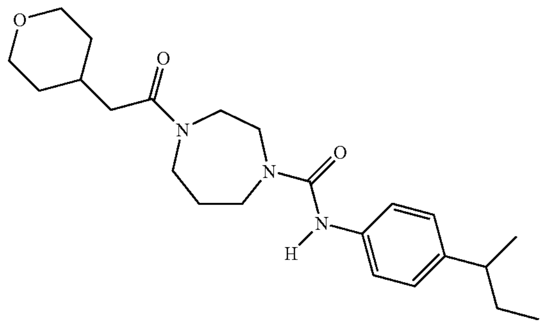 | 402 | E |
| 29 | 4-(2-Tetrahydro-pyran-4-yl-acetyl)-[1,4]diazepane-1-carboxylic acid (4-pentyl-phenyl)-amide | 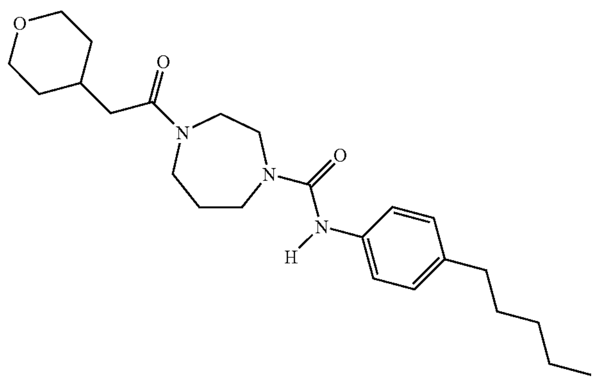 | 416 | E |
| 30 | 4-(2-Tetrahydro-pyran-4-yl-acetyl)-[1,4]diazepane-1-carboxylic acid (4-butyl-phenyl)-amide | 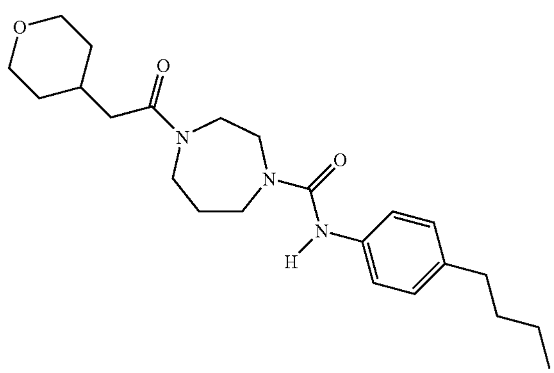 | 402 | E |
| 31 | 4-(2-Tetrahydro-pyran-4-yl-acetyl)-[1,4]diazepane-1-carboxylic acid (2-naphthyl)-amide | 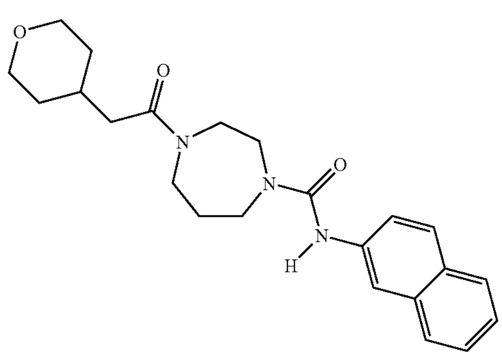 | 396 | E |

TABLE 1-continued

| Example | Name | Structure | LC-MS MH+ (amu) | Method |
|---|---|---|---|---|
| 32 | 4-(2-Tetrahydro-pyran-4-yl-acetyl)-[1,4]diazepane-1-carboxylic acid (4-methylsulfanyl-phenyl)-amide | 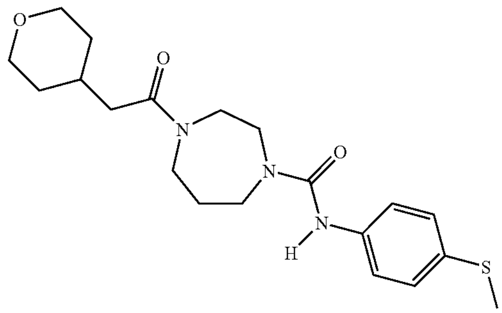 | 392 | E |
| 33 | 4-(2-Tetrahydro-pyran-4-yl-acetyl)-[1,4]diazepane-1-carboxylic acid (4-tert-butyl-phenyl)-amide | 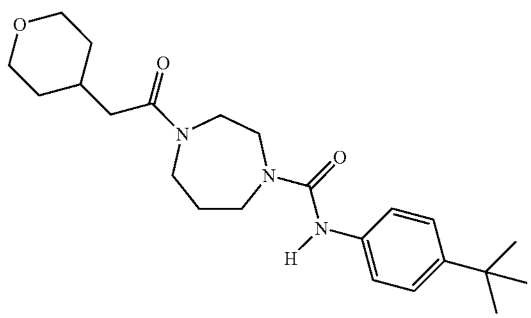 | 402 | E |
| 34 | 4-Cyclohexanecarbonyl-[1,4]diazepane-1-carboxylic acid (4-isopropyl-phenyl)-amide | 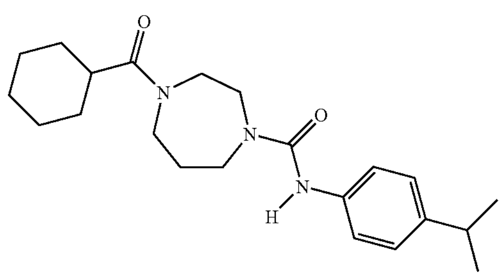 | 372 | C |
| 35 | 4-Benzoyl-[1,4]diazepane-1-carboxylic acid (4-isopropyl-phenyl)-amide | 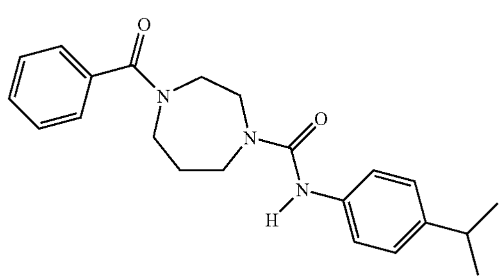 | 366 | C |
| 36 | 4-(2-Cyclohexyl-acetyl)-[1,4]diazepane-1-carboxylic acid (4-isopropyl-phenyl)-amide | 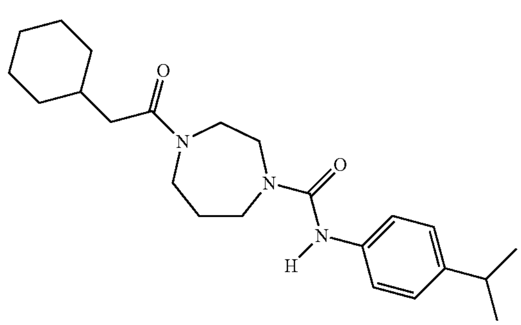 | 386 | C |

TABLE 1-continued

| Example | Name | Structure | LC-MS MH+ (amu) | Method |
|---|---|---|---|---|
| 37 | 4-(Pyridine-2-carbonyl)-[1,4]diazepane-1-carboxylic acid (4-isopropyl-phenyl)-amide | 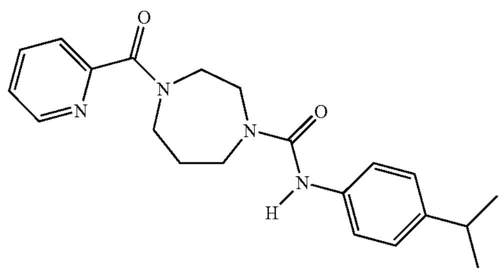 | 367 | D |
| 38 | 4-(Tetrahydro-pyran-4-carbonyl)-[1,4]diazepane-1-carboxylic acid (4-isopropyl-phenyl)-amide | 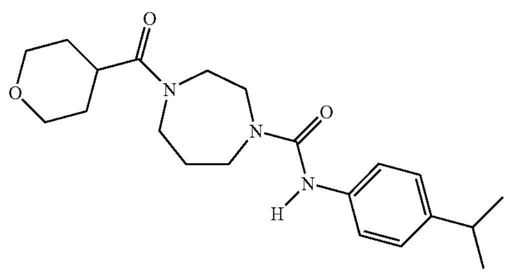 | 374 | C |
| 39 | 4-(Pyridine-4-carbonyl)-[1,4]diazepane-1-carboxylic acid (4-isopropyl-phenyl)-amide | 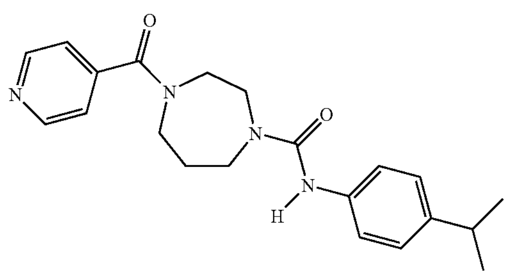 | 367 | D |
| 40 | 4-(3-Chloro-benzoyl)-[1,4]diazepane-1-carboxylic acid (4-isopropyl-phenyl)-amide | 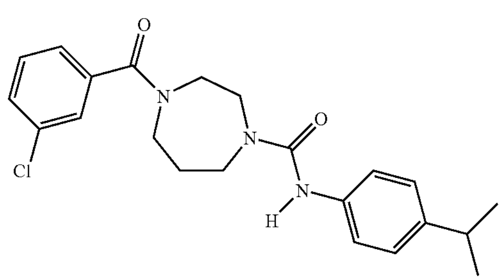 | 400 | D |
| 41 | 4-(4-Chloro-benzoyl)-[1,4]diazepane-1-carboxylic acid (4-isopropyl-phenyl)-amide | 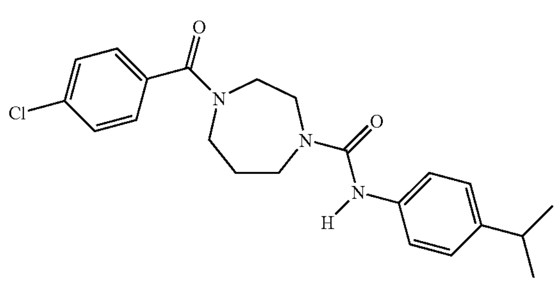 | 400 | D |

TABLE 1-continued

| Example | Name | Structure | LC-MS MH+ (amu) | Method |
|---|---|---|---|---|
| 42 | 4-(2-Tetrahydro-pyran-4-yl-acetyl)-[1,4]diazepane-1-carboxylic acid (2,2-difluoro-benzo[1,3]dioxol-5-yl)-amide | 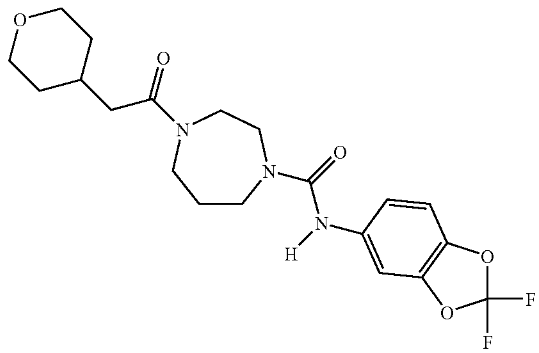 | 426 | E |
| 43 | 4-(2-Tetrahydro-pyran-4-yl-acetyl)-[1,4]diazepane-1-carboxylic acid (3,5-dichloro-phenyl)-amide | 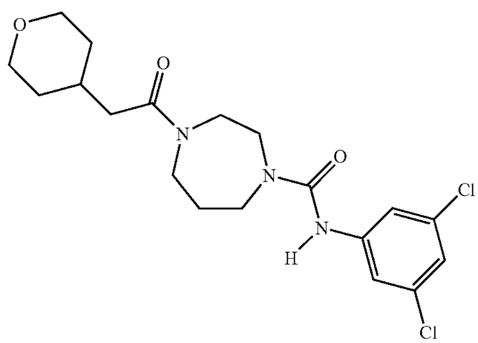 | 414 | E |
| 44 | 4-(2-Cyclopentyl-acetyl)-[1,4]diazepane-1-carboxylic acid (4-tert-butyl-phenyl)-amide | 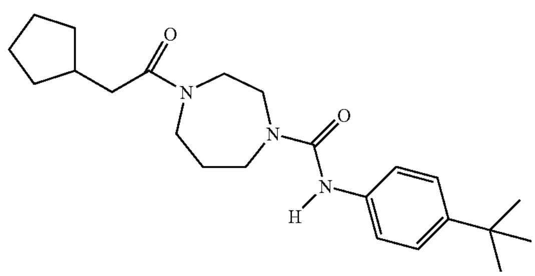 | 386 | E |
| 45 | 4-(2-Cyclopentyl-acetyl)-[1,4]diazepane-1-carboxylic acid (4-ethyl-phenyl)-amide | 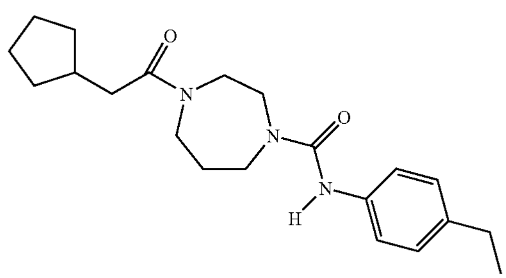 | 358 | E |

TABLE 1-continued

| Example | Name | Structure | LC-MS MH+ (amu) | Method |
|---|---|---|---|---|
| 46 | 4-(2-Cyclopentyl-acetyl)-[1,4]diazepane-1-carboxylic acid (1-acetyl-2,3-dihydro-1H-indol-6-yl)-amide | 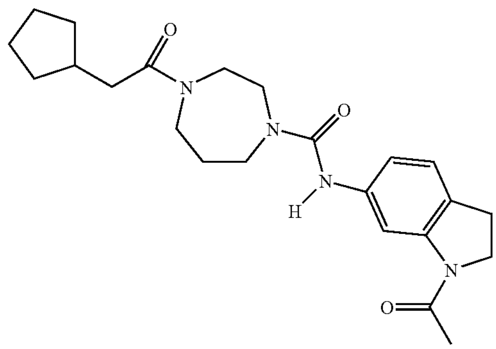 | 413 | E |
| 47 | 4-(2-Cyclopentyl-acetyl)-[1,4]diazepane-1-carboxylic acid (2,2-difluoro-benzo[1,3]dioxol-5-yl)-amide | 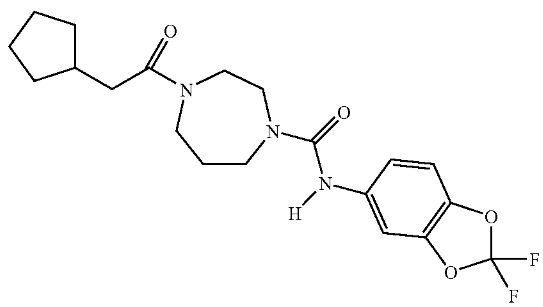 | 410 | E |
| 48 | 4-(2-Cyclopentyl-acetyl)-[1,4]diazepane-1-carboxylic acid (2-naphthyl)-amide | 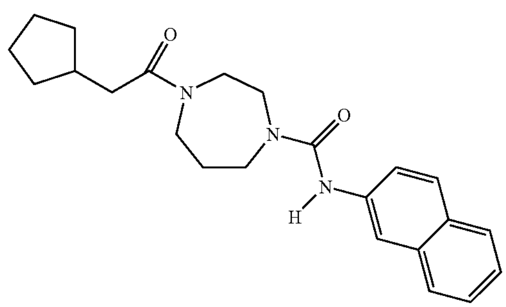 | 380 | E |
| 49 | 4-(2-Cyclopentyl-acetyl)-[1,4]diazepane-1-carboxylic acid (4-n-pentyl-phenyl)-amide | 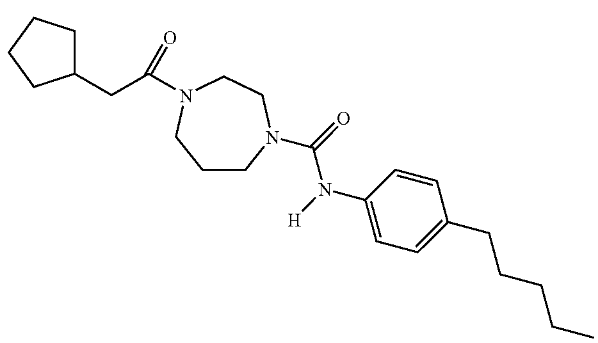 | 400 | E |
| 50 | 4-(2-Cyclopentyl-acetyl)-[1,4]diazepane-1-carboxylic acid (4-trifluoromethyl-phenyl)-amide | 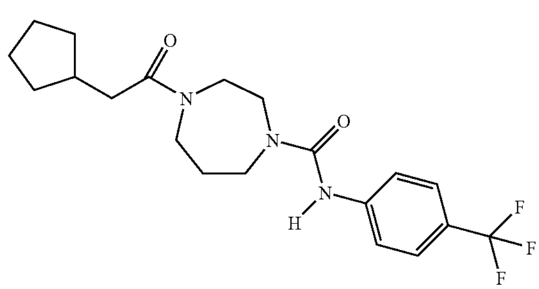 | 398 | E |

TABLE 1-continued

| Example | Name | Structure | LC-MS MH+ (amu) | Method |
| --- | --- | --- | --- | --- |
| 51 | 4-(2-Tetrahydro-pyran-4-yl-acetyl)[1,4]diazepane-1-carboxylic acid (4-trifluoromethyl-phenyl)-amide | 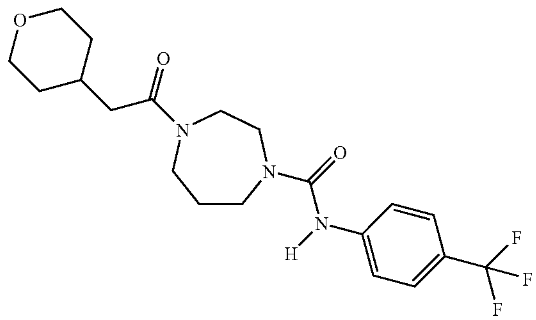 | 414 | E |
| 52 | 4-(2-Cyclopentyl-acetyl)-[1,4]diazepane-1-carboxylic acid (4-sec-butyl-phenyl)-amide | 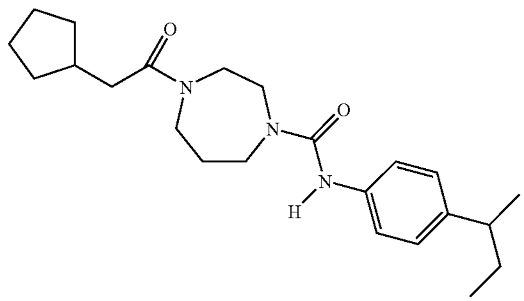 | 386 | E |
| 53 | 4-(2-Cyclopentyl-acetyl)-[1,4]diazepane-1-carboxylic acid (4-biphenyl)-amide | 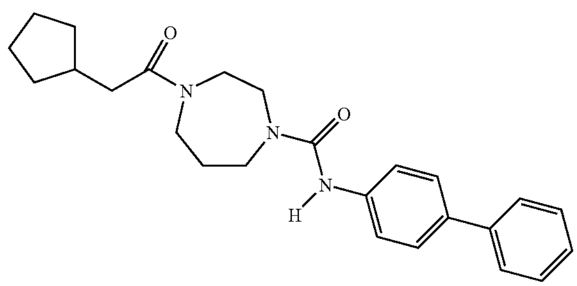 | 406 | E |
| 54 | 4-(2-Cyclopentyl-acetyl)-[1,4]diazepane-1-carboxylic acid (4-bromo-phenyl)-amide | 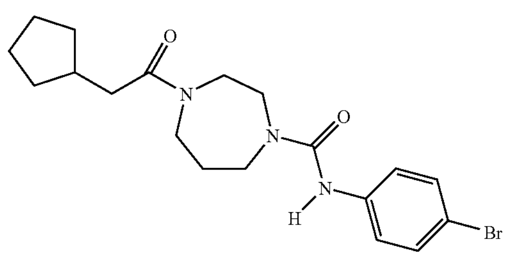 | 409 | E |
| 55 | 4-(3-Cyclopropyl-propionyl)-[1,4]diazepane-1-carboxylic acid (4-isopropyl-phenyl)-amide | 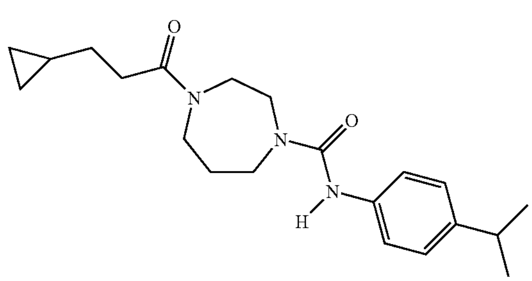 | 358 | D |

TABLE 1-continued

| Example | Name | Structure | LC-MS MH+ (amu) | Method |
|---|---|---|---|---|
| 56 | 4-(3-Cyclohexyl-propionyl)-[1,4]diazepane-1-carboxylic acid (4-isopropyl-phenyl)-amide | 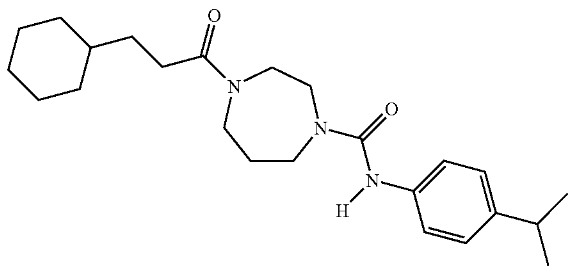 | 400 | D |
| 57 | 4-pivaloyl-[1,4]diazepane-1-carboxylic acid (4-isopropyl-phenyl)-amide | 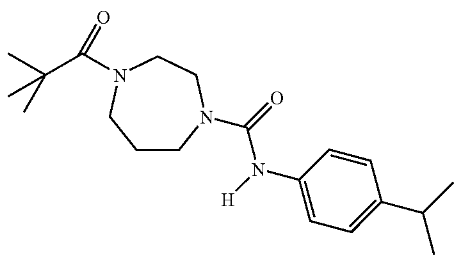 | 346 | D |
| 58 | 4-(4-Methyl-pentanoyl)-[1,4]diazepane-1-carboxylic acid (4-isopropyl-phenyl)-amide | 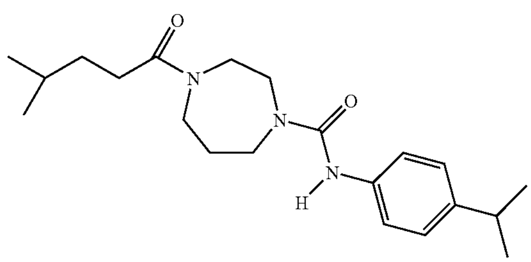 | 360 | D |
| 59 | 4-(4,4,4-Trifluoro-butyryl)-[1,4]diazepane-1-carboxylic acid (4-isopropyl-phenyl)-amide | 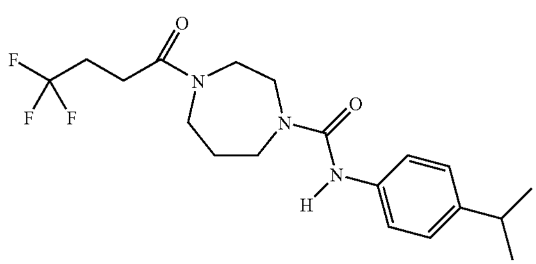 | 386 | D |
| 60 | 4-(3,3-Dimethyl-butyryl)-[1,4]diazepane-1-carboxylic acid (4-isopropyl-phenyl)-amide | 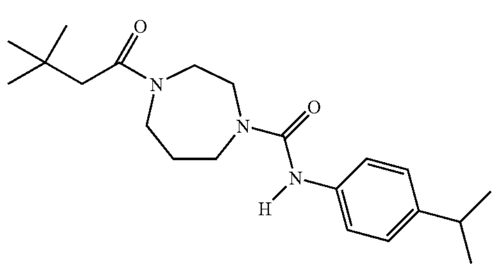 | 360 | D |

TABLE 1-continued

| Example | Name | Structure | LC-MS MH+ (amu) | Method |
|---|---|---|---|---|
| 61 | 4-(2-Cyclopentyl-acetyl)-[1,4]diazepane-1-carboxylic acid (2,4-dichloro-phenyl)-amide | 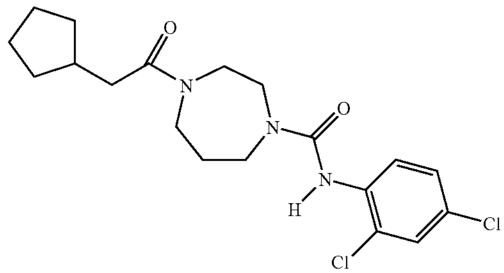 | 398 | E |
| 62 | 4-(2-Cyclopentyl-acetyl)-[1,4]diazepane-1-carboxylic acid (2,5-dichloro-phenyl)-amide | 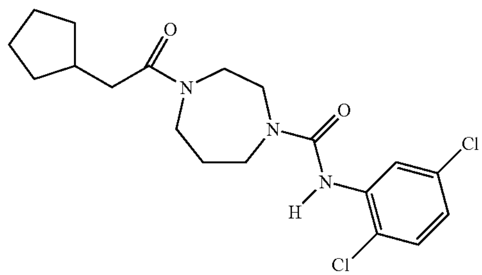 | 398 | E |
| 63 | 4-(2-Cyclopentyl-acetyl)-[1,4]diazepane-1-carboxylic acid (3,4-dichloro-phenyl)-amide | 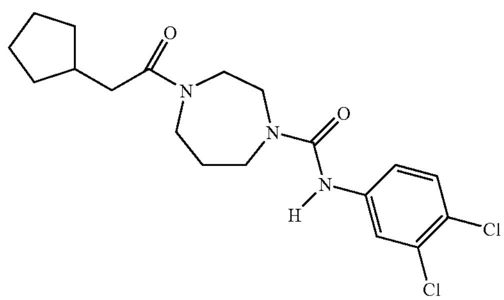 | 398 | E |
| 64 | 4-(2-Cyclopentyl-acetyl)-[1,4]diazepane-1-carboxylic acid (3,5-dichloro-phenyl)-amide | 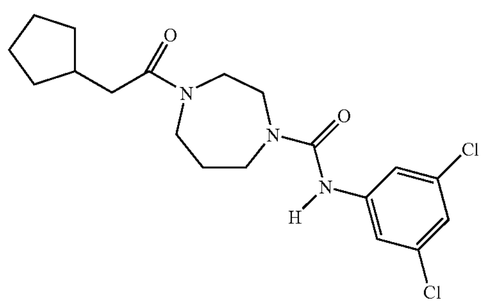 | 398 | E |
| 65 | 4-(2-Cyclohexyl-acetyl)-[1,4]diazepane-1-carboxylic acid (4-ethyl-phenyl)-amide | 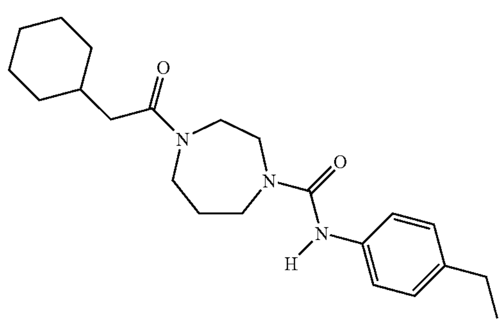 | 372 | E |

TABLE 1-continued

| Example | Name | Structure | LC-MS MH+ (amu) | Method |
|---|---|---|---|---|
| 66 | 4-(2-Cyclohexyl-acetyl)-[1,4]diazepane-1-carboxylic acid (2-naphthyl)-amide | 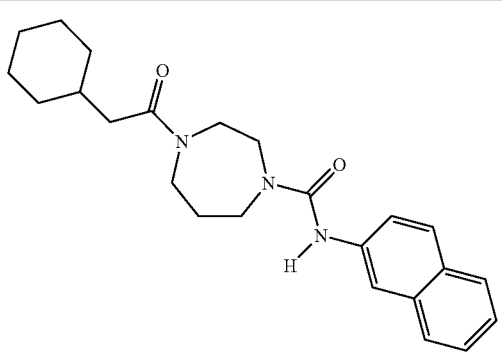 | 34 | E |
| 67 | 4-Cyclohexanecarbonyl-[1,4]diazepane-1-carboxylic acid (4-ethyl-phenyl)-amide | 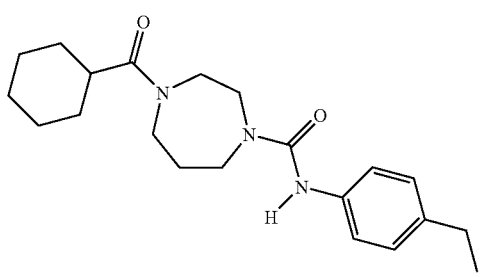 | 358 | E |
| 68 | 4-Cyclohexanecarbonyl-[1,4]diazepane-1-carboxylic acid naphthalen-2-ylamide | 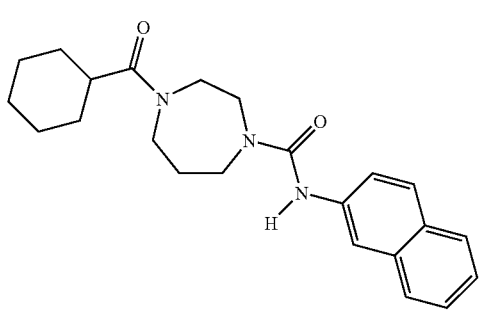 | 380 | E |
| 69 | 4-(4-Chloro-benzoyl)-[1,4]diazepane-1-carboxylic acid (4-tert-butyl-phenyl)-amide | 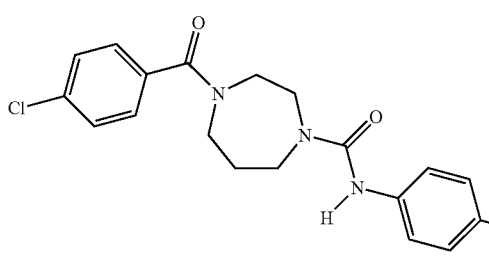 | 414 | D |
| 70 | 4-(4-Chloro-benzoyl)-[1,4]diazepane-1-carboxylic acid (4-trifluoromethyl-phenyl)-amide | 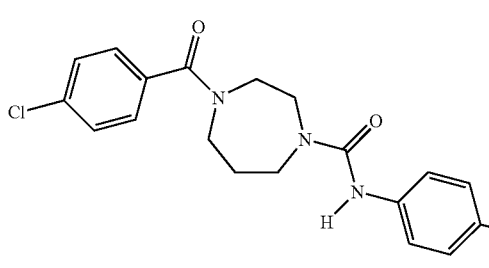 | 426 | D |

TABLE 1-continued

| Example | Name | Structure | LC-MS MH+ (amu) | Method |
|---|---|---|---|---|
| 71 | 4-(4-Chloro-benzoyl)-[1,4]diazepane-1-carboxylic acid (4-bromo-phenyl)-amide | 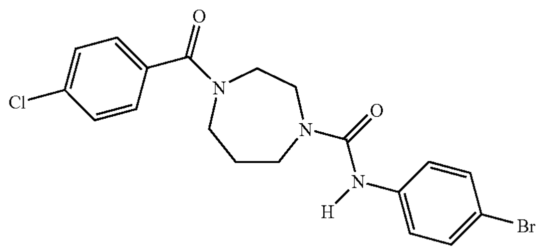 | 437 | E |
| 72 | 4-(4-Chloro-benzoyl)-[1,4]diazepane-1-carboxylic acid (3,4-dichloro-phenyl)-amide | 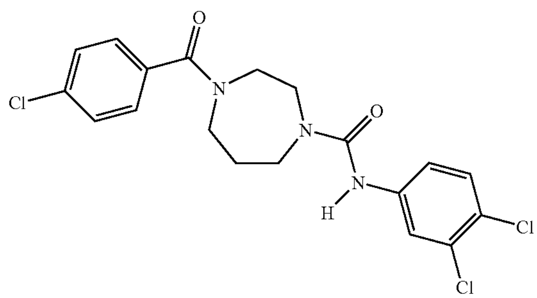 | 426 | E |
| 73 | 4-(4-Chloro-benzoyl)-[1,4]diazepane-1-carboxylic acid (3,5-dichloro-phenyl)-amide | 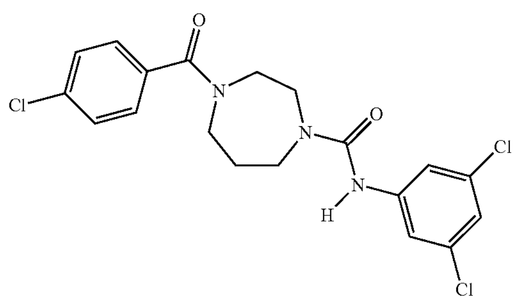 | 426 | E |
| 74 | 4-Cyclohexanecarbonyl-[1,4]diazepane-1-carboxylic acid (4-bromo-phenyl)-amide | 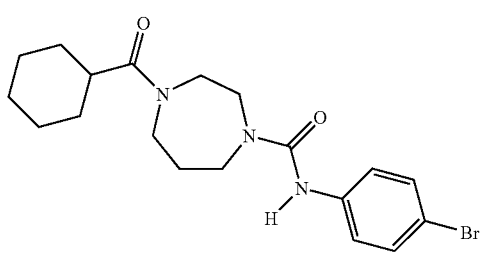 | 409 | E |
| 75 | 4-Cyclohexanecarbonyl-[1,4]diazepane-1-carboxylic acid (3,4-dichloro-phenyl)-amide | 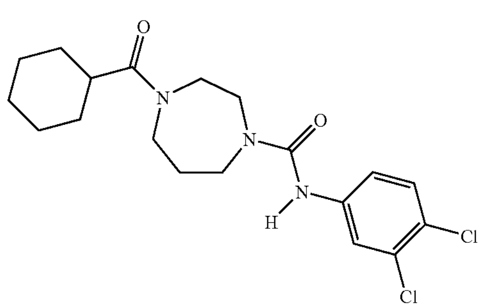 | 398 | E |

TABLE 1-continued

| Example | Name | Structure | LC-MS MH+ (amu) | Method |
|---|---|---|---|---|
| 76 | 4-Cyclohexanecarbonyl-[1,4]diazepane-1-carboxylic acid (3,5-dichloro-phenyl)-amide | 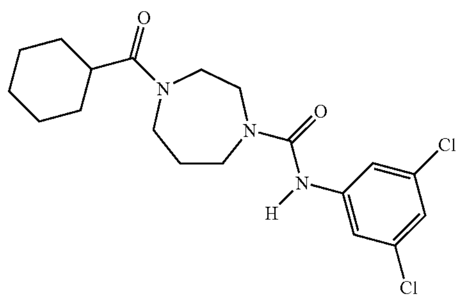 | 398 | E |
| 77 | 4-(Tetrahydro-pyran-4-carbonyl)-[1,4]diazepane-1-carboxylic acid (4-trifluoromethyl-phenyl)-amide | 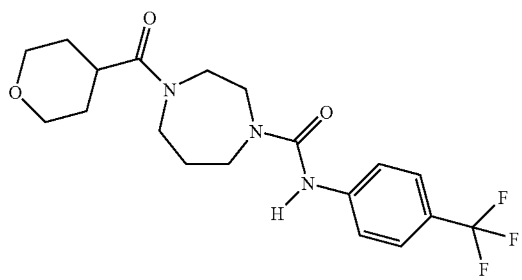 | 400 | D |
| 78 | 4-(4,4-Difluoro-cyclohexanecarbonyl)-[1,4]diazepane-1-carboxylic acid (4-trifluoromethyl-phenyl)-amide | 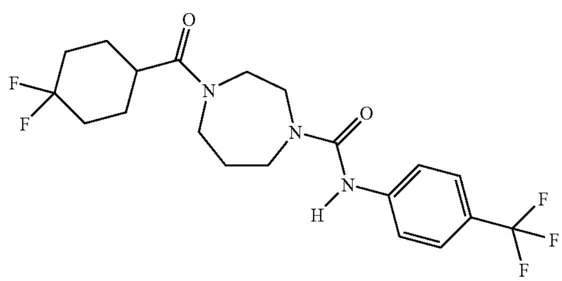 | 434 | D |
| 79 | 4-(4-Chloro-benzoyl)-[1,4]diazepane-1-carboxylic acid naphthalen-2-ylamide | 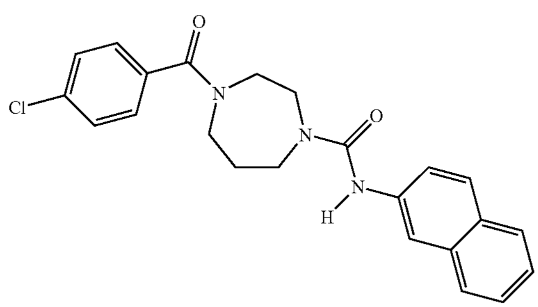 | 408 | E |
| 80 | 4-Cyclohexanecarbonyl-[1,4]diazepane-1-carboxylic acid (4-trifluoromethylsulfanyl-phenyl)-amide | 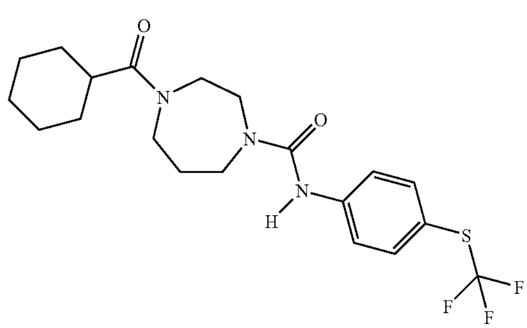 | 430 | E |

TABLE 1-continued

| Example | Name | Structure | LC-MS MH+ (amu) | Method |
|---|---|---|---|---|
| 81 | 4-(Tetrahydro-pyran-4-carbonyl)-[1,4]diazepane-1-carboxylic acid (4-trifluoromethylsulfanyl-phenyl)-amide | 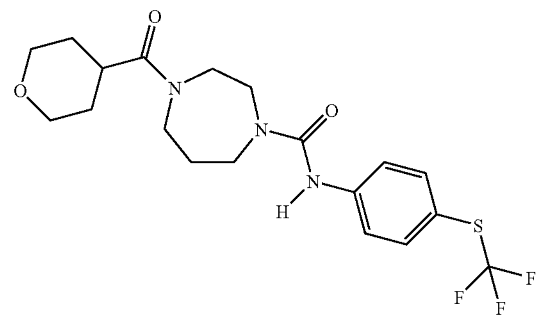 | 432 | E |
| 82 | 4-(2-cyclopentyl-acetyl)-[1,4]diazepane-1-carboxylic acid (4-trifluoromethylsulfanyl-phenyl)-amide | 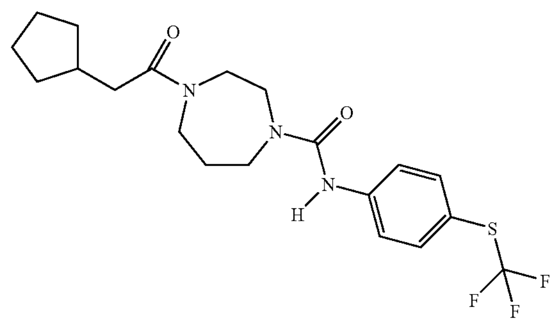 | 430 | E |
| 83 | 4-(2-Cyclopentyl-acetyl)-[1,4]diazepane-1-carboxylic acid (4-butyryl-phenyl)-amide | 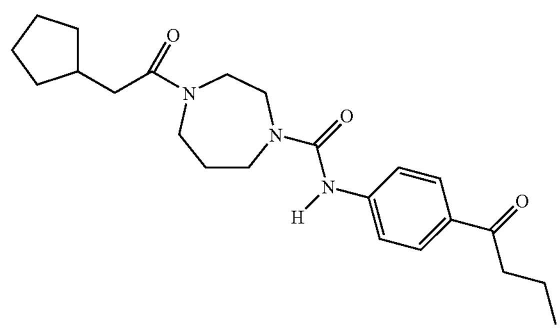 | 400 | E |
| 84 | 4-Cyclopentanecarbonyl-[1,4]diazepane-1-carboxylic acid naphthalen-2-ylamide | 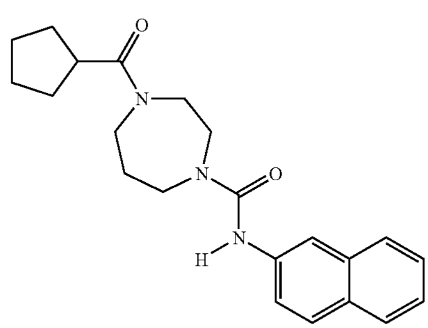 | 366 | C |

TABLE 1-continued

| Example | Name | Structure | LC-MS MH+ (amu) | Method |
|---|---|---|---|---|
| 85 | 4-(3-Cyclohexyl-propionyl)-[1,4]diazepane-1-carboxylic acid naphthalen-2-ylamide | 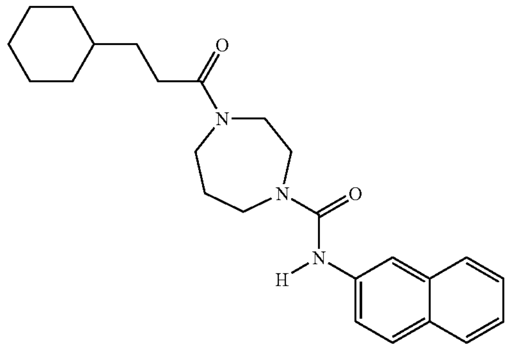 | 408 | C |
| 86 | 4-(3,4-Dichloro-benzoyl)-[1,4]diazepane-1-carboxylic acid naphthalen-2-ylamide | 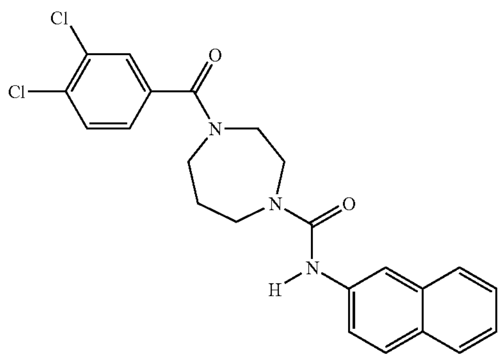 | 442 | C |
| 87 | 4-(3,5-Dichloro-benzoyl)-[1,4]diazepane-1-carboxylic acid naphthalen-2-ylamide | 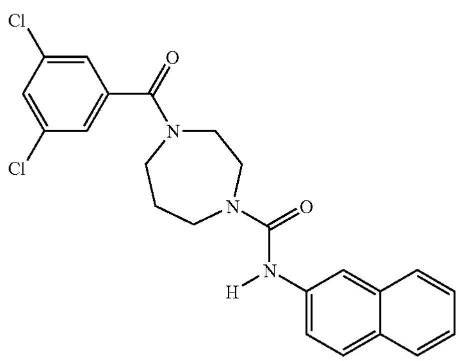 | 443 | C |
| 88 | 4-(4-Cyano-benzoyl)-[1,4]diazepane-1-carboxylic acid naphthalen-2-ylamide | 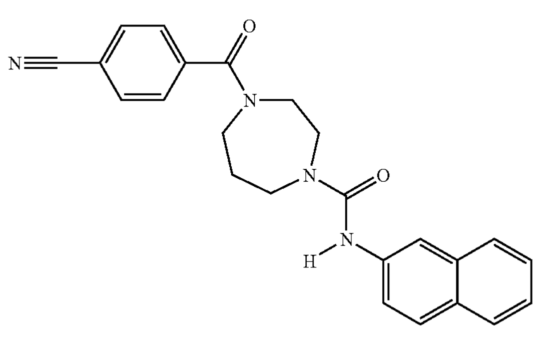 | 399 | C |

TABLE 1-continued

| Example | Name | Structure | LC-MS MH+ (amu) | Method |
|---|---|---|---|---|
| 89 | 4-(4-Dimethylamino-benzoyl)-[1,4]diazepane-1-carboxylic acid naphthalen-2-ylamide | 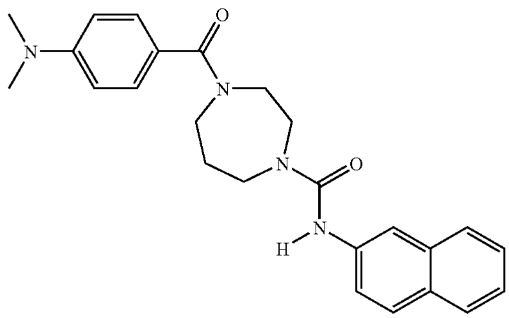 | 417 | C |
| 90 | 4-(2,5-Dichloro-benzoyl)-[1,4]diazepane-1-carboxylic acid naphthalen-2-ylamide | 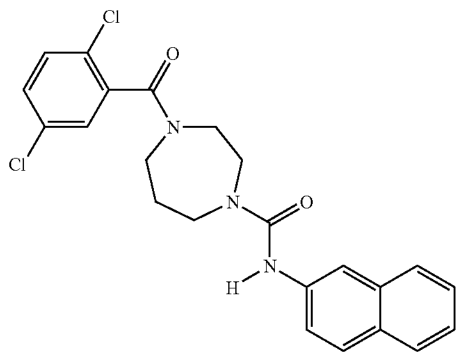 | 442 | C |
| 91 | 4-(4-Methoxy-benzoyl)-[1,4]diazepane-1-carboxylic acid naphthalen-2-ylamide | 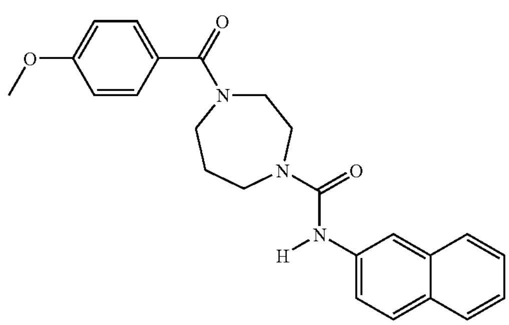 | 404 | C |
| 92 | 4-(4-Trifluoromethyl-benzoyl)-[1,4]diazepane-1-carboxylic acid naphthalen-2-ylamide | 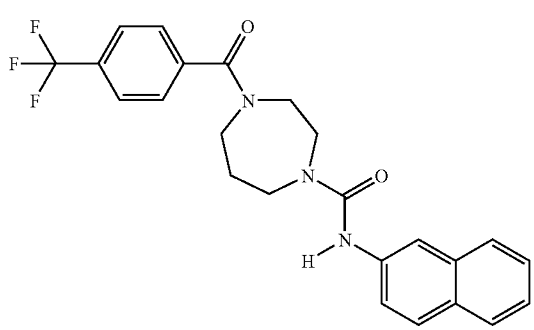 | 442 | C |

TABLE 1-continued

| Example | Name | Structure | LC-MS MH+ (amu) | Method |
|---|---|---|---|---|
| 93 | 4-(3,3-Dimethyl-butyryl)-[1,4]diazepane-1-carboxylic acid naphthalen-2-ylamide | 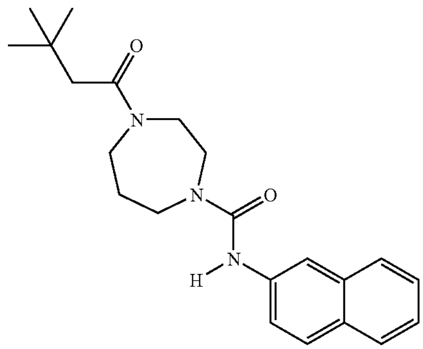 | 368 | C |
| 94 | 4-(4-Methyl-pentanoyl)-[1,4]diazepane-1-carboxylic acid naphthalen-2-ylamide | 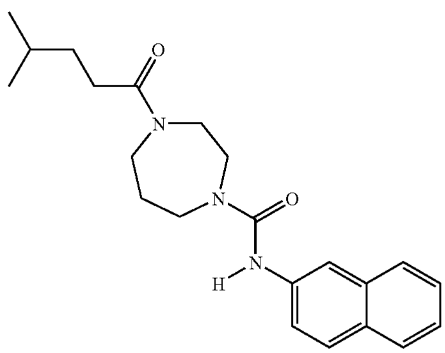 | 368 | C |
| 95 | 4-(2,2-Dimethyl-propionyl)-[1,4]diazepane-1-carboxylic acid naphthalen-2-ylamide | 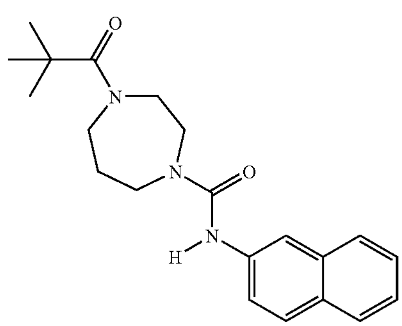 | 354 | C |
| 96 | 4-(2-Phenoxy-acetyl)-[1,4]diazepane-1-carboxylic acid naphthalen-2-ylamide | 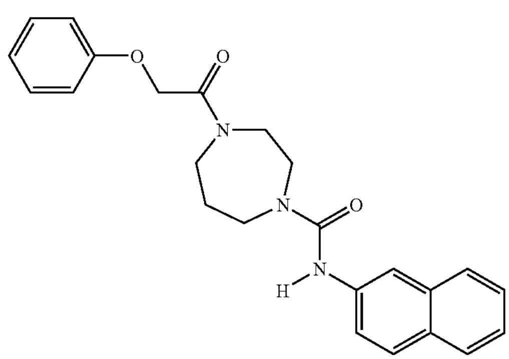 | 404 | C |

TABLE 1-continued

| Example | Name | Structure | LC-MS MH+ (amu) | Method |
|---------|------|-----------|-----------------|--------|
| 97 | 4-(4,4,4-Trifluoro-butyryl)-[1,4]diazepane-1-carboxylic acid naphthalen-2-ylamide | 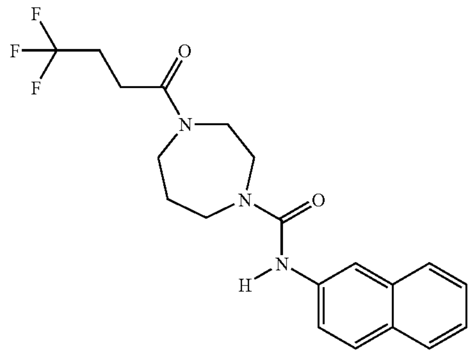 | 394 | C |
| 98 | 4-(3-Cyclopropyl-propionyl)-[1,4]diazepane-1-carboxylic acid naphthalen-2-ylamide | 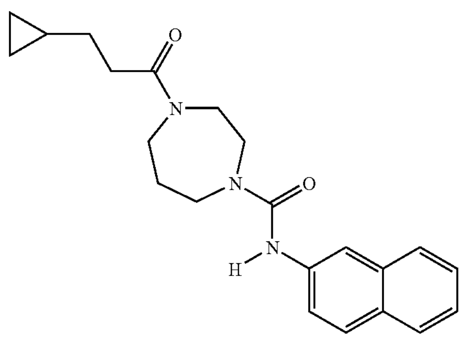 | 366 | C |
| 99 | 4-(2,4-Dichloro-benzoyl)-[1,4]diazepane-1-carboxylic acid naphthalen-2-ylamide | 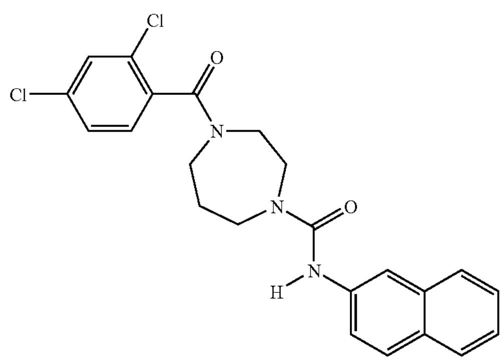 | 443 | C |
| 100 | 4-(4-Methyl-benzoyl)-[1,4]diazepane-1-carboxylic acid naphthalen-2-ylamide | 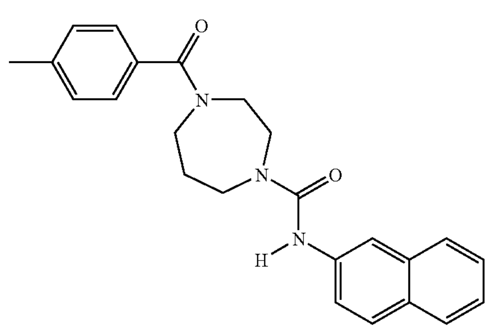 | 388 | C |

TABLE 1-continued

| Example | Name | Structure | LC-MS MH+ (amu) | Method |
|---|---|---|---|---|
| 101 | 4-(Tetrahydro-pyran-4-carbonyl)-[1,4]diazepane-1-carboxylic acid naphthalen-2-ylamide | 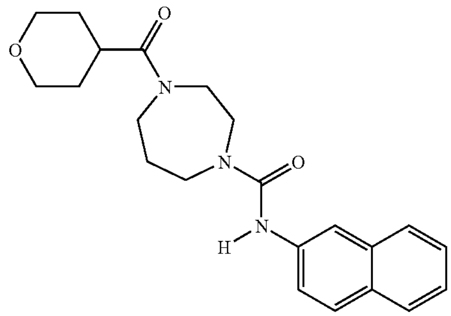 | 382 | C |
| 102 | 4-(3-Cyclopentyl-propionyl)-[1,4]diazepane-1-carboxylic acid (4-propyl-phenyl)-amide | 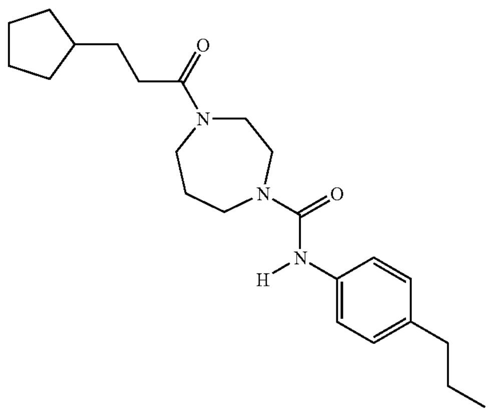 | 386 | C |
| 103 | 4-(2-Piperidin-1-yl-acetyl)-[1,4]diazepane-1-carboxylic acid naphthalen-2-ylamide | 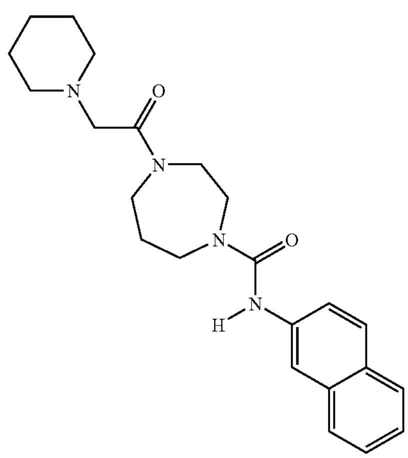 | 395 | C |
| 104 | 4-Cyclopentanecarbonyl-[1,4]diazepane-1-carboxylic acid (4-tert-butyl-phenyl)-amide | 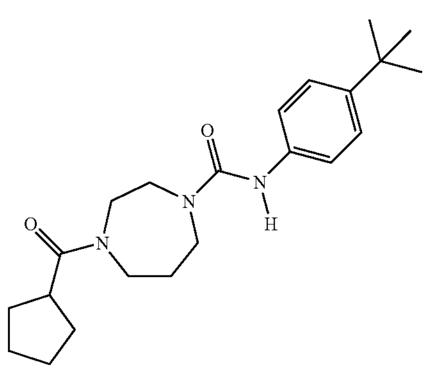 | 372 | C |

TABLE 1-continued

| Example | Name | Structure | LC-MS MH+ (amu) | Method |
|---|---|---|---|---|
| 105 | 4-(3-Cyclopentyl-propionyl)-[1,4]diazepane-1-carboxylic acid (4-tert-butyl-phenyl)-amide | 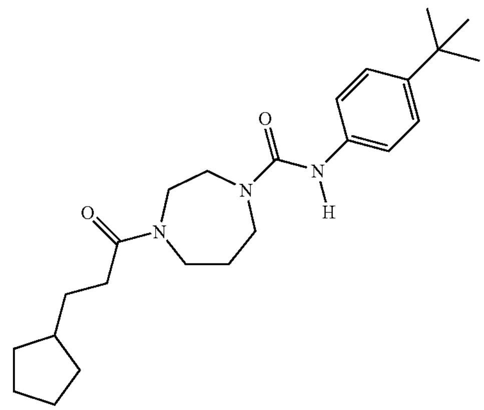 | 400 | C |
| 106 | 4-Cyclohexanecarbonyl-[1,4]diazepane-1-carboxylic acid (4-tert-butyl-phenyl)-amide | 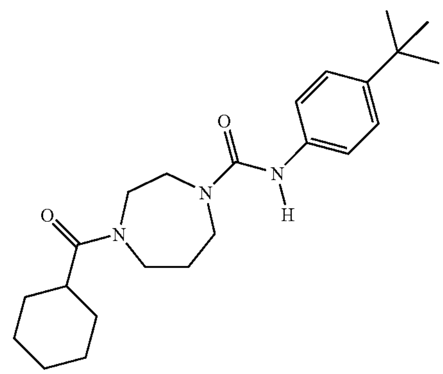 | 386 | C |
| 107 | 4-(2-Cyclohexyl-acetyl)-[1,4]diazepane-1-carboxylic acid (4-tert-butyl-phenyl)-amide | 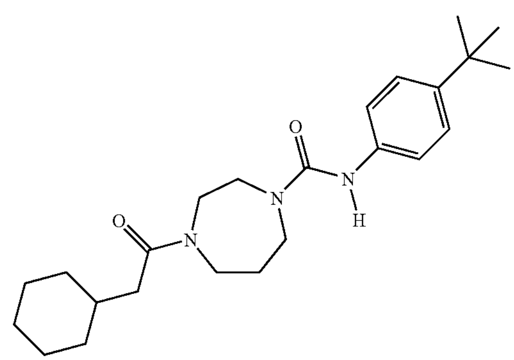 | 400 | C |
| 108 | 4-(3-Cyclohexyl-propionyl)-[1,4]diazepane-1-carboxylic acid (4-tert-butyl-phenyl)-amide | 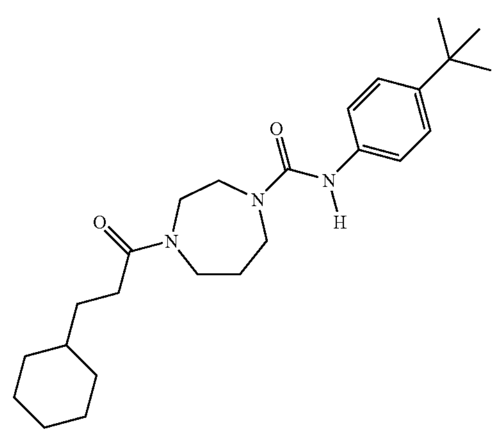 | 414 | C |

TABLE 1-continued

| Example | Name | Structure | LC-MS MH+ (amu) | Method |
|---|---|---|---|---|
| 109 | 4-(2,5-Dichloro-benzoyl)-[1,4]diazepane-1-carboxylic acid (4-tert-butyl-phenyl)-amide | 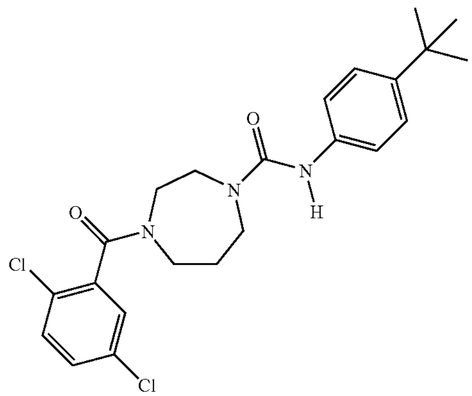 | 448 | C |
| 110 | 4-(3,4-Dichloro-benzoyl)-[1,4]diazepane-1-carboxylic acid (4-tert-butyl-phenyl)-amide | 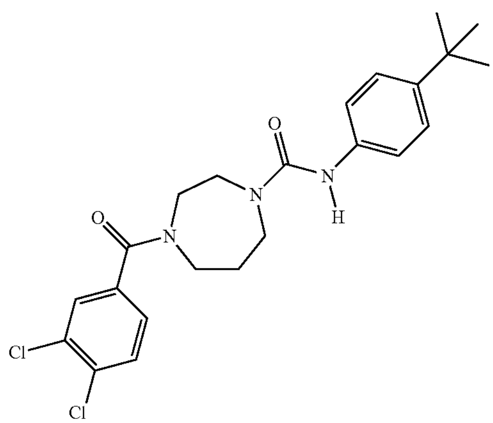 | 448 | C |
| 111 | 4-(3,5-Dichloro-benzoyl)-[1,4]diazepane-1-carboxylic acid (4-tert-butyl-phenyl)-amide | 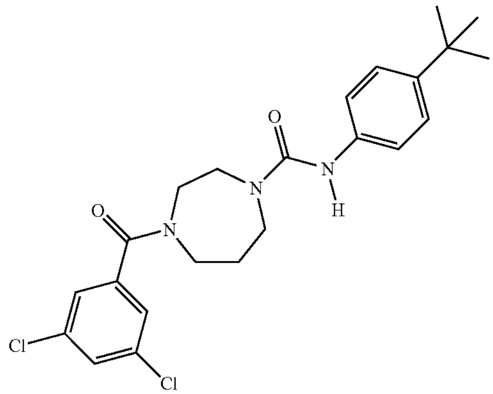 | 448 | C |

TABLE 1-continued

| Example | Name | Structure | LC-MS MH+ (amu) | Method |
|---|---|---|---|---|
| 112 | 4-(4-Cyano-benzoyl)-[1,4]diazepane-1-carboxylic acid (4-tert-butyl-phenyl)-amide | 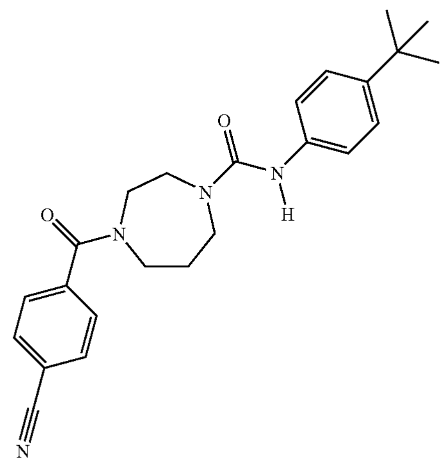 | 405 | C |
| 113 | 4-(4-Dimethylamino-benzoyl)-[1,4]diazepane-1-carboxylic acid (4-tert-butyl-phenyl)-amide | 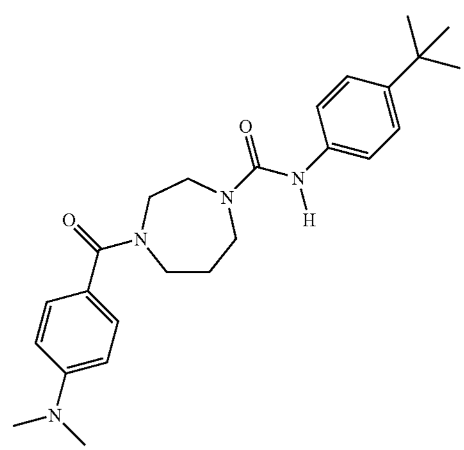 | 423 | C |
| 114 | 4-(4-Trifluoromethyl-benzoyl)-[1,4]diazepane-1-carboxylic acid (4-tert-butyl-phenyl)-amide | 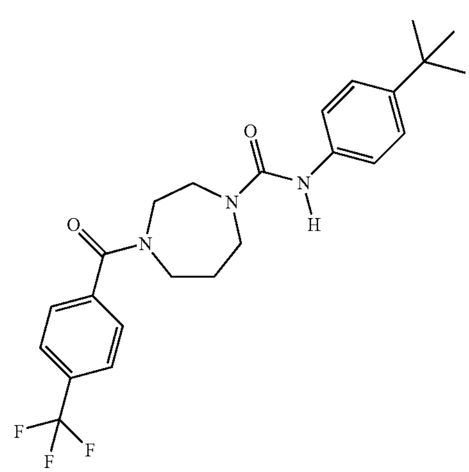 | 448 | C |

TABLE 1-continued

| Example | Name | Structure | LC-MS MH+ (amu) | Method |
|---|---|---|---|---|
| 115 | 4-(3,3-Dimethyl-butyryl)-[1,4]diazepane-1-carboxylic acid (4-tert-butyl-phenyl)-amide | 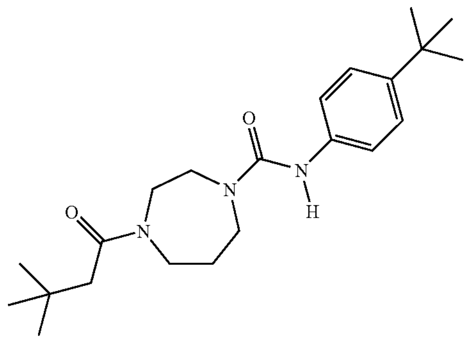 | 374 | C |
| 116 | 4-(4-Methyl-pentanoyl)-[1,4]diazepane-1-carboxylic acid (4-tert-butyl-phenyl)-amide | 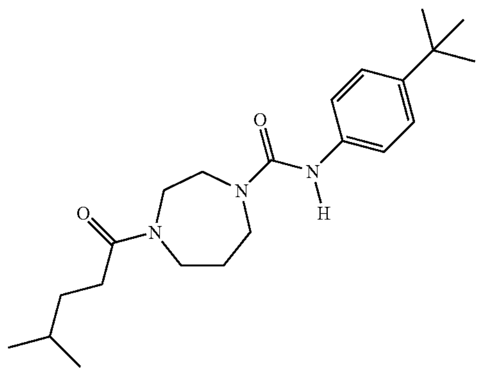 | 374 | C |
| 117 | 4-(2,2-Dimethyl-propionyl)-[1,4]diazepane-1-carboxylic acid (4-tert-butyl-phenyl)-amide | 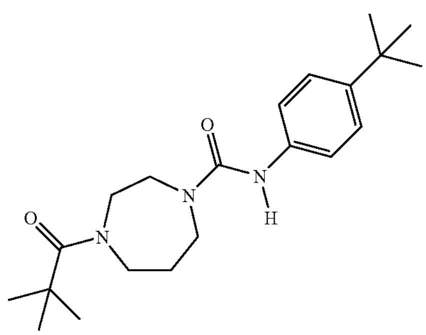 | 360 | C |
| 118 | 4-(2-Phenoxy-acetyl)-[1,4]diazepane-1-carboxylic acid (4-tert-butyl-phenyl)-amide | 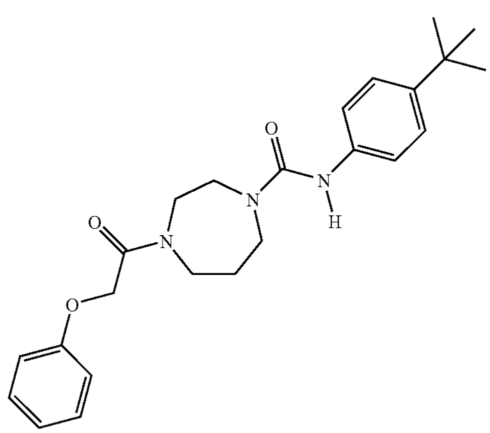 | 410 | C |

TABLE 1-continued
| Example | Name | Structure | LC-MS MH+ (amu) | Method |
|---|---|---|---|---|
| 119 | 4-(4,4,4-Trifluoro-butyryl)-[1,4]diazepane-1-carboxylic acid (4-tert-butyl-phenyl)-amide | 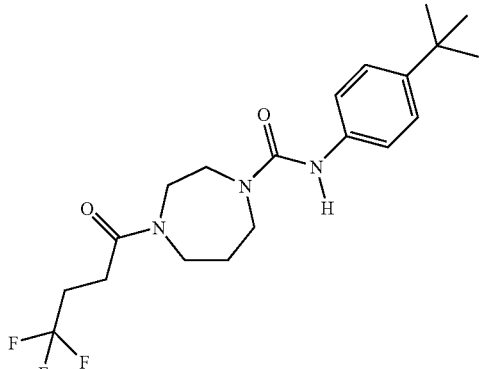 | 400 | C |
| 120 | 4-(3-Cyclopropyl-propionyl)-[1,4]diazepane-1-carboxylic acid (4-tert-butyl-phenyl)-amide | 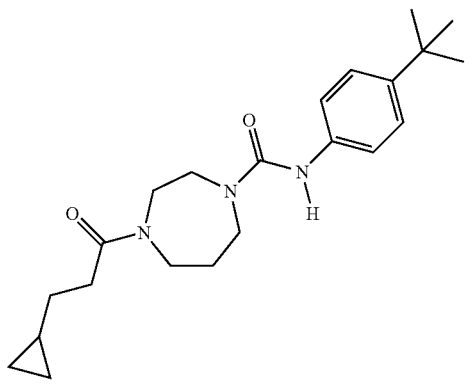 | 372 | C |
| 121 | 4-(2-Thiomorpholin-4-yl-acetyl)-[1,4]diazepane-1-carboxylic acid (4-tert-butyl-phenyl)-amide | 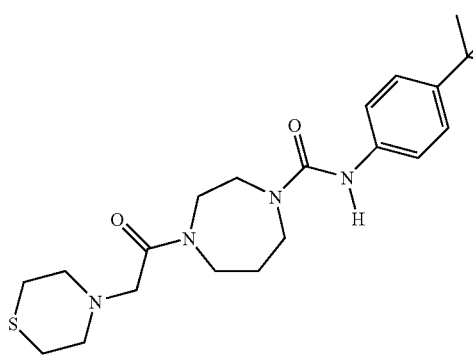 | 419 | C |
| 122 | 4-(4-Methyl-benzoyl)-[1,4]diazepane-1-carboxylic acid (4-tert-butyl-phenyl)-amide | 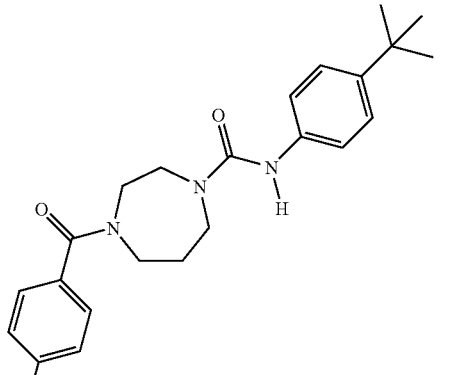 | 394 | C |

TABLE 1-continued

| Example | Name | Structure | LC-MS MH+ (amu) | Method |
|---|---|---|---|---|
| 123 | 4-(2-Phenylamino-acetyl)-[1,4]diazepane-1-carboxylic acid (4-tert-butyl-phenyl)-amide | 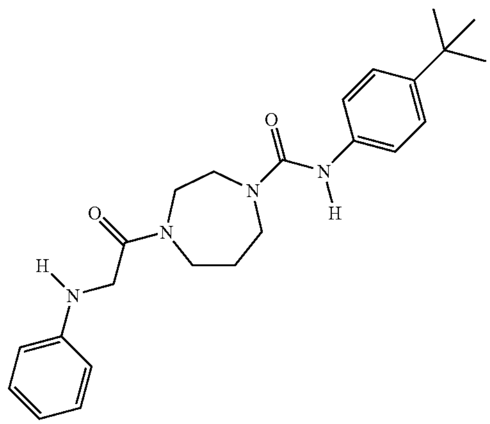 | 409 | C |
| 124 | 4-(Pyridine-2-carbonyl)-[1,4]diazepane-1-carboxylic acid (4-sec-butyl-phenyl)-amide | 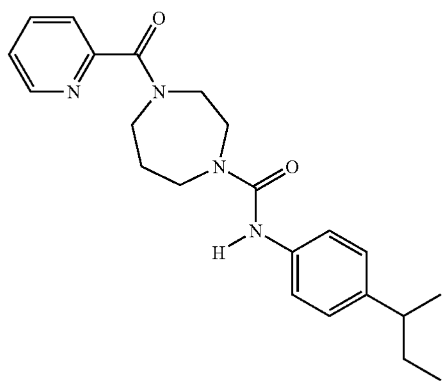 | 381 | C |
| 125 | 4-(Tetrahydro-pyran-4-carbonyl)-[1,4]diazepane-1-carboxylic acid (4-tert-butyl-phenyl)-amide | 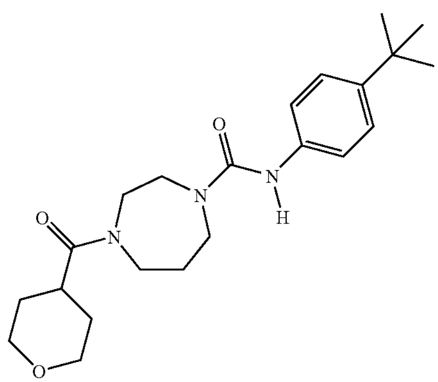 | 388 | C |
| 126 | 4-(2-Piperidin-1-yl-acetyl)-[1,4]diazepane-1-carboxylic acid (4-tert-butyl-phenyl)-amide | 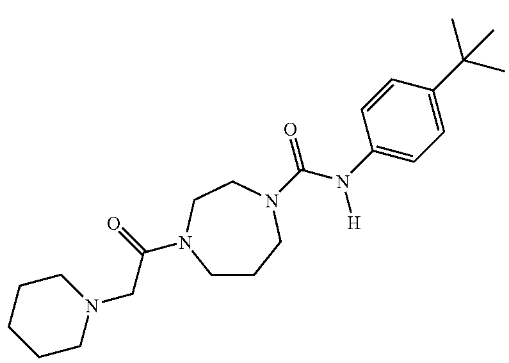 | 401 | C |

TABLE 1-continued

| Example | Name | Structure | LC-MS MH+ (amu) | Method |
|---|---|---|---|---|
| 127 | 4-(4-Trifluoromethyl-benzoyl)-[1,4]diazepane-1-carboxylic acid (4-trifluomethyl-phenyl)-amide | 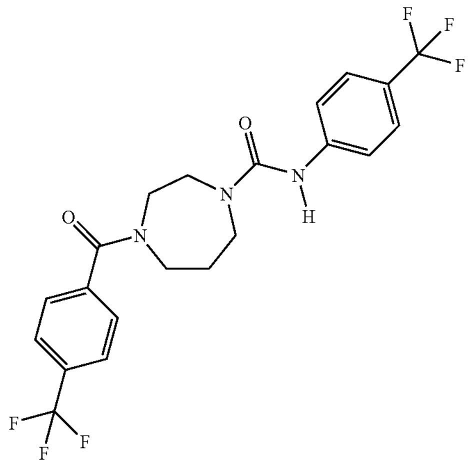 | 460 | D |
| 128 | 4-Cyclohexanecarbonyl-[1,4]diazepane-1-carboxylic acid (4-trifluoromethyl-phenyl)-amide | 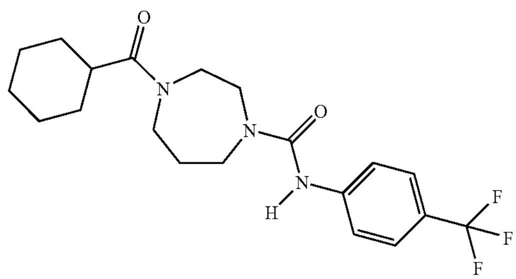 | 398 | D |
| 129 | 4-(4-Fluoro-benzoyl)-[1,4]diazepane-1-carboxylic acid (4-trifluoromethyl-phenyl)-amide | 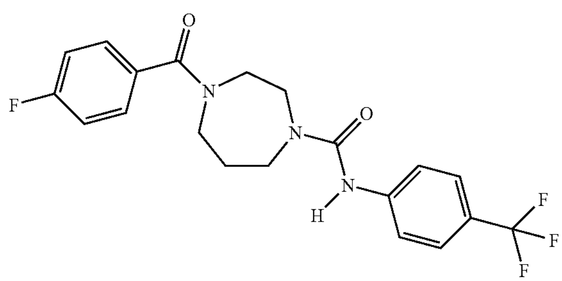 | 410 | D |
| 130 | 4-Benzoyl-[1,4]diazepane-1-carboxylic acid (4-trifluoromethyl-phenyl)-amide | 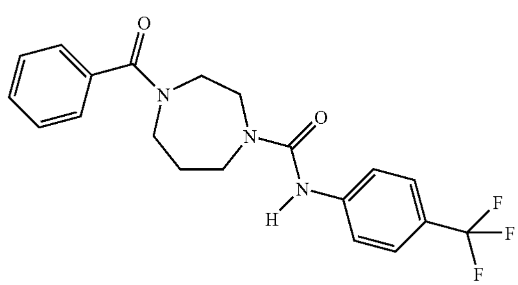 | 392 | D |
| 131 | 4-(2-Cyclopentyl-acetyl)-[1,4]diazepane-1-carboxylic acid (3-trifluoromethyl-phenyl)-amide | 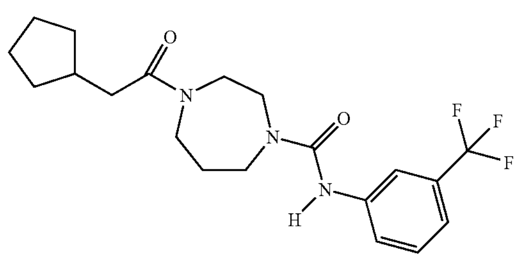 | 398 | E |

TABLE 1-continued

| Example | Name | Structure | LC-MS MH+ (amu) | Method |
|---|---|---|---|---|
| 132 | 4-(2-Cyclopentyl-acetyl)-[1,4]diazepane-1-carboxylic acid (4-bromo-3-trifluoromethyl-phenyl)-amide | 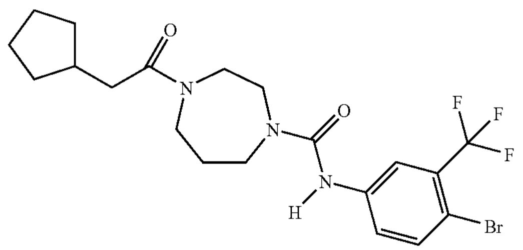 | 477 | E |
| 133 | 4-(Tetrahydro-pyran-4-carbonyl)-[1,4]diazepane-1-carboxylic acid (4-sec-butyl-phenyl)-amide | 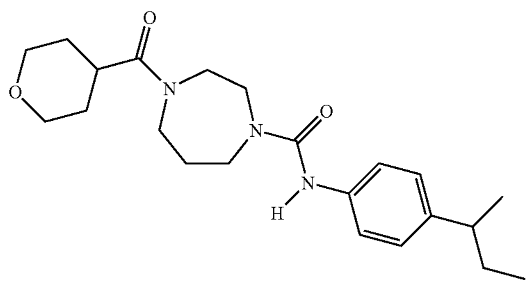 | 388 | D |
| 134 | 4-(3-Cyclopentyl-propionyl)-[1,4]diazepane-1-carboxylic acid cyclohexylmethyl-amide | 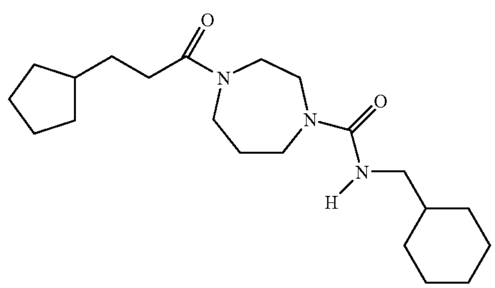 | 364 | B |
| 135 | 4-(3-Cyclopentyl-propionyl)-[1,4]diazepane-1-carboxylic acid cyclohexylamide | 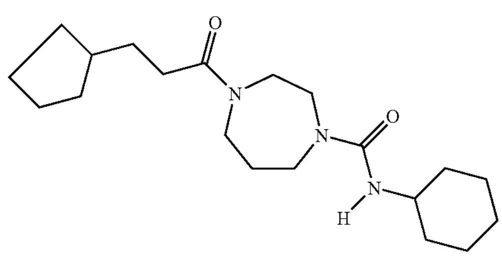 | 350 | B |
| 136 | 4-(2-Tetrahydro-pyran-4-yl-acetyl)-[1,4]diazepane-1-carboxylic acid (4-methanesulfonyl-phenyl)-amide | 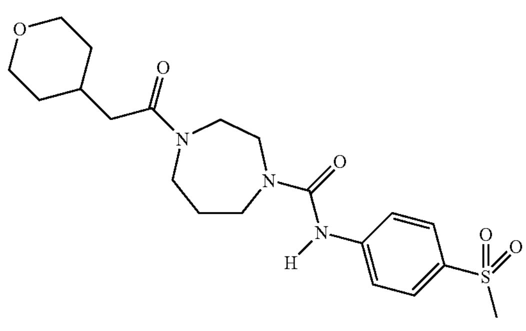 | 424 | F |

TABLE 1-continued

| Example | Name | Structure | LC-MS MH+ (amu) | Method |
|---|---|---|---|---|
| 137 | 4-(3-Cyclopentyl-propionyl)-[1,4]diazepane-1-carboxylic acid (4-methanesulfonyl-phenyl)-amide | 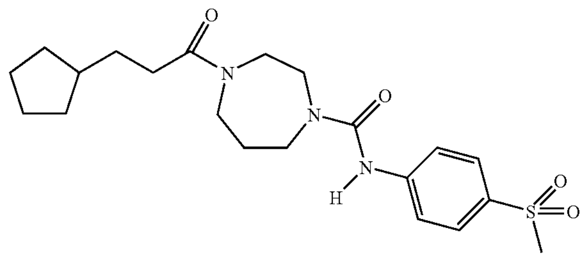 | 422 | F |
| 138 | 4-(2-Cyclopentyl-acetyl)-[1,4]diazepane-1-carboxylic acid (4-methanesulfonyl-phenyl)-amide | 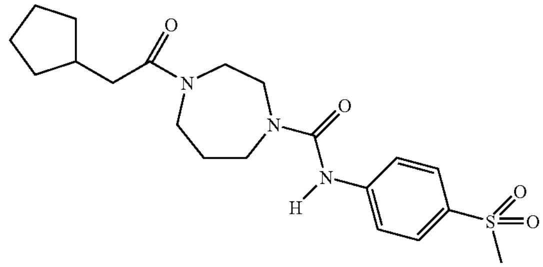 | 408 | F |
| 139 | 4-(Tetrahydro-pyran-4-carbonyl)-[1,4]diazepane-1-carboxylic acid [4-(2,2,2-trifluoro-1-methyl-ethyl)-phenyl]-amide | 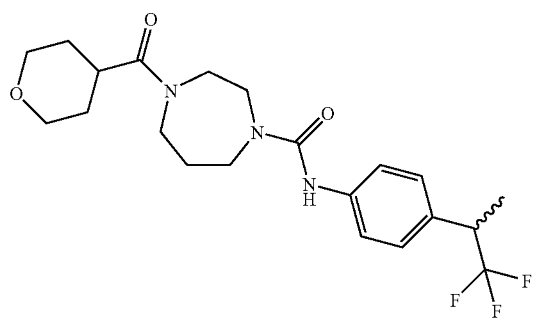 | 428 | G |
| 140 | 4-(2-Cyclopentyl-acetyl)-[1,4]diazepane-1-carboxylic acid (5-tert-butyl-isoxazol-3-yl)-amide | 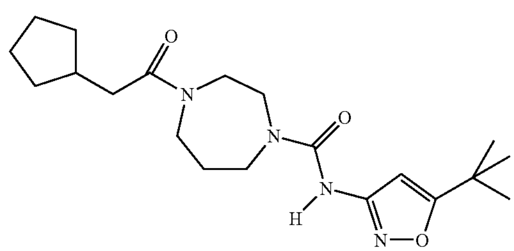 | 377 | H |
| 141 | 4-(4-Chloro-benzoyl)-[1,4]diazepane-1-carboxylic acid (5-tert-butyl-isoxazol-3-yl)-amide | 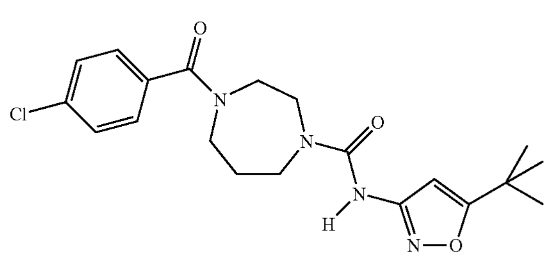 | 405 | H |

TABLE 1-continued

| Example | Name | Structure | LC-MS MH+ (amu) | Method |
|---|---|---|---|---|
| 142 | 4-(Tetrahydro-pyran-4-carbonyl)-[1,4]diazepane-1-carboxylic acid (5-tert-butyl-isoxazol-3-yl)-amide | 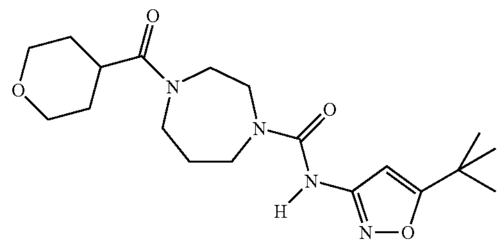 | 379 | H |
| 143 | 4-(1-Methyl-cyclohexanecarbonyl)-[1,4]diazepane-1-carboxylic acid (5-tert-butyl-isoxazol-3-yl)-amide | 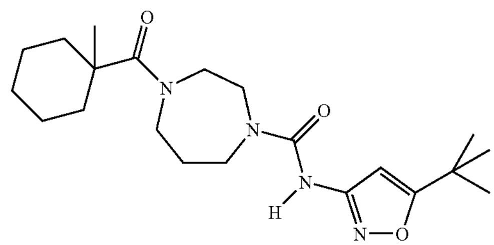 | 391 | H |
| 144 | 4-(4,4-Difluoro-cyclohexanecarbonyl)-[1,4]diazepane-1-carboxylic acid (5-tert-butyl-isoxazol-3-yl)-amide | 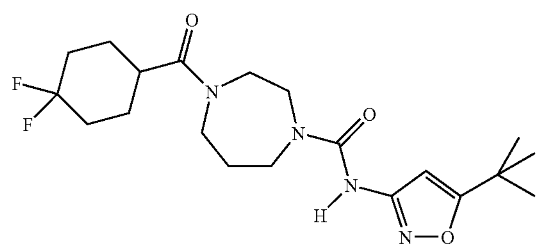 | 413 | H |
| 145 | 4-(4-Hydroxy-cyclohexanecarbonyl)-[1,4]diazepane-1-carboxylic acid (5-tert-butyl-isoxazol-3-yl)-amide | 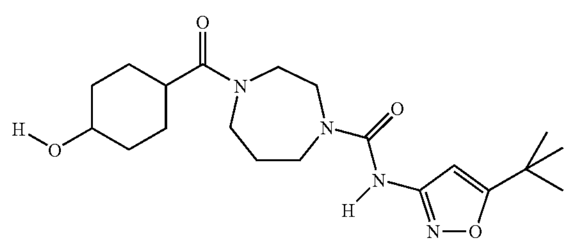 | 393 | H |
| 146 | 4-(Tetrahydro-pyran-2-carbonyl)-[1,4]diazepane-1-carboxylic acid (5-tert-butyl-isoxazol-3-yl)-amide | 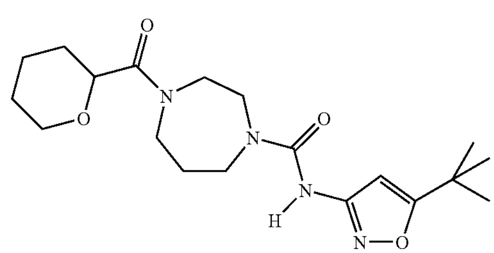 | 379 | H |
| 147 | 4-(Tetrahydro-pyran-3-carbonyl)-[1,4]diazepane-1-carboxylic acid (5-tert-butyl-isoxazol-3-yl)-amide | 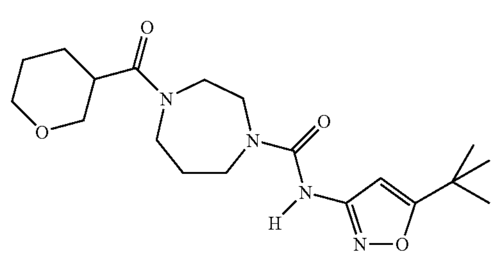 | 379 | H |

TABLE 1-continued

| Example | Name | Structure | LC-MS MH+ (amu) | Method |
|---|---|---|---|---|
| 148 | 4-(2-Tetrahydro-furan-2-yl-acetyl)-[1,4]diazepane-1-carboxylic acid (5-tert-butyl-isoxazol-3-yl)-amide | 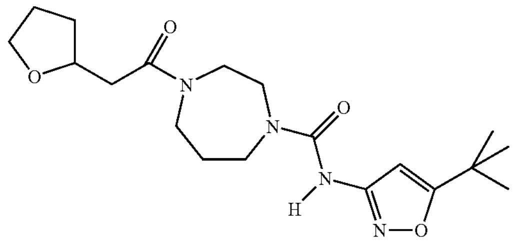 | 379 | H |
| 149 | 4-(Tetrahydro-furan-2-carbonyl)-[1,4]diazepane-1-carboxylic acid (5-tert-butyl-isoxazol-3-yl)-amide | 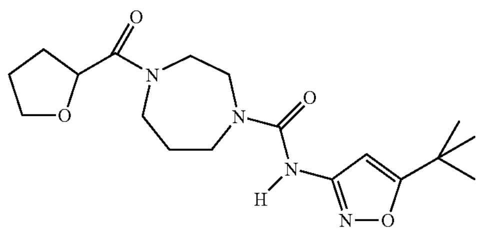 | 365 | H |
| 150 | 4-(Tetrahydro-furan-3-carbonyl)-[1,4]diazepane-1-carboxylic acid (5-tert-butyl-isoxazol-3-yl)-amide | 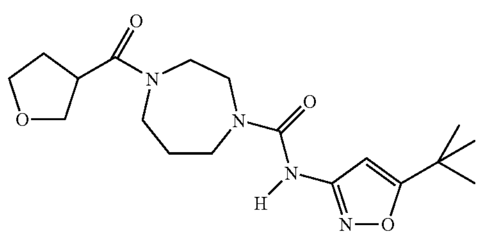 | 365 | H |
| 151 | 4-Cyclopentanecarbonyl-[1,4]diazepane-1-carboxylic acid (5-tert-butyl-isoxazol-3-yl)-amide | 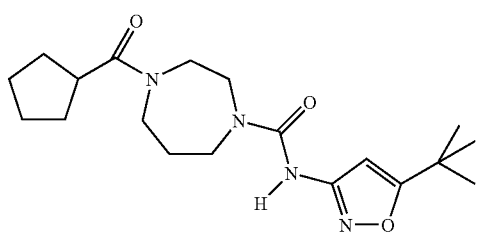 | 363 | H |
| 152 | 4-Cycloheptanecarbonyl-[1,4]diazepane-1-carboxylic acid (5-tert-butyl-isoxazol-3-yl)-amide | 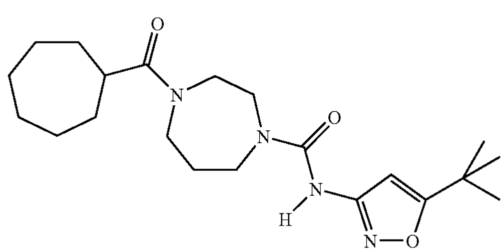 | 391 | H |
| 153 | 4-Cyclohexanecarbonyl-[1,4]diazepane-1-carboxylic acid (5-tert-butyl-isoxazol-3-yl)-amide | 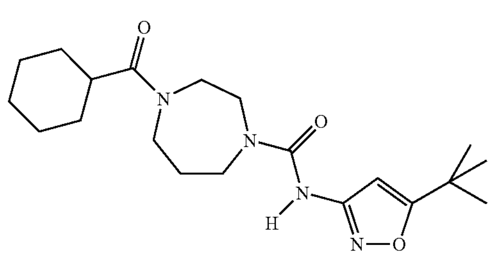 | 377 | H |

TABLE 1-continued

| Example | Name | Structure | LC-MS MH+ (amu) | Method |
|---|---|---|---|---|
| 154 | 4-(4-Trifluoromethyl-benzoyl)-[1,4]diazepane-1-carboxylic acid (5-tert-butyl-isoxazol-3-yl)-amide | 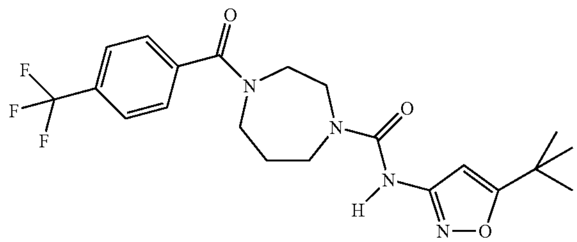 | 439 | H |
| 155 | 4-(4-Methoxy-cyclohexanecarbonyl)-[1,4]diazepane-1-carboxylic acid (5-tert-butyl-isoxazol-3-yl)-amide | 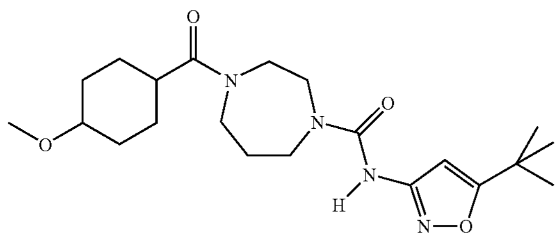 | 407 | H |
| 156 | 4-(2,2-Dimethyl-propionyl)-[1,4]diazepane-1-carboxylic acid (5-tert-butyl-isoxazol-3-yl)-amide | 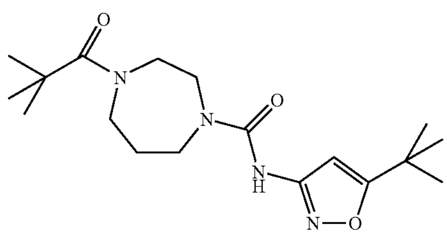 | 351 | H |
| 157 | 4-(3-Methyl-butyryl)-[1,4]diazepane-1-carboxylic acid (5-tert-butyl-isoxazol-3-yl)-amide | 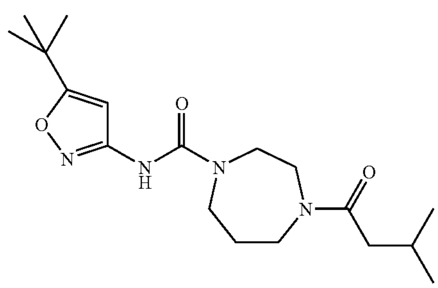 | 351 | H |
| 158 | 4-(4-Amino-cyclohexanecarbonyl)-[1,4]diazepane-1-carboxylic acid (5-tert-butyl-isoxazol-3-yl)-amide | 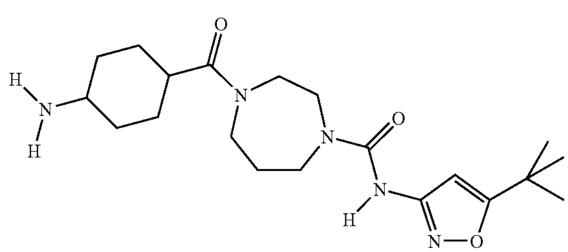 | 392 | J |
| 159 | 4-(Piperidine-4-carbonyl)-[1,4]diazepane-1-carboxylic acid (5-tert-butyl-isoxazol-3-yl)-amide | 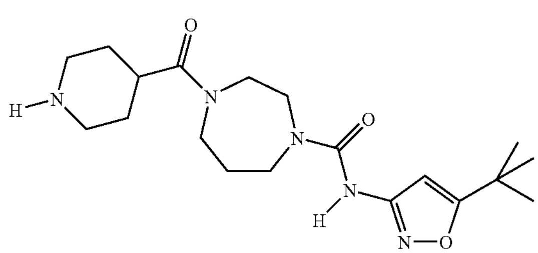 | 378 | J |

TABLE 1-continued

| Example | Name | Structure | LC-MS MH+ (amu) | Method |
|---|---|---|---|---|
| 160 | 4-(4-Acetylamino-cyclohexanecarbonyl)-[1,4]diazepane-1-carboxylic acid (5-tert-butyl-isoxazol-3-yl)-amide | 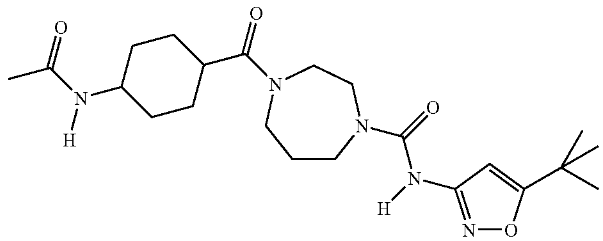 | 434 | J |
| 161 | 4-(4-Methanesulfonylamino-cyclohexanecarbonyl)-[1,4]diazepane-1-carboxylic acid (5-tert-butyl-isoxazol-3-yl)-amide | 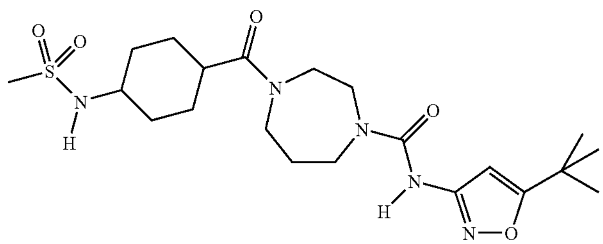 | 470 | J |
| 162 | 4-(1-Acetyl-piperidine-4-carbonyl)-[1,4]diazepane-1-carboxylic acid (5-tert-butyl-isoxazol-3-yl)-amide | 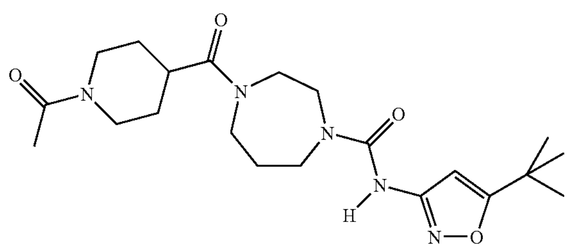 | 420 | J |
| 163 | 4-(1-Methanesulfonyl-piperidine-4-carbonyl)-[1,4]diazepane-1-carboxylic acid (5-tert-butyl-isoxazol-3-yl)-amide | 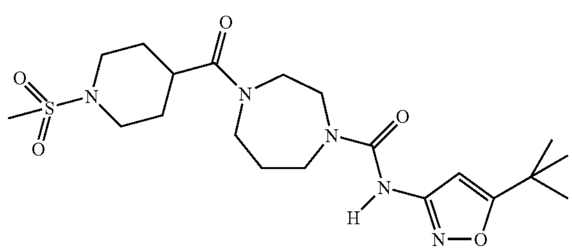 | 456 | J |
| 164 | 4-(Piperidine-3-carbonyl)-[1,4]diazepane-1-carboxylic acid (5-tert-butyl-isoxazol-3-yl)-amide | 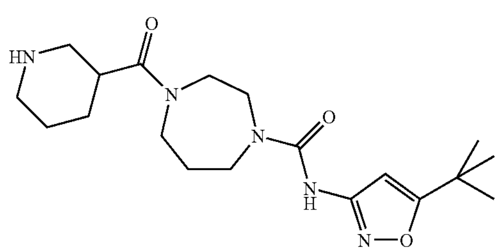 | 378 | J |
| 165 | 4-(1-Methanesulfonyl-piperidine-3-carbonyl)-[1,4]diazepane-1-carboxylic acid (5-tert-butyl-isoxazol-3-yl)-amide | 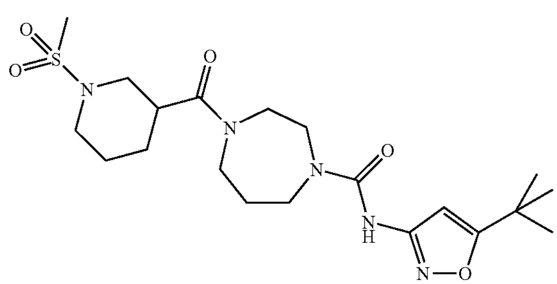 | 456 | J |

TABLE 1-continued

| Example | Name | Structure | LC-MS MH+ (amu) | Method |
|---|---|---|---|---|
| 166 | 4-(4-Chloro-benzoyl)-[1,4]diazepane-1-carboxylic acid (4-cyclopropyl-thiazol-2-yl)-amide | 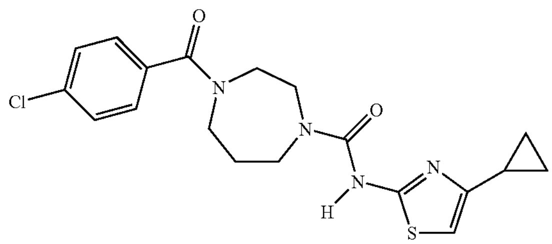 | 405 | K |
| 167 | 4-(4-Chloro-benzoyl)-[1,4]diazepane-1-carboxylic acid (4-phenyl-thiazol-2-yl)-amide | 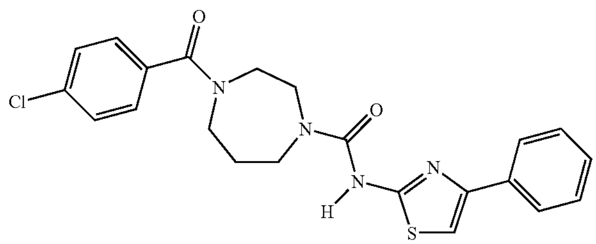 | 441 | K |
| 168 | 4-(4-Chloro-benzoyl)-[1,4]diazepane-1-carboxylic acid (4,5,6,7-tetrahydro-benzothiazol-2-yl)-amide | 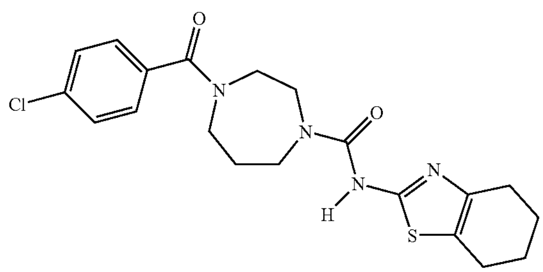 | 419 | K |
| 169 | 4-(4,4-Difluoro-cyclohexanecarbonyl)-[1,4]diazepane-1-carboxylic acid (5-tert-butyl-4-methyl-thiazol-2-yl)-amide | 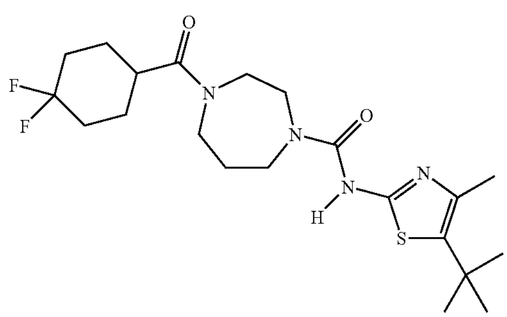 | 443 | K |
| 170 | 4-(Tetrahydro-pyran-4-carbonyl)-[1,4]diazepane-1-carboxylic acid (5-tert-butyl-thiazol-2-yl)-amide | 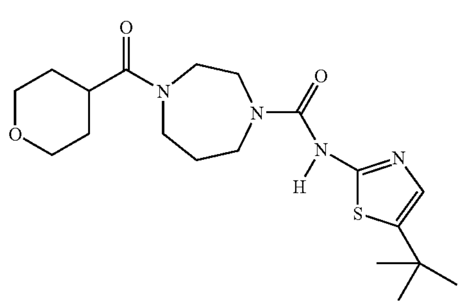 | 395 | K |

TABLE 1-continued

| Example | Name | Structure | LC-MS MH+ (amu) | Method |
|---|---|---|---|---|
| 171 | 4-(Tetrahydro-pyran-4-carbonyl)-[1,4]diazepane-1-carboxylic acid (4,5,6,7-tetrahydro-benzothiazol-2-yl)-amide | 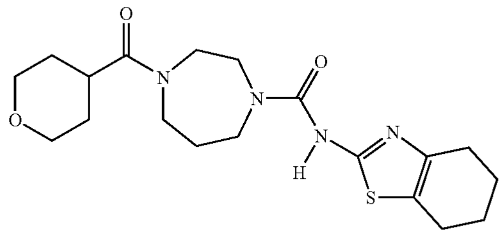 | 393 | K |
| 172 | 4-(Tetrahydro-pyran-4-carbonyl)-[1,4]diazepane-1-carboxylic acid (5-phenyl-thiazol-2-yl)-amide | 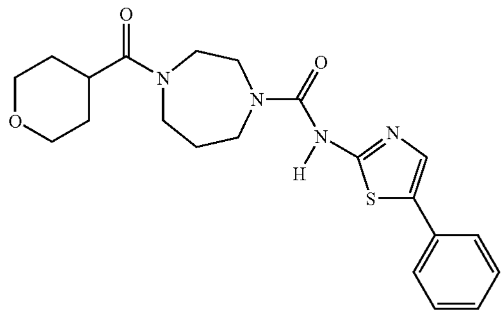 | 415 | K |
| 173 | 4-(4-Hydroxy-cyclohexanecarbonyl)-[1,4]diazepane-1-carboxylic acid (5-tert-butyl-thiazol-2-yl)-amide | 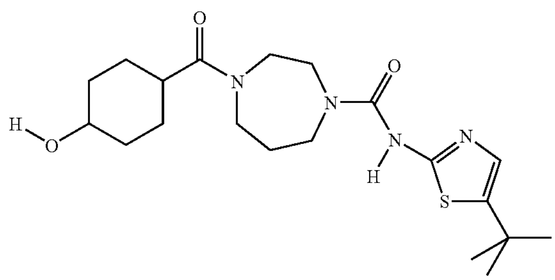 | 409 | K |
| 174 | 4-(4-Hydroxy-cyclohexanecarbonyl)-[1,4]diazepane-1-carboxylic acid (4-phenyl-thiazol-2-yl)-amide | 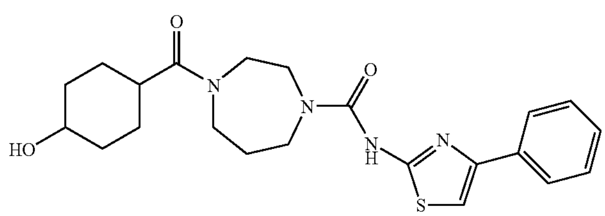 | 429 | K |
| 175 | 4-(Tetrahydro-pyran-4-carbonyl)-[1,4]diazepane-1-carboxylic acid (5-tert-butyl-2H-pyrazol-3-yl)-amide | 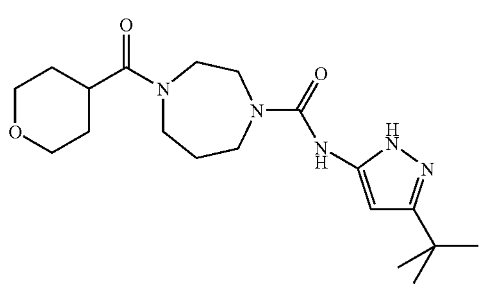 | 378 | K |

TABLE 1-continued

| Example | Name | Structure | LC-MS MH+ (amu) | Method |
|---|---|---|---|---|
| 176 | 4-(Tetrahydro-pyran-4-carbonyl)-[1,4]diazepane-1-carboxylic acid (5-isopropyl-thiazol-2-yl)-amide | 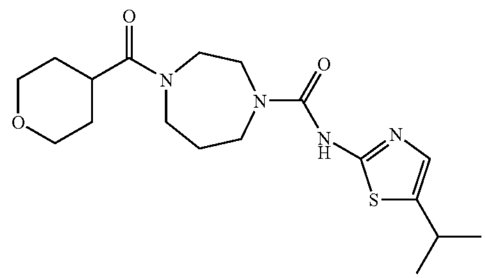 | 381 | K |
| 177 | 4-(Tetrahydro-pyran-4-carbonyl)-[1,4]diazepane-1-carboxylic acid (5-sec-butyl-2-methyl-2H-pyrazol-3-yl)-amide | 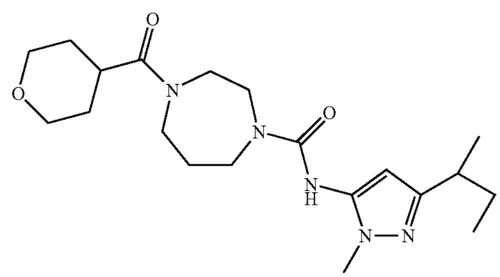 | 392 | K |
| 178 | 4-(Tetrahydro-pyran-4-carbonyl)-[1,4]diazepane-1-carboxylic acid (4-phenyl-thiazol-2-yl)-amide | 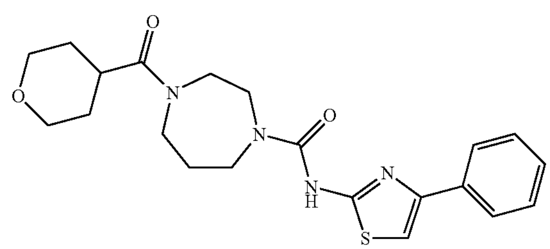 | 415 | K |
| 179 | 4-(Tetrahydro-pyran-4-carbonyl)-[1,4]diazepane-1-carboxylic acid (5-phenyl-isoxazol-3-yl)-amide | 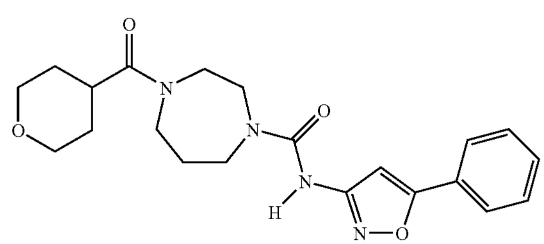 | 399 | L |
| 180 | 4-(Tetrahydro-pyran-4-carbonyl)-[1,4]diazepane-1-carboxylic acid (4-ethyl-pyridin-2-yl)-amide | 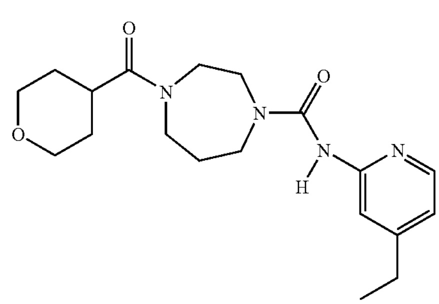 | 361 | L |

TABLE 1-continued

| Example | Name | Structure | LC-MS MH+ (amu) | Method |
|---|---|---|---|---|
| 181 | 4-(Tetrahydro-pyran-4-carbonyl)-[1,4]diazepane-1-carboxylic acid quinolin-3-ylamide | 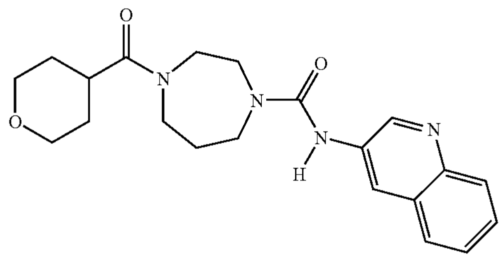 | 383 | L |
| 182 | 4-(Tetrahydro-pyran-4-carbonyl)-[1,4]diazepane-1-carboxylic acid (4-tert-butyl-thiazol-2-yl)-amide | 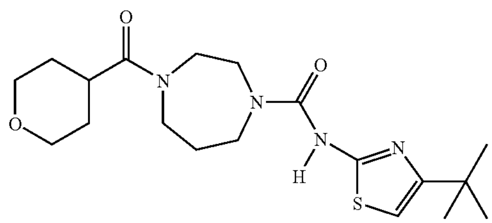 | 395 | M |
| 183 | 4-(Tetrahydro-pyran-4-carbonyl)-[1,4]diazepane-1-carboxylic acid (5-tert-butyl-4-methyl-thiazol-2-yl)-amide | 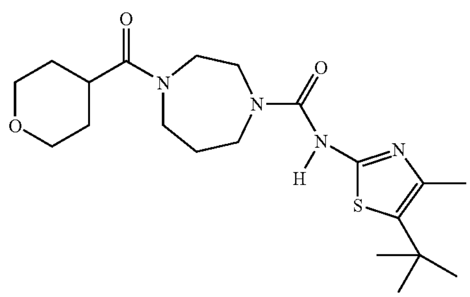 | 409 | N |
| 184 | 4-(Tetrahydro-pyran-4-carbonyl)-[1,4]diazepane-1-carboxylic acid (4-methyl-thiazol-2-yl)-amide | 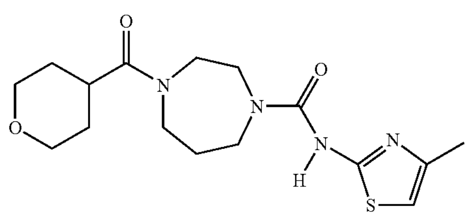 | 353 | N |
| 185 | 4-(Tetrahydro-pyran-4-carbonyl)-[1,4]diazepane-1-carboxylic acid (4,5-dimethyl-thiazol-2-yl)-amide | 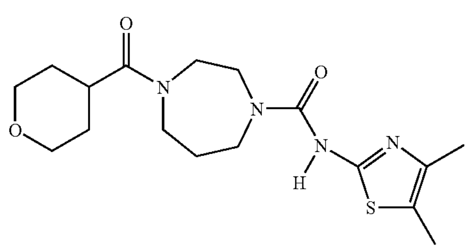 | 367 | N |
| 186 | 4-(Tetrahydro-pyran-4-carbonyl)-[1,4]diazepane-1-carboxylic acid (4-tert-butyl-5-methyl-thiazol-2-yl)-amide | 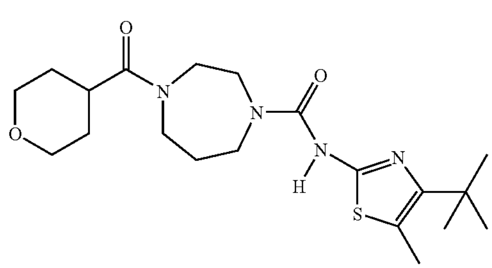 | 409 | N |

TABLE 1-continued

| Example | Name | Structure | LC-MS MH+ (amu) | Method |
|---|---|---|---|---|
| 187 | 4-(Tetrahydro-pyran-4-carbonyl)-[1,4]diazepane-1-carboxylic acid (4-trifluoromethyl-pyridin-2-yl)-amide | 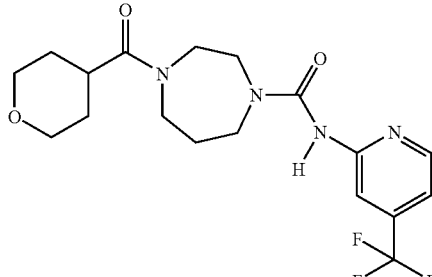 | 401 | N |
| 188 | 4-(Tetrahydro-pyran-4-carbonyl)-[1,4]diazepane-1-carboxylic acid (6-phenoxy-pyridin-3-yl)-amide | 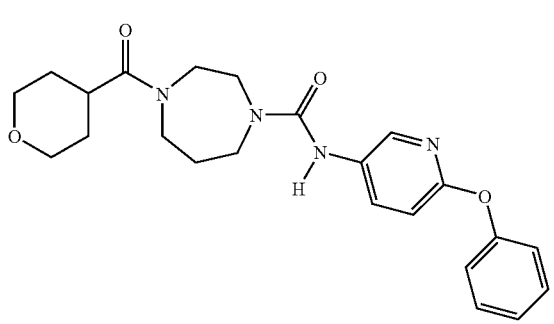 | 425 | N |
| 189 | 4-(Tetrahydro-pyran-4-carbonyl)-[1,4]diazepane-1-carboxylic acid (5-trifluoromethyl-pyridin-2-yl)-amide | 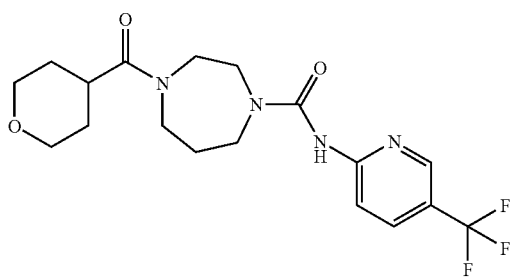 | 401 | N |
| 190 | 4-(Tetrahydro-pyran-4-carbonyl)-[1,4]diazepane-1-carboxylic acid (5-tert-butyl-2-methyl-2H-pyrazol-3-yl)-amide | 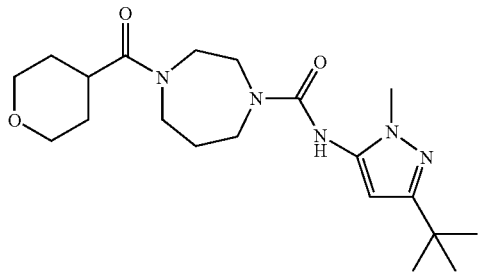 | 392 | N |
| 191 | 4-(Tetrahydro-pyran-4-carbonyl)-[1,4]diazepane-1-carboxylic acid (1-methyl-1H-benzoimidazol-2-yl)-amide | 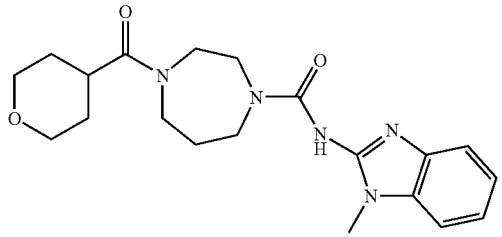 | 386 | N |

TABLE 1-continued

| Example | Name | Structure | LC-MS MH+ (amu) | Method |
|---|---|---|---|---|
| 192 | 4-(Tetrahydro-pyran-4-carbonyl)-[1,4]diazepane-1-carboxylic acid (2-methyl-5-phenyl-2H-pyrazol-3-yl)-amide | 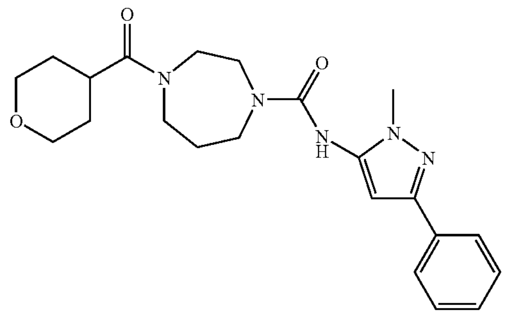 | 412 | N |
| 193 | 4-(Tetrahydro-pyran-4-carbonyl)-[1,4]diazepane-1-carboxylic acid (3-sec-butyl-isoxazol-5-yl)-amide | 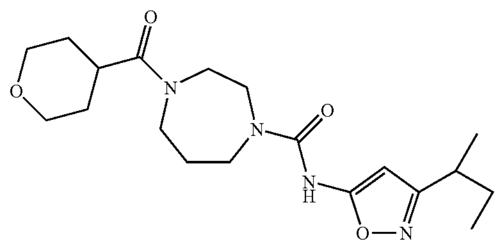 | 379 | P |
| 194 | 4-(Tetrahydro-pyran-4-carbonyl)-[1,4]diazepane-1-carboxylic acid (3-phenyl-isoxazol-5-yl)-amide | 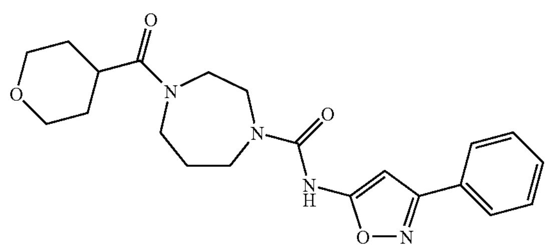 | 399 | P |
| 195 | 4-(Tetrahydro-pyran-4-carbonyl)-[1,4]diazepane-1-carboxylic acid (3-tert-butyl-isoxazol-5-yl)-amide | 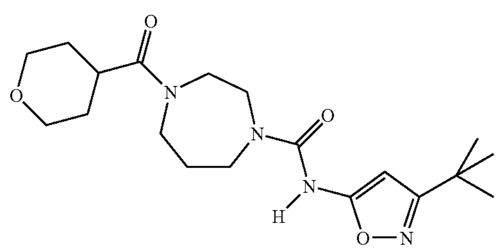 | 379 | P |
| 196 | 4-(Tetrahydro-pyran-4-carbonyl)-[1,4]diazepane-1-carboxylic acid (5-sec-butyl-pyridin-2-yl)-amide | 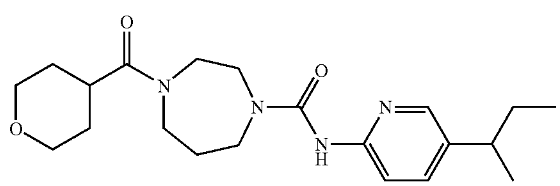 | 389 | Q |
| 197 | 4-(Morpholine-4-carbonyl)-[1,4]diazepane-1-carboxylic acid (5-tert-butyl-isoxazol-3-yl)-amide | 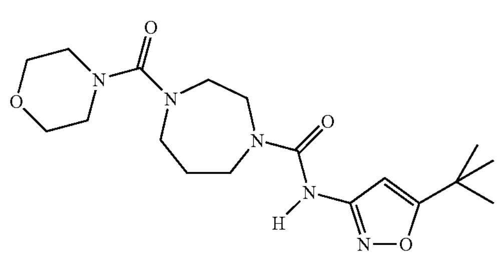 | 380 | R |

TABLE 1-continued

| Example | Name | Structure | LC-MS MH+ (amu) | Method |
|---|---|---|---|---|
| 198 | 4-(Piperidine-1-carbonyl)-[1,4]diazepane-1-carboxylic acid (5-tert-butyl-isoxazol-3-yl)-amide | 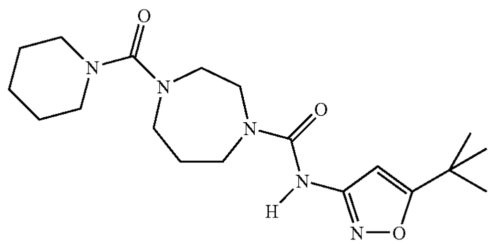 | 378 | R |
| 199 | 4-(4-Methanesulfonyl-piperidine-1-carbonyl)-[1,4]diazepane-1-carboxylic acid (5-tert-butyl-isoxazol-3-yl)-amide | 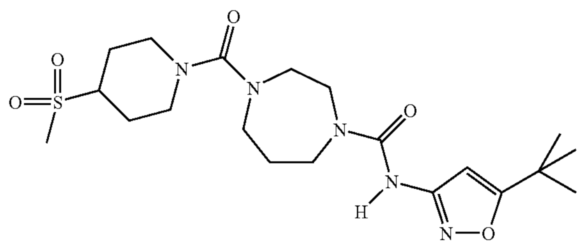 | 456 | R |
| 200 | 4-(1,1-Dioxo-1 $\lambda^6$-thiomorpholine-4-carbonyl)-[1,4]diazepane-1-carboxylic acid (5-tert-butyl-isoxazol-3-yl)-amide | 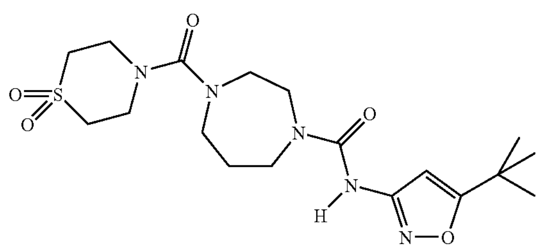 | 428 | R |
| 201 | 4-(4-Acetyl-piperazine-1-carbonyl)-[1,4]diazepane-1-carboxylic acid (5-tert-butyl-isoxazol-3-yl)-amide | 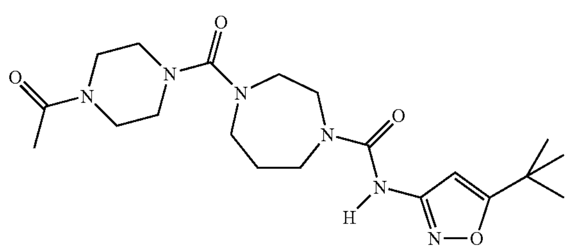 | 421 | R |
| 202 | 4-(4-Methanesulfonyl-piperazine-1-carbonyl)-[1,4]diazepane-1-carboxylic acid (5-tert-butyl-isoxazol-3-yl)-amide | 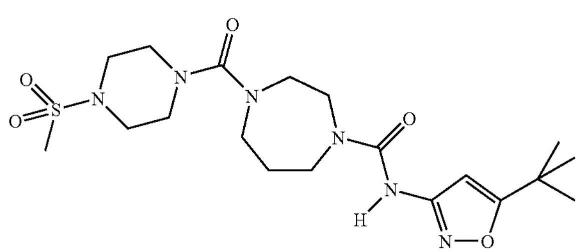 | 457 | R |
| 203 | 4-(Thiomorpholine-4-carbonyl)-[1,4]diazepane-1-carboxylic acid (5-tert-butyl-isoxazol-3-yl)-amide | 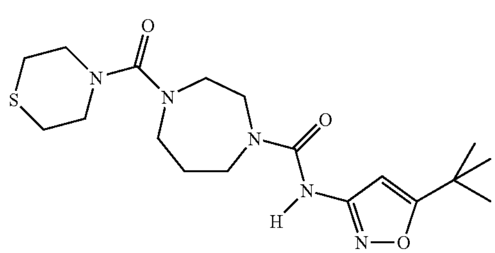 | 396 | R |

TABLE 1-continued

| Example | Name | Structure | LC-MS MH+ (amu) | Method |
|---|---|---|---|---|
| 204 | 4-(1-Oxo-1 $\lambda^4$-thiomorpholine-4-carbonyl)-[1,4]diazepane-1-carboxylic acid (5-tert-butyl-isoxazol-3-yl)-amide | 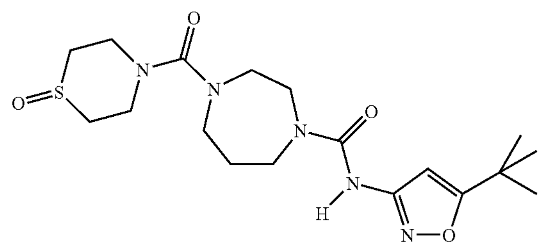 | 412 | R |
| 205 | 4-([1,4]Oxazepane-4-carbonyl)-[1,4]diazepane-1-carboxylic acid (5-tert-butyl-isoxazol-3-yl)-amide | 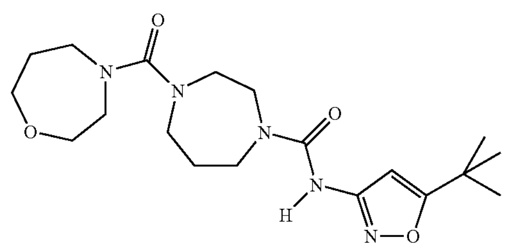 | 394 | R |
| 206 | 4-(4,4-Difluoro-piperidine-1-carbonyl)-[1,4]diazepane-1-carboxylic acid (5-tert-butyl-isoxazol-3-yl)-amide | 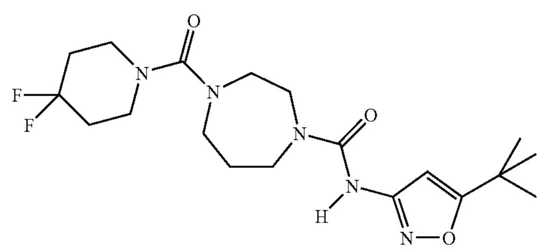 | 414 | R |
| 207 | 4-(1,1-Dioxo-1 $\lambda^6$-thiomorpholine-4-carbonyl)-[1,4]diazepane-1-carboxylic acid (4-sec-butyl-phenyl)-amide | 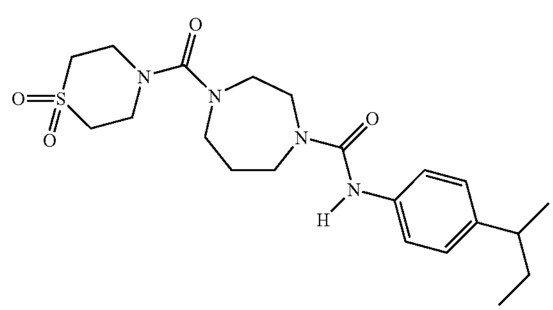 | 437 | R |
| 208 | 4-(1,1-Dioxo-1 $\lambda^6$-thiomorpholine-4-carbonyl)-[1,4]diazepane-1-carboxylic acid (4-tert-butyl-phenyl)-amide | 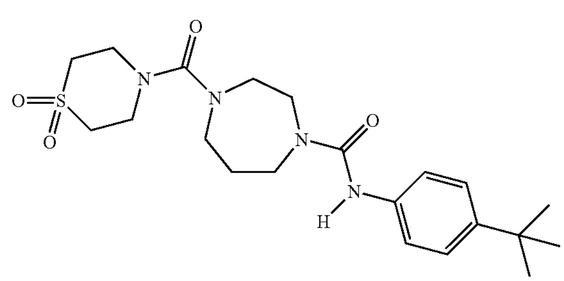 | 437 | R |

TABLE 1-continued

| Example | Name | Structure | LC-MS MH+ (amu) | Method |
|---|---|---|---|---|
| 209 | 4-(1,1-Dioxo-1 $\lambda^6$-thiomorpholine-4-carbonyl)-[1,4]diazepane-1-carboxylic acid [4-(2,2,2-trifluoro-1-methyl-ethyl)-phenyl]-amide | 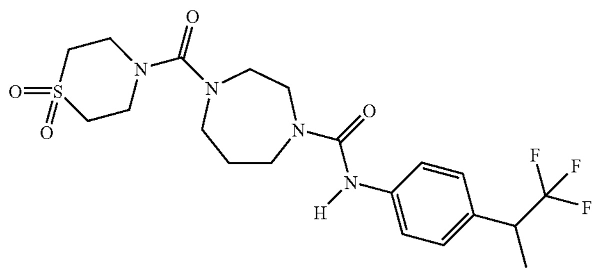 | 477 | R |
| 210 | 4-(1,1-Dioxo-1 $\lambda^6$-thiomorpholine-4-carbonyl)-[1,4]diazepane-1-carboxylic acid (3-tert-butyl-phenyl)-amide | 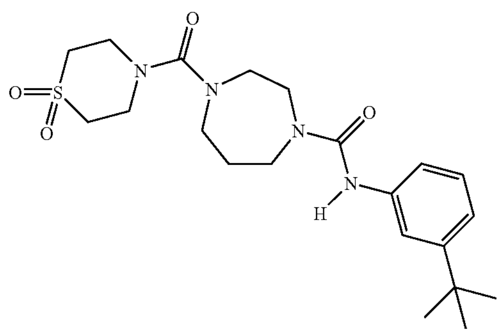 | 437 | R |
| 211 | 4-(1,1-Dioxo-1 $\lambda^6$-thiomorpholine-4-carbonyl)-[1,4]diazepane-1-carboxylic acid (3-tert-butyl-isoxazol-5-yl)-amide | 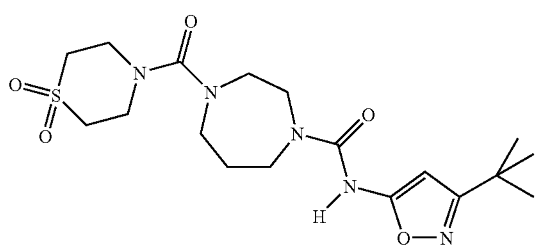 | 428 | R |
| 212 | [1,4]Diazepane-1,4-dicarboxylic acid 1-[(5-tert-butyl-isoxazol-3-yl)-amide] 4-cyclohexylamide | 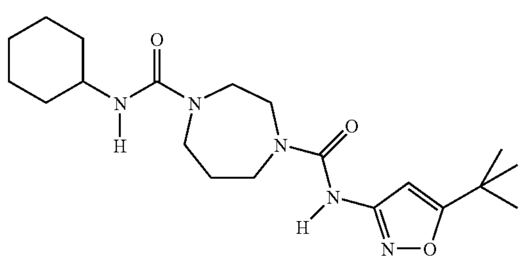 | 392 | R |
| 213 | 4-((2R,6S)-2,6-Dimethyl-morpholine-4-carbonyl)-[1,4]diazepane-1-carboxylic acid (5-tert-butyl-isoxazol-3-yl)-amide | 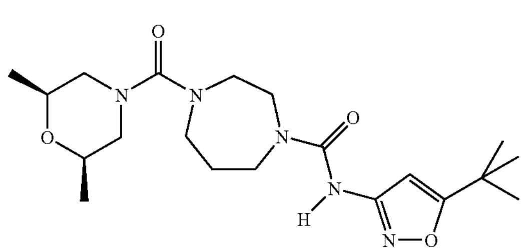 | 408 | R |

TABLE 1-continued

| Example | Name | Structure | LC-MS MH+ (amu) | Method |
|---|---|---|---|---|
| 214 | 4-(1,1-Dioxo-1 $\lambda^6$-thiomorpholine-4-carbonyl)-[1,4]diazepane-1-carboxylic acid (5-tert-butyl-thiazol-2-yl)-amide | 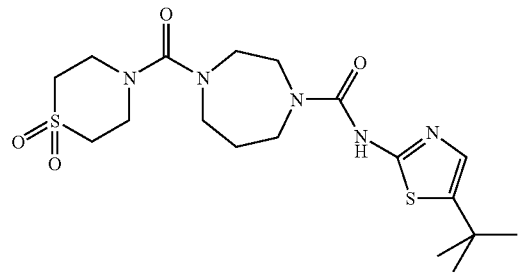 | 444 | R |
| 215 | 4-(1,1-Dioxo-1 $\lambda^6$-thiomorpholine-4-carbonyl)-[1,4]diazepane-1-carboxylic acid (5-isopropyl-thiazol-2-yl)-amide | 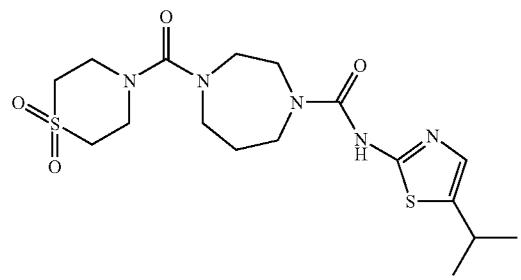 | 430 | R |
| 216 | 4-(1,1-Dioxo-1 $\lambda^6$-thiomorpholine-4-carbonyl)-[1,4]diazepane-1-carboxylic acid (4,5,6,7-tetrahydro-benzothiazol-2-yl)-amide | 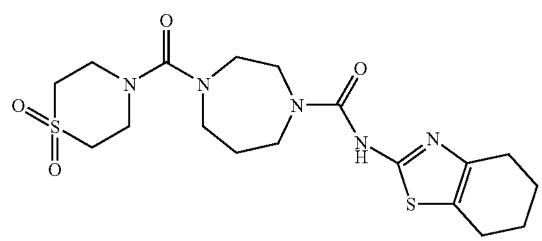 | 442 | R |
| 217 | [1,4]Diazepane-1,4-dicarboxylic acid 1-[(5-tert-butyl-isoxazol-3-yl)-amide] 4-cyclopentylamide | 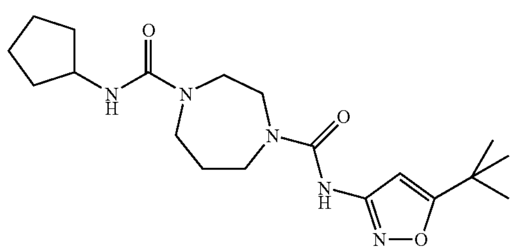 | 378 | R |
| 218 | 4-(Morpholine-4-carbonyl)-[1,4]diazepane-1-carboxylic acid (4-sec-butyl-phenyl)-amide | 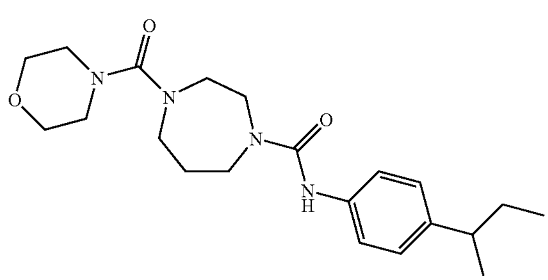 | 389 | R |

TABLE 1-continued

| Example | Name | Structure | LC-MS MH+ (amu) | Method |
|---|---|---|---|---|
| 219 | [1,4]Diazepane-1,4-dicarboxylic acid 1-[(5-tert-butyl-isoxazol-3-yl)-amide] 4-[(tetrahydro-pyran-4-yl)-amide] | 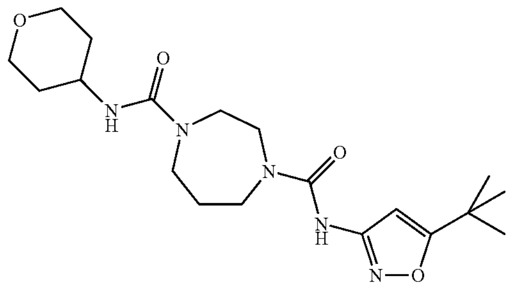 | 394 | R |
| 220 | [1,4]Diazepane-1,4-dicarboxylic acid 1-[(5-tert-butyl-isoxazol-3-yl)-amide] 4-phenylamide | 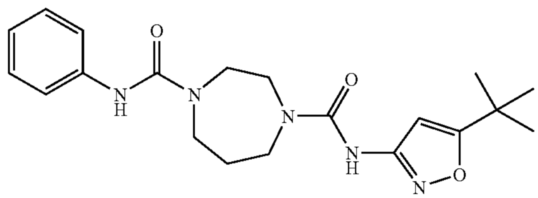 | 386 | R |
| 221 | 4-(Morpholine-4-carbonyl)-[1,4]diazepane-1-carboxylic acid (3-phenyl-isoxazol-5-yl)-amide | 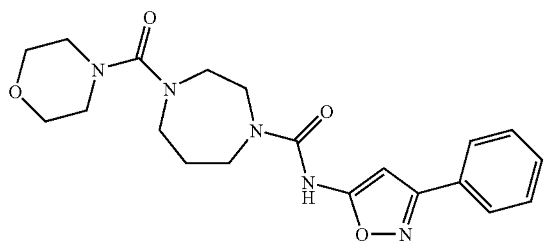 | 400 | R |
| 222 | 4-(Morpholine-4-carbonyl)-[1,4]diazepane-1-carboxylic acid (4-phenyl-thiazol-2-yl)-amide | 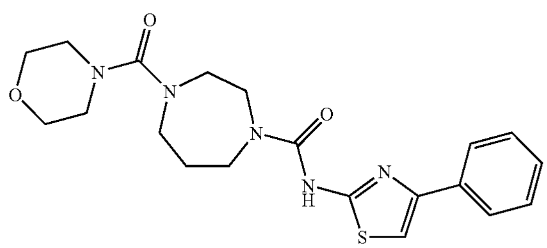 | 416 | R |
| 223 | 4-(Morpholine-4-carbonyl)-[1,4]diazepane-1-carboxylic acid (3-sec-butyl-isoxazol-5-yl)-amide | 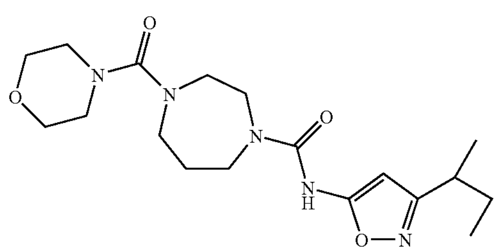 | 380 | R |
| 224 | 4-(4-Methoxy-piperidine-1-carbonyl)-[1,4]diazepane-1-carboxylic acid (3-tert-butyl-isoxazol-5-yl)-amide | 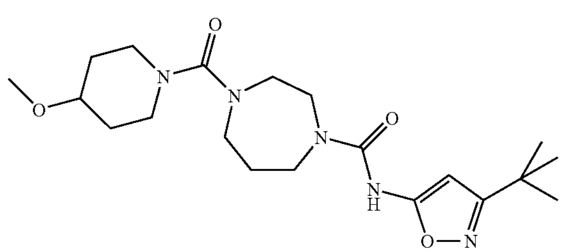 | 408 | R |

TABLE 1-continued

| Example | Name | Structure | LC-MS MH+ (amu) | Method |
|---|---|---|---|---|
| 225 | 4-(Morpholine-4-carbonyl)-[1,4]diazepane-1-carboxylic acid (3-tert-butyl-isoxazol-5-yl)-amide | 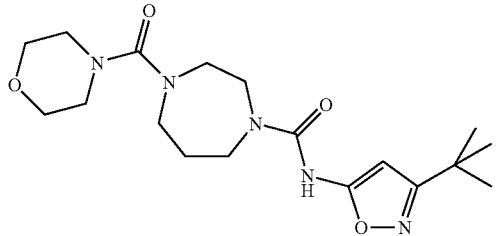 | 380 | R |
| 226 | 4-(2-Morpholin-4-yl-acetyl)-[1,4]diazepane-1-carboxylic acid (5-tert-butyl-isoxazol-3-yl)-amide | 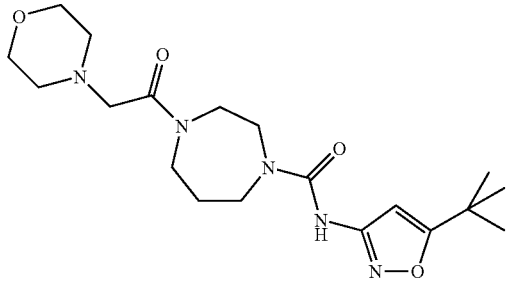 | 394 | S |
| 227 | 4-(2-Thiomorpholin-4-yl-acetyl)-[1,4]diazepane-1-carboxylic acid (5-tert-butyl-isoxazol-3-yl)-amide | 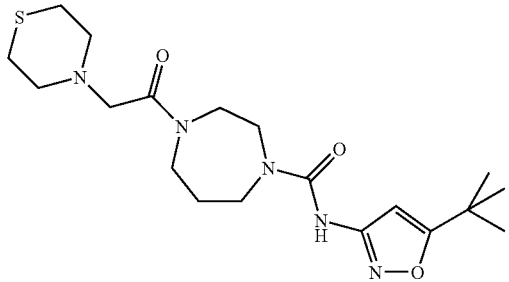 | 410 | S |
| 228 | 4-[2-(1,1-Dioxo-1 $\lambda^6$-thiomorpholin-4-yl)-acetyl]-[1,4]diazepane-1-carboxylic acid (5-tert-butyl-isoxazol-3-yl)-amide | 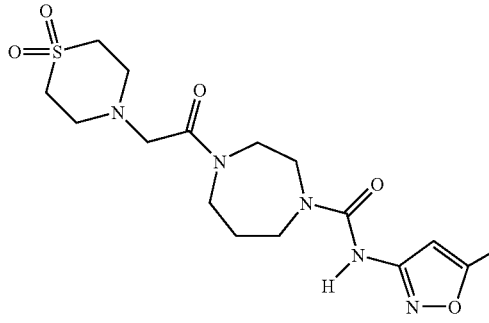 | 442 | S |
| 229 | 4-[2-(4,4-Difluoro-piperidin-1-yl)-acetyl]-[1,4]diazepane-1-carboxylic acid (5-tert-butyl-isoxazol-3-yl)-amide | 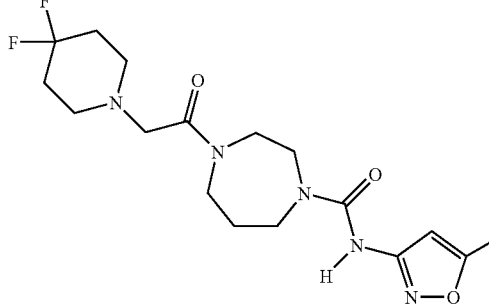 | 428 | S |

TABLE 1-continued

| Example | Name | Structure | LC-MS MH+ (amu) | Method |
|---|---|---|---|---|
| 230 | 4-[2-(1,1-Dioxo-1 $\lambda^6$-thiomorpholin-4-yl)-acetyl]-[1,4]diazepane-1-carboxylic acid (3-tert-butyl-isoxazol-5-yl)-amide | 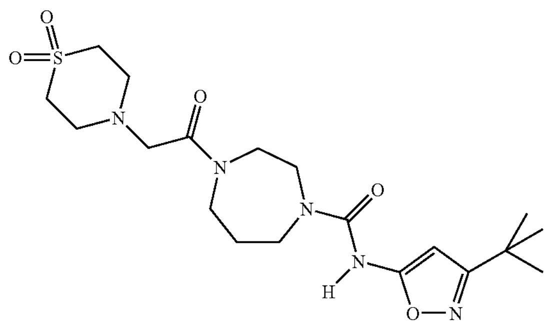 | 442 | S |
| 231 | 4-[2-((2R,6S)-2,6-Dimethyl-morpholin-4-yl)-acetyl]-[1,4]diazepane-1-carboxylic acid (5-tert-butyl-isoxazol-3-yl)-amide | 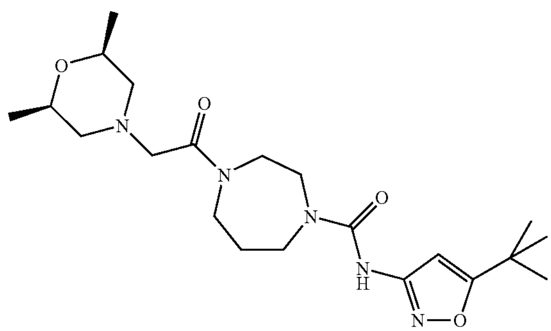 | 422 | S |
| 232 | 4-(4,4-Difluoro-cyclohexanecarbonyl)-[1,4]diazepane-1-carboxylic acid (3-tert-butyl-isoxazol-5-yl)-amide | 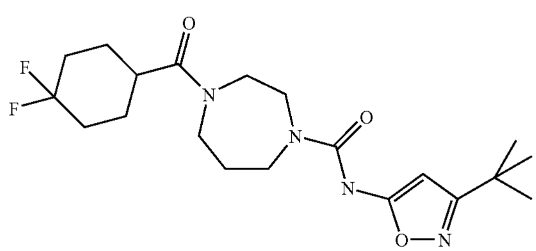 | 413 | P |
| 233 | 4-(Tetrahydro-pyran-4-carbonyl)-[1,4]diazapane-1-carboxylic acid (4,5-dimethyl-isoxazol-3-yl)-amide | 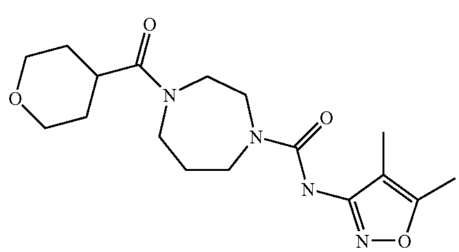 | 351 | L |

Example 18

Synthesis of 4-(4-Oxo-cyclohexanecarbonyl)-[1,4]diazepane-1-carboxylic acid (5-tert-butyl-isoxazol-3-yl)-amide (Compound 234)

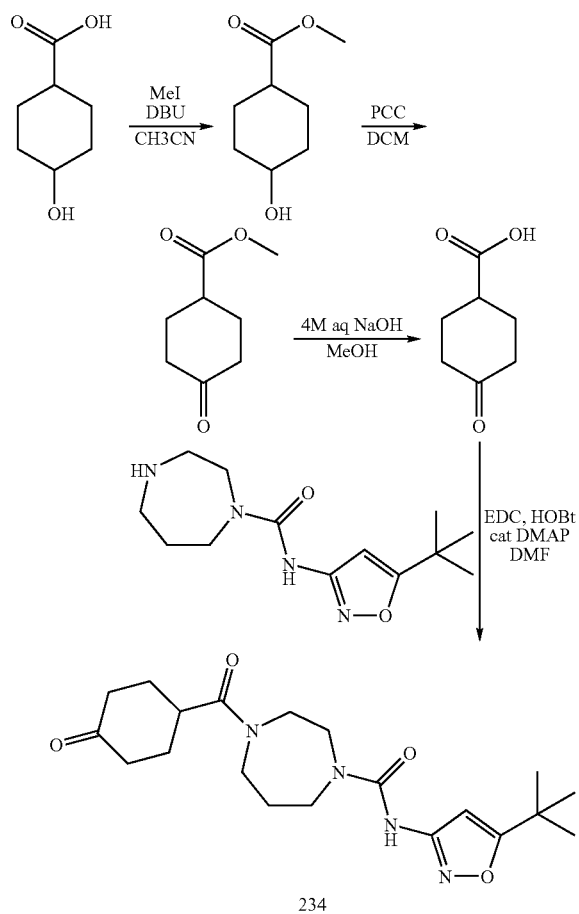

4-Hydroxycyclohexanecarboxylic acid (5 g; 34.68 mmol) was dispersed in 100 mL acetonitrile and cooled to 0° C. 1,8-diazabicyclo[5.4.0]undec-7-ene (DBU) (5.71 mL; 38.15 mmol) was added, followed by iodomethane (2.38 mL; 38.15 mmol). The resulting reaction mixture was stirred at room temperature overnight. The mixture was quenched with dilute aqueous ammonium chloride solution, and it was extracted with EtOAc twice. The organics were combined and washed with brine, dried over anhydrous sodium sulfate, filtered and concentrated in vacuo. The yellow oily residue was purified by flash column chromatography on silica gel using 50% EtOAc in hexanes mixture as eluent. The product was obtained as a colorless oil (4.147 g; 75.6% yield).

The 4-hydroxy methyl ester from above (4.147 g; 26.21 mmol) was dissolved in 150 mL DCM and pyridinium chlorochromate (PCC) (8.476 g; 39.32 mmol) was added. The reaction mixture was allowed to stir at room temperature overnight. The reaction mixture was diluted with ether and decanted. Solvents were removed and the residue was purified by flash column chromatography using 25% EtOAc in hexanes mixture as eluent. The product was obtained as a colorless oil (3.317 g; 81% yield).

To the solution of the above methyl ester (3.317 g, 21.24 mmol) in 50 mL methanol was added 4N sodium hydroxide aqueous solution (26.55 mL; 106.2 mmol). The reaction mixture was stirred at room temperature overnight. The solvents were evaporated in vacuo. The residue was extracted with ether once. The aqueous layer was acidified to pH~1 with 6N HCl and extracted with EtOAc three times. The combined organics were washed with brine, dried over anhydrous sodium sulfate, filtered and concentrated in vacuo. The product was obtained as a yellow oil (2.656 g; 88% yield).

To a solution of the above acid (92 mg; 0.647 mmol) and HOBt (104.1 mg; 0.77 mmol) in 2 mL DMF was added EDC (147.6 mg; 0.77 mmol). After stirring for 15 minutes at room temperature, the diazapane-isoxazole urea (150 mg; 0.56 mmol) was added, followed by DMAP (2.7 mg; 0.023 mmol). The mixture was left stirring at room temperature for 1 hour. Water was added to the reaction mixture. The mixture was extracted with EtOAc twice. The combined organics were washed with saturated aqueous sodium bicarbonate solution, saturated aqueous ammonium chloride solution, then brine. The organics were dried over anhydrous sodium sulfate, filtered and concentrated in vacuo. The residue was purified by flash column chromatography on silica gel using 2.5% methanol in DCM mixture as eluent. The title compound was obtained as a white foam (119 mg; 54% yield) ES+MS: 391 amu (MH+).

Example 19

Synthesis of 4-(4-Hydroxy-4-methyl-cyclohexanecarbonyl)-[1,4]diazepane-1-carboxylic acid (5-tert-butyl-isoxazol-3-yl)-amide (Compound 235)

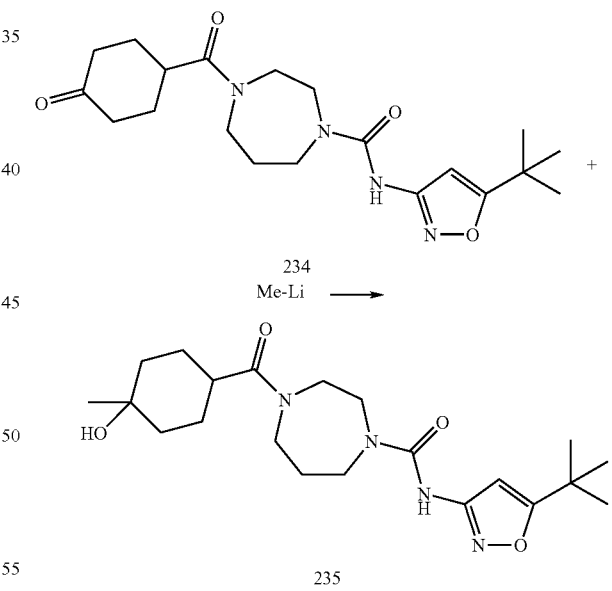

A methyllithium solution (1.6 M) in diethyl ether (0.95 mL; 01.525 mmol) was added dropwise to a stirred and cooled (−78° C.) solution of the ketone amide-urea (Compound 233) in anhydrous THF (3 mL) under inert atmosphere. The resulting mixture was stirred for 1 hour. The mixture was quenched with saturated aqueous ammonium chloride solution and extracted with DCM three times. The combined organics were washed with brine, dried over anhydrous sodium sulfate, filtered and concentrated in vacuo. The residue was purified by flash column chromatography on silica gel using 5% methanol in DCM mixture as eluent, followed by 10% methanol in DCM. The title compound was obtained as a colorless oil (85 mg; 69% yield). ES+MS: 407 amu (MH+).

Example 20

Synthesis of 4-(1,1-Dioxo-hexahydro-1λ⁶-thiopyran-4-carbonyl)-[1,4]diazepane-1-carboxylic acid (5-tert-butyl-isoxazol-3-yl)-amide (Compound 236)

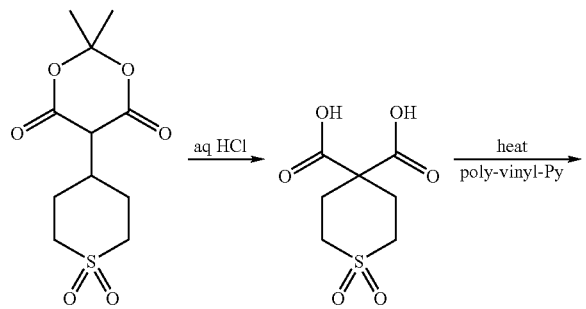

The sulfone meldrum's acid (100 mg; 0.38 mmol) was dispersed in 2M HCl aqueous solution (1 mL; 2 mmol) and heated in a microwave oven at 100° C. for 13 minutes. Water was added to the mixture and the aqueous layer was saturated with NaCl solid and extracted with 50% THF/EtOAc twice. The combined organics were dried over anhydrous sodium sulfate and concentrated in vacuo to give the malonic acid as an off white solid (70 mg; 83% yield). It was used as is for the next step.

To a microwave vial was added the sulfone malonic acid (67 mg; 0.302 mmol), poly-4-vinylpyridine (112 mg) and DMF (1.5 mL). The mixture was well mixed. The vial was placed into microwave oven for 10 mins at 95° C. The mixture was filtered through paper and washed with ether. The filtrate was concentrated to afford the carboxylic acid product as a yellow solid (64 mg; containing some DMF and impurities). It was used as is for the next step. The sulfone carboxylic acid (54 mg; 0.302 mmol), HOBt (49 mg; 0.36 mmol) and EDC (69 mg; 0.36 mmol) were combined in 2 mL anhydrous DMF. The mixture was stirred for 15 minutes at room temperature. Then the diazapane-isoxazole urea (70 mg; 0.26 mmol) and DMAP (1.3 mg; 0.011 mmol) were added. The reaction mixture was stirred at room temperature for 1 hour. Water was added to the mixture and it was extracted with EtOAc. The organic layer was washed sequentially with water, saturated aqueous sodium bicarbonate solution, saturated aqueous ammonium chloride solution, and brine. The organic layer was then dried over anhydrous sodium sulfate, filtered, and concentrated in vacuo. The residue was purified by flash column chromatography using 2.5% methanol in DCM mixture as eluent, followed by 5% methanol in DCM. The title compound was obtained in 86% purity as a colorless glassy material (24 mg; 21% yield). ES+MS: 427 amu (MH+).

Example 21

Synthesis of 4-(2-Cyclopentyl-acetyl)-[1,4]diazepane-1-carboxylic acid [4-(1-hydroxy-butyl)-phenyl]-amide (Compound 237)

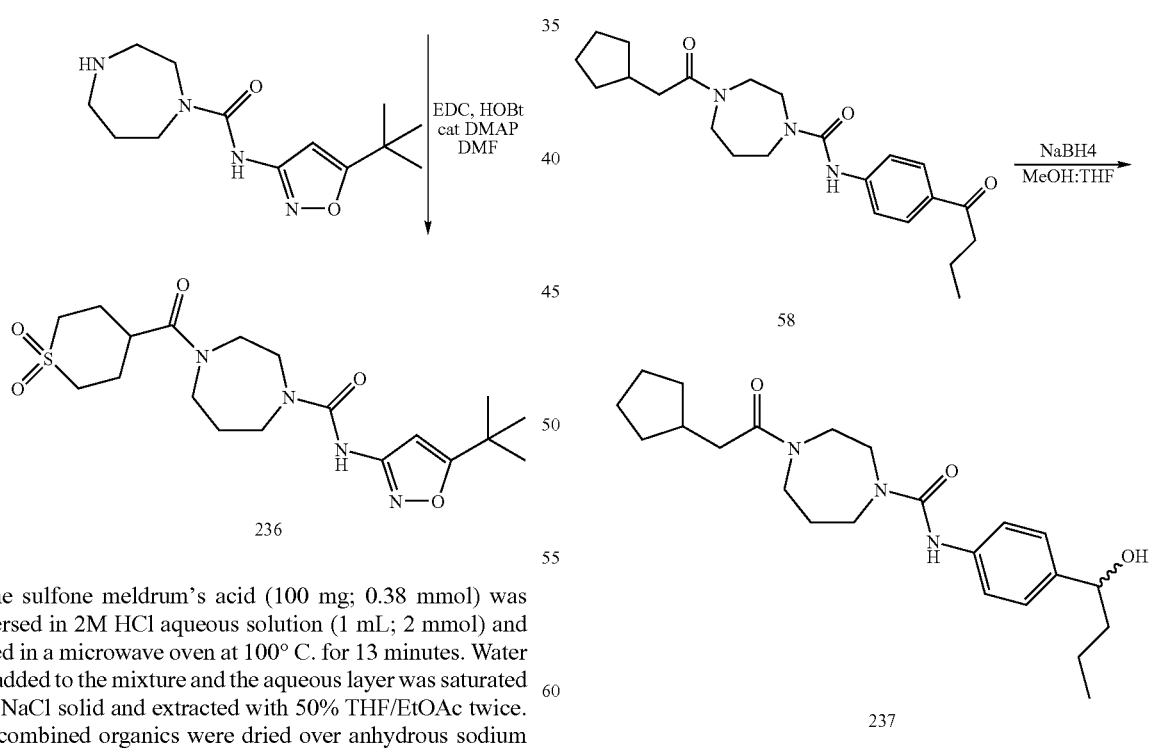

Compound 83 (87 mg; 0.22 mmol) was dissolved in 2 mL methanol:THF mixture (1:1) and treated at room temperature with sodium borohydride (25 mg; 0.35 mmol). The mixture was stirred for 1 hour, and then concentrated in vacuo, treated with 1M aqueous HCl solution and extracted with DCM. The combined organic layers were dried over anhydrous sodium sulfate, filtered, and the solvent was removed in vacuo. The title compound was obtained as a pale yellow foam, 79 mg, which was >99% pure by HPLC (97% yield). ES+MS: 402 amu (MH+).

Example 22

Synthesis of 4-(2-Cyclopentyl-acetyl)-[1,4]diazepane-1-carbothioic acid (4-isopropyl-phenyl)-amide (Compound 238)

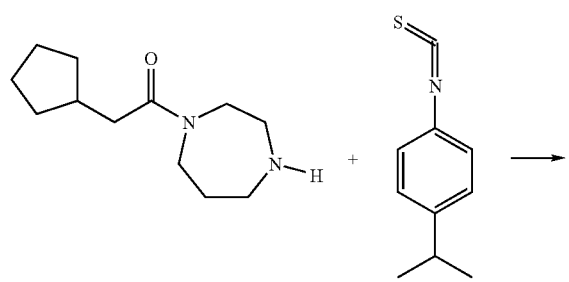

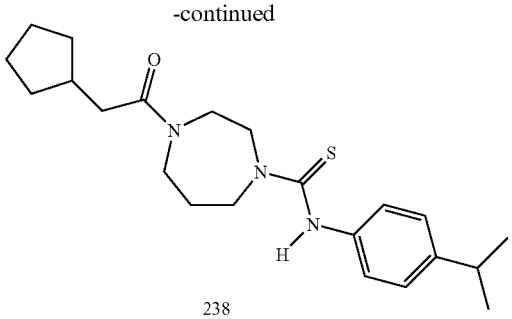

238

The 1-(2-cyclopentyl-acetyl)-1,4-diazepane (100 mg; 0.475 mmol) and 4-isopropylphenyl isothiocyanate (80 mg; 0.45 mmol) were mixed together at room temperature in 5 mL anhydrous THF. The reaction mixture was left stirring overnight, then 1 mL methanol was added and the solvents were evaporated in vacuo. The crude mixture was purified by flash column chromatography on SiO$_2$ using 0-50% EtOAc in hexanes mixtures as eluent, followed by 1-4% methanol in DCM mixtures. The desired product was isolated as a colorless foam, 180 mg (71% yield). ES+MS: 388 amu (MH+).

The compounds in Table 2 could be synthesized according to all the procedures described above.

For the compounds 248, 249, 259, 260, 261 (Table 2), the 1,5-diazocane core can be made as per Stetter et al, *Chem Ber* 1965, 98, 3228.

For the compounds 250, 251, 254 (Table 2) the 1,4-diazocane core can be made according to the scheme below.

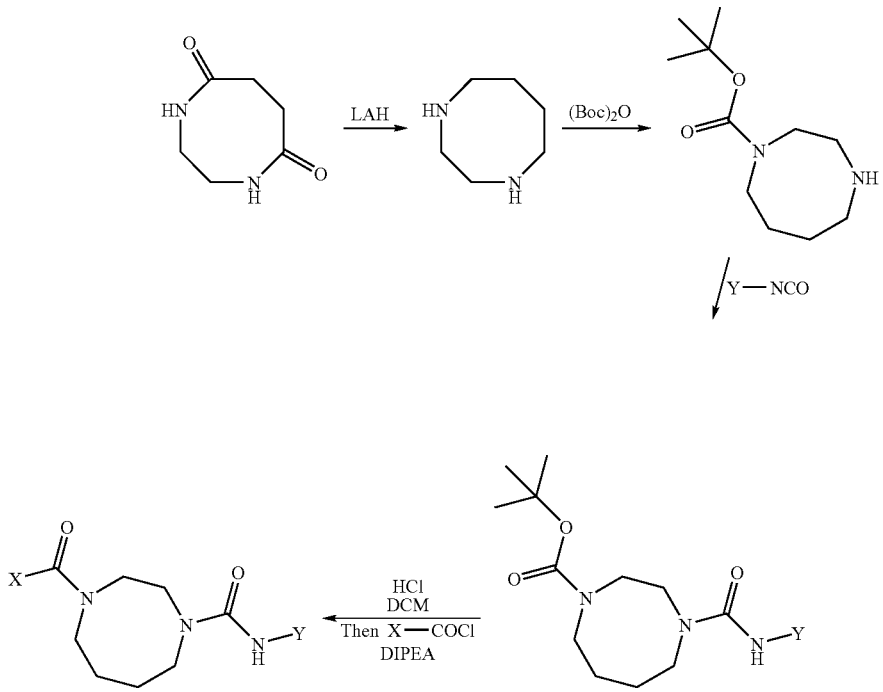

Commercially-available 1,4-diazocane-5,8-dione is treated with LAH in THF to obtain the reduced diamine, which, as above, is then mono-Boc-protected by treatment with di-tert-butyl dicarbonate in acetonitrile. Urea formation, de-protection with acid, and final amide or urea bond formation affords these compounds.

TABLE 2

| Example | Name | Structure |
|---|---|---|
| 239 | 4-(1,1-Dioxo-hexahydro-1λ⁶-thiopyran-4-carbonyl)-[1,4]diazepane-1-carboxylic acid (5-sec-butyl-pyridin-2-yl)-amide | 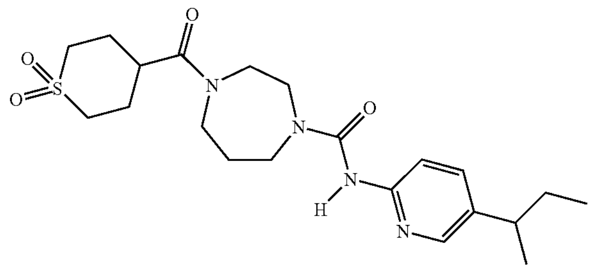 |
| 240 | 4-(1,1-Dioxo-hexahydro-1λ⁶-thiopyran-4-carbonyl)-[1,4]diazepane-1-carboxylic acid (5-tert-butyl-[1,2,4]oxadiazol-3-yl)-amide | 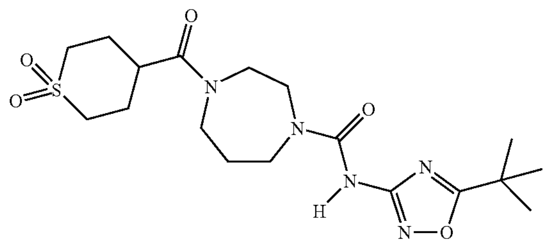 |
| 241 | 4-(1,1-Dioxo-hexahydro-1λ⁶-thiopyran-4-carbonyl)-[1,4]diazepane-1-carboxylic acid (5-tert-butyl-[1,3,4]oxadiazol-2-yl)-amide | 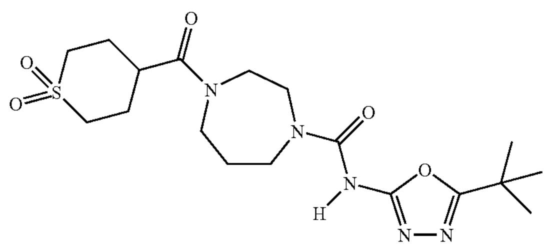 |
| 242 | 4-(1,1-Dioxo-hexahydro-1λ⁶-thiopyran-4-carbonyl)-[1,4]diazepane-1-carboxylic acid (5,6,7,8-tetrahydro-isoquinolin-3-yl)-amide | 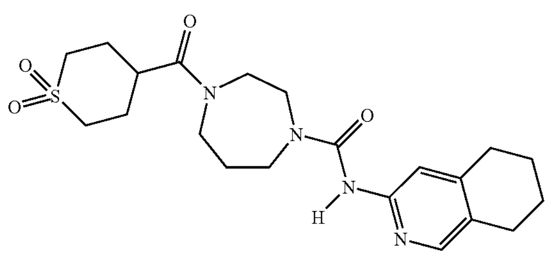 |
| 243 | 4-(6-Oxo-piperidine-3-carbonyl)-[1,4]diazepane-1-carboxylic acid (6-chloro-benzothiazol-2-yl)-amide | 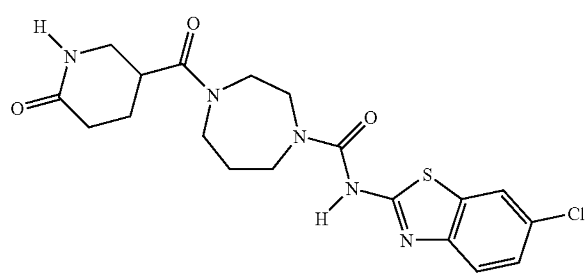 |
| 244 | 4-(1-Methyl-6-oxo-piperidine-3-carbonyl)-[1,4]diazepane-1-carboxylic acid (5-tert-butyl-thiazol-2-yl)-amide | 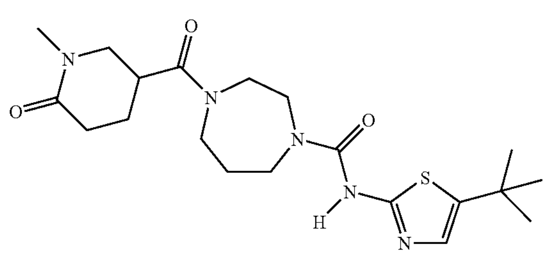 |

TABLE 2-continued

| Example | Name | Structure |
|---|---|---|
| 245 | 4-(2-Oxo-piperidine-4-carbonyl)-[1,4]diazepane-1-carboxylic acid (7,7-dimethyl-4,5,6,7-tetrahydro-benzothiazol-2-yl)-amide | 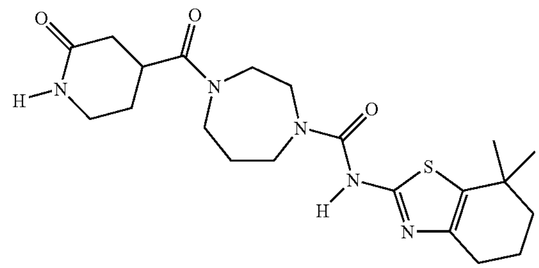 |
| 246 | 4-(1-Methyl-2-oxo-piperidine-4-carbonyl)-[1,4]diazepane-1-carboxylic acid (5-tert-butyl-[1,3,4]thiadiazol-2-yl)-amide | 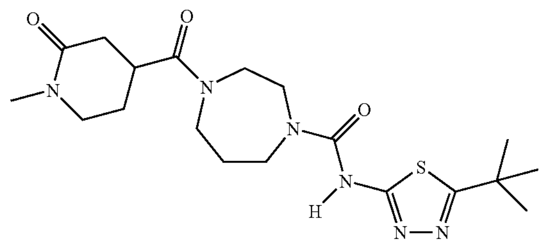 |
| 247 | 4-(1-Methanesulfonyl-piperidine-3-carbonyl)-[1,4]diazepane-1-carboxylic acid (5-tert-butyl-thiazol-2-yl)-amide | 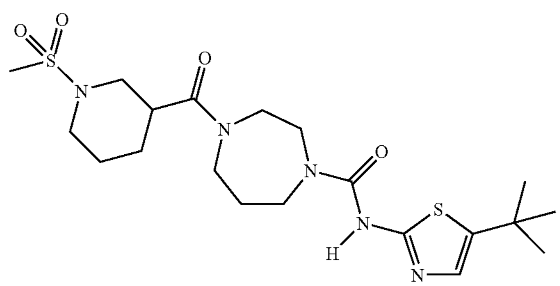 |
| 248 | 5-(Tetrahydro-pyran-4-carbonyl)-[1,5]diazocane-1-carboxylic acid (5-tert-butyl-isoxazol-3-yl)-amide | 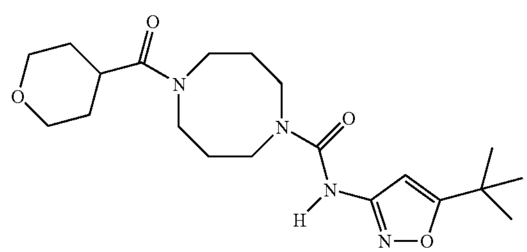 |
| 249 | 5-(1,1-Dioxo-hexahydro-1$\lambda^6$-thiopyran-4-carbonyl)-[1,5]diazocane-1-carboxylic acid (5-tert-butyl-isoxazol-3-yl)-amide | 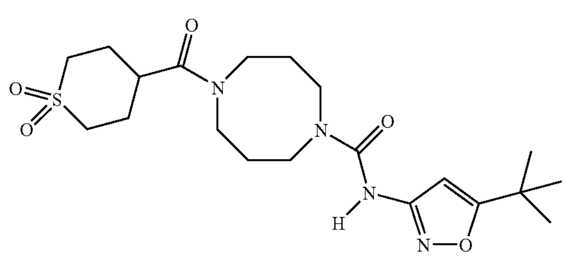 |
| 250 | 4-(Tetrahydro-pyran-4-carbonyl)-[1,4]diazocane-1-carboxylic acid (5-tert-butyl-isoxazol-3-yl)-amide | 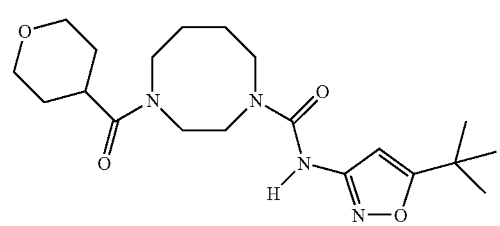 |

TABLE 2-continued

| Example | Name | Structure |
|---|---|---|
| 251 | 4-(1,1-Dioxo-hexahydro-1λ⁶-thiopyran-4-carbonyl)-[1,4]diazocane-1-carboxylic acid (5-tert-butyl-isoxazol-3-yl)-amide | 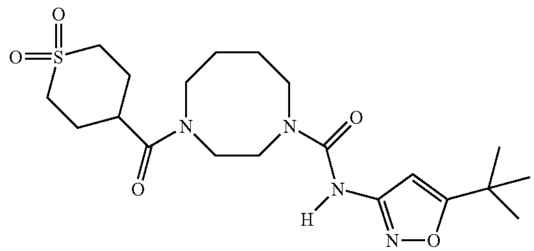 |
| 252 | 4-(Tetrahydro-pyran-4-carbonyl)-[1,4]diazepane-1-carboxylic acid [3-(1,1-dimethyl-propyl)-isoxazol-5-yl]amide | 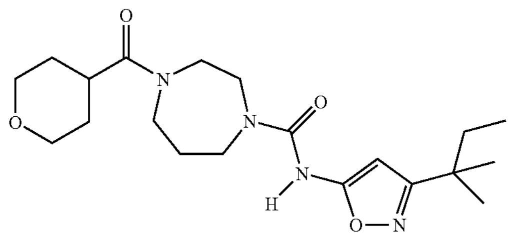 |
| 253 | 4-(Tetrahydro-pyran-4-carbonyl)-[1,4]diazepane-1-carboxylic acid (5-tert-butyl-pyridin-2-yl)-amide | 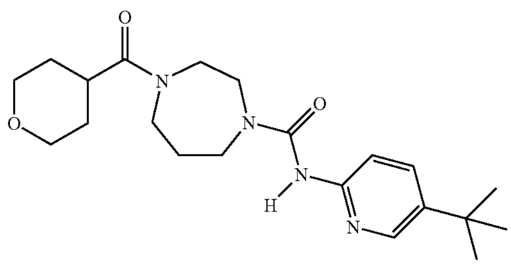 |
| 254 | 4-(Tetrahydro-pyran-4-carbonyl)-[1,4]diazocane-1-carboxylic acid [5-(1,1-dimethyl-propyl)-isoxazol-3-yl]-amide | 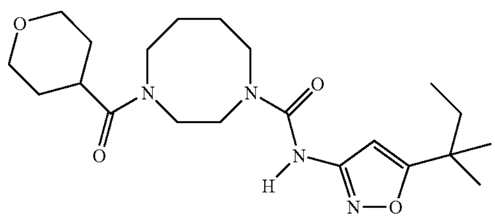 |
| 255 | 4-(Tetrahydro-pyran-4-carbonyl)-[1,4]diazepane-1-carboxylic acid [5-(1,1-dimethyl-propyl)-isoxazol-3-yl]-amide | 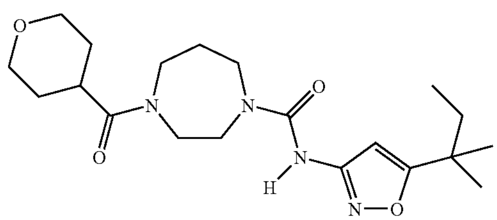 |
| 256 | 4-(Tetrahydro-pyran-4-carbonyl)-[1,4]diazepane-1-carboxylic acid [5-(1-methyl-cyclopropyl)-pyridin-2-yl]-amide | 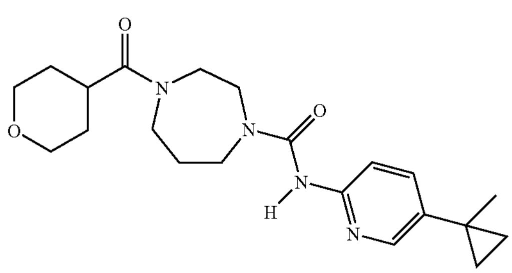 |

TABLE 2-continued

| Example | Name | Structure |
|---|---|---|
| 257 | 4-(6-Trifluoromethyl-pyridine-3-carbonyl)-[1,4]diazepane-1-carboxylic acid [5-(1,1-dimethyl-propyl)-isoxazol-3-yl]-amide | 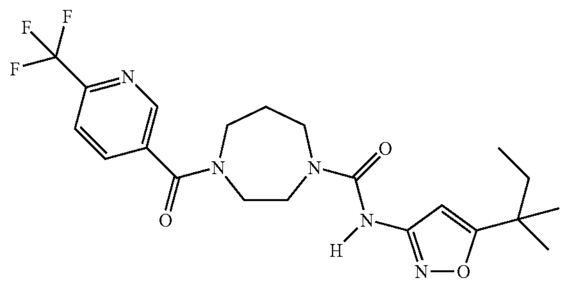 |
| 258 | 4-[4-(2,2,2-Trifluoro-ethyl)-piperazine-1-carbonyl]-[1,4]diazepane-1-carboxylic acid (5-tert-butyl-isoxazol-3-yl)-amide | 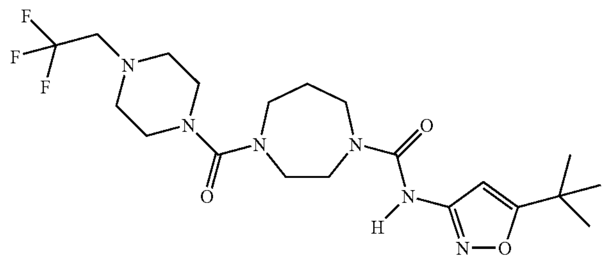 |
| 259 | 5-[4-(2,2,2-Trifluoro-ethyl)-piperazine-1-carbonyl]-[1,5]diazocane-1-carboxylic acid (5-tert-butyl-isoxazol-3-yl)-amide | 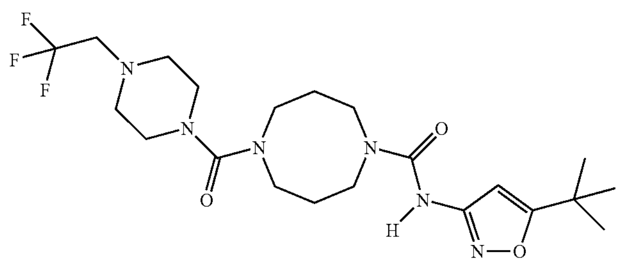 |
| 260 | 5-(1,1-Dioxo-1$\lambda^6$-thiomorpholine-4-carbonyl)-[1,5]diazocane-1-carboxylic acid (5-tert-butyl-isoxazol-3-yl)-amide | 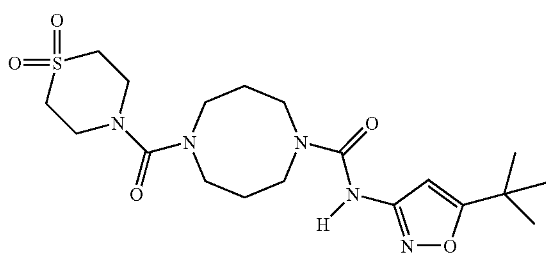 |
| 261 | 5-(1-Methanesulfonyl-piperidine-3-carbonyl)-[1,5]diazocane-1-carboxylic acid (5-tert-butyl-isoxazol-3-yl)-amide | 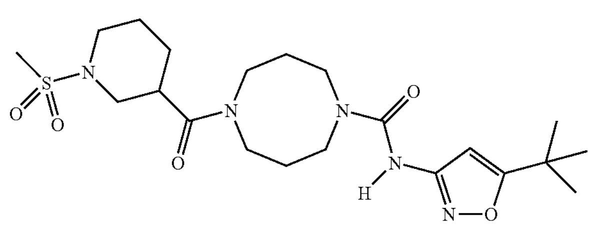 |
| 262 | 4-(4,4-Difluoro-piperidine-1-carbonyl)-[1,4]diazepane-1-carboxylic acid (3-tert-butyl-isoxazol-5-yl)-amide | 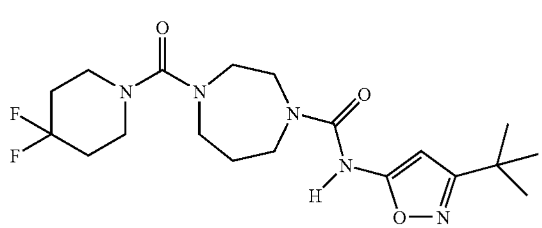 |

TABLE 2-continued

| Example | Name | Structure |
|---------|------|-----------|
| 263 | 4-(2-Piperidin-1-yl-acetyl)-[1,4]diazepane-1-carboxylic acid (4-sec-butyl-phenyl)-amide | 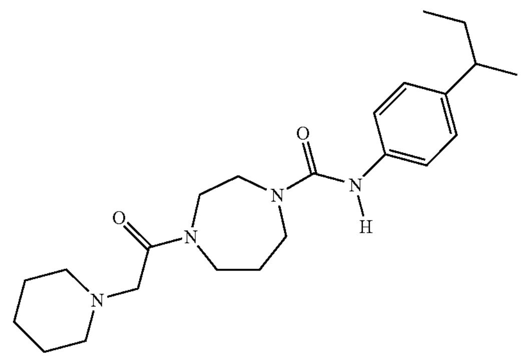 |
| 264 | 4-(Morpholine-4-carbonyl)-[1,4]diazepane-1-carboxylic acid (4-trifluoromethyl-phenyl)-amide | 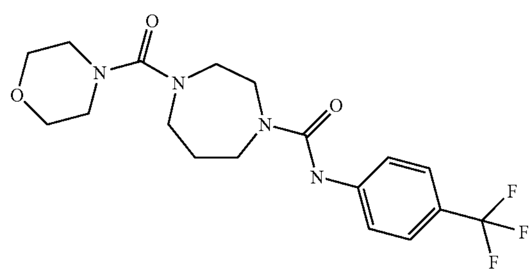 |
| 265 | 4-(Morpholine-4-carbonyl)-[1,4]diazepane-1-carboxylic acid (4-tert-butyl-phenyl)-amide | 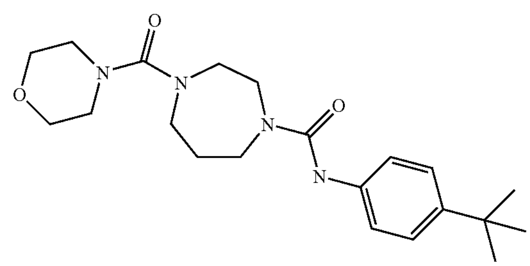 |
| 266 | 4-(Morpholine-4-carbonyl)-[1,4]diazepane-1-carboxylic acid (3-tert-butyl-phenyl)-amide | 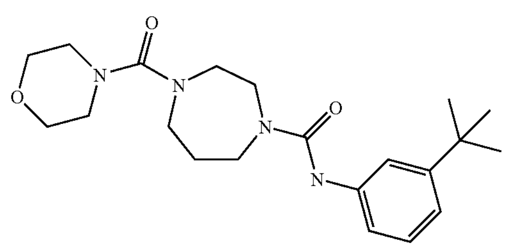 |
| 267 | 4-(Morpholine-4-carbonyl)-[1,4]diazepane-1-carboxylic acid (3-trifluoromethyl-4-bromo-phenyl)-amide | 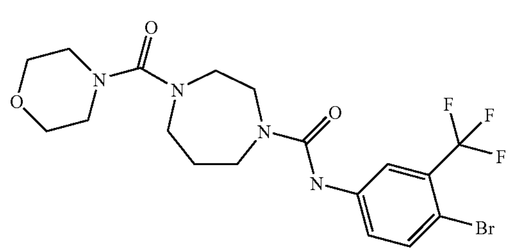 |

TABLE 2-continued

| Example | Name | Structure |
|---|---|---|
| 268 | 4-(Morpholine-4-carbonyl)-[1,4]diazepane-1-carboxylic acid (4-(1,1-difluoro)-propyl-phenyl)-amide | 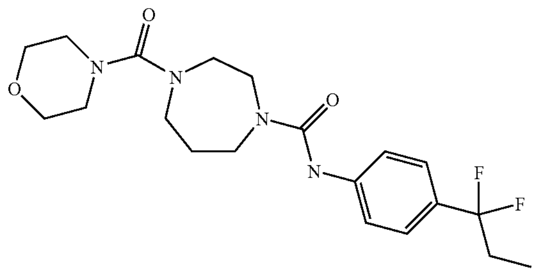 |
| 269 | 4-(Tetrahydro-pyran-4-carbonyl)-[1,4]diazepane-1-carboxylic acid (4-(1,1-difluoro)-ethyl-phenyl)-amide | 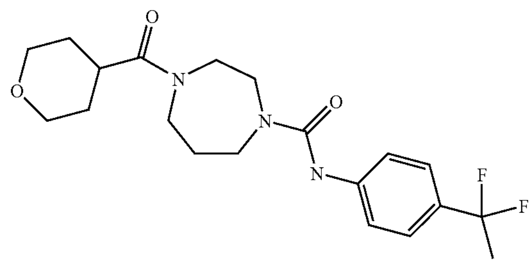 |
| 279 | 4-(Tetrahydro-pyran-4-carbonyl)-[1,4]diazepane-1-carboxylic acid (5-(1,1-difluoro)-ethyl-pyridin-2-yl)-amide | 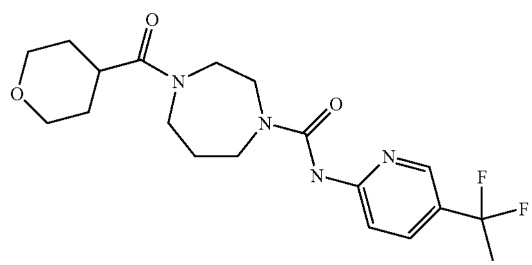 |

Assessment of Biological Properties

The biological properties of the compounds of the formula I were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Ga16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1 \times 10^{-5}$ M to $1 \times 10^{-10}$ M with 0.25% DMSO, final. The competition reaction was initiated with the addition of $^3$H—CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). $IC_{50}$ values for each compound were calculated as the concentration of compound that inhibits the specific binding of the radioactively labeled ligand to the receptor by 50% using the XLFit 4.1 four parameter logistic model. $IC_{50}$ values were converted to inhibition constant (Ki) values using Cheng-Prusoff equation.

B. CB2R Mediated Modulation of cAMP Synthesis:

Compounds of the invention were evaluated for their CB2 agonist or inverse agonistic activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R mediated modulation of cAMP synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Through the use of the above described assays, some of the compounds that exhibit agonistic activity are listed in Table 3 below.

TABLE 3

| Example number | hCB2 cAMP EC50 (nM) | Agonist Efficacy (%) |
|---|---|---|
| 1 | 66 | 56 |
| 11 | 74 | 65 |
| 17 | 47 | 80 |
| 19 | 35 | 104 |
| 34 | 23 | 102 |
| 36 | 29 | 95 |
| 41 | 43 | 95 |
| 44 | 60 | 95 |
| 48 | 53 | 100 |
| 49 | 48 | 73 |
| 52 | 7.1 | 98 |
| 55 | 89 | 105 |
| 56 | 22 | 103 |
| 60 | 78 | 71 |
| 68 | 26 | 99 |
| 69 | 10 | 96 |
| 78 | 71 | 87 |
| 79 | 46 | 100 |
| 80 | 12 | 99 |
| 81 | 120 | 96 |
| 82 | 36 | 92 |
| 86 | 52 | 92 |
| 88 | 36 | 97 |
| 90 | 20 | 91 |
| 92 | 14 | 96 |
| 94 | 89 | 98 |
| 99 | 100 | 102 |
| 105 | 29 | 94 |
| 106 | 20 | 102 |
| 107 | 100 | 94 |
| 108 | 21 | 96 |
| 109 | 87 | 72 |
| 110 | 64 | 97 |
| 112 | 19 | 109 |
| 113 | 62 | 78 |
| 114 | 2.7 | 99 |
| 116 | 96 | 94 |
| 121 | 36 | 103 |

TABLE 3-continued

| Example number | hCB2 cAMP EC50 (nM) | Agonist Efficacy (%) |
|---|---|---|
| 122 | 100 | 101 |
| 125 | 110 | 104 |
| 127 | 75 | 100 |
| 128 | 71 | 107 |
| 132 | 13 | 104 |
| 133 | 7.8 | 97 |
| 140 | 12 | 103 |
| 141 | 11 | 101 |
| 142 | 65 | 110 |
| 144 | 1.3 | 98 |
| 145 | 23 | 100 |
| 152 | 19 | 104 |
| 153 | 3.7 | 104 |
| 154 | 1.5 | 103 |
| 155 | 110 | 101 |
| 160 | 68 | 107 |
| 166 | 90 | 91 |
| 167 | 26 | 102 |
| 168 | 3.6 | 101 |
| 169 | 0.7 | 95 |
| 172 | 135 | 112 |
| 173 | 17 | 111 |
| 174 | 43 | 102 |
| 183 | 18 | 100 |
| 186 | 58 | 91 |
| 193 | 41 | 106 |
| 195 | 76 | 107 |
| 196 | 47 | 77 |
| 198 | 47 | 99 |
| 203 | 62 | 107 |
| 206 | 16 | 105 |
| 211 | 95 | 100 |
| 212 | 70 | 102 |
| 214 | 20 | 95 |
| 217 | 32 | 100 |
| 218 | 20 | 82 |
| 225 | 54 | 106 |
| 227 | 9.6 | 102 |
| 228 | 110 | 100 |
| 229 | 24 | 104 |
| 234 | 33 | 100 |

The following compounds were found to exhibit agonistic activity and thus to be particularly well suited for the treatment of pain as well as for the treatment of inflammation.

4-(3-Cyclopentyl-propionyl)-[1,4]diazepane-1-carboxylic acid (4-butyl-phenyl)-amide 4-(3-Cyclopentyl-propionyl)-[1,4]diazepane-1-carboxylic acid (4-isopropyl-phenyl)-amide 4-(3-Cyclopentyl-propionyl)-[1,4]diazepane-1-carboxylic acid (4-ethyl-phenyl)-amide 4-(3-Cyclopentyl-propionyl)-[1,4]diazepane-1-carboxylic acid (4-cyano-phenyl)-amide 4-(3-Cyclopentyl-propionyl)-[1,4]diazepane-1-carboxylic acid naphthalen-1-ylamide 4-(3-Cyclopentyl-propionyl)-[1,4]diazepane-1-carboxylic acid naphthalen-2-ylamide 4-(3-Cyclopentyl-propionyl)-[1,4]diazepane-1-carboxylic acid (4-chloro-phenyl)-amide 4-(3-Cyclopentyl-propionyl)-[1,4]diazepane-1-carboxylic acid m-tolylamide 4-(3-Cyclopentyl-propionyl)-[1,4]diazepane-1-carboxylic acid (4-dimethylamino-phenyl)-amide 4-(3-Cyclohexyl-propionyl)-[1,4]diazepane-1-carboxylic acid (4-butyl-phenyl)-amide 4-(2-Cyclopentyl-acetyl)-[1,4]diazepane-1-carboxylic acid (4-butyl-phenyl)-amide 4-Cyclopentanecarbonyl-[1,4]diazepane-1-carboxylic acid (4-butyl-phenyl)-amide 4-(4-Methyl-pentanoyl)-[1,4]diazepane-1-carboxylic acid (4-butyl-phenyl)-amide 4-(3-Cyclopentyl-propionyl)-[1,4]diazepane-1-carboxylic acid (4-pentyl-phenyl)-amide
4-(3-Cyclopentyl-propionyl)-[1,4]diazepane-1-carboxylic acid (4-trifluoromethyl-phenyl)-amide
4-Benzoyl-[1,4]diazepane-1-carboxylic acid (4-butyl-phenyl)-amide
4-(2-Cyclohexyl-acetyl)-[1,4]diazepane-1-carboxylic acid (4-butyl-phenyl)-amide
4-(3-Cyclopropyl-propionyl)-[1,4]diazepane-1-carboxylic acid (4-butyl-phenyl)-amide
4-Cyclohexanecarbonyl-[1,4]diazepane-1-carboxylic acid (4-butyl-phenyl)-amide
4-(Tetrahydro-pyran-4-carbonyl)-[1,4]diazepane-1-carboxylic acid (4-butyl-phenyl)-amide
4-(2-Cyclopentyl-acetyl)-[1,4]diazepane-1-carboxylic acid (4-trifluoromethoxy-phenyl)-amide
4-(2-Cyclopentyl-acetyl)-[1,4]diazepane-1-carboxylic acid (4-isopropyl-phenyl)-amide
4-(3-Cyclopentyl-propionyl)-[1,4]diazepane-1-carboxylic acid (4-methylsulfanyl-phenyl)-amide
4-(2-Cyclopentyl-acetyl)-[1,4]diazepane-1-carboxylic acid (4-methylsulfanyl-phenyl)-amide
4-(2-Tetrahydro-pyran-4-yl-acetyl)-[1,4]diazepane-1-carboxylic acid (4-isopropyl-phenyl)-amide
4-(2-Tetrahydro-pyran-4-yl-acetyl)-[1,4]diazepane-1-carboxylic acid (4-ethyl-phenyl)-amide
4-(2-Tetrahydro-pyran-4-yl-acetyl)-[1,4]diazepane-1-carboxylic acid (4-trifluoromethoxy-phenyl)-amide
4-(2-Tetrahydro-pyran-4-yl-acetyl)-[1,4]diazepane-1-carboxylic acid (4-sec-butyl-phenyl)-amide
4-(2-Tetrahydro-pyran-4-yl-acetyl)-[1,4]diazepane-1-carboxylic acid (4-pentyl-phenyl)-amide
4-(2-Tetrahydro-pyran-4-yl-acetyl)-[1,4]diazepane-1-carboxylic acid (4-butyl-phenyl)-amide
4-(2-Tetrahydro-pyran-4-yl-acetyl)-[1,4]diazepane-1-carboxylic acid (2-naphthyl)-amide
4-(2-Tetrahydro-pyran-4-yl-acetyl)-[1,4]diazepane-1-carboxylic acid (4-methylsulfanyl-phenyl)-amide
4-(2-Tetrahydro-pyran-4-yl-acetyl)-[1,4]diazepane-1-carboxylic acid (4-tert-butyl-phenyl)-amide
4-Cyclohexanecarbonyl-[1,4]diazepane-1-carboxylic acid (4-isopropyl-phenyl)-amide
4-Benzoyl-[1,4]diazepane-1-carboxylic acid (4-isopropyl-phenyl)-amide
4-(2-Cyclohexyl-acetyl)-[1,4]diazepane-1-carboxylic acid (4-isopropyl-phenyl)-amide
4-(Pyridine-2-carbonyl)-[1,4]diazepane-1-carboxylic acid (4-isopropyl-phenyl)-amide
4-(Tetrahydro-pyran-4-carbonyl)-[1,4]diazepane-1-carboxylic acid (4-isopropyl-phenyl)-amide
4-(Pyridine-4-carbonyl)-[1,4]diazepane-1-carboxylic acid (4-isopropyl-phenyl)-amide
4-(3-Chloro-benzoyl)-[1,4]diazepane-1-carboxylic acid (4-isopropyl-phenyl)-amide
4-(4-Chloro-benzoyl)-[1,4]diazepane-1-carboxylic acid (4-isopropyl-phenyl)-amide
4-(2-Tetrahydro-pyran-4-yl-acetyl)-[1,4]diazepane-1-carboxylic acid (2,2-difluoro-benzo[1,3]dioxol-5-yl)-amide
4-(2-Tetrahydro-pyran-4-yl-acetyl)-[1,4]diazepane-1-carboxylic acid (3,5-dichloro-phenyl)-amide
4-(2-Cyclopentyl-acetyl)-[1,4]diazepane-1-carboxylic acid (4-tert-butyl-phenyl)-amide
4-(2-Cyclopentyl-acetyl)-[1,4]diazepane-1-carboxylic acid (4-ethyl-phenyl)-amide
4-(2-Cyclopentyl-acetyl)-[1,4]diazepane-1-carboxylic acid (1-acetyl-2,3-dihydro-1H-indol-6-yl)-amide
4-(2-Cyclopentyl-acetyl)-[1,4]diazepane-1-carboxylic acid (2,2-difluoro-benzo[1,3]dioxol-5-yl)-amide
4-(2-Cyclopentyl-acetyl)-[1,4]diazepane-1-carboxylic acid (2-naphthyl)-amide
4-(2-Cyclopentyl-acetyl)-[1,4]diazepane-1-carboxylic acid (4-n-pentyl-phenyl)-amide
4-(2-Cyclopentyl-acetyl)-[1,4]diazepane-1-carboxylic acid (4-trifluoromethyl-phenyl)-amide
4-(2-Tetrahydro-pyran-4-yl-acetyl)-[1,4]diazepane-1-carboxylic acid (4-trifluoromethyl-phenyl)-amide
4-(2-Cyclopentyl-acetyl)-[1,4]diazepane-1-carboxylic acid (4-sec-butyl-phenyl)-amide
4-(2-Cyclopentyl-acetyl)-[1,4]diazepane-1-carboxylic acid (4-biphenyl)-amide
4-(2-Cyclopentyl-acetyl)-[1,4]diazepane-1-carboxylic acid (4-bromo-phenyl)-amide
4-(3-Cyclopropyl-propionyl)-[1,4]diazepane-1-carboxylic acid (4-isopropyl-phenyl)-amide
4-(3-Cyclohexyl-propionyl)-[1,4]diazepane-1-carboxylic acid (4-isopropyl-phenyl)-amide
4-pivaloyl-[1,4]diazepane-1-carboxylic acid (4-isopropyl-phenyl)-amide
4-(4-Methyl-pentanoyl)-[1,4]diazepane-1-carboxylic acid (4-isopropyl-phenyl)-amide
4-(4,4,4-Trifluoro-butyryl)-[1,4]diazepane-1-carboxylic acid (4-isopropyl-phenyl)-amide
4-(3,3-Dimethyl-butyryl)-[1,4]diazepane-1-carboxylic acid (4-isopropyl-phenyl)-amide
4-(2-Cyclopentyl-acetyl)-[1,4]diazepane-1-carboxylic acid (2,4-dichloro-phenyl)-amide
4-(2-Cyclopentyl-acetyl)-[1,4]diazepane-1-carboxylic acid (2,5-dichloro-phenyl)-amide
4-(2-Cyclopentyl-acetyl)-[1,4]diazepane-1-carboxylic acid (3,4-dichloro-phenyl)-amide
4-(2-Cyclopentyl-acetyl)-[1,4]diazepane-1-carboxylic acid (3,5-dichloro-phenyl)-amide
4-(2-Cyclohexyl-acetyl)-[1,4]diazepane-1-carboxylic acid (4-ethyl-phenyl)-amide
4-(2-Cyclohexyl-acetyl)-[1,4]diazepane-1-carboxylic acid (2-naphthyl)-amide
4-Cyclohexanecarbonyl-[1,4]diazepane-1-carboxylic acid (4-ethyl-phenyl)-amide
4-Cyclohexanecarbonyl-[1,4]diazepane-1-carboxylic acid naphthalen-2-ylamide
4-(4-Chloro-benzoyl)-[1,4]diazepane-1-carboxylic acid (4-tert-butyl-phenyl)-amide
4-(4-Chloro-benzoyl)-[1,4]diazepane-1-carboxylic acid (4-trifluoromethyl-phenyl)-amide
4-(4-Chloro-benzoyl)-[1,4]diazepane-1-carboxylic acid (4-bromo-phenyl)-amide
4-(4-Chloro-benzoyl)-[1,4]diazepane-1-carboxylic acid (3,4-dichloro-phenyl)-amide
4-(4-Chloro-benzoyl)-[1,4]diazepane-1-carboxylic acid (3,5-dichloro-phenyl)-amide
4-Cyclohexanecarbonyl-[1,4]diazepane-1-carboxylic acid (4-bromo-phenyl)-amide
4-Cyclohexanecarbonyl-[1,4]diazepane-1-carboxylic acid (3,4-dichloro-phenyl)-amide
4-Cyclohexanecarbonyl-[1,4]diazepane-1-carboxylic acid (3,5-dichloro-phenyl)-amide
4-(Tetrahydro-pyran-4-carbonyl)-[1,4]diazepane-1-carboxylic acid (4-trifluoromethyl-phenyl)-amide
4-(4,4-Difluoro-cyclohexanecarbonyl)-[1,4]diazepane-1-carboxylic acid (4-trifluoromethyl-phenyl)-amide
4-(4-Chloro-benzoyl)-[1,4]diazepane-1-carboxylic acid naphthalen-2-ylamide 4-Cyclohexanecarbonyl-[1,4]diazepane-1-carboxylic acid (4-trifluoromethylsulfanyl-phenyl)-amide
4-(Tetrahydro-pyran-4-carbonyl)-[1,4]diazepane-1-carboxylic acid (4-trifluoromethylsulfanyl-phenyl)-amide
4-(2-cyclopentyl-acetyl)-[1,4]diazepane-1-carboxylic acid (4-trifluoromethylsulfanyl-phenyl)-amide
4-(2-Cyclopentyl-acetyl)-[1,4]diazepane-1-carboxylic acid (4-butyryl-phenyl)-amide
4-Cyclopentanecarbonyl-[1,4]diazepane-1-carboxylic acid naphthalen-2-ylamide
4-(3-Cyclohexyl-propionyl)-[1,4]diazepane-1-carboxylic acid naphthalen-2-ylamide
4-(3,4-Dichloro-benzoyl)-[1,4]diazepane-1-carboxylic acid naphthalen-2-ylamide
4-(3,5-Dichloro-benzoyl)-[1,4]diazepane-1-carboxylic acid naphthalen-2-ylamide
4-(4-Cyano-benzoyl)-[1,4]diazepane-1-carboxylic acid naphthalen-2-ylamide
4-(4-Dimethylamino-benzoyl)-[1,4]diazepane-1-carboxylic acid naphthalen-2-ylamide
4-(2,5-Dichloro-benzoyl)-[1,4]diazepane-1-carboxylic acid naphthalen-2-ylamide
4-(4-Methoxy-benzoyl)-[1,4]diazepane-1-carboxylic acid naphthalen-2-ylamide
4-(4-Trifluoromethyl-benzoyl)-[1,4]diazepane-1-carboxylic acid naphthalen-2-ylamide
4-(3,3-Dimethyl-butyryl)-[1,4]diazepane-1-carboxylic acid naphthalen-2-ylamide
4-(4-Methyl-pentanoyl)-[1,4]diazepane-1-carboxylic acid naphthalen-2-ylamide
4-(2,2-Dimethyl-propionyl)-[1,4]diazepane-1-carboxylic acid naphthalen-2-ylamide
4-(2-Phenoxy-acetyl)-[1,4]diazepane-1-carboxylic acid naphthalen-2-ylamide
4-(4,4,4-Trifluoro-butyryl)-[1,4]diazepane-1-carboxylic acid naphthalen-2-ylamide
4-(3-Cyclopropyl-propionyl)-[1,4]diazepane-1-carboxylic acid naphthalen-2-ylamide
4-(2,4-Dichloro-benzoyl)-[1,4]diazepane-1-carboxylic acid naphthalen-2-ylamide
4-(4-Methyl-benzoyl)-[1,4]diazepane-1-carboxylic acid naphthalen-2-ylamide
4-(Tetrahydro-pyran-4-carbonyl)-[1,4]diazepane-1-carboxylic acid naphthalen-2-ylamide
4-(3-Cyclopentyl-propionyl)-[1,4]diazepane-1-carboxylic acid (4-propyl-phenyl)-amide
4-(2-Piperidin-1-yl-acetyl)-[1,4]diazepane-1-carboxylic acid naphthalen-2-ylamide
4-Cyclopentanecarbonyl-[1,4]diazepane-1-carboxylic acid (4-tert-butyl-phenyl)-amide
4-(3-Cyclopentyl-propionyl)-[1,4]diazepane-1-carboxylic acid (4-tert-butyl-phenyl)-amide
4-Cyclohexanecarbonyl-[1,4]diazepane-1-carboxylic acid (4-tert-butyl-phenyl)-amide
4-(2-Cyclohexyl-acetyl)-[1,4]diazepane-1-carboxylic acid (4-tert-butyl-phenyl)-amide
4-(3-Cyclohexyl-propionyl)-[1,4]diazepane-1-carboxylic acid (4-tert-butyl-phenyl)-amide
4-(2,5-Dichloro-benzoyl)-[1,4]diazepane-1-carboxylic acid (4-tert-butyl-phenyl)-amide
4-(3,4-Dichloro-benzoyl)-[1,4]diazepane-1-carboxylic acid (4-tert-butyl-phenyl)-amide
4-(3,5-Dichloro-benzoyl)-[1,4]diazepane-1-carboxylic acid (4-tert-butyl-phenyl)-amide
4-(4-Cyano-benzoyl)-[1,4]diazepane-1-carboxylic acid (4-tert-butyl-phenyl)-amide
4-(4-Dimethylamino-benzoyl)-[1,4]diazepane-1-carboxylic acid (4-tert-butyl-phenyl)-amide
4-(4-Trifluoromethyl-benzoyl)-[1,4]diazepane-1-carboxylic acid (4-tert-butyl-phenyl)-amide
4-(3,3-Dimethyl-butyryl)-[1,4]diazepane-1-carboxylic acid (4-tert-butyl-phenyl)-amide
4-(4-Methyl-pentanoyl)-[1,4]diazepane-1-carboxylic acid (4-tert-butyl-phenyl)-amide
4-(2,2-Dimethyl-propionyl)-[1,4]diazepane-1-carboxylic acid (4-tert-butyl-phenyl)-amide
4-(2-Phenoxy-acetyl)-[1,4]diazepane-1-carboxylic acid (4-tert-butyl-phenyl)-amide
4-(4,4,4-Trifluoro-butyryl)-[1,4]diazepane-1-carboxylic acid (4-tert-butyl-phenyl)-amide
4-(3-Cyclopropyl-propionyl)-[1,4]diazepane-1-carboxylic acid (4-tert-butyl-phenyl)-amide
4-(2-Thiomorpholin-4-yl-acetyl)-[1,4]diazepane-1-carboxylic acid (4-tert-butyl-phenyl)-amide
4-(4-Methyl-benzoyl)-[1,4]diazepane-1-carboxylic acid (4-tert-butyl-phenyl)-amide
4-(2-Phenylamino-acetyl)-[1,4]diazepane-1-carboxylic acid (4-tert-butyl-phenyl)-amide
4-(Pyridine-2-carbonyl)-[1,4]diazepane-1-carboxylic acid (4-sec-butyl-phenyl)-amide
4-(Tetrahydro-pyran-4-carbonyl)-[1,4]diazepane-1-carboxylic acid (4-tert-butyl-phenyl)-amide
4-(2-Piperidin-1-yl-acetyl)-[1,4]diazepane-1-carboxylic acid (4-tert-butyl-phenyl)-amide
4-(4-Trifluoromethyl-benzoyl)-[1,4]diazepane-1-carboxylic acid (4-trifluomethyl-phenyl)-amide
4-Cyclohexanecarbonyl-[1,4]diazepane-1-carboxylic acid (4-trifluoromethyl-phenyl)-amide
4-(4-Fluoro-benzoyl)-[1,4]diazepane-1-carboxylic acid (4-trifluoromethyl-phenyl)-amide
4-Benzoyl-[1,4]diazepane-1-carboxylic acid (4-trifluoromethyl-phenyl)-amide
4-(2-Cyclopentyl-acetyl)-[1,4]diazepane-1-carboxylic acid (3-trifluoromethyl-phenyl)-amide
4-(2-Cyclopentyl-acetyl)-[1,4]diazepane-1-carboxylic acid (4-bromo-3-trifluoromethyl-phenyl)-amide
4-(Tetrahydro-pyran-4-carbonyl)-[1,4]diazepane-1-carboxylic acid (4-sec-butyl-phenyl)-amide
4-(3-Cyclopentyl-propionyl)-[1,4]diazepane-1-carboxylic acid cyclohexylmethyl-amide
4-(3-Cyclopentyl-propionyl)-[1,4]diazepane-1-carboxylic acid cyclohexylamide
4-(2-Tetrahydro-pyran-4-yl-acetyl)-[1,4]diazepane-1-carboxylic acid (4-methanesulfonyl-phenyl)-amide
4-(3-Cyclopentyl-propionyl)-[1,4]diazepane-1-carboxylic acid (4-methanesulfonyl-phenyl)-amide
4-(2-Cyclopentyl-acetyl)-[1,4]diazepane-1-carboxylic acid (4-methanesulfonyl-phenyl)-amide
4-(Tetrahydro-pyran-4-carbonyl)-[1,4]diazepane-1-carboxylic acid [4-(2,2,2-trifluoro-1-methyl-ethyl)-phenyl]-amide
4-(2-Cyclopentyl-acetyl)-[1,4]diazepane-1-carboxylic acid (5-tert-butyl-isoxazol-3-yl)-amide
4-(4-Chloro-benzoyl)-[1,4]diazepane-1-carboxylic acid (5-tert-butyl-isoxazol-3-yl)-amide
4-(Tetrahydro-pyran-4-carbonyl)-[1,4]diazepane-1-carboxylic acid (5-tert-butyl-isoxazol-3-yl)-amide
4-(1-Methyl-cyclohexanecarbonyl)-[1,4]diazepane-1-carboxylic acid (5-tert-butyl-isoxazol-3-yl)-amide
4-(4,4-Difluoro-cyclohexanecarbonyl)-[1,4]diazepane-1-carboxylic acid (5-tert-butyl-isoxazol-3-yl)-amide
4-(4-Hydroxy-cyclohexanecarbonyl)-[1,4]diazepane-1-carboxylic acid (5-tert-butyl-isoxazol-3-yl)-amide 4-(Tetrahydro-pyran-2-carbonyl)-[1,4]diazepane-1-carboxylic acid (5-tert-butyl-isoxazol-3-yl)-amide
4-(Tetrahydro-pyran-3-carbonyl)-[1,4]diazepane-1-carboxylic acid (5-tert-butyl-isoxazol-3-yl)-amide
4-(2-Tetrahydro-furan-2-yl-acetyl)-[1,4]diazepane-1-carboxylic acid (5-tert-butyl-isoxazol-3-yl)-amide
4-(Tetrahydro-furan-2-carbonyl)-[1,4]diazepane-1-carboxylic acid (5-tert-butyl-isoxazol-3-yl)-amide
4-(Tetrahydro-furan-3-carbonyl)-[1,4]diazepane-1-carboxylic acid (5-tert-butyl-isoxazol-3-yl)-amide
4-Cyclopentanecarbonyl-[1,4]diazepane-1-carboxylic acid (5-tert-butyl-isoxazol-3-yl)-amide
4-Cycloheptanecarbonyl-[1,4]diazepane-1-carboxylic acid (5-tert-butyl-isoxazol-3-yl)-amide
4-Cyclohexanecarbonyl-[1,4]diazepane-1-carboxylic acid (5-tert-butyl-isoxazol-3-yl)-amide
4-(4-Trifluoromethyl-benzoyl)-[1,4]diazepane-1-carboxylic acid (5-tert-butyl-isoxazol-3-yl)-amide
4-(4-Methoxy-cyclohexanecarbonyl)-[1,4]diazepane-1-carboxylic acid (5-tert-butyl-isoxazol-3-yl)-amide
4-(2,2-Dimethyl-propionyl)-[1,4]diazepane-1-carboxylic acid (5-tert-butyl-isoxazol-3-yl)-amide
4-(3-Methyl-butyryl)-[1,4]diazepane-1-carboxylic acid (5-tert-butyl-isoxazol-3-yl)-amide
4-(4-Amino-cyclohexanecarbonyl)-[1,4]diazepane-1-carboxylic acid (5-tert-butyl-isoxazol-3-yl)-amide
4-(Piperidine-4-carbonyl)-[1,4]diazepane-1-carboxylic acid (5-tert-butyl-isoxazol-3-yl)-amide
4-(4-Acetylamino-cyclohexanecarbonyl)-[1,4]diazepane-1-carboxylic acid (5-tert-butyl-isoxazol-3-yl)-amide
4-(4-Methanesulfonylamino-cyclohexanecarbonyl)-[1,4]diazepane-1-carboxylic acid (5-tert-butyl-isoxazol-3-yl)-amide
4-(1-Acetyl-piperidine-4-carbonyl)-[1,4]diazepane-1-carboxylic acid (5-tert-butyl-isoxazol-3-yl)-amide
4-(1-Methanesulfonyl-piperidine-4-carbonyl)-[1,4]diazepane-1-carboxylic acid (5-tert-butyl-isoxazol-3-yl)-amide
4-(Piperidine-3-carbonyl)-[1,4]diazepane-1-carboxylic acid (5-tert-butyl-isoxazol-3-yl)-amide
4-(1-Methanesulfonyl-piperidine-3-carbonyl)-[1,4]diazepane-1-carboxylic acid (5-tert-butyl-isoxazol-3-yl)-amide
4-(4-Chloro-benzoyl)-[1,4]diazepane-1-carboxylic acid (4-cyclopropyl-thiazol-2-yl)-amide
4-(4-Chloro-benzoyl)-[1,4]diazepane-1-carboxylic acid (4-phenyl-thiazol-2-yl)-amide
4-(4-Chloro-benzoyl)-[1,4]diazepane-1-carboxylic acid (4,5,6,7-tetrahydro-benzothiazol-2-yl)-amide
4-(4,4-Difluoro-cyclohexanecarbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (5-tert-butyl-thiazol-2-yl)-amide
4-(Tetrahydro-pyran-4-carbonyl)-[1,4]diazepane-1-carboxylic acid (4,5,6,7-tetrahydro-benzothiazol-2-yl)-amide
4-(Tetrahydro-pyran-4-carbonyl)-[1,4]diazepane-1-carboxylic acid (5-phenyl-thiazol-2-yl)-amide
4-(4-Hydroxy-cyclohexanecarbonyl)-[1,4]diazepane-1-carboxylic acid (5-tert-butyl-thiazol-2-yl)-amide
4-(4-Hydroxy-cyclohexanecarbonyl)-[1,4]diazepane-1-carboxylic acid (4-phenyl-thiazol-2-yl)-amide
4-(Tetrahydro-pyran-4-carbonyl)-[1,4]diazepane-1-carboxylic acid (5-tert-butyl-2H-pyrazol-3-yl)-amide
4-(Tetrahydro-pyran-4-carbonyl)-[1,4]diazepane-1-carboxylic acid (5-isopropyl-thiazol-2-yl)-amide
4-(Tetrahydro-pyran-4-carbonyl)-[1,4]diazepane-1-carboxylic acid (5-sec-butyl-2-methyl-2H-pyrazol-3-yl)-amide
4-(Tetrahydro-pyran-4-carbonyl)-[1,4]diazepane-1-carboxylic acid (4-phenyl-thiazol-2-yl)-amide
4-(Tetrahydro-pyran-4-carbonyl)-[1,4]diazepane-1-carboxylic acid (5-phenyl-isoxazol-3-yl)-amide
4-(Tetrahydro-pyran-4-carbonyl)-[1,4]diazepane-1-carboxylic acid (4-ethyl-pyridin-2-yl)-amide
4-(Tetrahydro-pyran-4-carbonyl)-[1,4]diazepane-1-carboxylic acid quinolin-3-ylamide
4-(Tetrahydro-pyran-4-carbonyl)-[1,4]diazepane-1-carboxylic acid (4-tert-butyl-thiazol-2-yl)-amide
4-(Tetrahydro-pyran-4-carbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (4-methyl-thiazol-2-yl)-amide
4-(Tetrahydro-pyran-4-carbonyl)-[1,4]diazepane-1-carboxylic acid (4,5-dimethyl-thiazol-2-yl)-amide
4-(Tetrahydro-pyran-4-carbonyl)-[1,4]diazepane-1-carboxylic acid (4-tert-butyl-5-methyl-thiazol-2-yl)-amide
4-(Tetrahydro-pyran-4-carbonyl)-[1,4]diazepane-1-carboxylic acid (4-trifluoromethyl-pyridin-2-yl)-amide
4-(Tetrahydro-pyran-4-carbonyl)-[1,4]diazepane-1-carboxylic acid (6-phenoxy-pyridin-3-yl)-amide
4-(Tetrahydro-pyran-4-carbonyl)-[1,4]diazepane-1-carboxylic acid (5-trifluoromethyl-pyridin-2-yl)-amide
4-(Tetrahydro-pyran-4-carbonyl)-[1,4]diazepane-1-carboxylic acid (5-tert-butyl-2-methyl-2H-pyrazol-3-yl)-amide
4-(Tetrahydro-pyran-4-carbonyl)-[1,4]diazepane-1-carboxylic acid (1-methyl-1H-benzoimidazol-2-yl)-amide
4-(Tetrahydro-pyran-4-carbonyl)-[1,4]diazepane-1-carboxylic acid (2-methyl-5-phenyl-2H-pyrazol-3-yl)-amide
4-(Tetrahydro-pyran-4-carbonyl)-[1,4]diazepane-1-carboxylic acid (3-sec-butyl-isoxazol-5-yl)-amide
4-(Tetrahydro-pyran-4-carbonyl)-[1,4]diazepane-1-carboxylic acid (3-phenyl-isoxazol-5-yl)-amide
4-(Tetrahydro-pyran-4-carbonyl)-[1,4]diazepane-1-carboxylic acid (3-tert-butyl-isoxazol-5-yl)-amide
4-(Tetrahydro-pyran-4-carbonyl)-[1,4]diazepane-1-carboxylic acid (5-sec-butyl-pyridin-2-yl)-amide
4-(Morpholine-4-carbonyl)-[1,4]diazepane-1-carboxylic acid (5-tert-butyl-isoxazol-3-yl)-amide
4-(Piperidine-1-carbonyl)-[1,4]diazepane-1-carboxylic acid (5-tert-butyl-isoxazol-3-yl)-amide
4-(4-Methanesulfonyl-piperidine-1-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (5-tert-butyl-isoxazol-3-yl)-amide
4-(4-Acetyl-piperazine-1-carbonyl)-[1,4]diazepane-1-carboxylic acid (5-tert-butyl-isoxazol-3-yl)-amide
4-(4-Methanesulfonyl-piperazine-1-carbonyl)-[1,4]diazepane-1-carboxylic acid (5-tert-butyl-isoxazol-3-yl)-amide
4-(Thiomorpholine-4-carbonyl)-[1,4]diazepane-1-carboxylic acid (5-tert-butyl-isoxazol-3-yl)-amide
4-(1-Oxo-1$\lambda^4$-thiomorpholine-4-carbonyl)-[1,4]diazepane-1-carboxylic acid (5-tert-butyl-isoxazol-3-yl)-amide
4-([1,4]Oxazepane-4-carbonyl)-[1,4]diazepane-1-carboxylic acid (5-tert-butyl-isoxazol-3-yl)-amide
4-(4,4-Difluoro-piperidine-1-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (4-sec-butyl-phenyl)-amide 4-(1,1-Dioxo-1λ⁶-thiomorpholine-4-carbonyl)-[1,4]diazepane-1-carboxylic acid (4-tert-butyl-phenyl)-amide
4-(1,1-Dioxo-1λ⁶-thiomorpholine-4-carbonyl)-[1,4]diazepane-1-carboxylic acid [4-(2,2,2-trifluoro-1-methyl-ethyl)-phenyl]-amide
4-(1,1-Dioxo-1λ⁶-thiomorpholine-4-carbonyl)-[1,4]diazepane-1-carboxylic acid (3-tert-butyl-phenyl)-amide
4-(1,1-Dioxo-1λ⁶-thiomorpholine-4-carbonyl)-[1,4]diazepane-1-carboxylic acid (3-tert-butyl-isoxazol-5-yl)-amide
[1,4]Diazepane-1,4-dicarboxylic acid 1-[(5-tert-butyl-isoxazol-3-yl)-amide]-4-cyclohexylamide
4-((2R,6S)-2,6-Dimethyl-morpholine-4-carbonyl)-[1,4]diazepane-1-carboxylic acid (5-tert-butyl-isoxazol-3-yl)-amide
4-(1,1-Dioxo-1λ⁶-thiomorpholine-4-carbonyl)-[1,4]diazepane-1-carboxylic acid (5-tert-butyl-thiazol-2-yl)-amide
4-(1,1-Dioxo-1λ⁶-thiomorpholine-4-carbonyl)-[1,4]diazepane-1-carboxylic acid (5-isopropyl-thiazol-2-yl)-amide
4-(1,1-Dioxo-1λ⁶-thiomorpholine-4-carbonyl)-[1,4]diazepane-1-carboxylic acid (4,5,6,7-tetrahydro-benzothiazol-2-yl)-amide
[1,4]Diazepane-1,4-dicarboxylic acid 1-[(5-tert-butyl-isoxazol-3-yl)-amide]-4-cyclopentylamide
4-(Morpholine-4-carbonyl)-[1,4]diazepane-1-carboxylic acid (4-sec-butyl-phenyl)-amide
[1,4]Diazepane-1,4-dicarboxylic acid 1-[(5-tert-butyl-isoxazol-3-yl)-amide]-4-[(tetrahydro-pyran-4-yl)-amide][1,4]Diazepane-1,4-dicarboxylic acid 1-[(5-tert-butyl-isoxazol-3-yl)-amide]-4-phenylamide
4-(Morpholine-4-carbonyl)-[1,4]diazepane-1-carboxylic acid (3-phenyl-isoxazol-5-yl)-amide
4-(Morpholine-4-carbonyl)-[1,4]diazepane-1-carboxylic acid (4-phenyl-thiazol-2-yl)-amide
4-(Morpholine-4-carbonyl)-[1,4]diazepane-1-carboxylic acid (3-sec-butyl-isoxazol-5-yl)-amide
4-(4-Methoxy-piperidine-1-carbonyl)-[1,4]diazepane-1-carboxylic acid (3-tert-butyl-isoxazol-5-yl)-amide
4-(Morpholine-4-carbonyl)-[1,4]diazepane-1-carboxylic acid (3-tert-butyl-isoxazol-5-yl)-amide
4-(2-Morpholin-4-yl-acetyl)-[1,4]diazepane-1-carboxylic acid (5-tert-butyl-isoxazol-3-yl)-amide
4-(2-Thiomorpholin-4-yl-acetyl)-[1,4]diazepane-1-carboxylic acid (5-tert-butyl-isoxazol-3-yl)-amide
4-[2-(1,1-Dioxo-1λ⁶-thiomorpholin-4-yl)-acetyl]-[1,4]diazepane-1-carboxylic acid (5-tert-butyl-isoxazol-3-yl)-amide
4-[2-(4,4-Difluoro-piperidin-1-yl)-acetyl]-[1,4]diazepane-1-carboxylic acid (5-tert-butyl-isoxazol-3-yl)-amide
4-[2-(1,1-Dioxo-1λ⁶-thiomorpholin-4-yl)-acetyl]-[1,4]diazepane-1-carboxylic acid (3-tert-butyl-isoxazol-5-yl)-amide
4-[2-((2R,6S)-2,6-Dimethyl-morpholin-4-yl)-acetyl]-[1,4]diazepane-1-carboxylic acid (5-tert-butyl-isoxazol-3-yl)-amide
4-(4,4-Difluoro-cyclohexanecarbonyl)-[1,4]diazepane-1-carboxylic acid (3-tert-butyl-isoxazol-5-yl)-amide
4-(Tetrahydro-pyran-4-carbonyl)-[1,4]diazapane-1-carboxylic acid (4,5-dimethyl-isoxazol-3-yl)-amide
4-(4-Oxo-cyclohexanecarbonyl)-[1,4]diazepane-1-carboxylic acid (5-tert-butyl-isoxazol-3-yl)-amide
4-(4-Hydroxy-4-methyl-cyclohexanecarbonyl)-[1,4]diazepane-1-carboxylic acid (5-tert-butyl-isoxazol-3-yl)-amide
4-(1,1-Dioxo-hexahydro-1λ⁶-thiopyran-4-carbonyl)-[1,4]diazepane-1-carboxylic acid (5-tert-butyl-isoxazol-3-yl)-amide
4-(2-Cyclopentyl-acetyl)-[1,4]diazepane-1-carboxylic acid [4-(1-hydroxy-butyl)-phenyl]-amide
4-(2-Cyclopentyl-acetyl)-[1,4]diazepane-1-carbothioic acid (4-isopropyl-phenyl)-amide
Preferred compounds include:
4-(3-Cyclopentyl-propionyl)-[1,4]diazepane-1-carboxylic acid (4-butyl-phenyl)-amide
4-(3-Cyclopentyl-propionyl)-[1,4]diazepane-1-carboxylic acid (4-isopropyl-phenyl)-amide
4-(3-Cyclopentyl-propionyl)-[1,4]diazepane-1-carboxylic acid (4-ethyl-phenyl)-amide
4-(3-Cyclopentyl-propionyl)-[1,4]diazepane-1-carboxylic acid naphthalen-2-ylamide
4-(3-Cyclohexyl-propionyl)-[1,4]diazepane-1-carboxylic acid (4-butyl-phenyl)-amide
4-(2-Cyclopentyl-acetyl)-[1,4]diazepane-1-carboxylic acid (4-butyl-phenyl)-amide
4-Cyclopentanecarbonyl-[1,4]diazepane-1-carboxylic acid (4-butyl-phenyl)-amide
4-(4-Methyl-pentanoyl)-[1,4]diazepane-1-carboxylic acid (4-butyl-phenyl)-amide
4-Benzoyl-[1,4]diazepane-1-carboxylic acid (4-butyl-phenyl)-amide
4-(2-Cyclohexyl-acetyl)-[1,4]diazepane-1-carboxylic acid (4-butyl-phenyl)-amide
4-(3-Cyclopropyl-propionyl)-[1,4]diazepane-1-carboxylic acid (4-butyl-phenyl)-amide
4-Cyclohexanecarbonyl-[1,4]diazepane-1-carboxylic acid (4-butyl-phenyl)-amide
4-(Tetrahydro-pyran-4-carbonyl)-[1,4]diazepane-1-carboxylic acid (4-butyl-phenyl)-amide
4-(2-Cyclopentyl-acetyl)-[1,4]diazepane-1-carboxylic acid (4-isopropyl-phenyl)-amide
4-(2-Cyclopentyl-acetyl)-[1,4]diazepane-1-carboxylic acid (4-methylsulfanyl-phenyl)-amide
4-(2-Tetrahydro-pyran-4-yl-acetyl)-[1,4]diazepane-1-carboxylic acid (4-sec-butyl-phenyl)-amide
4-Cyclohexanecarbonyl-[1,4]diazepane-1-carboxylic acid (4-isopropyl-phenyl)-amide
4-Benzoyl-[1,4]diazepane-1-carboxylic acid (4-isopropyl-phenyl)-amide
4-(2-Cyclohexyl-acetyl)-[1,4]diazepane-1-carboxylic acid (4-isopropyl-phenyl)-amide
4-(Tetrahydro-pyran-4-carbonyl)-[1,4]diazepane-1-carboxylic acid (4-isopropyl-phenyl)-amide
4-(3-Chloro-benzoyl)-[1,4]diazepane-1-carboxylic acid (4-isopropyl-phenyl)-amide
4-(4-Chloro-benzoyl)-[1,4]diazepane-1-carboxylic acid (4-isopropyl-phenyl)-amide
4-(2-Cyclopentyl-acetyl)-[1,4]diazepane-1-carboxylic acid (4-tert-butyl-phenyl)-amide
4-(2-Cyclopentyl-acetyl)-[1,4]diazepane-1-carboxylic acid (4-ethyl-phenyl)-amide
4-(2-Cyclopentyl-acetyl)-[1,4]diazepane-1-carboxylic acid (2,2-difluoro-benzo[1,3]dioxol-5-yl)-amide
4-(2-Cyclopentyl-acetyl)-[1,4]diazepane-1-carboxylic acid (2-naphthyl)-amide
4-(2-Cyclopentyl-acetyl)-[1,4]diazepane-1-carboxylic acid (4-n-pentyl-phenyl)-amide
4-(2-Cyclopentyl-acetyl)-[1,4]diazepane-1-carboxylic acid (4-trifluoromethyl-phenyl)-amide
4-(2-Cyclopentyl-acetyl)-[1,4]diazepane-1-carboxylic acid (4-sec-butyl-phenyl)-amide
4-(2-Cyclopentyl-acetyl)-[1,4]diazepane-1-carboxylic acid (4-bromo-phenyl)-amide
4-(3-Cyclopropyl-propionyl)-[1,4]diazepane-1-carboxylic acid (4-isopropyl-phenyl)-amide 4-(3-Cyclohexyl-propionyl)-[1,4]diazepane-1-carboxylic acid (4-isopropyl-phenyl)-amide
4-(4-Methyl-pentanoyl)-[1,4]diazepane-1-carboxylic acid (4-isopropyl-phenyl)-amide
4-(4,4,4-Trifluoro-butyryl)-[1,4]diazepane-1-carboxylic acid (4-isopropyl-phenyl)-amide
4-(3,3-Dimethyl-butyryl)-[1,4]diazepane-1-carboxylic acid (4-isopropyl-phenyl)-amide
4-(2-Cyclopentyl-acetyl)-[1,4]diazepane-1-carboxylic acid (2,5-dichloro-phenyl)-amide
4-(2-Cyclopentyl-acetyl)-[1,4]diazepane-1-carboxylic acid (3,4-dichloro-phenyl)-amide
4-(2-Cyclopentyl-acetyl)-[1,4]diazepane-1-carboxylic acid (3,5-dichloro-phenyl)-amide
4-(2-Cyclohexyl-acetyl)-[1,4]diazepane-1-carboxylic acid (4-ethyl-phenyl)-amide
4-(2-Cyclohexyl-acetyl)-[1,4]diazepane-1-carboxylic acid (2-naphthyl)-amide
4-Cyclohexanecarbonyl-[1,4]diazepane-1-carboxylic acid (4-ethyl-phenyl)-amide
4-Cyclohexanecarbonyl-[1,4]diazepane-1-carboxylic acid naphthalen-2-ylamide
4-(4-Chloro-benzoyl)-[1,4]diazepane-1-carboxylic (4-tert-butyl-phenyl)-amide
4-(4-Chloro-benzoyl)-[1,4]diazepane-1-carboxylic acid (4-trifluoromethyl-phenyl)-amide
4-(4-Chloro-benzoyl)-[1,4]diazepane-1-carboxylic acid (4-bromo-phenyl)-amide
4-(4-Chloro-benzoyl)-[1,4]diazepane-1-carboxylic acid (3,4-dichloro-phenyl)-amide
4-Cyclohexanecarbonyl-[1,4]diazepane-1-carboxylic acid (4-bromo-phenyl)-amide
4-Cyclohexanecarbonyl-[1,4]diazepane-1-carboxylic acid (3,4-dichloro-phenyl)-amide
4-Cyclohexanecarbonyl-[1,4]diazepane-1-carboxylic acid (3,5-dichloro-phenyl)-amide
4-(4,4-Difluoro-cyclohexanecarbonyl)-[1,4]diazepane-1-carboxylic acid (4-trifluoromethyl-phenyl)-amide
4-(4-Chloro-benzoyl)-[1,4]diazepane-1-carboxylic acid naphthalen-2-ylamide
4-Cyclohexanecarbonyl-[1,4]diazepane-1-carboxylic acid (4-trifluoromethylsulfanyl-phenyl)-amide
4-(Tetrahydro-pyran-4-carbonyl)-[1,4]diazepane-1-carboxylic acid (4-trifluoromethylsulfanyl-phenyl)-amide
4-(2-cyclopentyl-acetyl)-[1,4]diazepane-1-carboxylic acid (4-trifluoromethylsulfanyl-phenyl)-amide
4-Cyclopentanecarbonyl-[1,4]diazepane-1-carboxylic acid naphthalen-2-ylamide
4-(3-Cyclohexyl-propionyl)-[1,4]diazepane-1-carboxylic acid naphthalen-2-ylamide
4-(3,4-Dichloro-benzoyl)-[1,4]diazepane-1-carboxylic acid naphthalen-2-ylamide
4-(4-Cyano-benzoyl)-[1,4]diazepane-1-carboxylic acid naphthalen-2-ylamide
4-(2,5-Dichloro-benzoyl)-[1,4]diazepane-1-carboxylic acid naphthalen-2-ylamide
4-(4-Trifluoromethyl-benzoyl)-[1,4]diazepane-1-carboxylic acid naphthalen-2-ylamide
4-(4-Methyl-pentanoyl)-[1,4]diazepane-1-carboxylic acid naphthalen-2-ylamide
4-(2-Phenoxy-acetyl)-[1,4]diazepane-1-carboxylic acid naphthalen-2-ylamide
4-(4,4,4-Trifluoro-butyryl)-[1,4]diazepane-1-carboxylic acid naphthalen-2-ylamide
4-(3-Cyclopropyl-propionyl)-[1,4]diazepane-1-carboxylic acid naphthalen-2-ylamide
4-(2,4-Dichloro-benzoyl)-[1,4]diazepane-1-carboxylic acid naphthalen-2-ylamide
4-(4-Methyl-benzoyl)-[1,4]diazepane-1-carboxylic acid naphthalen-2-ylamide
4-(Tetrahydro-pyran-4-carbonyl)-[1,4]diazepane-1-carboxylic acid naphthalen-2-ylamide
4-(3-Cyclopentyl-propionyl)-[1,4]diazepane-1-carboxylic acid (4-propyl-phenyl)-amide
4-Cyclopentanecarbonyl-[1,4]diazepane-1-carboxylic acid (4-tert-butyl-phenyl)-amide
4-(3-Cyclopentyl-propionyl)-[1,4]diazepane-1-carboxylic acid (4-tert-butyl-phenyl)-amide
4-Cyclohexanecarbonyl-[1,4]diazepane-1-carboxylic acid (4-tert-butyl-phenyl)-amide
4-(2-Cyclohexyl-acetyl)-[1,4]diazepane-1-carboxylic acid (4-tert-butyl-phenyl)-amide
4-(3-Cyclohexyl-propionyl)-[1,4]diazepane-1-carboxylic acid (4-tert-butyl-phenyl)-amide
4-(2,5-Dichloro-benzoyl)-[1,4]diazepane-1-carboxylic acid (4-tert-butyl-phenyl)-amide
4-(3,4-Dichloro-benzoyl)-[1,4]diazepane-1-carboxylic acid (4-tert-butyl-phenyl)-amide
4-(3,5-Dichloro-benzoyl)-[1,4]diazepane-1-carboxylic acid (4-tert-butyl-phenyl)-amide
4-(4-Cyano-benzoyl)-[1,4]diazepane-1-carboxylic acid (4-tert-butyl-phenyl)-amide
4-(4-Dimethylamino-benzoyl)-[1,4]diazepane-1-carboxylic acid (4-tert-butyl-phenyl)-amide
4-(4-Trifluoromethyl-benzoyl)-[1,4]diazepane-1-carboxylic acid (4-tert-butyl-phenyl)-amide
4-(4-Methyl-pentanoyl)-[1,4]diazepane-1-carboxylic acid (4-tert-butyl-phenyl)-amide
4-(4,4,4-Trifluoro-butyryl)-[1,4]diazepane-1-carboxylic acid (4-tert-butyl-phenyl)-amide
4-(3-Cyclopropyl-propionyl)-[1,4]diazepane-1-carboxylic acid (4-tert-butyl-phenyl)-amide
4-(2-Thiomorpholin-4-yl-acetyl)-[1,4]diazepane-1-carboxylic acid (4-tert-butyl-phenyl)-amide
4-(4-Methyl-benzoyl)-[1,4]diazepane-1-carboxylic acid (4-tert-butyl-phenyl)-amide
4-(Tetrahydro-pyran-4-carbonyl)-[1,4]diazepane-1-carboxylic acid (4-tert-butyl-phenyl)-amide
4-(2-Piperidin-1-yl-acetyl)-[1,4]diazepane-1-carboxylic acid (4-tert-butyl-phenyl)-amide
4-(4-Trifluoromethyl-benzoyl)-[1,4]diazepane-1-carboxylic acid (4-trifluomethyl-phenyl)-amide
4-Cyclohexanecarbonyl-[1,4]diazepane-1-carboxylic acid (4-trifluoromethyl-phenyl)-amide
4-(4-Fluoro-benzoyl)-[1,4]diazepane-1-carboxylic acid (4-trifluoromethyl-phenyl)-amide
4-(2-Cyclopentyl-acetyl)-[1,4]diazepane-1-carboxylic acid (3-trifluoromethyl-phenyl)-amide
4-(2-Cyclopentyl-acetyl)-[1,4]diazepane-1-carboxylic acid (4-bromo-3-trifluoromethyl-phenyl)-amide
4-(Tetrahydro-pyran-4-carbonyl)-[1,4]diazepane-1-carboxylic acid (4-sec-butyl-phenyl)-amide
4-(3-Cyclopentyl-propionyl)-[1,4]diazepane-1-carboxylic acid cyclohexylmethyl-amide
4-(Tetrahydro-pyran-4-carbonyl)-[1,4]diazepane-1-carboxylic acid [4-(2,2,2-trifluoro-1-methyl-ethyl)-phenyl]-amide
4-(2-Cyclopentyl-acetyl)-[1,4]diazepane-1-carboxylic acid (5-tert-butyl-isoxazol-3-yl)-amide
4-(4-Chloro-benzoyl)-[1,4]diazepane-1-carboxylic acid (5-tert-butyl-isoxazol-3-yl)-amide
4-(Tetrahydro-pyran-4-carbonyl)-[1,4]diazepane-1-carboxylic acid (5-tert-butyl-isoxazol-3-yl)-amide 4-(4,4-Difluoro-cyclohexanecarbonyl)-[1,4]diazepane-1-carboxylic acid (5-tert-butyl-isoxazol-3-yl)-amide
4-(4-Hydroxy-cyclohexanecarbonyl)-[1,4]diazepane-1-carboxylic acid (5-tert-butyl-isoxazol-3-yl)-amide
4-(Tetrahydro-pyran-2-carbonyl)-[1,4]diazepane-1-carboxylic acid (5-tert-butyl-isoxazol-3-yl)-amide
4-(2-Tetrahydro-furan-2-yl-acetyl)-[1,4]diazepane-1-carboxylic acid (5-tert-butyl-isoxazol-3-yl)-amide
4-Cyclopentanecarbonyl-[1,4]diazepane-1-carboxylic acid (5-tert-butyl-isoxazol-3-yl)-amide
4-Cycloheptanecarbonyl-[1,4]diazepane-1-carboxylic acid (5-tert-butyl-isoxazol-3-yl)-amide
4-Cyclohexanecarbonyl-[1,4]diazepane-1-carboxylic acid (5-tert-butyl-isoxazol-3-yl)-amide
4-(4-Trifluoromethyl-benzoyl)-[1,4]diazepane-1-carboxylic acid (5-tert-butyl-isoxazol-3-yl)-amide
4-(4-Methoxy-cyclohexanecarbonyl)-[1,4]diazepane-1-carboxylic acid (5-tert-butyl-isoxazol-3-yl)-amide
4-(3-Methyl-butyryl)-[1,4]diazepane-1-carboxylic acid (5-tert-butyl-isoxazol-3-yl)-amide
4-(4-Acetylamino-cyclohexanecarbonyl)-[1,4]diazepane-1-carboxylic acid (5-tert-butyl-isoxazol-3-yl)-amide
4-(4-Methanesulfonylamino-cyclohexanecarbonyl)-[1,4]diazepane-1-carboxylic acid (5-tert-butyl-isoxazol-3-yl)-amide
4-(4-Chloro-benzoyl)-[1,4]diazepane-1-carboxylic acid (4-cyclopropyl-thiazol-2-yl)-amide
4-(4-Chloro-benzoyl)-[1,4]diazepane-1-carboxylic acid (4-phenyl-thiazol-2-yl)-amide
4-(4-Chloro-benzoyl)-[1,4]diazepane-1-carboxylic acid (4,5,6,7-tetrahydro-benzothiazol-2-yl)-amide
4-(4,4-Difluoro-cyclohexanecarbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (5-tert-butyl-thiazol-2-yl)-amide
4-(Tetrahydro-pyran-4-carbonyl)-[1,4]diazepane-1-carboxylic acid (4,5,6,7-tetrahydro-benzothiazol-2-yl)-amide
4-(Tetrahydro-pyran-4-carbonyl)-[1,4]diazepane-1-carboxylic acid (5-phenyl-thiazol-2-yl)-amide
4-(4-Hydroxy-cyclohexanecarbonyl)-[1,4]diazepane-1-carboxylic acid (5-tert-butyl-thiazol-2-yl)-amide
4-(4-Hydroxy-cyclohexanecarbonyl)-[1,4]diazepane-1-carboxylic acid (4-phenyl-thiazol-2-yl)-amide
4-(Tetrahydro-pyran-4-carbonyl)-[1,4]diazepane-1-carboxylic acid (5-isopropyl-thiazol-2-yl)-amide
4-(Tetrahydro-pyran-4-carbonyl)-[1,4]diazepane-1-carboxylic acid (4-phenyl-thiazol-2-yl)-amide
4-(Tetrahydro-pyran-4-carbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (4-tert-butyl-5-methyl-thiazol-2-yl)-amide
4-(Tetrahydro-pyran-4-carbonyl)-[1,4]diazepane-1-carboxylic acid (5-trifluoromethyl-pyridin-2-yl)-amide
4-(Tetrahydro-pyran-4-carbonyl)-[1,4]diazepane-1-carboxylic acid (3-sec-butyl-isoxazol-5-yl)-amide
4-(Tetrahydro-pyran-4-carbonyl)-[1,4]diazepane-1-carboxylic acid (3-phenyl-isoxazol-5-yl)-amide
4-(Tetrahydro-pyran-4-carbonyl)-[1,4]diazepane-1-carboxylic acid (3-tert-butyl-isoxazol-5-yl)-amide
4-(Tetrahydro-pyran-4-carbonyl)-[1,4]diazepane-1-carboxylic acid (5-sec-butyl-pyridin-2-yl)-amide
4-(Morpholine-4-carbonyl)-[1,4]diazepane-1-carboxylic acid (5-tert-butyl-isoxazol-3-yl)-amide
4-(Piperidine-1-carbonyl)-[1,4]diazepane-1-carboxylic acid (5-tert-butyl-isoxazol-3-yl)-amide
4-(4-Methanesulfonyl-piperidine-1-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (5-tert-butyl-isoxazol-3-yl)-amide
4-(4-Acetyl-piperazine-1-carbonyl)-[1,4]diazepane-1-carboxylic acid (5-tert-butyl-isoxazol-3-yl)-amide
4-(Thiomorpholine-4-carbonyl)-[1,4]diazepane-1-carboxylic acid (5-tert-butyl-isoxazol-3-yl)-amide
4-([1,4]Oxazepane-4-carbonyl)-[1,4]diazepane-1-carboxylic acid (5-tert-butyl-isoxazol-3-yl)-amide
4-(4,4-Difluoro-piperidine-1-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (4-sec-butyl-phenyl)-amide
4-(1,1-Dioxo-1$\lambda^6$-thiomorpholine-4-carbonyl)-[1,4]diazepane-1-carboxylic acid (4-tert-butyl-phenyl)-amide
4-(1,1-Dioxo-1$\lambda^6$-thiomorpholine-4-carbonyl)-[1,4]diazepane-1-carboxylic acid [4-(2,2,2-trifluoro-1-methyl-ethyl)-phenyl]-amide
4-(1,1-Dioxo-1$\lambda^6$-thiomorpholine-4-carbonyl)-[1,4]diazepane-1-carboxylic acid (3-tert-butyl-phenyl)-amide
4-(1,1-Dioxo-1$\lambda^6$-thiomorpholine-4-carbonyl)-[1,4]diazepane-1-carboxylic acid (3-tert-butyl-isoxazol-5-yl)-amide
[1,4]Diazepane-1,4-dicarboxylic acid 1-[(5-tert-butyl-isoxazol-3-yl)-amide]-4-cyclohexylamide
4-(1,1-Dioxo-1$\lambda^6$-thiomorpholine-4-carbonyl)-[1,4]diazepane-1-carboxylic acid (5-tert-butyl-thiazol-2-yl)-amide
4-(1,1-Dioxo-1$\lambda^6$-thiomorpholine-4-carbonyl)-[1,4]diazepane-1-carboxylic acid (4,5,6,7-tetrahydro-benzothiazol-2-yl)-amide
[1,4]Diazepane-1,4-dicarboxylic acid 1-[(5-tert-butyl-isoxazol-3-yl)-amide]-4-cyclopentylamide
4-(Morpholine-4-carbonyl)-[1,4]diazepane-1-carboxylic acid (4-sec-butyl-phenyl)-amide
[1,4]Diazepane-1,4-dicarboxylic acid 1-[(5-tert-butyl-isoxazol-3-yl)-amide]-4-[(tetrahydro-pyran-4-yl)-amide]
4-(Morpholine-4-carbonyl)-[1,4]diazepane-1-carboxylic acid (3-phenyl-isoxazol-5-yl)-amide
4-(Morpholine-4-carbonyl)-[1,4]diazepane-1-carboxylic acid (4-phenyl-thiazol-2-yl)-amide
4-(Morpholine-4-carbonyl)-[1,4]diazepane-1-carboxylic acid (3-sec-butyl-isoxazol-5-yl)-amide
4-(4-Methoxy-piperidine-1-carbonyl)-[1,4]diazepane-1-carboxylic acid (3-tert-butyl-isoxazol-5-yl)-amide
4-(Morpholine-4-carbonyl)-[1,4]diazepane-1-carboxylic acid (3-tert-butyl-isoxazol-5-yl)-amide
4-(2-Morpholin-4-yl-acetyl)-[1,4]diazepane-1-carboxylic acid (5-tert-butyl-isoxazol-3-yl)-amide
4-(2-Thiomorpholin-4-yl-acetyl)-[1,4]diazepane-1-carboxylic acid (5-tert-butyl-isoxazol-3-yl)-amide
4-[2-(1,1-Dioxo-1$\lambda^6$-thiomorpholin-4-yl)-acetyl]-[1,4]diazepane-1-carboxylic acid (5-tert-butyl-isoxazol-3-yl)-amide
4-[2-(4,4-Difluoro-piperidin-1-yl)-acetyl]-[1,4]diazepane-1-carboxylic acid (5-tert-butyl-isoxazol-3-yl)-amide
4-[2-(1,1-Dioxo-1$\lambda^6$-thiomorpholin-4-yl)-acetyl]-[1,4]diazepane-1-carboxylic acid (3-tert-butyl-isoxazol-5-yl)-amide
4-(4,4-Difluoro-cyclohexanecarbonyl)-[1,4]diazepane-1-carboxylic acid (3-tert-butyl-isoxazol-5-yl)-amide
4-(4-Oxo-cyclohexanecarbonyl)-[1,4]diazepane-1-carboxylic acid (5-tert-butyl-isoxazol-3-yl)-amide 4-(4-Hydroxy-4-methyl-cyclohexanecarbonyl)-[1,4]diazepane-1-carboxylic acid (5-tert-butyl-isoxazol-3-yl)-amide
4-(1,1-Dioxo-hexahydro-1$\lambda^6$-thiopyran-4-carbonyl)-[1,4]diazepane-1-carboxylic acid
(5-tert-butyl-isoxazol-3-yl)-amide
4-(2-Cyclopentyl-acetyl)-[1,4]diazepane-1-carboxylic acid [4-(1-hydroxy-butyl)-phenyl]-amide
4-(2-Cyclopentyl-acetyl)-[1,4]diazepane-1-carbothioic acid (4-isopropyl-phenyl)-amide
Most preferred compounds include:
4-(3-Cyclopentyl-propionyl)-[1,4]diazepane-1-carboxylic acid (4-butyl-phenyl)-amide
4-(2-Cyclopentyl-acetyl)-[1,4]diazepane-1-carboxylic acid (4-butyl-phenyl)-amide
4-(2-Cyclohexyl-acetyl)-[1,4]diazepane-1-carboxylic acid (4-butyl-phenyl)-amide
4-Cyclohexanecarbonyl-[1,4]diazepane-1-carboxylic acid (4-butyl-phenyl)-amide
4-Cyclohexanecarbonyl-[1,4]diazepane-1-carboxylic acid (4-isopropyl-phenyl)-amide
4-(2-Cyclohexyl-acetyl)-[1,4]diazepane-1-carboxylic acid (4-isopropyl-phenyl)-amide
4-(4-Chloro-benzoyl)-[1,4]diazepane-1-carboxylic acid (4-isopropyl-phenyl)-amide
4-(2-Cyclopentyl-acetyl)-[1,4]diazepane-1-carboxylic acid (4-tert-butyl-phenyl)-amide
4-(2-Cyclopentyl-acetyl)-[1,4]diazepane-1-carboxylic acid (2-naphthyl)-amide
4-(2-Cyclopentyl-acetyl)-[1,4]diazepane-1-carboxylic acid (4-n-pentyl-phenyl)-amide
4-(2-Cyclopentyl-acetyl)-[1,4]diazepane-1-carboxylic acid (4-sec-butyl-phenyl)-amide
4-(3-Cyclopropyl-propionyl)-[1,4]diazepane-1-carboxylic acid (4-isopropyl-phenyl)-amide
4-(3-Cyclohexyl-propionyl)-[1,4]diazepane-1-carboxylic acid (4-isopropyl-phenyl)-amide
4-(3,3-Dimethyl-butyryl)-[1,4]diazepane-1-carboxylic acid (4-isopropyl-phenyl)-amide
4-(2-Cyclopentyl-acetyl)-[1,4]diazepane-1-carboxylic acid (2,5-dichloro-phenyl)-amide
4-Cyclohexanecarbonyl-[1,4]diazepane-1-carboxylic acid naphthalen-2-ylamide
4-(4-Chloro-benzoyl)-[1,4]diazepane-1-carboxylic acid (4-tert-butyl-phenyl)-amide
4-(4,4-Difluoro-cyclohexanecarbonyl)-[1,4]diazepane-1-carboxylic acid (4-trifluoromethyl-phenyl)-amide
4-(4-Chloro-benzoyl)-[1,4]diazepane-1-carboxylic acid naphthalen-2-ylamide
4-Cyclohexanecarbonyl-[1,4]diazepane-1-carboxylic acid (4-trifluoromethylsulfanyl-phenyl)-amide
4-(Tetrahydro-pyran-4-carbonyl)-[1,4]diazepane-1-carboxylic acid (4-trifluoromethylsulfanyl-phenyl)-amide
4-(2-cyclopentyl-acetyl)-[1,4]diazepane-1-carboxylic acid (4-trifluoromethylsulfanyl-phenyl)-amide
4-(3,4-Dichloro-benzoyl)-[1,4]diazepane-1-carboxylic acid naphthalen-2-ylamide
4-(4-Cyano-benzoyl)-[1,4]diazepane-1-carboxylic acid naphthalen-2-ylamide
4-(2,5-Dichloro-benzoyl)-[1,4]diazepane-1-carboxylic acid naphthalen-2-ylamide
4-(4-Trifluoromethyl-benzoyl)-[1,4]diazepane-1-carboxylic acid naphthalen-2-ylamide
4-(4-Methyl-pentanoyl)-[1,4]diazepane-1-carboxylic acid naphthalen-2-ylamide
4-(2,4-Dichloro-benzoyl)-[1,4]diazepane-1-carboxylic acid naphthalen-2-ylamide
4-(3-Cyclopentyl-propionyl)-[1,4]diazepane-1-carboxylic acid (4-tert-butyl-phenyl)-amide
4-Cyclohexanecarbonyl-[1,4]diazepane-1-carboxylic acid (4-tert-butyl-phenyl)-amide
4-(2-Cyclohexyl-acetyl)-[1,4]diazepane-1-carboxylic acid (4-tert-butyl-phenyl)-amide
4-(3-Cyclohexyl-propionyl)-[1,4]diazepane-1-carboxylic acid (4-tert-butyl-phenyl)-amide
4-(2,5-Dichloro-benzoyl)-[1,4]diazepane-1-carboxylic acid (4-tert-butyl-phenyl)-amide
4-(3,4-Dichloro-benzoyl)-[1,4]diazepane-1-carboxylic acid (4-tert-butyl-phenyl)-amide
4-(4-Cyano-benzoyl)-[1,4]diazepane-1-carboxylic acid (4-tert-butyl-phenyl)-amide
4-(4-Dimethylamino-benzoyl)-[1,4]diazepane-1-carboxylic acid (4-tert-butyl-phenyl)-amide
4-(4-Trifluoromethyl-benzoyl)-[1,4]diazepane-1-carboxylic acid (4-tert-butyl-phenyl)-amide
4-(4-Methyl-pentanoyl)-[1,4]diazepane-1-carboxylic acid (4-tert-butyl-phenyl)-amide
4-(2-Thiomorpholin-4-yl-acetyl)-[1,4]diazepane-1-carboxylic acid (4-tert-butyl-phenyl)-amide
4-(4-Methyl-benzoyl)-[1,4]diazepane-1-carboxylic acid (4-tert-butyl-phenyl)-amide
4-(Tetrahydro-pyran-4-carbonyl)-[1,4]diazepane-1-carboxylic acid (4-tert-butyl-phenyl)-amide
4-(4-Trifluoromethyl-benzoyl)-[1,4]diazepane-1-carboxylic acid (4-trifluomethyl-phenyl)-amide
4-Cyclohexanecarbonyl-[1,4]diazepane-1-carboxylic acid (4-trifluoromethyl-phenyl)-amide
4-(2-Cyclopentyl-acetyl)-[1,4]diazepane-1-carboxylic acid (4-bromo-3-trifluoromethyl-phenyl)-amide
4-(Tetrahydro-pyran-4-carbonyl)-[1,4]diazepane-1-carboxylic acid (4-sec-butyl-phenyl)-amide
4-(2-Cyclopentyl-acetyl)-[1,4]diazepane-1-carboxylic acid (5-tert-butyl-isoxazol-3-yl)-amide
4-(4-Chloro-benzoyl)-[1,4]diazepane-1-carboxylic acid (5-tert-butyl-isoxazol-3-yl)-amide
4-(Tetrahydro-pyran-4-carbonyl)-[1,4]diazepane-1-carboxylic acid (5-tert-butyl-isoxazol-3-yl)-amide
4-(4,4-Difluoro-cyclohexanecarbonyl)-[1,4]diazepane-1-carboxylic acid (5-tert-butyl-isoxazol-3-yl)-amide
4-(4-Hydroxy-cyclohexanecarbonyl)-[1,4]diazepane-1-carboxylic acid (5-tert-butyl-isoxazol-3-yl)-amide
4-Cycloheptanecarbonyl-[1,4]diazepane-1-carboxylic acid (5-tert-butyl-isoxazol-3-yl)-amide
4-Cyclohexanecarbonyl-[1,4]diazepane-1-carboxylic acid (5-tert-butyl-isoxazol-3-yl)-amide
4-(4-Trifluoromethyl-benzoyl)-[1,4]diazepane-1-carboxylic acid (5-tert-butyl-isoxazol-3-yl)-amide
4-(4-Methoxy-cyclohexanecarbonyl)-[1,4]diazepane-1-carboxylic acid (5-tert-butyl-isoxazol-3-yl)-amide
4-(4-Acetylamino-cyclohexanecarbonyl)-[1,4]diazepane-1-carboxylic acid (5-tert-butyl-isoxazol-3-yl)-amide
4-(4-Chloro-benzoyl)-[1,4]diazepane-1-carboxylic acid (4-cyclopropyl-thiazol-2-yl)-amide
4-(4-Chloro-benzoyl)-[1,4]diazepane-1-carboxylic acid (4-phenyl-thiazol-2-yl)-amide
4-(4-Chloro-benzoyl)-[1,4]diazepane-1-carboxylic acid (4,5,6,7-tetrahydro-benzothiazol-2-yl)-amide
4-(4,4-Difluoro-cyclohexanecarbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (5-phenyl-thiazol-2-yl)-amide
4-(4-Hydroxy-cyclohexanecarbonyl)-[1,4]diazepane-1-carboxylic acid (5-tert-butyl-thiazol-2-yl)-amide 4-(4-Hydroxy-cyclohexanecarbonyl)-[1,4]diazepane-1-carboxylic acid (4-phenyl-thiazol-2-yl)-amide
4-(Tetrahydro-pyran-4-carbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (4-tert-butyl-5-methyl-thiazol-2-yl)-amide
4-(Tetrahydro-pyran-4-carbonyl)-[1,4]diazepane-1-carboxylic acid (3-sec-butyl-isoxazol-5-yl)-amide
4-(Tetrahydro-pyran-4-carbonyl)-[1,4]diazepane-1-carboxylic acid (3-tert-butyl-isoxazol-5-yl)-amide
4-(Tetrahydro-pyran-4-carbonyl)-[1,4]diazepane-1-carboxylic acid (5-sec-butyl-pyridin-2-yl)-amide
4-(Piperidine-1-carbonyl)-[1,4]diazepane-1-carboxylic acid (5-tert-butyl-isoxazol-3-yl)-amide
4-(Thiomorpholine-4-carbonyl)-[1,4]diazepane-1-carboxylic acid (5-tert-butyl-isoxazol-3-yl)-amide
4-(4,4-Difluoro-piperidine-1-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (3-tert-butyl-isoxazol-5-yl)-amide
[1,4]Diazepane-1,4-dicarboxylic acid 1-[(5-tert-butyl-isoxazol-3-yl)-amide]-4-cyclohexylamide
4-(1,1-Dioxo-1$\lambda^6$-thiomorpholine-4-carbonyl)-[1,4]diazepane-1-carboxylic acid (5-tert-butyl-thiazol-2-yl)-amide
[1,4]Diazepane-1,4-dicarboxylic acid 1-[(5-tert-butyl-isoxazol-3-yl)-amide]-4-cyclopentylamide
4-(Morpholine-4-carbonyl)-[1,4]diazepane-1-carboxylic acid (4-sec-butyl-phenyl)-amide
4-(Morpholine-4-carbonyl)-[1,4]diazepane-1-carboxylic acid (3-tert-butyl-isoxazol-5-yl)-amide
4-(2-Thiomorpholin-4-yl-acetyl)-[1,4]diazepane-1-carboxylic acid (5-tert-butyl-isoxazol-3-yl)-amide
4-[2-(1,1-Dioxo-1$\lambda^6$-thiomorpholin-4-yl)-acetyl]-[1,4]diazepane-1-carboxylic acid (5-tert-butyl-isoxazol-3-yl)-amide
4-[2-(4,4-Difluoro-piperidin-1-yl)-acetyl]-[1,4]diazepane-1-carboxylic acid (5-tert-butyl-isoxazol-3-yl)-amide
4-(4,4-Difluoro-cyclohexanecarbonyl)-[1,4]diazepane-1-carboxylic acid (3-tert-butyl-isoxazol-5-yl)-amide
4-(4-Oxo-cyclohexanecarbonyl)-[1,4]diazepane-1-carboxylic acid (5-tert-butyl-isoxazol-3-yl)-amide Therapeutic Use As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine opthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lymphosarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

Combination Therapy

These compounds may also be employed in combination therapies with the following compounds to treat the above mentioned diseases:

non-steroidal antiinflammatory drugs (NSAIDs) including COX-2 inhibitors such as propionic acid derivatives (acetaminophen, alminoprofen, benoxaprofen, bucloxic acid, carprofen, fenhufen, fenoprofen, flurbiprofen, fluriprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxipinac, sulindac, tiopinac, tolmetin, zidometacin, and zomepirac), fenamic acid derivatives (meclofenamic acid, mefenamic acid, and tolfenamic acid), biphenyl-carboxylic acid derivatives, oxicams (isoxicam, meloxicam, piroxicam, sudoxicam and tenoxicam), salicylates (aspirin, acetyl salicylic acid, sulfasalazine choline magnesium salicylate, sodium salicylate, magnesium salicylate, choline salicylate,) and the pyrazolones (apazone, bezpiperylon, feprazone, mofebutazone, oxyphenbutazone, phenylbutazone), and the coxibs (celecoxib, valecoxib, rofecoxib and etoricoxib); diflunisal, etodolac, ketorolac tromethanime, meclofenamate sodium, nabumetone, lomoxicam, nimesulide, remifenzone, salsalate, flosulide, and the like; glucocorticosteroids such as betamethasone, budesonide, cortisone, dexamethasone, hydrocortisone, methylprednisolone, prednisolone, prednisone, triamcinolone and deflazacort; immunosuppressive, immunomodulatory, or cytsostatic drugs including but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab, IL-1 receptor antagonists such as but not limited to Kineret; interferon-beta, 1a or 1b including but not limited to Betaseron, Avonex and Rebif, interferon-alpha;

angiogenesis inhibitors such as but not limited to compounds directed against VEGF, taxol, pentoxyfylline opiate receptor agonists such as morphine, propoxyphene (Darvon), tramadol, buprenorphin;

sodium channel blockers such as carbamazepine, mexiletine, lamotrigine, pregabaline, tectin, NW-1029, CGX-1002;

N-type calcium channel blockers such as Ziconotide, NMED-160, SPI-860; serotonergic and noradrenergic modulators such as SR-57746, paroxetine, duloxetine, clonidine, amitriptyline, citalopram;

histamine H1 receptor antagonists such as bromopheniramine, chlorpheniramine, dexchlorpheniramine, triprolidine, clemastine, diphenhydramine, diphenylpyraline, tripelennamine, hydroxyzine, methdiazine, promethazine, trimeprazine, azatadine, cyproheptadine, antazoline, pheniramine pyrilamine, astemizole, terfenadine, loratadine, cetirizine, desloratadine, fexofenadine and levocetirizine;

histamine H2 receptor antagonists such as cimetidine, famotidine and ranitidine;

proton pump inhibitors such as omeprazole, pantoprazole and esomeprazole;

leukotriene antagonists and 5-lipoxygenase inhibitors such as zafirlukast, montelukast, pranlukast and zileuton;

local anesthetics such as ambroxol, lidocaine;

VR1 agonists and antagonists such as NGX-4010, WL-1002, ALGRX-4975, WL-10001, AMG-517;

nicotinic acetylcholine receptor agonists such as ABT-202, A-366833, ABT-594; BTG-102, A-85380, CGX1204;

P2X3 receptor antagonists such as A-317491, ISIS-13920, AZD-9056;

NGF agonists and antagonists such as RI-724, RI-1024, AMG-819, AMG-403, PPH 207;

NK1 and NK2 antagonists such as DA-5018, R-116301; CP-728663, ZD-2249;

NMDA antagonist such as NER-MD-11, CNS-5161, EAA-090, AZ-756, CNP-3381;

potassium channel modulators such as CL-888, ICA-69673, retigabine;

GABA modulators such as lacosamide;

serotonergic and noradrenergic modulators such as SR-57746, paroxetine, duloxetine, clonidine, amitriptyline, citalopram, flibanserin; and combination with anti-migraine drugs like sumatriptan, zolmitriptan, naratriptan, and eletriptan.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives,* Michael & Irene Ash (eds.), Gower, 1995; *Handbook of Pharmaceutical Excipients,* A. H. Kibbe (ed.), American Pharmaceutical Ass'n, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

Examples of Pharmaceutical Formulations

| A. TABLETS | |
|---|---|
| Component | Amount per tablet (mg) |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B. TABLETS | |
|---|---|
| Component | Amount per tablet (mg) |
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
| --- | --- |
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
| --- | --- |
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
| --- | --- |
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
| --- | --- |
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
| --- | --- |
| active substance | 0.005 |
| sorbitan trioleate | 0.1 |
| Monofluorotrichloromethane and difluorodichloromethane (2:3) | To 100 |

The suspension is transferred into a conventional aerosol container with a metering valve. Preferably, 50 µL of suspension are delivered per spray. The active substance may also be metered in higher doses if desired (e.g., 0.02% by weight).

H. POWDER FOR INHALATION

| Component | Amount |
| --- | --- |
| active substance | 1.0 mg |
| lactose monohydrate | to 25 mg |

I. POWDER FOR INHALATION

| Component | Amount |
| --- | --- |
| active substance | 2.0 mg |
| lactose monohydrate | to 25 mg |

J. POWDER FOR INHALATION

| Component | Amount |
| --- | --- |
| active substance | 1.0 mg |
| lactose monohydrate | to 5 mg |

K. POWDER FOR INHALATION

| Component | Amount |
| --- | --- |
| active substance | 2.0 mg |
| lactose monohydrate | to 5 mg |

In Examples H, I, J, and K, the powder for inhalation is produced in the usual way by mixing the individual ingredients together.

The invention claimed is:

1. A compound of the formula (I) wherein,

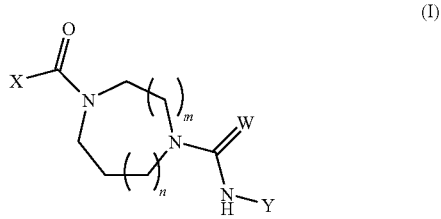

W is O,

X is $C_1$-$C_6$ alkyl, $C_3$-$C_{10}$ cycloalkyl, phenyl, naphthyl, quinolinyl, morpholinyl, thiomorpholinyl, dioxo-thiomorpholinyl, oxo-thiomorpholinyl, piperidinyl, piperazinyl, tetrahydropyranyl, tetrahydrofuranyl, pyridinyl, thiazolyl, oxazolyl, isoxazolyl, imidazolyl, hexahydrothiopyran, dioxo-hexahydrothiopyran, oxazepanyl or thienyl, each X is optionally substituted with 1-3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, amino$C_1$-$C_6$ acyl, $C_1$-$C_6$ acylamino, $C_1$-$C_6$ alkoxycarbonyl, $C_1$-$C_6$ alkoxycarbonylamino, $C_3$-$C_6$ cycloalkyl, morpholinyl, thiomorpholinyl, dioxo-thiomorpholinyl, piperidinyl, pyrrolidinyl, tetrahydrofuranyl, tetrahydropyranyl, phenoxy, phenylamino, halogen, cyano, $C_1$-$C_6$ dialkylamino, oxo, hydroxyl, phenyl, pyridinyl and $SO_2R^4$, each of the above ring substituents for X are further optionally substituted with 1 to 2 halogen or $C_1$-$C_4$ alkyl optionally substituted with halogen; or X is $R^2R^3N$—, wherein $R^2$ and $R^3$ are independently hydrogen, $C_1$-$C_6$ alkyl (optionally substituted by 1 to 3 halogen atoms), $C_3$-$C_6$ cycloalkyl, phenyl, benzyl, quinolinyl, morpholinyl, thiomorpholinyl, piperidinyl, piperazinyl, thiazolyl, oxazolyl, isoxazolyl, imidazolyl, triazolyl, oxadiazolyl, thiadiazolyl, indolyl, azaindolyl, benzoxazolyl, benzothiazolyl, benzimidazolyl, tetrahydrobenzothiazolyl, tetrahydrobenzimidazolyl, tetrahydrobenzoxazolyl, tetrahydroisoquinolinyl or pyridinyl each of the above ring substituents are optionally substituted with 1 to 2 $C_1$-$C_4$ alkyl optionally substituted with halogen;

$R^4$ is $C_1$-$C_6$ alkyl (optionally substituted by 1 to 3 halogen atoms), $C_3$-$C_6$ cycloalkyl, phenyl or benzyl;

Y is $C_1$-$C_6$ alkyl, $C_3$-$C_{10}$ cycloalkyl, phenyl, naphthyl, quinolinyl, morpholinyl, thiomorpholinyl, piperidinyl, piperazinyl, tetrahydropyranyl, tetrahydrofuranyl, pyridinyl, thiazolyl, oxazolyl, isoxazolyl, imidazolyl, triazolyl, oxadiazolyl, thiadiazolyl, indolyl, azaindolyl, benzoxazolyl, benzothiazolyl, benzimidazolyl, tetrahydrobenzothiazolyl, tetrahydrobenzimidazolyl, tetrahydrobenzoxazolyl, tetrahydroisoquinolinyl, and thienyl each optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, $C_3$-$C_6$ cycloalkyl, phenoxy, $C_1$-$C_6$ alkylthio (which is optionally substituted with 1 to 3 halogen atoms), halogen, $C_1$-$C_6$ dialkylamino, $C_1$-$C_6$ dialkylamino$C_1$-$C_6$ alkyl, phenyl (which is optionally substituted with 1 to 2 halogen atoms or $C_1$-$C_4$ alkyl optionally substituted with halogen), thienyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^5$ wherein $R^5$ is $C_1$-$C_6$ alkyl (optionally substituted by one to 3 halogen atoms) and m and n are 1;

or a pharmaceutically acceptable salt thereof.

2. The compound according to claim 1 and wherein,

X is methyl, ethyl, propyl, butyl, pentyl, cyclopropyl, cyclobutyl, cyclopentyl, cyclohexyl, cycloheptyl, phenyl, naphthyl, quinolinyl, morpholinyl, thiomorpholinyl, dioxothiomorpholinyl, oxo-thiomorpholinyl, piperidinyl, piperazinyl, tetrahydropyranyl, tetrahydrofuranyl, pyridinyl, thiazolyl, oxazolyl, isoxazolyl, imidazolyl, hexahydrothiopyran, dioxo-hexahydrothiopyran, oxazepanyl, and thienyl, each X is optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, $C_1$-$C_6$ acylamino, $C_3$-$C_6$ cycloalkyl, phenoxy, halogen, cyano, $C_1$-$C_6$ dialkylamino, morpholinyl, tetrahydrofuranyl, tetrahydropyranyl, piperidinyl, pyrrolidinyl, thiomorpholinyl, dioxo-thiomorpholinyl, oxo, hydroxyl, phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^4$;

or X is $R^2R^3N$—, wherein $R^2$ and $R^3$ are independently hydrogen, $C_1$-$C_6$ alkyl (optionally substituted by 1 to 3 halogen atoms), $C_3$-$C_6$ cycloalkyl, phenyl, benzyl or morpholinyl;

Y is methyl, ethyl, propyl, butyl, pentyl, cyclopropyl, cyclobutyl, cyclopentyl, cyclohexyl, cycloheptyl, phenyl, naphthyl, quinolinyl, morpholinyl, thiomorpholinyl, piperidinyl, piperazinyl, tetrahydropyranyl, tetrahydrofuranyl, pyridinyl, thiazolyl, oxazolyl, isoxazolyl, imidazolyl, indolyl, azaindolyl, benzoxazolyl, benzothiazolyl, benzimidazolyl, tetrahydrobenzothiazolyl, tetrahydrobenzimidazolyl, tetrahydrobenzoxazolyl and thienyl each optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_3$-$C_6$ cycloalkyl, phenoxy, $C_1$-$C_6$ alkylthio (which is optionally substituted with 1 to 3 halogens), halogen, dimethylamino $C_1$-$C_6$ alkyl, phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^5$ wherein $R^5$ is $C_1$-$C_6$ alkyl (optionally substituted by one to 3 halogen atoms);

$R^4$ is $C_1$-$C_6$ alkyl (optionally substituted by 1 to 3 halogen atoms), $C_3$-$C_6$ cycloalkyl, phenyl or benzyl.

3. The compound according to claim 2 and wherein,

X is methyl, ethyl, propyl, cyclopentyl, cyclohexyl, phenyl, naphthyl, quinolinyl, tetrahydropyranyl, cycloheptyl, dioxo-hexahydrothiopyran, each optionally substituted with 1-3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_1$-$C_6$ acyl, $C_1$-$C_6$acylamino, $C_3$-$C_6$ cycloalkyl, phenoxy, halogen, hydroxyl, oxo, cyano, $C_1$-$C_6$dialkylamino, morpholinyl, thiomorpholinyl, dioxo-thiomorpholinyl, piperidinyl pyrrolidinyl, phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^4$;

Y is phenyl, naphthyl, quinolinyl, pyridinyl, thiazolyl, oxazolyl, isoxazolyl, imidazolyl, tetrahydrobenzothiazolyl, and thienyl each optionally substituted with 1 to 3 substituents chosen from $C_1$-$C_6$ alkyl (which is optionally substituted with 1 to 3 halogen atoms), $C_1$-$C_6$ alkoxy (which is optionally substituted with 1 to 3 halogen atoms), $C_3$-$C_6$ cycloalkyl, phenoxy, halogen, $C_1$-$C_6$ alkylthio (which is optionally substituted with 1-3 halogens) dimethylamino $C_1$-$C_6$ alkyl, phenyl (which is optionally substituted with 1 to 2 halogen atoms or $C_1$-$C_4$ alkyl optionally substituted with halogen), pyridinyl (which is optionally substituted with 1 to 2 $C_1$-$C_4$ alkyl optionally substituted with halogen) and $SO_2R^5$ wherein $R^5$ is $C_1$-$C_6$ alkyl (optionally substituted by 1 to 3 halogen atoms)

or X is $R^2R^3N—$, wherein $R^2$ and $R^3$ are independently hydrogen, $C_1$-$C_6$ alkyl (optionally substituted by 1 to 3 halogen atoms), or morpholinyl;

$R^4$ is $C_1$-$C_6$ alkyl (optionally substituted by 1 to 3 halogen atoms), $C_3$-$C_6$ cycloalkyl, phenyl or benzyl.

4. A compound chosen from:

4-(3-Cyclopentyl-propionyl)-[1,4]diazepane-1-carboxylic acid (4-butyl-phenyl)-amide
4-(3-Cyclopentyl-propionyl)-[1,4]diazepane-1-carboxylic acid (4-isopropyl-phenyl)-amide
4-(3-Cyclopentyl-propionyl)-[1,4]diazepane-1-carboxylic acid (4-ethyl-phenyl)-amide
4-(3-Cyclopentyl-propionyl)-[1,4]diazepane-1-carboxylic acid (4-cyano-phenyl)-amide
4-(3-Cyclopentyl-propionyl)-[1,4]diazepane-1-carboxylic acid naphthalen-1-ylamide
4-(3-Cyclopentyl-propionyl)-[1,4]diazepane-1-carboxylic acid naphthalen-2-ylamide
4-(3-Cyclopentyl-propionyl)-[1,4]diazepane-1-carboxylic acid (4-chloro-phenyl)-amide
4-(3-Cyclopentyl-propionyl)-[1,4]diazepane-1-carboxylic acid m-tolylamide
4-(3-Cyclopentyl-propionyl)-[1,4]diazepane-1-carboxylic acid (4-dimethylamino-phenyl)-amide
4-(3-Cyclohexyl-propionyl)-[1,4]diazepane-1-carboxylic acid (4-butyl-phenyl)-amide
4-(2-Cyclopentyl-acetyl)-[1,4]diazepane-1-carboxylic acid (4-butyl-phenyl)-amide
4-Cyclopentanecarbonyl-[1,4]diazepane-1-carboxylic acid (4-butyl-phenyl)-amide
4-(4-Methyl-pentanoyl)-[1,4]diazepane-1-carboxylic acid (4-butyl-phenyl)-amide
4-(3-Cyclopentyl-propionyl)-[1,4]diazepane-1-carboxylic acid (4-pentyl-phenyl)-amide
4-(3-Cyclopentyl-propionyl)-[1,4]diazepane-1-carboxylic acid (4-trifluoromethyl-phenyl)-amide
4-Benzoyl-[1,4]diazepane-1-carboxylic acid (4-butyl-phenyl)-amide
4-(2-Cyclohexyl-acetyl)-[1,4]diazepane-1-carboxylic acid (4-butyl-phenyl)-amide
4-(3-Cyclopropyl-propionyl)-[1,4]diazepane-1-carboxylic acid (4-butyl-phenyl)-amide
4-Cyclohexanecarbonyl-[1,4]diazepane-1-carboxylic acid (4-butyl-phenyl)-amide
4-(Tetrahydro-pyran-4-carbonyl)-[1,4]diazepane-1-carboxylic acid (4-butyl-phenyl)-amide
4-(2-Cyclopentyl-acetyl)-[1,4]diazepane-1-carboxylic acid (4-trifluoromethoxy-phenyl)-amide
4-(2-Cyclopentyl-acetyl)-[1,4]diazepane-1-carboxylic acid (4-isopropyl-phenyl)-amide
4-(3-Cyclopentyl-propionyl)-[1,4]diazepane-1-carboxylic acid (4-methylsulfanyl-phenyl)-amide
4-(2-Cyclopentyl-acetyl)-[1,4]diazepane-1-carboxylic acid (4-methylsulfanyl-phenyl)-amide
4-(2-Tetrahydro-pyran-4-yl-acetyl)-[1,4]diazepane-1-carboxylic acid (4-isopropyl-phenyl)-amide
4-(2-Tetrahydro-pyran-4-yl-acetyl)-[1,4]diazepane-1-carboxylic acid (4-ethyl-phenyl)-amide
4-(2-Tetrahydro-pyran-4-yl-acetyl)-[1,4]diazepane-1-carboxylic acid (4-trifluoromethoxy-phenyl)-amide
4-(2-Tetrahydro-pyran-4-yl-acetyl)-[1,4]diazepane-1-carboxylic acid (4-sec-butyl-phenyl)-amide
4-(2-Tetrahydro-pyran-4-yl-acetyl)-[1,4]diazepane-1-carboxylic acid (4-pentyl-phenyl)-amide
4-(2-Tetrahydro-pyran-4-yl-acetyl)-[1,4]diazepane-1-carboxylic acid (4-butyl-phenyl)-amide
4-(2-Tetrahydro-pyran-4-yl-acetyl)-[1,4]diazepane-1-carboxylic acid (2-naphthyl)-amide
4-(2-Tetrahydro-pyran-4-yl-acetyl)-[1,4]diazepane-1-carboxylic acid (4-methylsulfanyl-phenyl)-amide
4-(2-Tetrahydro-pyran-4-yl-acetyl)-[1,4]diazepane-1-carboxylic acid (4-tert-butyl-phenyl)-amide
4-Cyclohexanecarbonyl-[1,4]diazepane-1-carboxylic acid (4-isopropyl-phenyl)-amide
4-Benzoyl-[1,4]diazepane-1-carboxylic acid (4-isopropyl-phenyl)-amide
4-(2-Cyclohexyl-acetyl)-[1,4]diazepane-1-carboxylic acid (4-isopropyl-phenyl)-amide
4-(Pyridine-2-carbonyl)-[1,4]diazepane-1-carboxylic acid (4-isopropyl-phenyl)-amide
4-(Tetrahydro-pyran-4-carbonyl)-[1,4]diazepane-1-carboxylic acid (4-isopropyl-phenyl)-amide
4-(Pyridine-4-carbonyl)-[1,4]diazepane-1-carboxylic acid (4-isopropyl-phenyl)-amide
4-(3-Chloro-benzoyl)-[1,4]diazepane-1-carboxylic acid (4-isopropyl-phenyl)-amide
4-(4-Chloro-benzoyl)-[1,4]diazepane-1-carboxylic acid (4-isopropyl-phenyl)-amide
4-(2-Tetrahydro-pyran-4-yl-acetyl)-[1,4]diazepane-1-carboxylic acid (2,2-difluoro-benzol-[1,3]-dioxol-5-yl)-amide
4-(2-Tetrahydro-pyran-4-yl-acetyl)-[1,4]diazepane-1-carboxylic acid (3,5-dichloro-phenyl)-amide
4-(2-Cyclopentyl-acetyl)-[1,4]diazepane-1-carboxylic acid (4-tert-butyl-phenyl)-amide
4-(2-Cyclopentyl-acetyl)-[1,4]diazepane-1-carboxylic acid (4-ethyl-phenyl)-amide
4-(2-Cyclopentyl-acetyl)-[1,4]diazepane-1-carboxylic acid (1-acetyl-2,3-dihydro-1H-indol-6-yl)-amide
4-(2-Cyclopentyl-acetyl)-[1,4]diazepane-1-carboxylic acid (2,2-difluoro-benzol-[1,3]-dioxol-5-yl)-amide
4-(2-Cyclopentyl-acetyl)-[1,4]diazepane-1-carboxylic acid (2-naphthyl)-amide
4-(2-Cyclopentyl-acetyl)-[1,4]diazepane-1-carboxylic acid (4-n-pentyl-phenyl)-amide
4-(2-Cyclopentyl-acetyl)-[1,4]diazepane-1-carboxylic acid (4-trifluoromethyl-phenyl)-amide
4-(2-Tetrahydro-pyran-4-yl-acetyl)-[1,4]diazepane-1-carboxylic acid (4-trifluoromethyl-phenyl)-amide
4-(2-Cyclopentyl-acetyl)-[1,4]diazepane-1-carboxylic acid (4-sec-butyl-phenyl)-amide 4-(2-Cyclopentyl-acetyl)-[1,4]diazepane-1-carboxylic acid (4-biphenyl)-amide
4-(2-Cyclopentyl-acetyl)-[1,4]diazepane-1-carboxylic acid (4-bromo-phenyl)-amide
4-(3-Cyclopropyl-propionyl)-[1,4]diazepane-1-carboxylic acid (4-isopropyl-phenyl)-amide
4-(3-Cyclohexyl-propionyl)-[1,4]diazepane-1-carboxylic acid (4-isopropyl-phenyl)-amide
4-pivaloyl-[1,4]diazepane-1-carboxylic acid (4-isopropyl-phenyl)-amide
4-(4-Methyl-pentanoyl)-[1,4]diazepane-1-carboxylic acid (4-isopropyl-phenyl)-amide
4-(4,4,4-Trifluoro-butyryl)-[1,4]diazepane-1-carboxylic acid (4-isopropyl-phenyl)-amide
4-(3,3-Dimethyl-butyryl)-[1,4]diazepane-1-carboxylic acid (4-isopropyl-phenyl)-amide
4-(2-Cyclopentyl-acetyl)-[1,4]diazepane-1-carboxylic acid (2,4-dichloro-phenyl)-amide
4-(2-Cyclopentyl-acetyl)-[1,4]diazepane-1-carboxylic acid (2,5-dichloro-phenyl)-amide
4-(2-Cyclopentyl-acetyl)-[1,4]diazepane-1-carboxylic acid (3,4-dichloro-phenyl)-amide
4-(2-Cyclopentyl-acetyl)-[1,4]diazepane-1-carboxylic acid (3,5-dichloro-phenyl)-amide
4-(2-Cyclohexyl-acetyl)-[1,4]diazepane-1-carboxylic acid (4-ethyl-phenyl)-amide
4-(2-Cyclohexyl-acetyl)-[1,4]diazepane-1-carboxylic acid (2-naphthyl)-amide
4-Cyclohexanecarbonyl-[1,4]diazepane-1-carboxylic acid (4-ethyl-phenyl)-amide
4-Cyclohexanecarbonyl-[1,4]diazepane-1-carboxylic acid naphthalen-2-ylamide
4-(4-Chloro-benzoyl)-[1,4]diazepane-1-carboxylic acid (4-tert-butyl-phenyl)-amide
4-(4-Chloro-benzoyl)-[1,4]diazepane-1-carboxylic acid (4-trifluoromethyl-phenyl)-amide
4-(4-Chloro-benzoyl)-[1,4]diazepane-1-carboxylic acid (4-bromo-phenyl)-amide
4-(4-Chloro-benzoyl)-[1,4]diazepane-1-carboxylic acid (3,4-dichloro-phenyl)-amide
4-(4-Chloro-benzoyl)-[1,4]diazepane-1-carboxylic acid (3,5-dichloro-phenyl)-amide
4-Cyclohexanecarbonyl-[1,4]diazepane-1-carboxylic acid (4-bromo-phenyl)-amide
4-Cyclohexanecarbonyl-[1,4]diazepane-1-carboxylic acid (3,4-dichloro-phenyl)-amide
4-Cyclohexanecarbonyl-[1,4]diazepane-1-carboxylic acid (3,5-dichloro-phenyl)-amide
4-(Tetrahydro-pyran-4-carbonyl)-[1,4]diazepane-1-carboxylic acid (4-trifluoromethyl-phenyl)-amide
4-(4,4-Difluoro-cyclohexanecarbonyl)-[1,4]diazepane-1-carboxylic acid (4-trifluoromethyl-phenyl)-amide
4-(4-Chloro-benzoyl)-[1,4]diazepane-1-carboxylic acid naphthalen-2-ylamide
4-Cyclohexanecarbonyl-[1,4]diazepane-1-carboxylic acid (4-trifluoromethylsulfanyl-phenyl)-amide
4-(Tetrahydro-pyran-4-carbonyl)-[1,4]diazepane-1-carboxylic acid (4-trifluoromethylsulfanyl-phenyl)-amide
4-(2-cyclopentyl-acetyl)-[1,4]diazepane-1-carboxylic acid (4-trifluoromethylsulfanyl-phenyl)-amide
4-(2-Cyclopentyl-acetyl)-[1,4]diazepane-1-carboxylic acid (4-butyryl-phenyl)-amide
4-Cyclopentanecarbonyl-[4,1]diazepane-1-carboxylic acid naphthalen-2-ylamide
4-(3-Cyclohexyl-propionyl)-[1,4]diazepane-1-carboxylic acid naphthalen-2-ylamide
4-(3,4-Dichloro-benzoyl)-[1,4]diazepane-1-carboxylic acid naphthalen-2-ylamide
4-(3,5-Dichloro-benzoyl)-[1,4]diazepane-1-carboxylic acid naphthalen-2-ylamide
4-(4-Cyano-benzoyl)-[1,4]diazepane-1-carboxylic acid naphthalen-2-ylamide
4-(4-Dimethylamino-benzoyl)-[1,4]diazepane-1-carboxylic acid naphthalen-2-ylamide
4-(2,5-Dichloro-benzoyl)-[1,4]diazepane-1-carboxylic acid naphthalen-2-ylamide
4-(4-Methoxy-benzoyl)-[1,4]diazepane-1-carboxylic acid naphthalen-2-ylamide
4-(4-Trifluoromethyl-benzoyl)-[1,4]diazepane-1-carboxylic acid naphthalen-2-ylamide
4-(3,3-Dimethyl-butyryl)-[1,4]diazepane-1-carboxylic acid naphthalen-2-ylamide
4-(4-Methyl-pentanoyl)-[1,4]diazepane-1-carboxylic acid naphthalen-2-ylamide
4-(2,2-Dimethyl-propionyl)-[1,4]diazepane-1-carboxylic acid naphthalen-2-ylamide
4-(2-Phenoxy-acetyl)-[1,4]diazepane-1-carboxylic acid naphthalen-2-ylamide
4-(4,4,4-Trifluoro-butyryl)-[1,4]diazepane-1-carboxylic acid naphthalen-2-ylamide
4-(3-Cyclopropyl-propionyl)-[1,4]diazepane-1-carboxylic acid naphthalen-2-ylamide
4-(2,4-Dichloro-benzoyl)-[1,4]diazepane-1-carboxylic acid naphthalen-2-ylamide
4-(4-Methyl-benzoyl)-[1,4]diazepane-1-carboxylic acid naphthalen-2-ylamide
4-(Tetrahydro-pyran-4-carbonyl)-[1,4]diazepane-1-carboxylic acid naphthalen-2-ylamide
4-(3-Cyclopentyl-propionyl)-[1,4]diazepane-1-carboxylic acid (4-propyl-phenyl)-amide
4-(2-Piperidin-1-yl-acetyl)-[1,4]diazepane-1-carboxylic acid naphthalen-2-ylamide
4-Cyclopentanecarbonyl-[1,4]diazepane-1-carboxylic acid (4-tert-butyl-phenyl)-amide
4-(3-Cyclopentyl-propionyl)-[1,4]diazepane-1-carboxylic acid (4-tert-butyl-phenyl)-amide
4-Cyclohexanecarbonyl-[4,1]diazepane-1-carboxylic acid (4-tert-butyl-phenyl)-amide
4-(2-Cyclohexyl-acetyl)-[1,4]diazepane-1-carboxylic acid (4-tert-butyl-phenyl)-amide
4-(3-Cyclohexyl-propionyl)-[1,4]diazepane-1-carboxylic acid (4-tert-butyl-phenyl)-amide
4-(2,5-Dichloro-benzoyl)-[1,4]diazepane-1-carboxylic acid (4-tert-butyl-phenyl)-amide
4-(3,4-Dichloro-benzoyl)-[1,4]diazepane-1-carboxylic acid (4-tert-butyl-phenyl)-amide
4-(3,5-Dichloro-benzoyl)-[1,4]diazepane-1-carboxylic acid (4-tert-butyl-phenyl)-amide
4-(4-Cyano-benzoyl)-[1,4]diazepane-1-carboxylic acid (4-tert-butyl-phenyl)-amide
4-(4-Dimethylamino-benzoyl)-[1,4]diazepane-1-carboxylic acid (4-tert-butyl-phenyl)-amide
4-(4-Trifluoromethyl-benzoyl)-[1,4]diazepane-1-carboxylic acid (4-tert-butyl-phenyl)-amide
4-(3,3-Dimethyl-butyryl)-[1,4]diazepane-1-carboxylic acid (4-tert-butyl-phenyl)-amide
4-(4-Methyl-pentanoyl)-[1,4]diazepane-1-carboxylic acid (4-tert-butyl-phenyl)-amide
4-(2,2-Dimethyl-propionyl)-[1,4]diazepane-1-carboxylic acid (4-tert-butyl-phenyl)-amide
4-(2-Phenoxy-acetyl)-[1,4]diazepane-1-carboxylic acid (4-tert-butyl-phenyl)-amide 4-(4,4,4-Trifluoro-butyryl)-[1,4]diazepane-1-carboxylic acid (4-tert-butyl-phenyl)-amide
4-(3-Cyclopropyl-propionyl)-[1,4]diazepane-1-carboxylic acid (4-tert-butyl-phenyl)-amide
4-(2-Thiomorpholin-4-yl-acetyl)-[1,4]diazepane-1-carboxylic acid (4-tert-butyl-phenyl)-amide
4-(4-Methyl-benzoyl)-[1,4]diazepane-1-carboxylic acid (4-tert-butyl-phenyl)-amide
4-(2-Phenylamino-acetyl)-[1,4]diazepane-1-carboxylic acid (4-tert-butyl-phenyl)-amide
4-(Pyridine-2-carbonyl)-[1,4]diazepane-1-carboxylic acid (4-sec-butyl-phenyl)-amide
4-(Tetrahydro-pyran-4-carbonyl)-[1,4]diazepane-1-carboxylic acid (4-tert-butyl-phenyl)-amide
4-(2-Piperidin-1-yl-acetyl)-[1,4]diazepane-1-carboxylic acid (4-tert-butyl-phenyl)-amide
4-(4-Trifluoromethyl-benzoyl)-[1,4]diazepane-1-carboxylic acid (4-trifluomethyl-phenyl)-amide
4-Cyclohexanecarbonyl-[1,4]diazepane-1-carboxylic acid (4-trifluoromethyl-phenyl)-amide
4-(4-Fluoro-benzoyl)-[1,4]diazepane-1-carboxylic acid (4-trifluoromethyl-phenyl)-amide
4-Benzoyl-[1,4]diazepane-1-carboxylic acid (4-trifluoromethyl-phenyl)-amide
4-(2-Cyclopentyl-acetyl)-[1,4]diazepane-1-carboxylic acid (3-trifluoromethyl-phenyl)-amide
4-(2-Cyclopentyl-acetyl)-[1,4]diazepane-1-carboxylic acid (4-bromo-3-trifluoromethyl-phenyl)-amide
4-(Tetrahydro-pyran-4-carbonyl)-[1,4]diazepane-1-carboxylic acid (4-sec-butyl-phenyl)-amide
4-(3-Cyclopentyl-propionyl)-[1,4]diazepane-1-carboxylic acid cyclohexylmethyl-amide
4-(3-Cyclopentyl-propionyl)-[1,4]diazepane-1-carboxylic acid cyclohexylamide
4-(2-Tetrahydro-pyran-4-yl-acetyl)-[1,4]diazepane-1-carboxylic acid (4-methanesulfonyl-phenyl)-amide
4-(3-Cyclopentyl-propionyl)-[1,4]diazepane-1-carboxylic acid (4-methanesulfonyl-phenyl)-amide
4-(2-Cyclopentyl-acetyl)-[1,4]diazepane-1-carboxylic acid (4-methanesulfonyl-phenyl)-amide
4-(Tetrahydro-pyran-4-carbonyl)-[1,4]diazepane-1-carboxylic acid [4-(2,2,2-trifluoro-1-methyl-ethyl)-phenyl]-amide
4-(2-Cyclopentyl-acetyl)-[1,4]diazepane-1-carboxylic acid (5-tert-butyl-isoxazol-3-yl)-amide
4-(4-Chloro-benzoyl)-[1,4]diazepane-1-carboxylic acid (5-tert-butyl-isoxazol-3-yl)-amide
4-(Tetrahydro-pyran-4-carbonyl)-[1,4]diazepane-1-carboxylic acid (5-tert-butyl-isoxazol-3-yl)-amide
4-(1-Methyl-cyclohexanecarbonyl)-[1,4]diazepane-1-carboxylic acid (5-tert-butyl-isoxazol-3-yl)-amide
4-(4,4-Difluoro-cyclohexanecarbonyl)-[1,4]diazepane-1-carboxylic acid (5-tert-butyl-isoxazol-3-yl)-amide
4-(4-Hydroxy-cyclohexanecarbonyl)-[1,4]diazepane-1-carboxylic acid (5-tert-butyl-isoxazol-3-yl)-amide
4-(Tetrahydro-pyran-2-carbonyl)-[1,4]diazepane-1-carboxylic acid (5-tert-butyl-isoxazol-3-yl)-amide
4-(Tetrahydro-pyran-3-carbonyl)-[1,4]diazepane-1-carboxylic acid (5-tert-butyl-isoxazol-3-yl)-amide
4-(2-Tetrahydro-furan-2-yl-acetyl)-[1,4]diazepane-1-carboxylic acid (5-tert-butyl-isoxazol-3-yl)-amide
4-(Tetrahydro-furan-2-carbonyl)-[1,4]diazepane-1-carboxylic acid (5-tert-butyl-isoxazol-3-yl)-amide
4-(Tetrahydro-furan-3-carbonyl)-[1,4]diazepane-1-carboxylic acid (5-tert-butyl-isoxazol-3-yl)-amide
4-Cyclopentanecarbonyl-[4,1]diazepane-1-carboxylic acid (5-tert-butyl-isoxazol-3-yl)-amide
4-Cycloheptanecarbonyl-[1,4]diazepane-1-carboxylic acid (5-tert-butyl-isoxazol-3-yl)-amide
4-Cyclohexanecarbonyl-[1,4]diazepane-1-carboxylic acid (5-tert-butyl-isoxazol-3-yl)-amide
4-(4-Trifluoromethyl-benzoyl)-[1,4]diazepane-1-carboxylic acid (5-tert-butyl-isoxazol-3-yl)-amide
4-(4-Methoxy-cyclohexanecarbonyl)-[1,4]diazepane-1-carboxylic acid (5-tert-butyl-isoxazol-3-yl)-amide
4-(2,2-Dimethyl-propionyl)-[1,4]diazepane-1-carboxylic acid (5-tert-butyl-isoxazol-3-yl)-amide
4-(3-Methyl-butyryl)-[1,4]diazepane-1-carboxylic acid (5-tert-butyl-isoxazol-3-yl)-amide
4-(4-Amino-cyclohexanecarbonyl)-[1,4]diazepane-1-carboxylic acid (5-tert-butyl-isoxazol-3-yl)-amide
4-(Piperidine-4-carbonyl)-[1,4]diazepane-1-carboxylic acid (5-tert-butyl-isoxazol-3-yl)-amide
4-(4-Acetylamino-cyclohexanecarbonyl)-[1,4]diazepane-1-carboxylic acid (5-tert-butyl-isoxazol-3-yl)-amide
4-(4-Methanesulfonylamino-cyclohexanecarbonyl)-[1,4]diazepane-1-carboxylic acid (5-tert-butyl-isoxazol-3-yl)-amide
4-(1-Acetyl-piperidine-4-carbonyl)-[1,4]diazepane-1-carboxylic acid (5-tert-butyl-isoxazol-3-yl)-amide
4-(1-Methanesulfonyl-piperidine-4-carbonyl)-[1,4]diazepane-1-carboxylic acid (5-tert-butyl-isoxazol-3-yl)-amide
4-(Piperidine-3-carbonyl)-[1,4]diazepane-1-carboxylic acid (5-tert-butyl-isoxazol-3-yl)-amide
4-(1-Methanesulfonyl-piperidine-3-carbonyl)-[1,4]diazepane-1-carboxylic acid (5-tert-butyl-isoxazol-3-yl)-amide
4-(4-Chloro-benzoyl)-[1,4]diazepane-1-carboxylic acid (4-cyclopropyl-thiazol-2-yl)-amide
4-(4-Chloro-benzoyl)-[1,4]diazepane-1-carboxylic acid (4-phenyl-thiazol-2-yl)-amide
4-(4-Chloro-benzoyl)-[1,4]diazepane-1-carboxylic acid (4,5,6,7-tetrahydro-benzothiazol-2-yl)-amide
4-(4,4-Difluoro-cyclohexanecarbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (5-tert-butyl-thiazol-2-yl)-amide
4-(Tetrahydro-pyran-4-carbonyl)-[1,4]diazepane-1-carboxylic acid (4,5,6,7-tetrahydro-benzothiazol-2-yl)-amide
4-(Tetrahydro-pyran-4-carbonyl)-[1,4]diazepane-1-carboxylic acid (5-phenyl-thiazol-2-yl)-amide
4-(4-Hydroxy-cyclohexanecarbonyl)-[1,4]diazepane-1-carboxylic acid (5-tert-butyl-thiazol-2-yl)-amide
4-(4-Hydroxy-cyclohexanecarbonyl)-[1,4]diazepane-1-carboxylic acid (4-phenyl-thiazol-2-yl)-amide
4-(Tetrahydro-pyran-4-carbonyl)-[1,4]diazepane-1-carboxylic acid (5-tert-butyl-2H-pyrazol-3-yl)-amide
4-(Tetrahydro-pyran-4-carbonyl)-[1,4]diazepane-1-carboxylic acid (5-isopropyl-thiazol-2-yl)-amide
4-(Tetrahydro-pyran-4-carbonyl)-[1,4]diazepane-1-carboxylic acid (5-sec-butyl-2-methyl-2H-pyrazol-3-yl)-amide
4-(Tetrahydro-pyran-4-carbonyl)-[1,4]diazepane-1-carboxylic acid (4-phenyl-thiazol-2-yl)-amide
4-(Tetrahydro-pyran-4-carbonyl)-[1,4]diazepane-1-carboxylic acid (5-phenyl-isoxazol-3-yl)-amide
4-(Tetrahydro-pyran-4-carbonyl)-[1,4]diazepane-1-carboxylic acid (4-ethyl-pyridin-2-yl)-amide
4-(Tetrahydro-pyran-4-carbonyl)-[1,4]diazepane-1-carboxylic acid quinolin-3-ylamide 4-(Tetrahydro-pyran-4-carbonyl)-[1,4]diazepane-1-carboxylic acid (4-tert-butyl-thiazol-2-yl)-amide
4-(Tetrahydro-pyran-4-carbonyl)-[1,4]diazepane-1-carboxylic acid (5-tert-butyl-4-methyl-thiazol-2-yl)-amide
4-(Tetrahydro-pyran-4-carbonyl)-[1,4]diazepane-1-carboxylic acid (4-methyl-thiazol-2-yl)-amide
4-(Tetrahydro-pyran-4-carbonyl)-[1,4]diazepane-1-carboxylic acid (4,5-dimethyl-thiazol-2-yl)-amide
4-(Tetrahydro-pyran-4-carbonyl)-[1,4]diazepane-1-carboxylic acid (4-tert-butyl-5-methyl-thiazol-2-yl)-amide
4-(Tetrahydro-pyran-4-carbonyl)-[1,4]diazepane-1-carboxylic acid (4-trifluoromethyl-pyridin-2-yl)-amide
4-(Tetrahydro-pyran-4-carbonyl)-[1,4]diazepane-1-carboxylic acid (6-phenoxy-pyridin-3-yl)-amide
4-(Tetrahydro-pyran-4-carbonyl)-[1,4]diazepane-1-carboxylic acid (5-trifluoromethyl-pyridin-2-yl)-amide
4-(Tetrahydro-pyran-4-carbonyl)-[1,4]diazepane-1-carboxylic acid (5-tert-butyl-2-methyl-2H-pyrazol-3-yl)-amide
4-(Tetrahydro-pyran-4-carbonyl)-[1,4]diazepane-1-carboxylic acid (1-methyl-1H-benzoimidazol-2-yl)-amide
4-(Tetrahydro-pyran-4-carbonyl)-[1,4]diazepane-1-carboxylic acid (2-methyl-5-phenyl-2H-pyrazol-3-yl)-amide
4-(Tetrahydro-pyran-4-carbonyl)-[1,4]diazepane-1-carboxylic acid (3-sec-butyl-isoxazol-5-yl)-amide
4-(Tetrahydro-pyran-4-carbonyl)-[1,4]diazepane-1-carboxylic acid (3-phenyl-isoxazol-5-yl)-amide
4-(Tetrahydro-pyran-4-carbonyl)-[1,4]diazepane-1-carboxylic acid (3-tert-butyl-isoxazol-5-yl)-amide
4-(Tetrahydro-pyran-4-carbonyl)-[1,4]diazepane-1-carboxylic acid (5-sec-butyl-pyridin-2-yl)-amide
4-(Morpholine-4-carbonyl)-[1,4]diazepane-1-carboxylic acid (5-tert-butyl-isoxazol-3-yl)-amide
4-(Piperidine-1-carbonyl)-[1,4]diazepane-1-carboxylic acid (5-tert-butyl-isoxazol-3-yl)-amide
4-(4-Methanesulfonyl-piperidine-1-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (5-tert-butyl-isoxazol-3-yl)-amide
4-(4-Acetyl-piperazine-1-carbonyl)-[1,4]diazepane-1-carboxylic acid (5-tert-butyl-isoxazol-3-yl)-amide
4-(4-Methanesulfonyl-piperazine-1-carbonyl)-[1,4]diazepane-1-carboxylic acid (5-tert-butyl-isoxazol-3-yl)-amide
4-(Thiomorpholine-4-carbonyl)-[1,4]diazepane-1-carboxylic acid (5-tert-butyl-isoxazol-3-yl)-amide
4-(1-Oxo-1$\lambda^4$-thiomorpholine-4-carbonyl)-[1,4]diazepane-1-carboxylic acid (5-tert-butyl-isoxazol-3-yl)-amide
4-([1,4]Oxazepane-4-carbonyl)-[1,4]diazepane-1-carboxylic acid (5-tert-butyl-isoxazol-3-yl)-amide
4-(4,4-Difluoro-piperidine-1-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (4-sec-butyl-phenyl)-amide
4-(1,1-Dioxo-1$\lambda^6$-thiomorpholine-4-carbonyl)-[1,4]diazepane-1-carboxylic acid (4-tert-butyl-phenyl)-amide
4-(1,1-Dioxo-1$\lambda^6$-thiomorpholine-4-carbonyl)-[1,4]diazepane-1-carboxylic acid [4-(2,2,2-trifluoro-1-methyl-ethyl)-phenyl]-amide
4-(1,1-Dioxo-1$\lambda^6$-thiomorpholine-4-carbonyl)-[1,4]diazepane-1-carboxylic acid (3-tert-butyl-phenyl)-amide
4-(1,1-Dioxo-1$\lambda^6$-thiomorpholine-4-carbonyl)-[1,4]diazepane-1-carboxylic acid (3-tert-butyl-isoxazol-5-yl)-amide
[1,4]Diazepane-1,4-dicarboxylic acid 1-[(5-tert-butyl-isoxazol-3-yl)-amide]-4-cyclohexylamide
4-((2R,6S)-2,6-Dimethyl-morpholine-4-carbonyl)-[1,4]diazepane-1-carboxylic acid (5-tert-butyl-isoxazol-3-yl)-amide
4-(1,1-Dioxo-1$\lambda^6$-thiomorpholine-4-carbonyl)-[1,4]diazepane-1-carboxylic acid (5-tert-butyl-thiazol-2-yl)-amide
4-(1,1-Dioxo-1$\lambda^6$-thiomorpholine-4-carbonyl)-[1,4]diazepane-1-carboxylic acid (5-isopropyl-thiazol-2-yl)-amide
4-(1,1-Dioxo-1$\lambda^6$-thiomorpholine-4-carbonyl)-[1,4]diazepane-1-carboxylic acid (4,5,6,7-tetrahydro-benzothiazol-2-yl)-amide
[1,4]Diazepane-1,4-dicarboxylic acid 1-[(5-tert-butyl-isoxazol-3-yl)-amide]-4-cyclopentylamide
4-(Morpholine-4-carbonyl)-[1,4]diazepane-1-carboxylic acid (4-sec-butyl-phenyl)-amide
[1,4]Diazepane-1,4-dicarboxylic acid 1-[(5-tert-butyl-isoxazol-3-yl)-amide]-4-[(tetrahydro-pyran-4-yl)-amide]
[1,4]Diazepane-1,4-dicarboxylic acid 1-[(5-tert-butyl-isoxazol-3-yl)-amide]-4-phenylamide
4-(Morpholine-4-carbonyl)-[1,4]diazepane-1-carboxylic acid (3-phenyl-isoxazol-5-yl)-amide
4-(Morpholine-4-carbonyl)-[1,4]diazepane-1-carboxylic acid (4-phenyl-thiazol-2-yl)-amide
4-(Morpholine-4-carbonyl)-[1,4]diazepane-1-carboxylic acid (3-sec-butyl-isoxazol-5-yl)-amide
4-(4-Methoxy-piperidine-1-carbonyl)-[1,4]diazepane-1-carboxylic acid (3-tert-butyl-isoxazol-5-yl)-amide
4-(Morpholine-4-carbonyl)-[1,4]diazepane-1-carboxylic acid (3-tert-butyl-isoxazol-5-yl)-amide
4-(2-Morpholin-4-yl-acetyl)-[1,4]diazepane-1-carboxylic acid (5-tert-butyl-isoxazol-3-yl)-amide
4-(2-Thiomorpholin-4-yl-acetyl)-[1,4]diazepane-1-carboxylic acid (5-tert-butyl-isoxazol-3-yl)-amide
4-[2-(1,1-Dioxo-1$\lambda^6$-thiomorpholin-4-yl)-acetyl]-[1,4]diazepane-1-carboxylic acid (5-tert-butyl-isoxazol-3-yl)-amide
4-[2-(4,4-Difluoro-piperidin-1-yl)-acetyl]-[1,4]diazepane-1-carboxylic acid (5-tert-butyl-isoxazol-3-yl)-amide
4-[2-(1,1-Dioxo-1$\lambda^6$-thiomorpholin-4-yl)-acetyl]-[1,4]diazepane-1-carboxylic acid (3-tert-butyl-isoxazol-5-yl)-amide
4-[2-((2R,6S)-2,6-Dimethyl-morpholin-4-yl)-acetyl]-[1,4]diazepane-1-carboxylic acid (5-tert-butyl-isoxazol-3-yl)-amide
4-(4,4-Difluoro-cyclohexanecarbonyl)-[1,4]diazepane-1-carboxylic acid (3-tert-butyl-isoxazol-5-yl)-amide
4-(Tetrahydro-pyran-4-carbonyl)-[1,4]diazapane-1-carboxylic acid (4,5-dimethyl-isoxazol-3-yl)-amide
4-(4-Oxo-cyclohexanecarbonyl)-[1,4]diazepane-1-carboxylic acid (5-tert-butyl-isoxazol-3-yl)-amide
4-(4-Hydroxy-4-methyl-cyclohexanecarbonyl)-[1,4]diazepane-1-carboxylic acid (5-tert-butyl-isoxazol-3-yl)-amide
4-(1,1-Dioxo-hexahydro-1$\lambda^6$-thiopyran-4-carbonyl)-[1,4]diazepane-1-carboxylic acid (5-tert-butyl-isoxazol-3-yl)-amide
4-(2-Cyclopentyl-acetyl)-[1,4]diazepane-1-carboxylic acid [4-(1-hydroxy-butyl)-phenyl]-amide 4-(2-Cyclopentyl-acetyl)-[1,4]diazepane-1-carbothioic acid (4-isopropyl-phenyl)-amide or a pharmaceutically acceptable salt thereof.

5. A pharmaceutical composition comprising a therapeutically effective amount of a compound according to claim 1 and one or more pharmaceutically acceptable carriers and/or adjuvants.

6. A method of treating pain comprising administering a therapeutically effective amount of a compound of the formula (I) according to claim 1.

7. The method according to claim 6 wherein pain is chosen from acute pain, visceral pain, neuropathic pain, inflammatory and nociceptive pain, cancer pain and headache.

8. The method according to claim 7 wherein neuropathic pain is chosen from low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

\* \* \* \* \*